United States Patent
Liu et al.

(10) Patent No.: US 10,679,488 B2
(45) Date of Patent: Jun. 9, 2020

(54) SYSTEM AND METHOD FOR IMPROVING COMPLIANCE WITH ONE OR MORE PROTOCOLS INCLUDING HAND HYGIENE AND PERSONAL PROTECTIVE EQUIPMENT PROTOCOLS

(71) Applicant: Microsensor Labs, LLC, Chicago, IL (US)

(72) Inventors: Peng Liu, Chicago, IL (US); Yang Liu, Beijing (CN); Jiapeng Huang, Louisville, KY (US)

(73) Assignee: Microsensor Labs, LLC, Chicago, IL (US)

( * ) Notice: Subject to any disclaimer, the term of this patent is extended or adjusted under 35 U.S.C. 154(b) by 0 days.

(21) Appl. No.: 16/148,683

(22) Filed: Oct. 1, 2018

(65) Prior Publication Data

US 2019/0043337 A1 Feb. 7, 2019

Related U.S. Application Data

(63) Continuation-in-part of application No. 15/946,537, filed on Apr. 5, 2018, now Pat. No. 10,403,121.
(Continued)

(51) Int. Cl.
*G08B 21/24* (2006.01)
*G16H 50/30* (2018.01)
*G16H 40/20* (2018.01)

(52) U.S. Cl.
CPC ........... *G08B 21/245* (2013.01); *G16H 40/20* (2018.01); *G16H 50/30* (2018.01)

(58) Field of Classification Search
CPC ....... G16H 50/30; G16H 40/20; G08B 21/245
See application file for complete search history.

(56) References Cited

U.S. PATENT DOCUMENTS 5,870,015 A 2/1999 Hinkel
6,028,520 A 2/2000 Maehre
(Continued)

FOREIGN PATENT DOCUMENTS

EP 3118828 A1 1/2017
WO WO2015179262 A1 11/2015
(Continued)

OTHER PUBLICATIONS

U.S. Office Action for U.S. Appl. No. 15/946,537 dated Oct. 18, 2018.
(Continued)

*Primary Examiner* — Hongmin Fan
(74) *Attorney, Agent, or Firm* — Lempia Summerfield Katz LLC

(57) ABSTRACT

A system and method for detecting personal protective equipment (PPE) compliance is disclosed. Personal protective equipment, such as gloves, gowns, masks, protective eyewear, may be used to limit transmission of illness either from the patient to the care giver or vice-versa. Compliance with PPE is important in various contexts, including hospital settings, home settings, work settings, and school settings. For example, a healthcare provider may wear a wristband, which may interact with a stationary controller that is associated with an entrance and/or an exit to an area for the patient (such as the stationary controller integrated with or proximate to a hand cleaning agent dispenser) proximate to the entrance and/or exit. The interaction may be used to determine whether the healthcare provider has complied with PPE protocols. Further, the system may be used to train healthcare providers or others in PPE hygiene. In addition, the wristband may be used to check for compliance of a plurality of protocols, such as PPE protocols and hand hygiene (HH) protocols. In this way, the system may be used
(Continued)

for safely interacting with patients in order to reduce cross-contamination.

32 Claims, 61 Drawing Sheets

Related U.S. Application Data

(60) Provisional application No. 62/482,146, filed on Apr. 5, 2017.

(56) References Cited

U.S. PATENT DOCUMENTS

| | | | |
|---|---|---|---|
| 6,417,773 | B1 | 7/2002 | Vlahos et al. |
| 6,937,155 | B2 | 8/2005 | Ballard |
| 8,648,724 | B2 | 2/2014 | Forsberg et al. |
| 8,698,637 | B2 | 4/2014 | Raichman |
| 9,135,805 | B2 | 9/2015 | Freedman et al. |
| 9,483,930 | B1 | 11/2016 | Haaland |
| 9,695,981 | B2 | 7/2017 | Au |
| 9,747,760 | B2 * | 8/2017 | Fletcher .................. G08B 3/10 |
| 2006/0191068 | A1 | 8/2006 | Vlahos et al. |
| 2009/0195385 | A1 | 8/2009 | Huang et al. |
| 2010/0073162 | A1 | 3/2010 | Johnson et al. |
| 2010/0164728 | A1 | 7/2010 | Plost |
| 2010/0193703 | A1 | 8/2010 | Kimura et al. |
| 2012/0062382 | A1 | 3/2012 | Taneff |
| 2012/0256742 | A1 * | 10/2012 | Snodgrass .............. G16H 40/20 340/539.12 |
| 2012/0268277 | A1 | 10/2012 | Best |
| 2013/0300572 | A1 | 11/2013 | Mould-Millman |
| 2014/0266692 | A1 | 9/2014 | Freedman et al. |
| 2014/0313055 | A1 | 10/2014 | Warkentin et al. |
| 2014/0345726 | A1 | 11/2014 | Seggio et al. |
| 2016/0379456 | A1 | 12/2016 | Nongpiur et al. |
| 2017/0004287 | A1 | 1/2017 | O'Toole |
| 2017/0294106 | A1 | 10/2017 | Thyroff |
| 2017/0372216 | A1 | 12/2017 | Awiszus |
| 2018/0151054 | A1 | 5/2018 | Pi |
| 2018/0357886 | A1 * | 12/2018 | Tavori .................. G08B 21/245 |

FOREIGN PATENT DOCUMENTS

| | | |
|---|---|---|
| WO | WO2017011911 A1 | 1/2017 |
| WO | WO2017094016 A1 | 6/2017 |

OTHER PUBLICATIONS

International Search Report for PCT Application No. US2018/026238, dated Jul. 23, 2018.
Written Opinion of the International Searching Authority for PCT Application No. US2018/026238, dated Jul. 23, 2018.
PCT International Search Report and Written Opinion of International Searching Authority, corresponding to PCT International Application No. PCT/US2019/025751 dated Sep. 11, 2019.

* cited by examiner

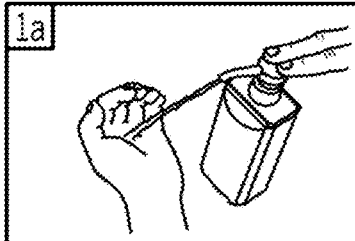 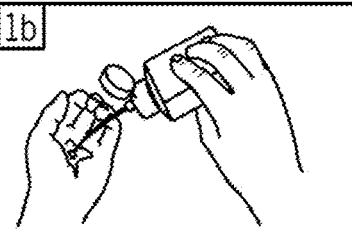 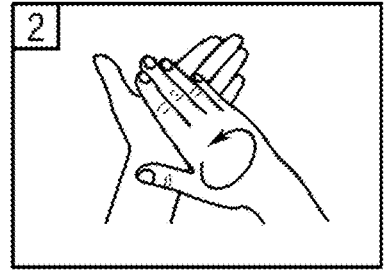

Apply a palmful of the product in a cupped hand, covering all surfaces;   Rub hands palm to palm;

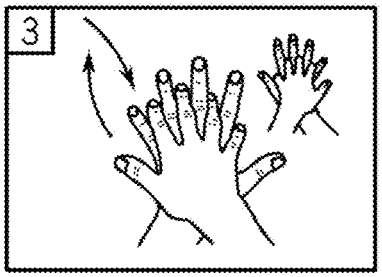 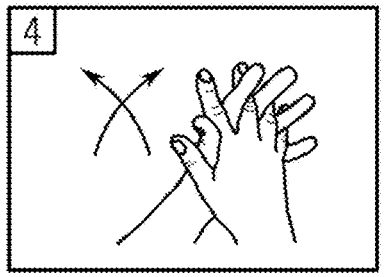 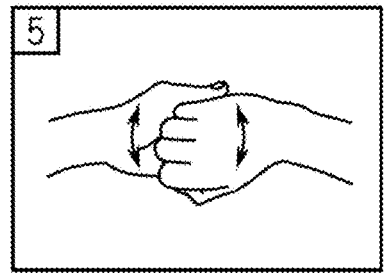

Right palm over left dorsum with interlaced fingers and vice versa;   Palm to palm with fingers interlaced;   Backs of fingers to opposing palms with fingers interlocked;

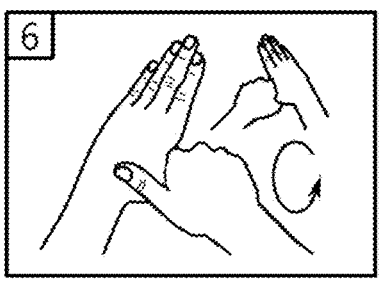 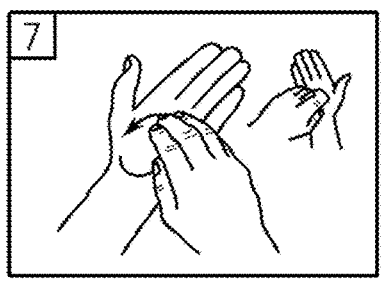 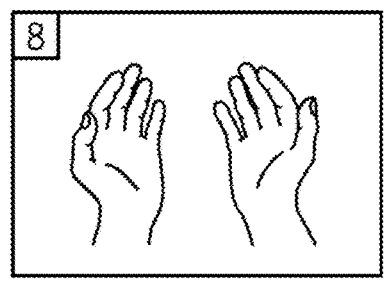

Rotational rubbing of left thumb clasped in right palm and vice versa;   Rotational rubbing, backwards and forward with clasped fingers of right hand in left palm and vice versa;   Once dry; your hands are safe.

FIG. 10A

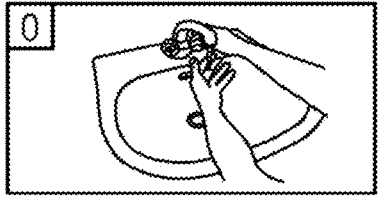
Wet hands with water;

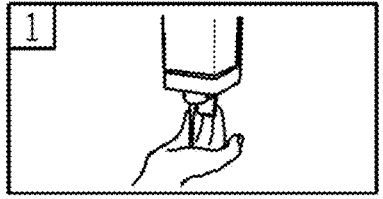
Apply enough soap to cover all hand surfaces;

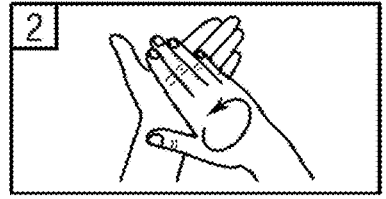
Rub hands palm to palm;

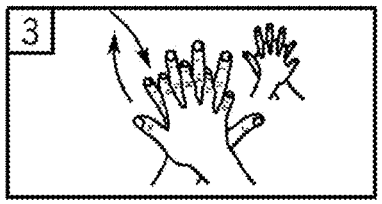
Right palm over left dorsum with interlaced fingers and vice versa;

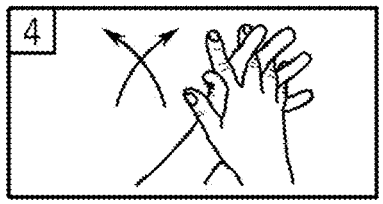
Palm to palm with fingers interlaced;

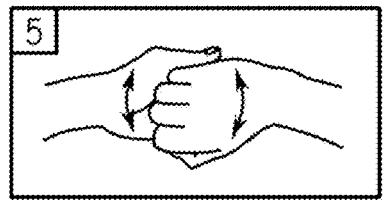
Backs of fingers to opposing palms with fingers interlocked;

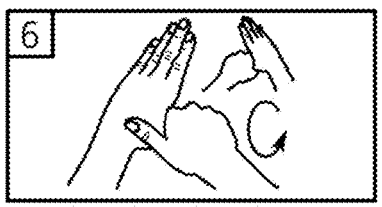
Rotational rubbing of left thumb clasped in right palm and vice versa;

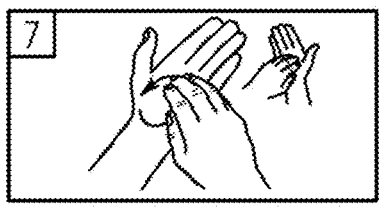
Rotational rubbing, backwards and forward with clasped fingers of right hand in left palm and vice versa;

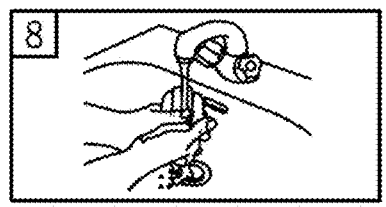
Rinse hands with water;

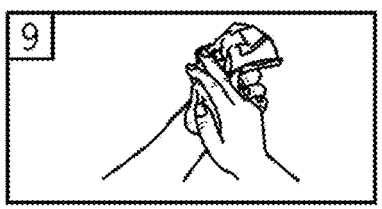
Dry hands thoroughly with a single use towel;

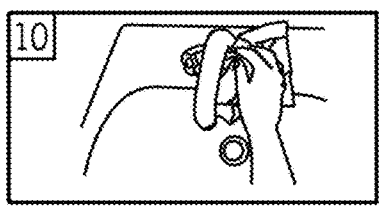
Use towel to turn off faucet;

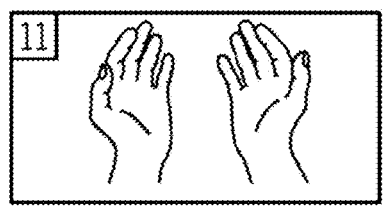
Your hands are safe.

FIG. 10B

SYSTEM AND METHOD FOR IMPROVING COMPLIANCE WITH ONE OR MORE PROTOCOLS INCLUDING HAND HYGIENE AND PERSONAL PROTECTIVE EQUIPMENT PROTOCOLS

REFERENCE TO RELATED APPLICATIONS

This application is a continuation-in-part of U.S. patent application Ser. No. 15/946,537 (filed on Apr. 5, 2018), which claims the benefit of U.S. Provisional Application No. 62/482,146 filed on Apr. 5, 2017, the entirety of both of which are incorporated by reference herein.

GOVERNMENT LICENSE RIGHTS

This invention was made with United States government support under grant number 1R43NR017373-01A1 and grant number 1R44AG060848-01 awarded by the National Institutes of Health (NIH) Small Business Innovation Research (SBIR). The United States Government has certain rights in the invention.

BACKGROUND

Healthcare-Associated Infections (HAIs) imposes devastating medical and economic consequences. Severe HAIs lead to extended hospital stays, lasting side effects and ultimately increased costs and risks of mortality. Treating these infections costs the health care system billions of dollars every year.

A good personal protective equipment practice is important to reduce transmission of pathogenic microorganisms to patients and to protect workers (e.g., pursuant to Occupational Safety and Health Administration (OSHA) standards). For example, health care providers may wear various types of personal protective equipment, such as any one, any combination, or all of: gloves, mask, gown, or protective eyewear. Typically, the personal protective equipment is placed outside of a patient's room for the healthcare provider to wear.

BRIEF DESCRIPTION OF THE DRAWINGS

The accompanying drawings, which are incorporated in and constitute a part of this specification, illustrate various aspects of the invention and together with the description, serve to explain its principles. Wherever convenient, the same reference numbers will be used throughout the drawings to refer to the same or like elements.

FIG. 10A illustrates a series of pictures which highlights the recommended hand rubbing techniques with alcohol-based formulation in World Health Organization (WHO) guidelines on hand hygiene in health care, with the duration of the hand hygiene motions (picture #2-7) recommended to last 20-30 seconds. Thus, the alcohol-based hand rub (ABHR) is one example of a hand hygiene technique. Another example of a hand hygiene technique is using soap (or other type of cleanings product) and water.

FIG. 10B illustrates a series of pictures which highlights the recommended hand washing techniques with soap and water in WHO guidelines on hand hygiene in health care, with the duration of the procedure recommended to last 40-60 seconds.

DETAILED DESCRIPTION OF EMBODIMENTS

Overview

Figure 1A:
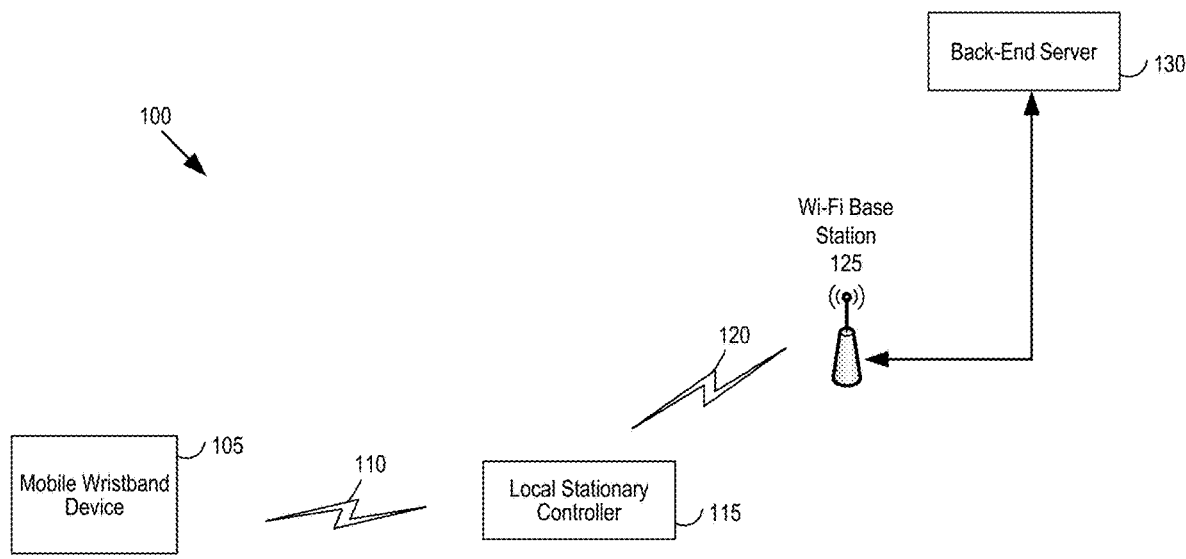
FIG. 1A is a first example block diagram of a hand hygiene system, with a mobile wristband device, a local stationary controller and a back-end server.

A method and system are disclosed that detects hand hygiene compliance and in turn, addresses hospitals' needs to reduce HAI rates and re-admission rates, improve patient care and decrease HAI-related costs.

A method and system are disclosed that detects personal protective equipment compliance and in turn, addresses hospitals' needs to reduce HAI rates and re-admission rates, improve patient care and decrease HAI-related costs. As discussed in further detail below, the detection of hand hygiene compliance and the detection of personal protective equipment compliance may be performed separately from one another, or may be performed in combination with one another. For example, in one implementation, the system may only detect hand hygiene compliance (without detecting personal protective equipment compliance). In another implementation, the system may only detect personal protective equipment compliance (without detecting hand hygiene compliance). In still another implementation, the system may detect both hand hygiene compliance and personal protective equipment compliance. In a specific implementation, the detection of the hand hygiene (HH) compliance and the detection of personal protective equipment (PPE) compliance may at least be partly dependent on one another, as discussed in further detail below. As one example, the trigger to detect HH compliance and PPE compliance may be dependent on one another (e.g., a common trigger for both HH compliance and PPE compliance; a trigger for HH compliance in turn results in a trigger for PPE compliance; a trigger for PPE compliance in turn results in a trigger for HH compliance). As another example, the detection of movements for HH compliance and PPE compliance may be dependent on one another (e.g., movements are checked for HH compliance and movements thereafter are checked for PPE compliance; movements are checked for PPE compliance and movements thereafter are checked for HH compliance).

By way of background, both the World Health Organization (WHO) and the Centers for Disease Control (CDC) provide detailed hand hygiene techniques and durations in their guidelines that are intended to be implemented in all health care settings. For instance, in WHO guidelines on hand hygiene in health care, hand hygiene with alcohol-based formulation is recommended for routine hygienic hand antisepsis with various hand-rubbing motions lasting for 20-30 seconds. One example hand hygiene technique is handwashing using soap and water. Another hand hygiene technique is hand rubbing, such as with alcohol-based formulations. As used herein, any discussion for hand hygiene is applicable to both handwashing and hand rubbing. Likewise, any discussion regarding hand rubbing is applicable to handwashing, and any discussion regarding handwashing is applicable to hand rubbing.

An example of this is illustrated in FIG. 10A. In particular, FIG. 10A illustrates the recommended hand rubbing techniques with alcohol-based formulation in WHO guidelines on hand hygiene in health care, with the duration of the hand hygiene motions (as shown in pictures #2-7 of FIG. 10A) that is recommended to last 20-30 seconds. In contrast, handwashing with soap is recommended for cleaning soiled hands, with the same hand-rubbing motions plus extra steps of rinsing and drying, for a total duration of 40-60 seconds. An example of this is illustrated in FIG. 10B. Thus, in one implementation, the hand movements associated with cleaning hands using the alcohol based-formulation is the same as the hand movements associated with cleaning hands using soap/water (e.g., pictures #2-7 of FIG. 10A). Alternatively, different hand movements are required for cleaning hands using the alcohol based-formulation versus using soap/water.

Separate from, or in combination with, movements may be monitored for compliance with one or more PPE protocols. As discussed above, to reduce the spread of diseases, health care providers may don personal protective equipment (e.g., gloves, gown, mask, protective eyewear). The wearing of the personal protective equipment may be dictated by the one or more PPE protocols. In this regard, compliance with PPE protocols may be recommended in certain situations when interacting with patients.

Figure 10C:
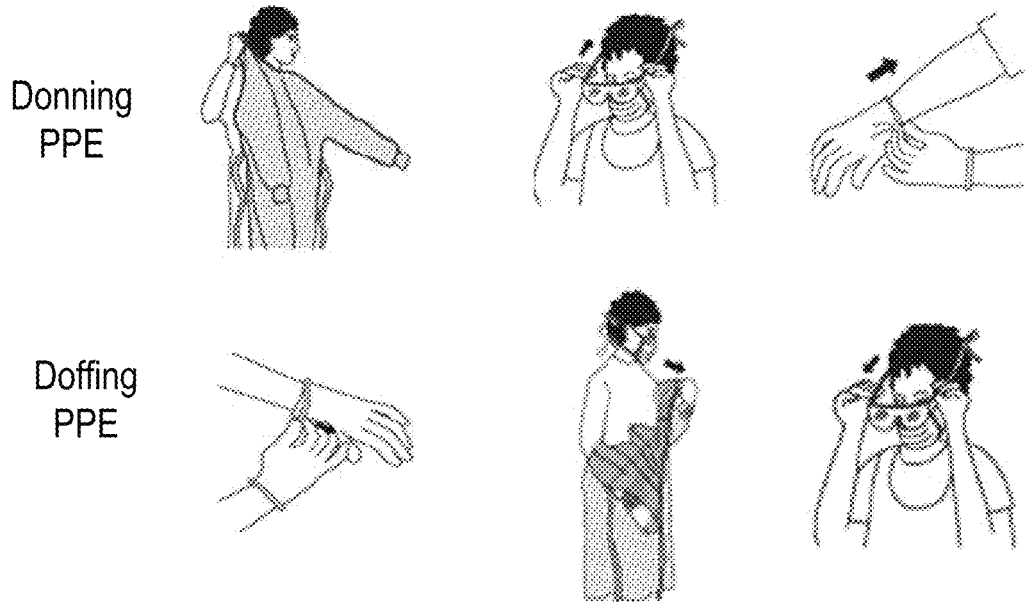
FIG. 10C illustrates a series of pictures which highlights the donning and doffing of personal protective equipment (PPE).

FIG. 10C illustrates a series of pictures which highlights best practices for donning and doffing of personal protective equipment (PPE). Examples are illustrated at http://www.nipcm.hps.scot.nhs.uk/appendices/appendix-6-best-practice-putting-on-and-removing-ppe/. As shown in FIG. 10C, donning PPE may include first putting on a gown, then putting on protective face wear (e.g., first a mask and then google), and finally putting on gloves, while doffing PPE includes first removing the gloves, then removing the gown, and finally removing the protective face wear. Combinations of PPE types (e.g., gloves, masks, goggle, respirator, gown or apron) are available to protect all or parts of the healthcare provider from contact with potentially infectious material. For instance, gloves protect the hands; gowns or aprons protect the skin and/or clothing; masks and respirators protect the mouth and nose; goggles protect the eyes; and face shields protect the entire face. The selection of PPE may be determined by the isolation precautions required for the patient and/or the nature of the patient contact. The Centers for Disease Control and Prevention (CDC) have suggested steps for donning and removing PPEs. Specifically, the CDC recommends donning or doffing PPEs in the proper steps to prevent contamination of skin and clothing.

Alternatively, protocols may be issued by another governing body, such as the Occupational Safety and Health Administration (OSHA). As one example, OSHA (or another governing body) may issue protocols for: eye and face protection; respiratory protection; head protection; foot protection; electrical protective devices; and hand protection. In this regard, any discussion regarding compliance with hand hygiene or personal protective equipment may likewise be applied to compliance with any type of protocol. As one specific example, OSHA promulgates protocols for training, such as for hazardous material handling. In this regard, the systems and methods used for training in hand hygiene or personal protective equipment compliance may likewise be applied to training for other protocols, such as OSHA training protocols.

In one implementation, a hand hygiene monitoring system and method is disclosed. The hand hygiene monitoring system may be used in various settings, such as in a hospital setting, a nursing home setting, a home setting, or the like. In a first specific implementation, the hand hygiene monitoring system comprises one or more mobile electronic devices and one or more stationary electronic devices. The mobile electronic device may be configured to be attached or associated (such as by the shape of the mobile electronic device or a hook or clip associated with the electronic device) with a person, such as a health care provider, a child, an elderly person, or the like. As discussed in more detail below, the mobile electronic device in one implementation may comprise a wristband electronic device configured to be worn on a person's wrist. Alternatively, the mobile electronic device may be attached to other parts of the person's body. The stationary electronic device may be fixedly attached to a part of a premises. The part of the premises may be itself stationary (such as a stationary hand cleaning agent dispenser) or may move (such as a door or a drawer). For example, as discussed in more detail below, the stationary electronic device may be fixedly attached in relation to a hand cleaning agent dispenser (e.g., as part of (or within) the hand cleaning agent dispenser or in fixed relation and proximate to or adjacent to the hand cleaning agent dispenser). In a second specific implementation, the hand hygiene monitoring system comprises one or more mobile electronic devices, one or more stationary electronic devices, and central analytics. The central analytics may be configured to analyze one or more aspects of the hand hygiene monitoring system, as discussed further below.

Figure 1B:
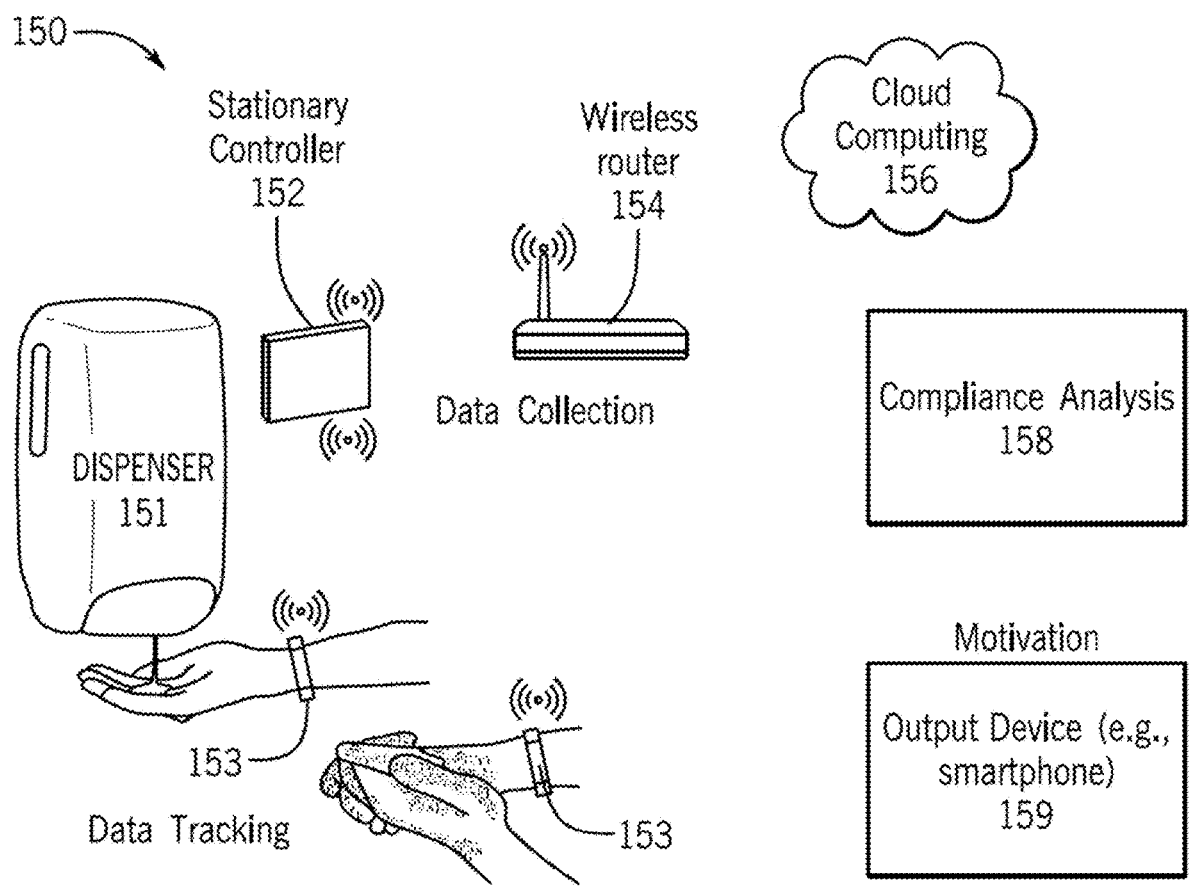
FIG. 1B is a second example block diagram of a hand hygiene system, with a mobile wristband device, a dispenser, a local stationary controller, compliance analysis, one or more output devices, and cloud computing.
Figure 1C:
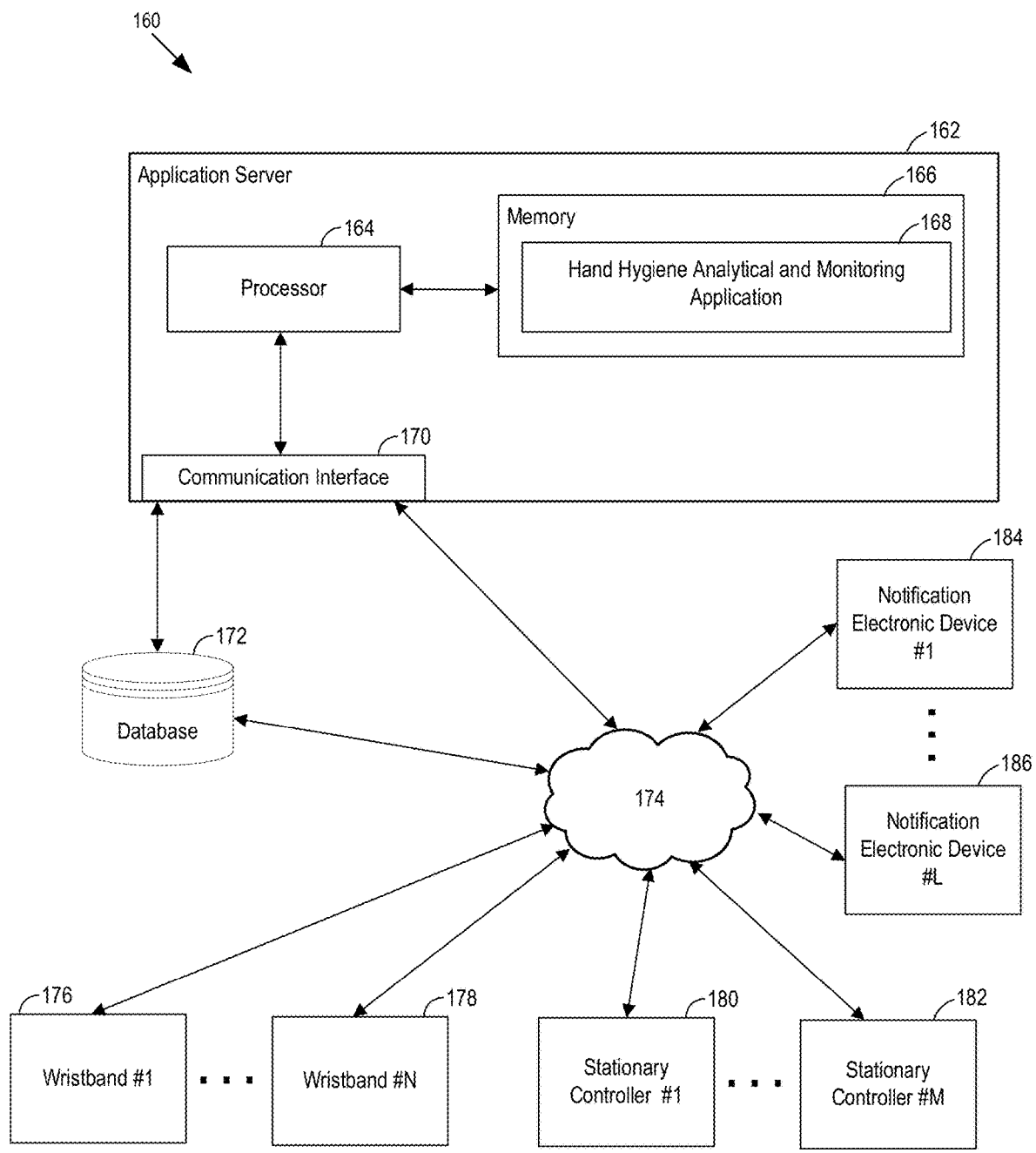
FIG. 1C is a third example block diagram of a hand hygiene system, with an application server, a database, one or more wristbands, one or more stationary controllers, and one or more notification electronic devices.
Figure 2:
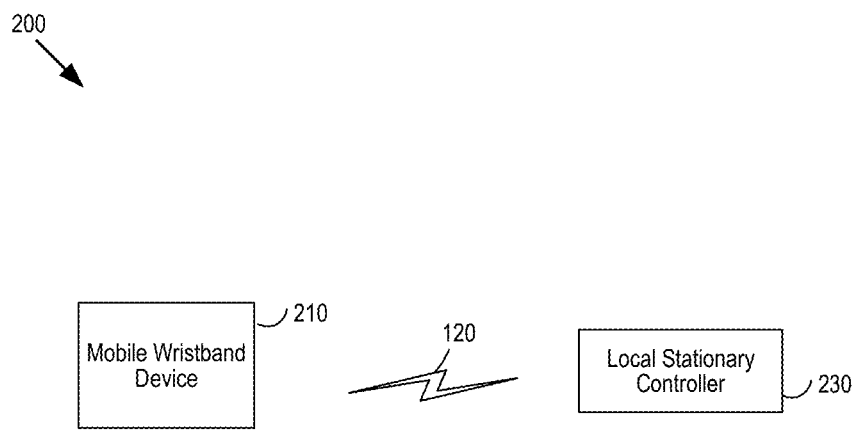
FIG. 2 is a fourth example block diagram of a hand hygiene system, with a mobile wristband device and a local stationary controller.

Thus, in one implementation, the hand hygiene monitoring system may comprise a hand hygiene compliance system configured for use in a hospital setting or other healthcare setting, whereby one or more healthcare providers wear wristbands and whereby stationary controllers may be associated with a dispenser (e.g., mounted proximate to (such as within sound sensor range) or within the dispenser) and/or an entrance to a room, and back-end analytics (such as cloud computing). Examples of this are illustrated in FIGS. 1A-C. Alternatively, the hand hygiene compliance system includes the wristband and a stationary controller, an example of which is illustrated in FIG. 2.

As discussed in more detail below, a mobile electronic device is configured with one or more sensors that measure movement of a person, such as the healthcare provider. The mobile electronic device may include a housing that is attached or somehow associated with the person. As one example, the mobile electronic device may comprise a wristband electronic device, whereby the wristband electronic device is affixed to the wrist of the person. In one specific example, the wristband electronic device fully encircles the wrist of the healthcare provider. In another specific example, the wristband electronic device only partly encircles the wrist of the healthcare provider. Alternatively, the mobile electronic device may be clipped or strapped to the wrist of the healthcare provider (such as tying a strap to the wrist of the healthcare provider). Discussed below are various applications of the wristband. Any discussion below regarding the wristband comprises a wristband electronic device, and may likewise be applied to any other type of electronic device, such as another type of wearable electronic device, that can be attached or otherwise associated with the person that may measure hand movements or other type of body movements of the healthcare provider.

The wristband may record sensor data from one or more sensors. In one implementation, the wristband includes a single motion sensor. In an alternate implementation, the wristband includes multiple motion sensors, such as a first type of motion sensor and a second type of motion sensor, with the first type of motion sensor being different than the second type of motion sensor. In a first specific implementation, the first type of motion sensor is configured to sense a first type of movement, and the second type of motion sensor is configured to sense a second type of movement.

For example, the first type of motion sensor comprises a micro-vibration sensor configured to sense basic movement, and the second type of motion sensor comprises an accelerometer configured to sense acceleration in one, two, or three axes. One example of a micro-vibration sensor comprises a Sensolute Version MVS0608.02 micro-vibration sensor. The micro-vibration sensor may be omnidirectional with sensitivity independent of sensor orientation and may be suitable for basic motion-detection, whereas the accelerometer is configured to detect more advanced motions, such as acceleration. In operation, the wristband may operate in low power mode, such that one or more sections of the wristband do not draw power (or draw less power than in normal operation) and other sections of the wristband draw power and are in normal operation mode. When the wristband is in low power mode, example sections subject to low power mode comprise the controller and the accelerometer (or other type of motion sensor configured to sense more complex motions) and an example section of the wristband that draws power and in normal mode may comprise the micro-vibration sensor. Further, in operation, the micro-vibration sensor may sense basic motions, and responsive to detecting the basic motions, may wake-up the wristband from low power mode (such as resuming normal operation of the accelerometer and the controller). In this way, the wristband may conserve power by operating in low power mode, and may use a combination of motion sensors to sense a hand washing event (such as by resuming normal mode (and waking up the accelerometer) triggered by the output of the micro-vibration sensor and by sensing the hand washing motions using the accelerometer).

In still an alternate implementation, the wristband includes three or more motion sensors, such as a first type of motion sensor, a second type of motion sensor, and a third type of motion sensor, with each type being different from the other. As discussed further below, the wristband may include any one, any two, any three, or all four of: a micro-vibration sensor; an accelerometer; a gyroscope; and a magnetometer.

Responsive to the one or more sensors generating sensor data, the sensor data may be analyzed. In one implementation, the wristband analyzes the sensor data, with the wristband making the determination, based on the analysis, whether the hand movements were sufficient or insufficient according to the guidelines. Thereafter, the wristband may output the determination (e.g., generating an output indicative of the sufficiency and/or insufficiency of the hand movements according to the guidelines) and may transmit the determination (e.g., sufficiency and/or insufficiency of hand movements according to the guidelines) to an external device, such as the stationary controller and/or the back-end analytics. In another implementation, the stationary controller receives the sensor data from the wristband and analyzes the sensor data, thereby making the determination as to sufficiency and/or insufficiency of hand movements. Thereafter, the stationary controller transmits the determination (e.g., sufficiency and/or insufficiency of hand movements according to the guidelines) to an external device, such as the wristband (for outputting an indication of sufficiency and/or insufficiency according to the guidelines) or the back-end analytics. Alternatively, or in addition, the stationary controller may determine both whether hand cleaning agent (such as sanitizer, soap, or the like) has been dispensed and whether the hand movements were sufficient to meet compliance. In still another implementation, the back-end analytics receives the sensor data from the wristband and analyzes the sensor data, thereby making the determination as to sufficiency and/or insufficiency of hand movements according to the guidelines. Thereafter, the back-end analytics transmits the determination (e.g., sufficiency and/or insufficiency of hand movements) to an external device, such as the wristband (for outputting an indication of sufficiency and/or insufficiency) or the stationary controller.

Alternatively, more than one device may determine hand hygiene compliance. As one example, the wristband and the stationary controller, in combination, may determine hand hygiene compliance. Specifically, the stationary controller may determine whether hand cleaning agent (such as sanitizer, soap, or the like) has been dispensed, and the wristband may determine whether the hand movements were sufficient (e.g., the hand movements were for at least a predetermined amount of time; the hand movements were at least a certain level of vigorousness (e.g., as measured by an accelerometer); or the hand movements with a certain level of vigorousness were for at least the predetermined amount of time). As another example, the wristband and the back-end analytics, in combination, may determine hand hygiene compliance.

As discussed above, the analytics may analyze the sensor data in one or more respects to determine hand hygiene compliance. In one implementation, the analytics may determine whether or not the person performed any act related to hand washing (such as whether the hand cleaning agent was dispensed from the dispenser). In another implementation, the analytics may determine a duration of the hand hygiene motions. As discussed in more detail below, the wristband (and/or the stationary controller) may analyze sensor output from the motion sensor(s) (such as the accelerometer) to determine whether the sensor output is indicative of hand hygiene motions (as opposed to other hand motions) for a predetermined amount of time (e.g., for 20 seconds). In a more specific implementation, the analytics may sum the amount of time that the sensor data is indicative of the hand hygiene motion(s) in a predetermined time window. For example, responsive to the wristband being triggered by the stationary controller to monitor hand hygiene motion(s), the wristband may track the hand hygiene motion(s) for the subsequent 60 seconds, one example of the predetermined time window. In that 60 seconds, the wristband may analyze the sensor data generated by the accelerometer and/or gyroscope and/or magnetometer for the hand hygiene motion(s). In practice, the user may start and stop the hand hygiene motion(s), such as a starting time at time=1 second to time=10 seconds perform the hand hygiene motion(s), stop performing the hand hygiene motion(s) from a stopping time of time=11 seconds to time=14 seconds, and resume the hand hygiene motion(s) from a restarting time of time=15 seconds to time=28 seconds. The wristband may track that from time=1-10 a total of 9 seconds of hand hygiene motion(s) were performed (with the wristband incrementing a counter so that the value of the counter is indicative of 9 seconds of hand hygiene motion(s)), from time=11-14, may track no hand hygiene motion(s) were performed (so that the counter is not incremented such that the value of the counter remains indicative of 9 seconds of hand hygiene motion(s)), and may track at least from time=15-26 seconds of hand hygiene motion(s) (for a total of 20 seconds of hand hygiene motion(s)). In this way, the wristband may determine that the minimum amount of time (e.g., 20 seconds) of hand hygiene motion(s) was performed within the predetermined time window, even though the user started and stopped the hand hygiene motion(s). Further, in one implementation, once the wristband tracks the minimum amount of time (e.g., 20 seconds) of hand hygiene motion(s), the wristband may return to sleep mode. Alternatively, the wristband may track a total amount of time of hand hygiene motion(s) within the predetermined time window.

In another implementation, the analysis of the sensor data may be configured to identify a plurality of discrete motions. As illustrated in FIG. 10A, the WHO recommends a plurality of discrete motions, such as the 6-step hand hygiene technique as indicated in steps 2-7. The analytics may determine whether the sensor data is indicative of any one, any combination, or all of a set of discrete motions, such as the motions as indicated in steps 2-7. In one implementation, the analytics may determine whether all of the motions in the discrete set of motions were performed regardless of sequences (e.g., steps 2-7 are performed in sequence; steps 2, 4, 6, 3, 5, 7). In an alternate implementation, the analytics may determine whether all of the motions in the discrete set of motions were performed in a predetermined sequence (e.g., steps 2-7 are performed in sequence). Further, in one implementation, the analytics may track an amount of time (such as a minimum amount of time) that each of the motions in the discrete set of motions is performed. By way of example, the analytics may determine "sufficient" hand hygiene motions if each of steps 2-7 is performed for 3 seconds each. Alternatively, the analytics may determine "sufficient" hand hygiene motions if each of steps 2-5 is performed for 3 seconds each and steps 6-7 are each performed for 4 seconds. The analytics may track whether the total amount of time for each of the steps tracked is at least the predetermined amount (e.g., either 3 or 4 seconds). Further, the analytics may assign one or more counters to track a total amount of time for each of the steps tracked in order to account for starting/stopping of hand hygiene motions for a respective step. In this way, the analytics may track the recommended different steps in order to determine whether the hand hygiene motions are sufficient.

In one implementation, the analysis of the sensor data may be directed to the vigorousness of the hand hygiene motions. As one example, the analysis may be based on frequency of at least one aspect of the sensor data. In particular, the frequency of movement of the sensor data may be analyzed, such as the peak frequency of movement. As discussed in more detail below, different body movements result in different frequencies of movement. Hand movements, such as predetermined hand movements associated with hand washing, may have a higher frequency than other body movements (such as arm swinging, walking, etc.). In this regard, the peak frequency of the movement may be analyzed in order to determine whether the movement is attributable to hand washing or to another body movement. Further, because hand washing movements may have higher frequencies than other types of movements, such as arm swinging, the analysis may use a frequency filter (e.g., use a high pass filter to filter out frequencies lower than a predetermined frequency in order to filter out frequencies due to walking or arm swinging), as discussed further below. Thus, if the wristband performs the analysis, the wristband may include a high-pass filter to filter out non-hand washing movements.

Further, in one implementation, the sensor data is analyzed in each of the three dimensions. In an alternate implementation, the sensor data is analyzed in fewer than all of the three dimensions. In a first specific implementation, the sensor data is analyzed in only two dimensions (e.g., analyzing for large acceleration in both the x- and y-axis). In a second specific implementation, the sensor data is analyzed in only one dimension (e.g., analyzing for large rotation rate along the y-axis (pitch) or for large acceleration along the z-axis).

In another implementation, the sensor data may be analyzed for power spectrum density (PSD). In one example, the PSD of the signal may describe the power present in the signal as a function of frequency, per unit frequency. In particular, the analysis may focus on peak power in determining whether the sensor data is associated with hand washing movements.

In still another implementation, the method and system limits analysis to a discrete window of sensor data. In particular, a triggering event may identify a potential hand hygiene event, thereby beginning the sequence of analyzing the sensor data for the hand hygiene event. As discussed in more detail below, the wristband and the stationary controller work in combination for the triggering event. In one example, the stationary controller sends a beacon. Responsive to the wristband coming within range of near-field communication (e.g., within Bluetooth communication range for at least a predetermined amount of time), the wristband may be triggered to record sensor data in order to determine whether hand hygiene movements have occurred. In another example, the wristband may send a beacon, such as a Bluetooth signal or RFID signal. The stationary controller may sense the signal (e.g., the stationary controller may determine, based on the strength of the beacon, how close the wristband is to the stationary controller). Responsive to the stationary controller determining that the wristband is proximate (e.g., within a predetermined distance for at least a predetermined amount of time), the stationary controller may transmit a wake-up signal to the wristband to record the sensor data for analysis. Further, the analysis of the sensor data generated within the discrete window may be based on a contrast of hand hygiene motions with other periodic motions that may occur within the discrete window. As one example, the time period associated with the discrete window may be 60 seconds when the healthcare provider is walking into a patient's room. In that regard, the analysis may focus on contrasting hand hygiene movements with other periodic movements that may be performed within the 60 second discrete window (e.g., walking, knocking on a door, etc.). For example, the analysis may focus on frequency and/or power to differentiate hand hygiene movements with other periodic movements. In this regard, accuracy of analysis may be increased by: (1) using data in the discrete window; and (2) analyzing hand hygiene actions and contrasting those hand hygiene actions without other periodic actions (e.g., walking, knocking on door) within that discrete window.

Figure 4A:
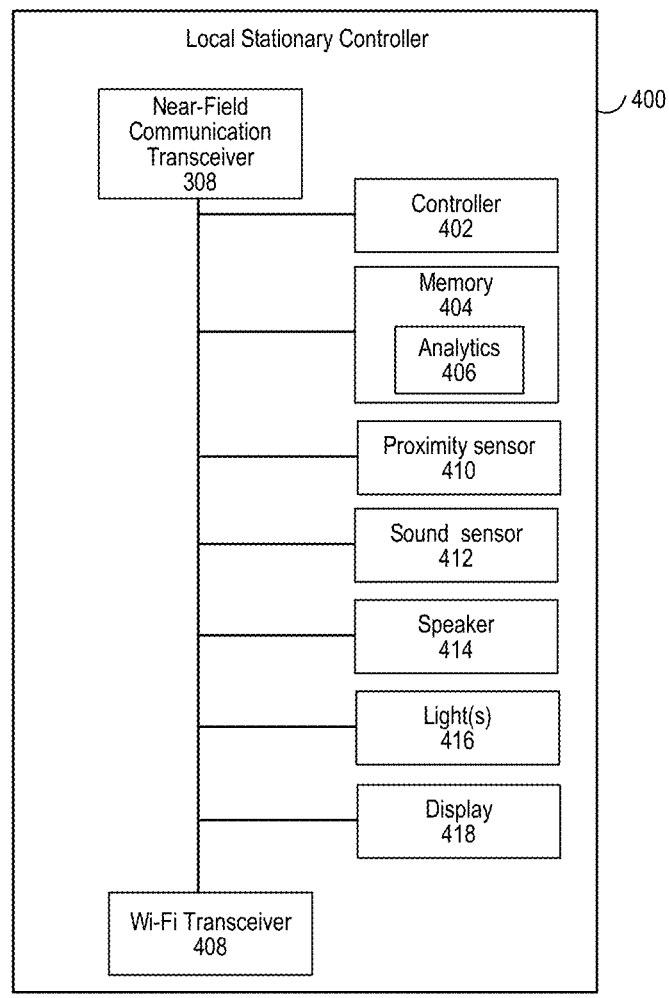
FIG. 4A is a first example block diagram of the local stationary controller.
Figure 4B:
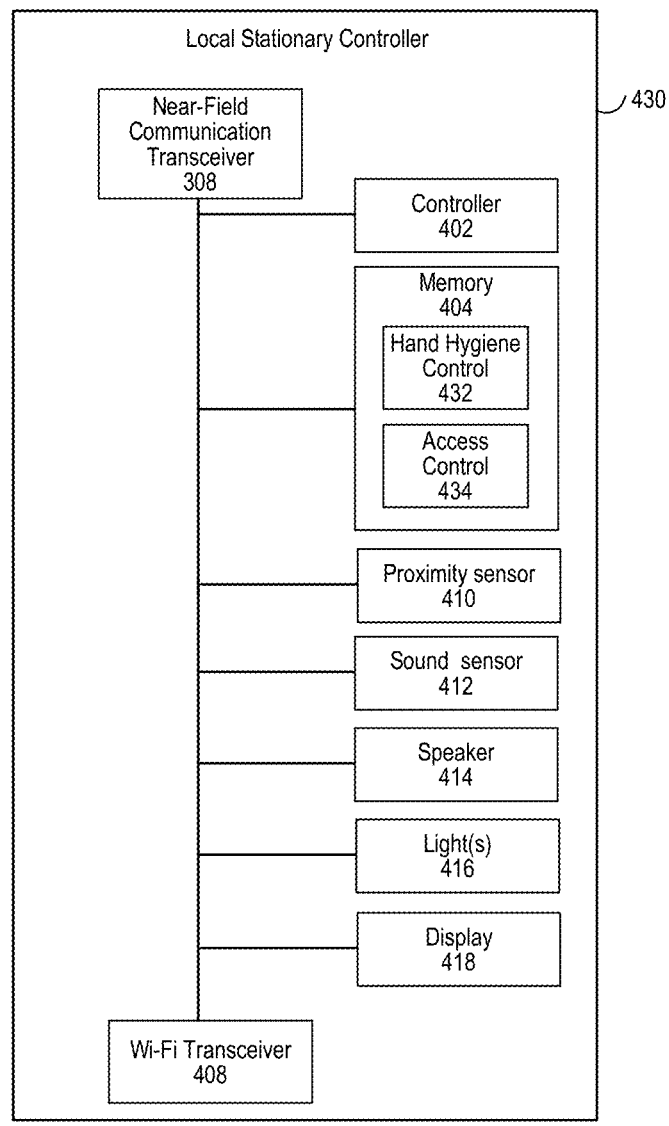
FIG. 4B is a second example block diagram of the local stationary controller.

In the present implementation, the motion sensor may operate for a very short time (~1 minute) only when a hand hygiene event is detected (such as by the stationary controller as illustrated in FIGS. 4A-B). For most of the time, at least a part of the wristband, such as one or more of the motion sensors within the wristband, is in sleep mode. For example, within sleep mode, power may be reduced or completely withheld from one or more parts of the wristband, such as the motion sensor. This achieves both low power dissipation and reliable hygiene compliance detection. Selection of low-power chips further reduces the wristband's power consumption, as discussed further below. In particular, since the wristband is activated in the discrete window, the wristband may have a longer battery life, thereby reducing the burden from the healthcare provider to recharge or replace the battery as often. Further, since the wristband is activated in the discrete window, the wristband may focus on events that may occur within the window, thereby more accurately detecting compliance during a hand hygiene event, and avoiding false alarms from any interfering motions (e.g., walking) or motions in a non-hygiene event.

In one implementation, the analysis uses one or more static thresholds in analyzing whether the sensor data is indicative of hand hygiene movements. For example, the frequency and/or the power associated with the sensor data may be compared with static thresholds (e.g., use a static filter to filter periodic walking movement from hand rubbing movement; use a static threshold to analyze in the magnitude domain (such as power)). With regard to frequency, one or more thresholds, such as a lower threshold (to filter out other periodic movements, such as walking) and/or an upper threshold (to filter out overly vigorous hand hygiene movements) may be used. In an alternate implementation, the analysis may use one or more dynamic thresholds in order to dynamically adapt the analytics. For example, based on previous sensor data, the thresholds and/or ranges for frequency and/or power analysis may be adapted. In a particular example, the analysis may use machine learning that adapts to an individual healthcare provider's hygiene habit. For example, the individual healthcare provider may perform hand hygiene movements multiple times in a certain period (e.g., in a day, week, month, etc.). The machine learning may extract one or more characteristics associated with the hygiene habits of the individual healthcare provider and then store those parameters correlated to this individual healthcare provider. Thus, the thresholds, such as the frequency and/or magnitude for analysis, may be tailored to the individual healthcare provider.

As discussed in more detail below, the wristband may operate in a lower power mode. In one implementation, the wristband may operate in a discrete window (such as for 60 seconds) in order to detect the hand hygiene movements. Within this discrete window, one or more operations of the wristband, such as the motion sensor(s), are awakened for recording sensor data.

Further, in one implementation, the wristband may operate in a sleep mode (in which a part of the electronics within the wristband are turned off or are consuming less power) and may operate in a normal mode (in which some or all of the electronics within the wristband that are turned off or are consuming less power in sleep mode are turned on or consume a greater amount of power). As one example, the wristband may include one or more sensors, with some or all of the sensors being turned off or inactive in sleep mode, and some or all of the sensors being turned on or active in normal mode.

The wristband may be triggered to exit from sleep mode in one of several ways. In one way, the wristband may make the decision to exit sleep mode on its own and without any input from an external device. For example, the wristband may have one or more sensors that remain active in sleep mode, with the data generated by the one or more sensors active in sleep mode being used to determine whether to exit sleep mode. In particular, the wristband may include a micro-vibration sensor. The micro-vibration sensor draws less power than other motion sensors, such as accelerometers or gyroscopes. Responsive to the micro-vibration sensor, active in sleep mode, indicating motion, the wristband may wake-up the microcontroller and/or other sensors on the wristband, such as the accelerometer and/or gyroscope and/or magnetometer, thereby exiting sleep mode. In another way, the wristband may make the decision to exit sleep mode based on input from another electronic device. For example, the wristband may work in combination with an external device, such as the stationary controller, in order to determine when a hand hygiene event begins (and, in turn, when for the wristband is to "wake up"). As discussed above, the wristband may send a beacon to the stationary controller, or may receive a beacon from the stationary controller in order to trigger the wake up of the wristband.

After which, the wristband may generate and record sensor data. After the hand hygiene event (e.g., after no more than 60 seconds), the wristband may go back into sleep mode (either due to determining that the hand hygiene event is successful or not).

In still another implementation, one or more operations of hand hygiene monitoring may be divided amongst the wristband and the stationary controller. As discussed in more detail below, the stationary controller may be associated with the dispenser (e.g., antibacterial dispenser) and/or the entrance of the room. For example, one operation of hand hygiene monitoring is a trigger for beginning the hand hygiene monitoring. In this example, one of the wristband or the stationary controller may send a beacon, and another of the wristband or the stationary controller may detect the beacon, thereby triggering the beginning of the hand hygiene monitoring. In particular, the wristband may send an RFID or Bluetooth signal, which may be sensed by the stationary controller. In the example of Bluetooth, the stationary controller, based on the signal strength of the Bluetooth signal and/or the time elapsed of receiving the Bluetooth signal, may determine the closeness of the devices to one another. In response to the stationary controller determining that the wristband is within a predetermined distance for a predetermined period of time, the stationary controller may send a wake-up signal to the wristband to begin monitoring for hand hygiene. In another implementation, the stationary controller may transmit a beacon, which upon receipt by the wristband wakes up at least a part of the wristband, such as the motion sensor(s) on the wristband. More specifically, in one implementation, responsive to the wristband sensing the beacon signal from the stationary controller for a predetermined amount of time, the wristband may wake-up the motion sensor(s) on the wristband.

Alternatively, or in addition, the hand hygiene monitoring system may generate one or more outputs associated with the hand hygiene monitoring. A first output may be generated to alert the healthcare provider to perform the hand hygiene movements. A second output may be generated to alert the healthcare provider as to whether the hand hygiene movements were sufficient and/or insufficient. In one implementation, the stationary controller may generate the alert to the healthcare provider to perform the hand hygiene movements, and the wristband may generate the alert to the healthcare provider as to whether the hand hygiene movements were sufficient and/or insufficient. Alternatively, the wristband may generate the alert to the healthcare provider to perform the hand hygiene movements, and the stationary controller may generate the alert to the healthcare provider as to whether the hand hygiene movements were sufficient and/or insufficient. In either implementation, the alerts may be divided amongst the stationary controller and the wristband. In still another implementation, only one device (e.g., either the stationary controller or the wristband) generates both the alert to the healthcare provider to perform the hand hygiene movements, and the alert to the healthcare provider as to whether the hand hygiene movements were sufficient and/or insufficient.

Generally speaking, the analytics may determine any one, any combination, or all of: compliance; partial compliance; or non-compliance. Further, the analytics may determine any one, any combination or all of: whether the user took hand cleaning agent; whether the user perform hand movements indicative of hand hygiene; whether the user performed hand movements indicative of hand hygiene for at least a predetermined amount of time; whether the user performed a series of hand movements indicative of hand hygiene; whether the user performed a series of hand movements indicative of hand hygiene each for a respective period of time; and whether the data was indeterminate of compliance.

Responsive to the determination of the analytics, one or more outputs may be generated using output functionality. In one implementation, the wristband may generate one or more outputs based on a determination of any one, any combination, or all of: compliance, partial compliance and/or non-compliance. The one or more outputs from the wristband may comprise audio and/or visual outputs, such as sound(s) (such as different sounds), light(s) (such as different lights or different combinations of lights), vibration(s) (such as different patterns of vibrations), or the like. For example, a first sound may be indicative of compliance and a second sound, different from the first sound, may be indicative of non-compliance. As another example, a first sound may be indicative of compliance, a second sound may be indicative of partial compliance, and a third sound may be indicative of non-compliance. As still another example, a first light may be indicative of compliance (e.g., a green colored light) and a second sound (e.g., a red colored light) may be indicative of non-compliance. As yet still another example, the wristband may escalate the outputs based on a determination of partial compliance and/or non-compliance. In particular, the wristband may initially output a sound and/or light responsive to determining a hand hygiene event. Responsive to determining non-compliance (and/or partial compliance) with the hand hygiene event, the wristband may generate a different type of output, such as a louder sound (e.g., louder than the output responsive to determining a hand hygiene event) and/or a brighter light (e.g., brighter lights or a greater number of lights than the output responsive to determining a hand hygiene event).

Alternatively, or in addition, the stationary controller may generate one or more outputs based on a determination of any one, any combination, or all of: compliance, partial compliance and/or non-compliance. The one or more outputs from the stationary controller may comprise audio and/or visual outputs, such as sound(s), light(s), or the like. Alternatively, or in addition, an electronic device separate from the wristband and the stationary controller may generate one or more outputs based on a determination of any one, any combination, or all of: compliance, partial compliance and/or non-compliance. In one implementation, the determination as to compliance, partial compliance and/or non-compliance, either transmitted to or determined by the back-end analytics, may result in the back-end analytics transmitting an alert to a separate electronic device. For example, the separate electronic device (e.g., a smartphone) may be associated with the user who is the subject of the compliant, partial compliant and/or non-compliant hand hygiene event. As another example, the separate electronic device may be associated with a third party separate from the user subject to the hand hygiene event. In particular, the separate electronic device may be associated with an administrator tasked with hand hygiene compliance in a hospital setting or a responsible administrator for a section of the hospital (e.g., the head nurse in the ICU).

Alternatively, or in addition, one or more aspects of the wristband, the stationary controller or the back-end analytics may change responsive to a determination of any one, any combination, or all of: compliance; partial compliance; or non-compliance. As one example, responsive to a determination of partial and/or non-compliance, the wristband and/or stationary controller may modify its operation responsive to a new hand hygiene event. In one implementation, the outputs generated by the wristband and/or stationary controller may be different than those outputs during a previous wristband event. As one example, the audio outputs generated by the wristband and/or stationary controller may be louder than those outputs during the previous wristband event responsive to determination of partial compliance and/or non-compliance. As another example, an output, not generated during the previous hand hygiene event, may be generated in a subsequent hand hygiene event based on compliance, partial compliance, and/or non-compliance. In particular, responsive to determining that the user partially complied and or non-complied during the previous hand hygiene event, a display on the wristband may be activated to output a countdown of 20 seconds. In this way, the user may receive more guidance to wash for a predetermined amount of time (e.g., 20 seconds) responsive to determination of partial or non-compliance. Alternatively, or in addition, the analytics to determine compliance may be different than the analytics used during the previous wristband event. For example, the analytics may be stricter (e.g., requiring a longer time to detect hand hygiene motions for determining compliance) than previously used analytics.

Alternatively, or in addition, the hand hygiene monitoring system may track the dispensing of hand cleaning agent from the dispenser. In one implementation, the stationary controller tracks at least one aspect related to the dispensing. In a more specific implementation, the stationary controller tracks the operation of the dispenser as opposed to hand movement. For example, the stationary controller may include a sensor, such as a sound sensor, to determine whether the dispenser has dispensed the hand cleaning solution. In particular, the sound sensor may record data that the stationary controller may later analyze to determine whether the dispenser has performed an internal movement that is indicative of dispensing hand cleaning solution (e.g., whether the data recorded from the sound sensor is indicative of a motor on the dispenser dispensing hand cleaning agent). For example, the stationary controller may perform frequency domain analysis to determine whether the motor has dispensed hand cleaning solution. One or both of graphs of background sound (FIG. 6E) and dispensing sound (FIG. 6F) may be used by the stationary controller to perform the frequency domain analysis for the determination.

In an alternate implementation, multiple types of hand cleaning solution may be dispensed. One type comprises an alcohol-based cleaning solution, which is dispensed from a first dispenser. Another type comprises a soap-based cleaning solution, which is dispensed from a second dispenser. In one implementation, one or more stationary controllers may determine whether the respective dispenser (alcohol-based cleaning solution dispenser or soap dispenser) has dispensed cleaning agent. For example, one or more sound sensors may generate sound data for the sound from the respective dispenser, with the sound data being analyzed to determine whether the sound is more closely related to the sound when dispensing the alcohol-based cleaning solution from the alcohol-based cleaning solution dispenser or more closely related to the sound when dispensing the soap-based cleaning solution from the soap-based cleaning solution dispenser. In this regard, the stationary controller may record the sound, and determine whether the sound is indicative of dispensing from the first dispenser (and thus dispensing the alcohol-based cleaning solution) or is indicative of dispensing from the second dispenser (and thus dispensing the soap-based cleaning solution). Alternatively, multiple indicators (such as multiple sounds) may indicate compliance with the hand hygiene protocol. As discussed above, one hand hygiene protocol comprises using soap and water. In this way, one or more sound sensors may sense first sound data emanating from the dispenser (such as the soap dispenser) and sense second sound data emanating from the faucet (to determine whether water is flowing from the faucet). Responsive to determining that the first sound data is indicative of dispensing from the soap dispenser and second sound data is indicative of water flow, the stationary controller may determine compliance with the soap/water protocol. In this way, the stationary controller may determine, based on sound, which of the multiple types of hand cleaning solution were dispensed.

Alternatively, the wristband, via a microphone resident on the wristband, may input sound data and may determine itself whether the sound data is indicative of the sound of the motor dispensing hand cleaning agent. Or, in the instance of multiple types of hand cleaning solution, the wristband may determine, from analysis of the sound, which dispenser dispensed the hand cleaning agent, and in turn the type of hand cleaning agent. As another example, the stationary controller may be integrated with the electronics of the dispenser such that a signal from the dispenser motor, which is configured to dispense hand cleaning solution, may be input to the stationary controller. In that regard, responsive to the signal from the dispenser motion indicating that the motor dispensed hand cleaning solution, the stationary controller may determine that hand cleaning solution has been dispensed.

In still another implementation, the system may include a back-end electronic device, such as a server, that performs analytics, as discussed above. The analytics may be configured to perform any one, any combination, or all of: determine compliance (e.g., full, partial or non-compliance); generate compliance reports, to identify trends based on time of shift, protocols, and other desired metrics; identify patients and/or health care providers that are the source of cross-contamination; generate alerts responsive to compliance determinations, identifying trends, identifying patients and/or health care providers that are the source of cross-contamination, or the like; generating displays or other types of graphical users interfaces to output statistics based on one or more criteria, such as based on an event (e.g., full, partial, or non-compliance), based on people (e.g., analysis based on all doctors, all nurses, or individuals), and/or based on location (e.g., based on the particular floor of a hospital, the particular wing of a hospital, based on a department of the hospital (e.g., ICU-A, ICU-B, ICU-C)).

In one implementation, one or more electronic devices may work in combination with the wristband in order to instruct a user as to proper hand hygiene. For example, a user may follow instructions of requested movements that are output (e.g., displayed on a display) on an electronic device. The wristband, worn by the user, may register movements of the user. The electronic device may compare the requested movements with the registered movements in order to provide feedback to the user. In a first implementation, the user may comprise an adult healthcare provider, with the feedback to the user for instructional purposes. The feedback may comprise instructions as to one or more of the following: information as to deficiencies in hand hygiene movements; or information as to deficiencies in the amount of time of hand hygiene. The feedback may include a score, with the score based on improvement or worsening of the hand hygiene (e.g., improvement or worsening based on a previous training session). In a second implementation, the user may comprise a child, with the feedback to the user for instructing the child on hand hygiene. The feedback may take one or more forms. In one form, the feedback may be similar to the feedback to educate a healthcare provider. Alternatively, or in addition, the form of the feedback may be in the form of scoring for a video game type output or gamification. As one example, the feedback may be in the form of a score, which may be translated in a video game type feedback. As another example, the gamification may use game-design elements and game principles in non-game contexts, such as in the context of teaching hand hygiene.

In still another implementation, hand hygiene monitoring may be integrated with another type of system, such as an access control system. Various types of access control systems are contemplated. In one example, the access control may comprise physical access, such as access to a premises. In another example, the access control may comprise information access, such as computer access to a resource, such as information. In either type, the access control system may determine whether a user is authorized for access.

In one implementation, the access control may be determined based on an identification code associated with the user. Various types of identification codes may be used. In a first type, the identification code may be transmitted via radio frequency. In particular, radio frequency identification (RFID) technology may be used. RFID may use electromagnetic fields to automatically identify a user. For example, RFID tags may contain electronically-stored information indicative of an identification code of the user. Different types of RFID tags may be used. One type of RFID tag comprises a passive RFID tag, which collects energy from a nearby RFID reader's interrogating radio waves. Another type of RFID tag comprises an active RFID tag, which has a local power source (such as a battery). In this regard, an RFID tag may be used or incorporated within or somehow associated with the wristband. Thus, the wristband may be held within a certain distance of the RFID reader to authenticate the user. In another type, the identification code may be transmitted via a communication protocol, such as near-field communication (e.g., Bluetooth) and/or Wi-Fi.

In a first specific implementation, the access control system and the hand hygiene system may operate independently of one another, with the wristband including both types of functionality (e.g., hand hygiene functionality including one or more motion sensors and/or hand hygiene analytics and access control functionality including access control identification (e.g., RFID tag), with the hand hygiene functionality and access control functionality operating independently of one another). In a second specific implementation, hand hygiene monitoring and access control may be integrated. In one aspect, both hand hygiene monitoring and access control may be analyzed in order to determine whether to grant access to a person, such as a healthcare provider, to a premises, such as a room, a floor, a building, or the like. The analysis may comprise: (1) whether the hand hygiene monitoring system has determined that the person has sufficiently met hand hygiene protocol(s) (e.g., the person has taken sanitizer; whether the person performed a hand hygiene rubbing motion (such as for at least a predetermined time); whether the person performed a set of predetermined rubbing motions; etc.); and (2) whether the access control system has determined that the person is authorized to enter (e.g., the identification code associated with the person indicates access to premises should be granted). Performing (1) and (2) may be in any sequence in order to determine whether to grant access, such as: first (1) and then (2); first (2) and then (1); or both (1) and (2) are examined simultaneously.

Further, different devices may perform (1) and/or (2). In one implementation, the wristband may perform (1) and an external device, such as a stationary RFID local access control panel or a central RFID control system, may perform (2). In another implementation, the stationary controller may perform (1) and an external device, such as a stationary RFID local access control panel or a central RFID control system, may perform (2). In still another implementation, a hand hygiene central monitoring system may perform (1) and an external device, such as a stationary RFID local access control panel or a central RFID control system, may perform (2).

As discussed above, the wristband may include functionality for both monitoring hand hygiene and for access control. In one implementation, the wristband may include one or more sensors for monitoring hand hygiene (and optionally functionality for determining whether the hand hygiene was sufficient), and may include functionality for the identification code associated with the person (e.g., an RFID tag that is associated with the person; an identification code that may be transmitted via Bluetooth or Wi-Fi or the like). In this regard, the information (such as identification code and the hand hygiene information) may be transmitted via different protocols (e.g., RFID vs. Bluetooth or Wi-Fi) or may be transmitted via the same protocol (e.g., Bluetooth or Wi-Fi). Further, the wristband may transmit the information in a predetermined sequence. As one example, the wristband may transmit the identification code and the hand hygiene information independent of one another. As another example, the wristband may transmit the identification code and the hand hygiene information dependent on one another, such as transmitting the identification code only in response to the wristband determining that the hand hygiene is sufficient.

In still another implementation, a proximity sensing-output generating device is disclosed. In a specific implementation, the proximity sensing-output generating device may be positioned in different sections of a premises, and may be configured to sense one or more events or tasks. For example, the proximity sensing-output generating device may be fixedly attached to a part of the premises, such as to a wall, a door, a drawer, an electrical appliance (e.g., a refrigerator), or the like. The events or tasks may comprise leaving a premises, entering a premises, preparing food, using the toilet, using the faucet, or the like. These events or tasks may not follow a predefined schedule and may thus be difficult to track.

The proximity sensing-output generating device may identify the event or task based on one or more sensors resident in the proximity sensing-output generating device. In one implementation, the one or more sensors comprise one or more motion sensors (e.g., micro-vibration sensor, accelerometer, gyroscope). The motion sensor(s) may sense movement of the part of the premises to which the proximity sensing-output generating device is attached (e.g., sense movement of the door, the drawer, etc.) or may sense movement proximate to the proximity sensing-output generating device (e.g., in a hallway of the premises). In one implementation, the motion sensor(s) sense direction of opening (such as whether a door is being opened or closed; drawer/cabinet is being opened or closed). As discussed further below, the motion sensors may sense whether an event or a task will happen, or whether an event or a task is happening. As one example, responsive to the motion sensor sensing that a door to the bathroom has opened, the proximity sensing-output generating device may determine that the person is using the bathroom. As another example, responsive to the motion sensor sensing that a door to the residence has opened, the proximity sensing-output generating device may determine that the person is exiting the residence. As still another example, responsive to the motion sensor sensing that a drawer, a cabinet, and/or an appliance in the kitchen has been opened, the proximity sensing-output generating device may determine that the person is using the kitchen.

Alternatively, or in addition, the proximity sensing-output generating device may include a sound sensor (e.g., a microphone or the like) configured to sense one or more sounds in the premises in order to determine whether the event or task is occurring. Responsive to the sensor(s) determining that an event or task is occurring or will occur, the proximity sensing-output generating device may take one or more actions. In one implementation, the proximity sensing-output generating device may wake-up at least a part of the proximity sensing-output generating device. As one example, the sound sensor may sense one aspect in order to wake up in anticipation of monitoring an event or a task. In particular, the sound sensor may sense a toilet flushing or a person walking in the vicinity in order to wake up one or more circuits in the proximity sensing-output generating device. As another example, the micro-vibration sensor may sense vibration in order to wake up at least a part of the proximity sensing-output generating device.

Alternatively, or in addition, the proximity sensing-output generating device may generate an output. For example, responsive to the sound sensor detecting an event or a task, such as a door opening, a cabinet opening, or the like, the proximity sensing-output generating device may generate an output (e.g., responsive to sensing that the bathroom door opening, the proximity sensing-output generating device may generate an audio output reminding to "flush the toilet after use"; responsive to the sound sensor sensing that the toilet has flushed, the proximity sensing-output generating device may generate an audio output reminding to "wash hands in the sink"; etc.).

As another example, responsive to the sound sensor not detecting an event or a task, such as not detecting that the water in the bathroom has been shut off, the proximity sensing-output generating device may generate an output (e.g., responsive to the sound sensor continuing to sense for greater than a predetermined amount of time that the faucet is still running water, the proximity sensing-output generating device may generate an audio output reminding to "shut off the faucet in the bathroom").

As still another example, responsive to the motion sensor detecting an event or task, the proximity sensing-output generating device may generate an output (e.g., responsive to the door sensor detecting the opening of the front door, the proximity sensing-output generating device may generate an audio output reminding to "take your mobile phone and identification with you").

Further, the proximity sensing-output generating device may sense a series of sounds and/or a series of movements in sequence (including the presence/absence of a sound, and/or the presence/absence of a movement). In the example of monitoring the event or task of using the restroom, the proximity sensing-output generating device may monitor the series of sounds including: (1) toilet flushing (e.g., the presence of a sound that the toilet has flushed); and (2) the absence of water running (or first the presence of water running indicating that the faucet has been used, and thereafter the absence of water running to monitor that the faucet has been turned off). Responsive to monitoring each of the series of sounds, the proximity sensing-output generating device may generate an output.

Thus, at any point in the detected event or task, the proximity sensing-output generating device may generate one or more outputs. The outputs may take one of several forms, including an aural output (such as via a speaker), a visual output (such as via display), or a combination thereof. Further, the outputs may be generated in anticipation of reminding a person of an expected event or task, or reminding a person in case the event or task has not occurred.

The aural outputs may be pre-recorded sound. For example, the proximity sensing-output generating device may include a button or trigger in order to input the aural output so that a familiar voice, such as from a family member, may be output as a reminder.

A series of proximity sensing-output generating devices may be positioned in various parts of a residence, such as in the kitchen, in the entranceway, in the bathrooms, or the like. Further, the proximity sensing-output generating devices may communicate with one another and/or with a central hub via wireless communication (e.g., Wi-Fi communication). In this regard, the proximity sensing-output generating devices may communicate with other proximity sensing-output generating devices locally (e.g., point-to-point) or with a hub centrally (e.g., hub and spoke). In this regard, one proximity sensing-output generating device may sense an event and may communicate with the hub and/or another proximity sensing-output generating device in order for the output to be generated by another proximity sensing-output generating device. As discussed above, in the context of a faucet running in the bathroom, since the person has left the bathroom and the faucet running, the proximity sensing-output generating device positioned near or in the bathroom may communicate (either directly or via a hub) with another proximity sensing-output generating device. The another proximity sensing-output generating device may then generate an output in order to remind the resident to turn the faucet off in the bathroom. Alternatively, or in addition, the proximity sensing-output generating device positioned near or in the bathroom may communicate (either directly or via a hub) with an electronic device external to the premises (e.g., sending an alert to a central authority, which in turn relays the alert to a mobile phone of a family member of the resident, or sending the alert to the mobile phone of the family member directly) alerting the electronic device of the event (e.g., the failure to turn off the faucet or the exit of the resident from the residence).

The proximity sensing-output generating device may take one of several forms, such as a small form factor for placement on a door, a wall, a drawer (e.g., such as in the shape of a pull-knob for a drawer), an appliance, or the like. Further, the proximity sensing-output generating device may include a multi-position switch in order to indicate the placement of the proximity sensing-output generating device. As one example, the proximity sensing-output generating device may include a 3-position switch, with a first position indicative of bathroom placement, a second position indicative of kitchen placement, and a third position indicative of entranceway placement. Responsive to the position of the switch, the proximity sensing-output generating device may activate different modes in the device (e.g., a kitchen mode in order to sense events related to the kitchen and generate outputs thereto, a bathroom mode in order to sense events related to the bathroom and generate outputs thereto, and an entranceway mode in order to sense events related to the entranceway and generate outputs thereto).

In yet another implementation, the wristband may include multiple monitoring functionalities, such as hand hygiene monitoring functionality and non-hand hygiene monitoring (e.g., fitness monitoring). As discussed above, the wristband may monitor one or more activities, which may relate to hand hygiene or to fitness monitoring. The wristband may include algorithms that distinguish between the hand hygiene motions and other fitness type motions, such as walking. For example, the wristband may include separate algorithms that analyze the hand hygiene motions and other fitness type motions, such as walking. As another example, the wristband may include a single algorithm that analyzes both the hand hygiene motions and other fitness type motions in combination. In this regard, the wristband, which includes both functionalities, may act synergistically to analyze the hand hygiene motions and the non-hand hygiene motions (such as walking or stepping).

Thus, in one implementation, the sensor-based system, discussed in more detail below, is configured to track and analyze the HH and/or PPE of healthcare providers (e.g., provide 24 hours a day and 7 days a week monitoring, and provide real-time intervention and feedback).

In one implementation, a PPE monitoring system and method is disclosed. Similar to the HH monitoring system, the PPE system may be used in various settings, such as in a hospital setting, a nursing home setting, a home setting, or the like. In a first specific implementation, the PPE monitoring system comprises one or more mobile electronic devices and one or more stationary electronic devices. The mobile electronic device may be configured to be attached or associated (such as by the shape of the mobile electronic device or a hook or clip associated with the electronic device) with a person, such as a health care provider, a child, an elderly person, or the like. As discussed in more detail below, the mobile electronic device in one implementation may comprise a wristband electronic device configured to be worn on a person's wrist. Alternatively, the mobile electronic device may be attached to other parts of the person's body. The stationary electronic device may be fixedly attached to a part of a premises. The part of the premises may be itself stationary (such as a stationary hand cleaning agent dispenser proximate to or associated with an entrance or an exit to a patient area (such as a patient room)) or may move (such as a door or a drawer). For example, as discussed in more detail below, the stationary electronic device may be fixedly attached in relation to a hand cleaning agent dispenser (e.g., as part of (or within) the hand cleaning agent dispenser or in fixed relation and proximate to or adjacent to the hand cleaning agent dispenser). In a second specific implementation, the PPE monitoring system comprises one or more mobile electronic devices, one or more stationary electronic devices, and central analytics. The central analytics may be configured to analyze one or more aspects of the PPE monitoring system, as discussed further below.

Thus, in one implementation, the PPE monitoring system may comprise a PPE compliance system configured for use in a hospital setting or other healthcare setting, whereby one or more healthcare providers wear wristbands and whereby stationary controllers may be associated with an entrance and/or exit to a room, and back-end analytics (such as cloud computing). Though disclosed in the context of a HH monitoring system, examples of this are likewise illustrated in FIGS. 1A-C. Alternatively, the PPE compliance system includes the wristband and a stationary controller, an example of which is illustrated in FIG. 2.

Similar to HH monitoring, the mobile electronic device is configured with one or more sensors that measure movement of a person, such as the healthcare provider, and may comprise a wristband electronic device, whereby the wristband electronic device is affixed to the wrist of the person. Any discussion below regarding a wristband for HH monitoring may likewise be applied to PPE monitoring. As merely one example, the wristband may record sensor data from one or more sensors, with the wristband including a single motion sensor, or multiple motion sensors (e.g., a first type of motion sensor and a second type of motion sensor, with the first type of motion sensor being different than the second type of motion sensor).

Similar to the discussion for the wristband monitoring HH movement, the first type of motion sensor comprises a micro-vibration sensor configured to sense basic movement, and the second type of motion sensor comprises an accelerometer configured to sense acceleration in one, two, or three axes. In still an alternate implementation, the wristband includes three or more motion sensors, such as a first type of motion sensor, a second type of motion sensor, and a third type of motion sensor, with each type being different from the other. As discussed further below, the wristband may include any one, any two, any three, or all four of: a micro-vibration sensor; an accelerometer; a gyroscope; and a magnetometer.

Responsive to the one or more sensors generating sensor data, the sensor data may be analyzed for PPE compliance. In one implementation, the wristband analyzes the sensor data, with the wristband making the determination, based on the analysis, whether the PPE movements were sufficient or insufficient according to the PPE protocols. Thereafter, the wristband may output the determination (e.g., generating an output indicative of the sufficiency and/or insufficiency of the PPE movements according to the PPE protocols) and may transmit the determination (e.g., sufficiency and/or insufficiency of PPE movements according to the guidelines) to an external device, such as the stationary controller and/or the back-end analytics. Alternatively, or in addition, the wristband may determine compliance with multiple protocols, such as both HH protocols and PPE protocols.

In another implementation, the stationary controller receives the sensor data from the wristband and analyzes the sensor data, thereby making the determination as to sufficiency and/or insufficiency of PPE movements. Thereafter, the stationary controller transmits the determination (e.g., sufficiency and/or insufficiency of PPE movements according to the guidelines) to an external device, such as the wristband (for outputting an indication of sufficiency and/or insufficiency according to the guidelines) or the back-end analytics.

Alternatively, or in addition, the stationary controller may determine compliance with multiple protocols, such as both HH protocols and PPE protocols. The determination as to compliance with HH protocols may be achieved in one of several ways, including any one, any combination, or all of: whether hand cleaning agent (such as sanitizer, soap, or the like) has been dispensed; whether the hand movements were for a sufficient period of time; or whether the hand movements were sufficient to meet compliance. In still another implementation, the back-end analytics receives the sensor data from the wristband and analyzes the sensor data, thereby making the determination as to sufficiency and/or insufficiency of PPE and/or HH movements according to the guidelines. Thereafter, the back-end analytics transmits the determination (e.g., sufficiency and/or insufficiency of PPE and/or HH movements) to an external device, such as the wristband (for outputting an indication of sufficiency and/or insufficiency) or the stationary controller.

Alternatively, more than one device may determine PPE compliance. As one example, the wristband and the stationary controller, in combination, may determine PPE and HH compliance. As another example, the wristband and the back-end analytics, in combination, may determine PPE compliance.

As discussed above, the analytics may analyze the sensor data in one or more respects to determine PPE compliance. In one implementation, the analytics may determine whether or not the person performed any act related to putting on or taking off personal protective equipment (such as whether the healthcare provider put on or took off latex rubber gloves). As one example, the analysis of the sensor data may be configured to identify a plurality of discrete motions that are indicative of performing certain predetermined movements associated with putting on or taking off personal protective equipment. In one implementation, the analytics may determine whether all the predetermined PPE motions in the discrete set of PPE motions were performed in a specific sequence (e.g., motion associated with putting on gloves is detected last; motion associated with putting on gloves is detected first). In an alternate implementation, the analytics may determine whether all of the predetermined PPE motions in the discrete set of PPE motions were performed in any sequence.

As discussed above, various PPE protocols may be used. In one implementation, an entire area (such as a section of a floor in a hospital (e.g., Intensive Care Unit)), an entire floor, or an entire building (e.g., an entire hospital building) may be subject to the same PPE protocol. In another implementation, the PPE protocol used may depend on a specific patient area, such as a patient room. As one example, a first patient may be in a first patient area (such as a first patient room) and a second patient may be in a second patient area (such as a second patient room). The first patient may have a first illness that has associated therewith a first PPE protocol, and the second patient may have a second illness that has associated therewith a second PPE protocol, with the first PPE protocol being different from the second PPE protocol. In particular, the first PPE protocol may require gloves, and the second PPE protocol may require gloves, gown and a mask.

Further, PPE protocols may be dependent on whether a person is entering or exiting a patient area, as discussed in more detail below. Thus, one or more devices may determine whether the person (e.g., the healthcare worker) is entering or exiting a patient area (e.g., a patient room). In one implementation, one or more stationary controllers may perform the determination.

For example, a single stationary controller may be used to determine whether the person is entering or exiting the patient area. In one implementation, the stationary controller may make this determination based on timing and/or based on an identification of the person. As one example, the wristband may include a particular identification associated with the healthcare worker. A particular stationary controller, communicating with the wristband, may receive the particular identification. Responsive to the particular stationary controller determining that it has not communicated with the wristband with this particular identification within a certain period of time (e.g., 2 minutes, 5 minutes, etc.), the stationary controller may determine that the healthcare worker has entered the patient area. Responsive to the particular stationary controller determining that it has communicated with the wristband with this particular identification within the certain period of time, the stationary controller may determine that the healthcare worker is exiting the patient area.

As another example, multiple stationary controllers may be used to determine whether the person is entering or exiting the patient area. The multiple stationary controllers may be stationed in different positions relative to the patient area (e.g., a first stationary controller positioned outside of the patient area and a second stationary controller positioned inside of the patient area). In one implementation, the stationary controllers may interact with a wristband (such as via Bluetooth communication). Responsive to the interaction, the respective stationary controller may determine whether the healthcare worker (who is wearing the wristband) is entering or exiting the patient area. For example, responsive to the first stationary controller communicating via Bluetooth with the wristband for a certain period or time (or the first stationary controller communicating via Bluetooth with the wristband without the second stationary controller communicating via Bluetooth with the wristband; or the first stationary controller first communicating via Bluetooth with the wristband before the second stationary controller communicates via Bluetooth with the wristband), the first stationary controller (which is positioned outside the patient area) may determine that the healthcare worker is entering the patient area. As another example, responsive to the second stationary controller communicating via Bluetooth with the wristband for a certain period or time (or the second stationary controller communicating via Bluetooth with the wristband without the first stationary controller communicating via Bluetooth with the wristband; or the second stationary controller first communicating via Bluetooth with the wristband before the first stationary controller communicates via Bluetooth with the wristband), the second stationary controller (which is positioned inside the patient area) may determine that the healthcare worker is exiting the patient area.

In another implementation, the wristband may perform the determination as to whether the person is entering or exiting the patient area. In a first specific implementation, the wristband may analyze the sensor data (e.g., data from the gyroscope and/or accelerometer) responsive to detecting communication from a stationary controller. For example, responsive to communicating via Bluetooth with a stationary controller, the wristband may store sensor data from one or more sensors (e.g., gyroscope and/or accelerometer) and analyze the sensor data in order to determine whether the sensor data is indicative of a pulling motion or a pushing motion. Responsive to determining that the sensor data is indicative of a pulling motion and responsive to a pulling motion being indicative of entering an area (e.g., the wristband is pre-programmed to indicate that pulling motions are indicative of entering an area), the wristband and/or stationary controller may determine that the healthcare worker has entered the patient area. Responsive to determining that the sensor data is indicative of a pushing motion and responsive to a pushing motion being indicative of exiting an area (e.g., the wristband is pre-programmed to indicate that pushing motions are indicative of exiting an area), the wristband and/or stationary controller may determine that the healthcare worker has exited the patient area. In a second specific implementation, the wristband may analyze the sensor data (e.g., data from the gyroscope and/or accelerometer) continuously to determine whether a pulling motion or a pushing motion has occurred.

In yet another implementation, a device separate from the stationary controllers and the wristband may be used in determining whether the healthcare worker is entering or exiting the patient area. As discussed above, a part of the proximity sensing and output generating device may be used to indicate movement of a door, such as movement associated with opening and/or closing of the door. In one implementation, the proximity sensing and output generating device may only sense a movement (such as the door has been opened and closed), but cannot sense whether the movement is associated with an entrance or an exit. In this regard, the proximity sensing and output generating device may be used in combination with one or both of the wristband or the stationary controller in order to determine whether the person is entering or exiting the patient area. As one example, responsive to the proximity sensing and output generating device determining movement of the door, the proximity sensing and output generating device may generate an output indicative of the determination of the movement of the door. The wristband and/or the stationary controller may receive the output, and responsive to receipt, may analyze its sensor data in order to make the determination as to whether the healthcare worker is entering or exiting the patient area. For example, responsive to receiving the output, the wristband may analyze its sensor data in order to determine whether it has recorded a pulling motion or a pushing motion, and responsive to this determination, determine whether the healthcare worker is entering or exiting the patient area. As another example, the proximity sensing and output generating device may have a unique identification, and send the unique identification in the output to the stationary controller. Using the output, with the unique identification, the stationary controller may determine whether the healthcare worker is entering or exiting the patient area.

The device which makes the determination of PPE protocol compliance may receive the respective protocol in one of several ways. In the example where the wristband performs the determination as to PPE protocol compliance, the wristband may receive an indication as to the specific PPE protocol from a separate electronic device (e.g., the stationary controller). In particular, a stationary controller may be associated with a specific patient area, such as first patient area or second patient area. The stationary controller may send one or both of an indication of the PPE protocol or the required movements for the PPE protocol. In the example, discussed above, responsive to the wristband being proximate to the first stationary controller, the first stationary controller may transmit to the wristband an indication of the first PPE protocol (e.g., the first PPE protocol may comprise a gown and gloves, with the first stationary controller transmitting to the wristband an indication of the gown and gloves, such as upon entering the room and indication of putting on the gown first and then the gloves).

Further, in one implementation, the sensor data for PPE movement is analyzed in each of the three dimensions. In an alternate implementation, the sensor data for PPE movement is analyzed in fewer than all of the three dimensions. In a first specific implementation, the sensor data is analyzed in only two dimensions (e.g., analyzing for large acceleration in both the x- and y-axis). In a second specific implementation, the sensor data is analyzed in only one dimension (e.g., analyzing for large rotation rate along the y-axis (pitch) or for large acceleration along the z-axis).

In still another implementation, the method and system for PPE compliance limits analysis to a discrete window of sensor data. In particular, a triggering event may identify a potential PPE event, thereby beginning the sequence of analyzing the sensor data for the PPE event. As discussed in more detail below, the wristband and the stationary controller work in combination for the triggering event. In one example, the stationary controller sends a beacon. Responsive to the wristband coming within range of near-field communication (e.g., within Bluetooth communication range for at least a predetermined amount of time), the wristband may be triggered to record sensor data in order to determine whether PPE movements have occurred. In another example, the wristband may send a beacon, such as a Bluetooth signal or RFID signal. The stationary controller may sense the signal (e.g., the stationary controller may determine, based on the strength of the beacon, how close the wristband is to the stationary controller). Responsive to the stationary controller determining that the wristband is proximate (e.g., within a predetermined distance for at least a predetermined amount of time), the stationary controller may transmit a wake-up signal to the wristband to record the sensor data for analysis. Further, the analysis of the sensor data generated within the discrete window may be based on a contrast of PPE motions with other periodic motions that may occur within the discrete window. As one example, the time period associated with the discrete window may be 60 seconds when the healthcare provider is walking into a patient's room. In that regard, the analysis may focus on contrasting PPE movements with other periodic movements that may be performed within the 60 second discrete window (e.g., walking, knocking on a door, etc.). For example, the analysis may focus on frequency and/or power to differentiate PPE movements with other periodic movements. In this regard, accuracy of analysis may be increased by: (1) using data in the discrete window; and (2) analyzing PPE actions and contrasting those PPE actions without other periodic actions (e.g., walking, knocking on door) within that discrete window.

In the present implementation, the motion sensor may operate for a very short time (~1 minute) only when a PPE event is detected. For most of the time, at least a part of the wristband, such as one or more of the motion sensors within the wristband, is in sleep mode. For example, within sleep mode, power may be reduced or completely withheld from one or more parts of the wristband, such as the motion sensor. This achieves both low power dissipation and reliable PPE compliance detection. Selection of low-power chips further reduces the wristband's power consumption, as discussed further below. In particular, since the wristband is activated in the discrete window, the wristband may have a longer battery life, thereby reducing the burden from the healthcare provider to recharge or replace the battery as often. Further, since the wristband is activated in the discrete window, the wristband may focus on events that may occur within the window, thereby more accurately detecting compliance during a PPE event, and avoiding false alarms from any interfering motions (e.g., walking) or motions in a non-PPE event.

In one implementation, the analysis uses one or more static thresholds in analyzing whether the sensor data is indicative of PPE movements. For example, the frequency and/or the power associated with the sensor data may be compared with static thresholds (e.g., use a static filter to filter periodic walking movement from PPE movement; use a static threshold to analyze in the magnitude domain (such as power)). With regard to frequency, one or more thresholds, such as a lower threshold (to filter out other periodic movements, such as walking) and/or an upper threshold (to filter out overly PPE movements) may be used. In an alternate implementation, the analysis may use one or more dynamic thresholds in order to dynamically adapt the analytics. For example, based on previous sensor data, the thresholds and/or ranges for frequency and/or power analysis may be adapted. In a particular example, the analysis may use machine learning that adapts to an individual healthcare provider's PPE habit. For example, the individual healthcare provider may perform PPE movements multiple times in a certain period (e.g., in a day, week, month, etc.). The machine learning may extract one or more characteristics associated with the PPE habits of the individual healthcare provider and then store those parameters correlated to this individual healthcare provider. Thus, the thresholds, such as the frequency and/or magnitude for analysis, may be tailored to the individual healthcare provider.

As discussed in more detail below, the wristband may operate in a lower power mode. In one implementation, the wristband may operate in a discrete window (such as for 60 seconds) in order to detect the hand hygiene movements. Within this discrete window, one or more operations of the wristband, such as the motion sensor(s), are awakened for recording sensor data.

Further, in one implementation, the wristband may operate in a sleep mode (in which a part of the electronics within the wristband are turned off or are consuming less power) and may operate in a normal mode (in which some or all of the electronics within the wristband that are turned off or are consuming less power in sleep mode are turned on or consume a greater amount of power). As one example, the wristband may include one or more sensors, with some or all of the sensors being turned off or inactive in sleep mode, and some or all of the sensors being turned on or active in normal mode.

The wristband may be triggered to exit from sleep mode in one of several ways. In one way, the wristband may make the decision to exit sleep mode on its own and without any input from an external device. For example, the wristband may have one or more sensors that remain active in sleep mode, with the data generated by the one or more sensors active in sleep mode being used to determine whether to exit sleep mode. In particular, the wristband may include a micro-vibration sensor. The micro-vibration sensor draws less power than other motion sensors, such as accelerometers or gyroscopes. Responsive to the micro-vibration sensor, active in sleep mode, indicating motion, the wristband may wake-up the microcontroller and/or other sensors on the wristband, such as the accelerometer and/or gyroscope and/or magnetometer, thereby exiting sleep mode. In another way, the wristband may make the decision to exit sleep mode based on input from another electronic device. For example, the wristband may work in combination with an external device, such as the stationary controller, in order to determine when a PPE event begins (and, in turn, when for the wristband is to "wake up"). As discussed above, the wristband may send a beacon to the stationary controller, or may receive a beacon from the stationary controller in order to trigger the wake up of the wristband. After which, the wristband may generate and record sensor data. After the PPE event (e.g., after no more than 60 seconds), the wristband may go back into sleep mode (either due to determining that the PPE event is successful or not).

In still another implementation, one or more operations of PPE monitoring may be divided amongst the wristband and the stationary controller. As discussed in more detail below, the stationary controller may be associated with an entrance or exit to a room. For example, one operation of PPE monitoring is a trigger for beginning the PPE monitoring. In this example, one of the wristband or the stationary controller may send a beacon, and another of the wristband or the stationary controller may detect the beacon, thereby triggering the beginning of the PPE monitoring. In particular, the wristband may send an RFID or Bluetooth signal, which may be sensed by the stationary controller. In the example of Bluetooth, the stationary controller, based on the signal strength of the Bluetooth signal and/or the time elapsed of receiving the Bluetooth signal, may determine the closeness of the devices to one another. In response to the stationary controller determining that the wristband is within a predetermined distance for a predetermined period of time, the stationary controller may send a wake-up signal to the wristband to begin monitoring for PPE. In another implementation, the stationary controller may transmit a beacon, which upon receipt by the wristband wakes up at least a part of the wristband, such as the motion sensor(s) on the wristband. More specifically, in one implementation, responsive to the wristband sensing the beacon signal from the stationary controller for a predetermined amount of time, the wristband may wake-up the motion sensor(s) on the wristband.

Alternatively, or in addition, the PPE monitoring system may generate one or more outputs associated with the PPE monitoring. A first output may be generated to alert the healthcare provider to perform the PPE movements. A second output may be generated to alert the healthcare provider as to whether the PPE movements were sufficient and/or insufficient. In one implementation, the stationary controller may generate the alert to the healthcare provider to perform the PPE movements, and the wristband may generate the alert to the healthcare provider as to whether the PPE movements were sufficient and/or insufficient. Alternatively, the wristband may generate the alert to the healthcare provider to perform the PPE movements, and the stationary controller may generate the alert to the healthcare provider as to whether the PPE movements were sufficient and/or insufficient. In either implementation, the alerts may be divided amongst the stationary controller and the wristband. In still another implementation, only one device (e.g., either the stationary controller or the wristband) generates both the alert to the healthcare provider to perform the PPE movements, and the alert to the healthcare provider as to whether the PPE movements were sufficient and/or insufficient.

Generally speaking, the analytics may determine any one, any combination, or all of: compliance; partial compliance; or non-compliance. Further, the analytics may determine any one, any combination or all of: whether the person put on or took off the required PPE; whether the person put on or took off the required PPE in the required sequence; whether the person complied with PPE and HH protocols; or whether the person complied with PPE and HH protocols in the required sequence.

Responsive to the determination of the analytics, one or more outputs may be generated using output functionality. In one implementation, the wristband may generate one or more outputs based on a determination of any one, any combination, or all of: compliance, partial compliance and/or non-compliance. The one or more outputs from the wristband may comprise audio and/or visual outputs, such as sound(s) (such as different sounds), light(s) (such as different lights or different combinations of lights), vibration(s) (such as different patterns of vibrations), or the like. For example, a first sound may be indicative of compliance and a second sound, different from the first sound, may be indicative of non-compliance. As another example, a first sound may be indicative of compliance, a second sound may be indicative of partial compliance, and a third sound may be indicative of non-compliance. As still another example, a first light may be indicative of compliance (e.g., a green colored light) and a second sound (e.g., a red colored light) may be indicative of non-compliance. As yet still another example, the wristband may escalate the outputs based on a determination of partial compliance and/o non-compliance. In particular, the wristband may initially output a sound and/or light responsive to determining a hand hygiene event. Responsive to determining non-compliance (and/or partial compliance) with the hand hygiene event, the wristband may generate a different type of output, such as a louder sound (e.g., louder than the output responsive to determining a hand hygiene event) and/or a brighter light (e.g., brighter lights or a greater number of lights than the output responsive to determining a hand hygiene event).

Alternatively, or in addition, the stationary controller may generate one or more outputs based on a determination of any one, any combination, or all of: compliance, partial compliance and/or non-compliance. The one or more outputs from the stationary controller may comprise audio and/or visual outputs, such as sound(s), light(s), or the like. Alternatively, or in addition, an electronic device separate from the wristband and the stationary controller may generate one or more outputs based on a determination of any one, any combination, or all of: compliance, partial compliance and/or non-compliance. In one implementation, the determination as to compliance, partial compliance and/or non-compliance, either transmitted to or determined by the back-end analytics, may result in the back-end analytics transmitting an alert to a separate electronic device. For example, the separate electronic device (e.g., a smartphone) may be associated with the user who is the subject of the compliant, partial compliant and/or non-compliant PPE event. As another example, the separate electronic device may be associated with a third party separate from the user subject to the PPE event. In particular, the separate electronic device may be associated with an administrator tasked with PPE compliance in a hospital setting or a responsible administrator for a section of the hospital (e.g., the head nurse in the ICU). As another example, the separate electronic device may be associated with a teacher tasked to train healthcare providers in PPE protocols.

Alternatively, or in addition, one or more aspects of the wristband, the stationary controller or the back-end analytics may change responsive to a determination of any one, any combination, or all of: compliance; partial compliance; or non-compliance. As one example, responsive to a determination of partial and/or non-compliance, the wristband and/ or stationary controller may modify its operation responsive to a new PPE event. In one implementation, the outputs generated by the wristband and/or stationary controller may be different than those outputs during a previous wristband event. As one example, the audio outputs generated by the wristband and/or stationary controller may be louder than those outputs during the previous wristband event responsive to determination of partial compliance and/or non-compliance. As another example, an output, not generated during the previous PPE event, may be generated in a subsequent PPE event based on compliance, partial compliance, and/or non-compliance. In particular, responsive to determining that the user partially complied and or non-complied during the previous PPE event, a display on the wristband may be activated to output a countdown of 20 seconds. In this way, the user may receive more guidance to put on or take off the protective garments within a predetermined amount of time (e.g., 20 seconds) responsive to determination of partial or non-compliance. Alternatively, or in addition, the analytics to determine compliance may be different than the analytics used during the previous wristband event. For example, the analytics may be stricter than previously used analytics.

In still another implementation, the PPE monitoring system may include a back-end electronic device, such as a server, that performs analytics, as discussed above. The analytics may be configured to perform any one, any combination, or all of: determine compliance (e.g., full, partial or non-compliance); generate compliance reports, to identify trends based on time of shift, protocols, and other desired metrics; identify patients and/or health care providers that are the source of cross-contamination; generate alerts responsive to compliance determinations, identifying trends, identifying patients and/or health care providers that are the source of cross-contamination, or the like; generating displays or other types of graphical users interfaces to output statistics based on one or more criteria, such as based on an event (e.g., full, partial, or non-compliance), based on people (e.g., analysis based on all doctors, all nurses, or individuals), and/or based on location (e.g., based on the particular floor of a hospital, the particular wing of a hospital, based on a department of the hospital (e.g., ICU-A, ICU-B, ICU-C)).

In one implementation, one or more electronic devices may work in combination with the wristband in order to instruct a user as to proper PPE. For example, a user may follow instructions of requested movements that are output (e.g., displayed on a display) on an electronic device. The wristband, worn by the user, may register movements of the user. The electronic device may compare the requested movements with the registered movements in order to provide feedback to the user. In a first implementation, the user may comprise an adult healthcare provider, with the feedback to the user for instructional purposes. The feedback may comprise instructions as to one or more of the following: information as to deficiencies in PPE movements; or information as to deficiencies in the sequence of PPE movements. The feedback may include a score, with the score based on improvement or worsening of the PPE (e.g., improvement or worsening based on a previous training session).

FIG. 1A is a first example block diagram of a hand hygiene system 100, with a mobile wristband device 105, a local stationary controller 115 and a back-end server 130. As discussed above, the mobile wristband device 105 and the local stationary controller 115 may communicate wirelessly, such as via 110. Example wireless protocols may comprise near-field communication protocols, such as RFID, Bluetooth, ZigBee or the like. The local stationary controller 115 may likewise communicate with back-end server 130. As shown in FIG. 1A, the communication between the local stationary controller 115 and back-end server 130 is wireless 120 via a Wi-Fi base station 125. Other methods of communication are contemplated.

FIG. 1B is a second example block diagram of a hand hygiene system 150, with a mobile wristband device 153, a dispenser 151, a local stationary controller 152, wireless router 154 (e.g., Wi-Fi transceiver), cloud computing 156, compliance analysis 158, and output device 159 (e.g., smartphone or tablet). The system 150 is configured to perform any one, any combination, or all of the following four functions: data tracking, data collection, data analysis and healthcare provider motivation. Each healthcare provider wears a wristband 153 with built-in motion sensors, discussed in more detail below. In one implementation, each wristband is assigned to and worn by only one person (e.g., healthcare provider). Further, there is a one-to-one mapping between the person's information (e.g., name, role, etc) and the MAC address of the wristband. As discussed further below, stationary controllers (e.g., positioned inside and/or outside a patient room) may be mapped to a particular area (e.g., a room location).

When the healthcare provider approaches the entrance of a patient's room, the wristband sensor on wristband 153 detects the beacon from the controller 152 installed close to, adjacent to, or proximate to the sanitizer dispenser 151 and send a hand hygiene alert to the healthcare provider. Alternatively, the wristband 153 may transmit a beacon to the controller 152, which in turn may detect the wristband 153, with the controller 152 sending a signal to wristband 153, as discussed above. The wristband sensor in wristband 153 records the healthcare provider's hand motion data during the hand hygiene event, which is transmitted via the controller 152 and wireless router 154 to cloud computing 156, which may comprise a hospital server.

As discussed above, controller 152 may be mounted proximate to dispenser 151, such as within or less than 1 inch, within or less than 2 inches, within or less than 3 inches, etc. of dispenser 151. Controller 152 may include electronics that performs one or more functions. For example, controller 152 may generate a beacon (or other wireless signal) that is received by the wristband 153. As discussed above, in response to receiving the beacon, the wristband 153 is configured to generate an output indicative of the hand hygiene alert (e.g., an audible output and/or a visual output indicative to the healthcare provider to perform the hand cleaning process). In this regard, the controller 152 generates the beacon that begins the hand hygiene notification process. Alternatively, controller 152 may receive a beacon from wristband 153, such as a Bluetooth signal. In response, controller 152 may determine a proximity to wristband 153, and if sufficiently proximate, send a wake-up signal to wristband 153 to begin motion sensor monitoring.

As another example, the controller 152 may monitor one or more operations related to dispenser 151. In one implementation, the controller 152 may monitor at least one aspect of the dispenser 151 itself. For example, the controller 152 may monitor an internal operation of the dispenser 151. In a first specific implementation, the controller 152 may include a sensor, such as a sound sensor, that may monitor the internal operation of dispenser 151 (e.g., a sound sensor that senses sound generated by a motor within dispenser 151 that dispenses antibacterial product into the hand of the healthcare provider). Thus, in the first specific implementation, the controller 152 may monitor the dispenser 151, as opposed to movement of the healthcare provider. In a second specific implementation, the controller 152 may include a sensor, such as an infrared sensor, that may monitor the movement of the healthcare provider in an area proximate to the dispenser 151. In a third specific implementation, the controller 152 may include multiple sensors that monitor the internal operation of the dispenser 151 and the movement of the healthcare provider in an area proximate to the dispenser 151.

Responsive to the controller 152 determining that the monitored aspect of the dispenser 151 has occurred (e.g., the controller 152 determining that the dispenser 151 has dispensed the antibacterial product and/or the controller 152 determining that the healthcare provider is proximate to the dispenser 151), the controller 152 may send a communication to the wristband 153. Responsive to the communication, the wristband 153 may begin to track the hand movements of the healthcare provider. Alternatively, the wristband 153 may begin to track the hand movements responsive to receiving the beacon from the controller 152.

The wristband 153 may thus record the healthcare provider's hand motion data during the hand hygiene event. In one implementation, the wristband 153 may analyze the hand motion data locally (within the wristband 153), and transmit the analysis (and/or the hand motion data) to the controller 152. Alternatively (or in addition), the wristband 153 may transmit the hand motion data to controller 152 for analysis by the controller 152 and/or for analysis by cloud computing 156.

After the analysis of the hand motion data (either by wristband 153, controller 152 and/or cloud computing 156), an indication of the results of the analysis may be transmitted to the healthcare provider. In one implementation, the indication may be output on wristband 153. In one example, the wristband 153 may perform the analysis and may output the indication of the results of the analysis (e.g., whether the healthcare provider adequately cleaned his/her hands; whether the healthcare provider inadequately cleaned his/her hands; an indication how to improve hand cleaning (e.g., aurally outputting to the healthcare provider to clean the hands for a longer period of time, such as for 10 more seconds)). In another example, the controller 152 may perform the analysis and may transmit to the wristband 153 the indication for output by the wristband 153 of the indication of the results of the analysis. In still another example, the controller 152 may perform the analysis and may transmit to cloud computing 156 the indication, which may transmit to (or may available for download by) a mobile app running on a mobile electronic device associated with the healthcare provider. In yet another example, cloud computing 156 may perform the analysis using compliance analysis 158 (e.g., a computer associated with the infection control team may analyze hand hygiene data) and may transmit to (or may available for download by) a mobile app running on a mobile electronic device associated with the healthcare provider (e.g., output device 159).

In this way, separate from feedback from the wristband 153, each healthcare provider may also check his/her performance through the mobile app on output device 159, thereby being provided motivation to comply with hygiene standards.

In one implementation, the hygiene protocol, including the hand hygiene protocol, is standard and consistent for different locations within a premises. Generally speaking, the hygiene protocol may include any one, any combination, or all of the following: hand hygiene protocol; mask protocol (e.g., whether or not to wear a face mask); gown protocol (e.g., whether or not to wear a hospital gown); gloves protocol (e.g., whether or not to wear latex rubber gloves); footwear protocol (e.g., whether or not to wear booties over the shoes); etc. For example, the hygiene protocol may be the same for a first hospital room and a second hospital room, or may be the same for a first section of the hospital and a second section of the hospital. As discussed further below, various hand hygiene protocols may be used, such as those issued by WHO. Alternatively, the hygiene protocol is different for different locations within a premises. For example, a first hospital room may have a first hygiene protocol and a second hospital room may have a second hygiene protocol, with the first hygiene protocol being different than the second hygiene protocol. In particular, the first hygiene protocol may be different from the second hygiene protocol in any one, any combination, or all of: hand hygiene protocol, mask protocol, gown protocol, or footwear protocol. As another example, a first section of the hospital, such as the ICU (or ICU-A), may have the first hygiene protocol whereas a second section of the hospital, such as the neonatal unit or ICU B, may have the second hygiene protocol (e.g., the ICU requires face masks whereas the neonatal unit requires gowns).

The hygiene protocol may be communicated to one or both of the stationary controller or the wristband in one of several ways. In one way, the stationary controller may have the specific protocol pre-programmed thereon (either upon installation or sent from the server). For example, responsive to a determination that a patient with pneumonia is staying in a particular room, the server may send a communication to the stationary controller (assigned to that particular room) to indicate the hygiene protocol for a patient with pneumonia. Similarly, the wristband may determine the specific protocol in one of several ways. In one way, the stationary controller in the specific location may send or push the protocol to the wristband. For example, a stationary controller in the first section of the hospital may send the first protocol (e.g., the correct hand movements or the requirement of a face mask) to the wristband in response to the stationary controller determining that the wristband is in proximity (see 638 of FIG. 6C). In another way, the wristband may, itself, determine its location, transmit the location to a server, which in response may send the specific protocol.

In practice, the stationary controller and/or the wristband may generate an output indicating the protocol (e.g., the deviation in the protocol, such as wearing a face mask). For example, responsive to the stationary controller determining that the wristband is in proximity, the stationary controller may generate an output (e.g., an audio output stating: "please put on a face mask"). As another example, the wristband may generate the output, such as the audio output.

Further, the output may be dependent on the status of the person. Status may be defined in one of several ways, such as: a trainee (e.g., a new employee); an existing employee; a visitor; etc. In this regard, the output, either from the stationary controller and/or from the wristband, may be dependent on the status of the person. As one example, the status of the person may be an employee. The status may be stored, for example, on the wristband. In the example of the stationary controller generating the output, the stationary controller may first receive the status of the person (e.g., the wristband transmitting the status of "trainee" to the stationary controller upon the wristband coming into proximity with the stationary controller). The stationary controller may determine whether to generate the output (e.g., generating a reminder to wear a mask) dependent on whether the person is designated as a trainee. If so, the stationary controller may generate the output. Conversely, in the event that the person is an "employee" (meaning more experienced than a trainee in the protocols of the hospital), responsive to the stationary controller determining the status of the person as "employee", the stationary controller may determine not to generate the output (e.g., not generate a reminder to wear a mask). Similarly, in the context of the wristband generating the output, the wristband may determine whether to generate the output based on the status of the person. As discussed above, the wristband may determine, either based on a communication from the stationary controller or from another external device, to output a particular protocol for a specific room or section of a hospital. The wristband may condition the output of the particular protocol on the status of the person. Specifically, the wristband may indicate that the wearer is a trainee. Responsive to the wristband determining that the wearer is a trainee, the wristband may determine to output the special protocol (e.g., generate a vibration, generate an audio and/or display output). Conversely, responsive to the wristband determining that the wearer is an "employee", the wristband may determine to output the special protocol (e.g., generate a vibration, generate an audio and/or display output).

Thus, in one implementation, the wristband may comprise an ultra-low-power device. Optionally, the wristband may be any one, any combination, or all of the following: waterproof; easy to clean; provide output to the healthcare provider (e.g., a warning vibrating alert if no or incomplete hand hygiene detected). To minimize the change on healthcare providers' workflow, the wristband may be configured such that power consumption may be reduced so that battery life is extended (e.g., approximately 12 months), as discussed in more detail below.

Since the sensors may be worn on different parts of the body, such as at the wrist, the sensors are not in direct contact with patients most of the time and are less likely to be contaminated. Nevertheless, the wristbands may be designed such that they can be easily cleaned with UV lights or sanitizer when needed.

Alternatively, or in addition, the wristband may include a simple and robust algorithm for hand rubbing detection. Rubbing hands with an alcohol-based formulation is one manner for routine hygienic hand antisepsis. Alternatively, soap and water may be used mostly for cleaning soiled hands. When using an alcohol-based formulation, healthcare providers can walk while rubbing hands. Therefore, a robust motion algorithm may be used to detect the hand rubbing motions, separate from noise factors such as walking and arm swing. Since the wristband tracks and stores the hand hygiene information and provide real-time intervening, the embedded algorithm may be straightforward in order to minimize the computing power and thus increase battery life of the wristband. In a first specific implementation, the wristband's sole focus is directed to hand hygiene compliance. In a second specific implementation, the wristband has multiple purposes, including hand hygiene compliance and access control (e.g., RFID tag) and/or including hand hygiene compliance and activity tracking (e.g., pedometer, movement tracker, or the like). In this regard, the wristband may include algorithms to track different types of movements, such as hand hygiene movements, arm swinging movements, step movements, and the like. The wristband may thus analyze movements against multiple algorithms in order to determine the mostly likely type of movement. For example, the wristband may analyze the sensor output to determine whether the sensor output is more indicative of hand hygiene movements or arm swinging movements. Therefore, including algorithms directed to identifying different types of movements may improve operation of the hand hygiene compliance.

In still another implementation, the wristband may generate sensor data that may be analyzed by hand hygiene analytics. In particular, the sensor data may be stored in a hand hygiene database, which provides a variety of data to hospital management team and individual healthcare providers. Detailed hand hygiene compliance reports generated by date, location (floor, unit or room), or department are available to hospital administrators and can be used to set up incentive/penalty programs to motivate healthcare providers. Infection control professionals also have access to the information to differentiate between staff groups and identify trends based on time of shift, protocols, or other desired metrics. Further, a mobile app may be used, whereby healthcare providers can compare their performance to their colleagues' and be motivated through peer pressure and team competition.

FIG. 1C is a third example block diagram of a hand hygiene system 160, with an application server 162, a database 172, one or more wristbands (wristband #1 (176) to wristband # N (178)), one or more stationary controllers (stationary controller #1 (180) to stationary controller # M (182)), and one or more notification electronic devices (electronic device #1 (184) to electronic device # L (186)). FIG. 1C shows N wristbands, M stationary controllers and L electronic devices. Any numbers of wristbands, stationary controllers, and electronic devices are contemplated.

The application server 162 is configured to include the hardware, software, firmware, and/or middleware for operating the hand hygiene analytical and monitoring application 168. Application server 162 is shown to include a processor 164, a memory 166, and a communication interface 170. The hand hygiene analytical and monitoring application 168 is described in terms of functionality to manage various stages of managing the hand hygiene data as generated by one or more wristbands (wristband #1 (176) to wristband # N (178)) and/or one or more stationary controllers (stationary controller #1 (180) to stationary controller # M (182)), and for notification via electronic device #1 (184) to electronic device # L (186).

Hand hygiene analytical and monitoring application 168 (and hand hygiene analytics 306 and access control 374, 482 resident in wristband and hand hygiene control 432 and access control 434 in stationary controller, discussed further below), may be a representation of software, hardware, firmware, and/or middleware configured to implement the management of any one, any combination, or all of the stages of hand hygiene compliance.

The system 160 may further include a database 172 for storing data for use by the hand hygiene analytical and monitoring application 168. For example, data generated by one or both of wristbands 176, 178 and stationary controllers 180, 182 may be stored in database 172.

The application server 162 may communicate with the database 172 directly to access the data. Alternatively, the application server 162 may also communicate with the database 172 via network 174 (e.g., the Internet). Though FIG. 1C illustrates direct and indirect communication, in one implementation, only direct communication is used, in an alternate implementation, only indirect communication is used, and still in an alternate implementation, both direct and indirect communication is used.

The application server 162 may communicate with any number and type of communication devices via network 174. As illustrated in FIG. 1C, application server 162 may communicate with electronic devices associated with one or more users. For example, FIG. 1C depicts N wristbands 176, 178, M stationary controllers 180, 182, and L electronic devices 184, 186. The wristbands 176, 178 may communication directly with application server 162 or may communicate via stationary controllers 180, 182 (not shown). The depiction in FIG. 1C is merely for illustration purposes. Fewer or greater numbers of wristbands, stationary controllers, and electronic devices are contemplated.

Electronic device #1 (184) to electronic device # L (186) shown in FIG. 1C may be used to notify one or more individuals, such as the healthcare provider associated with one of wristbands 176, 178, or another healthcare provider not associated with one of wristbands 176, 178. Further, electronic device #1 (184) to electronic device # L (186) may comprise smartphones, tablet computers, personal computers (PCs), server computers, handheld or laptop devices, multiprocessor systems, microprocessor-based systems, network PCs, or devices, and the like.

Figure 1D:
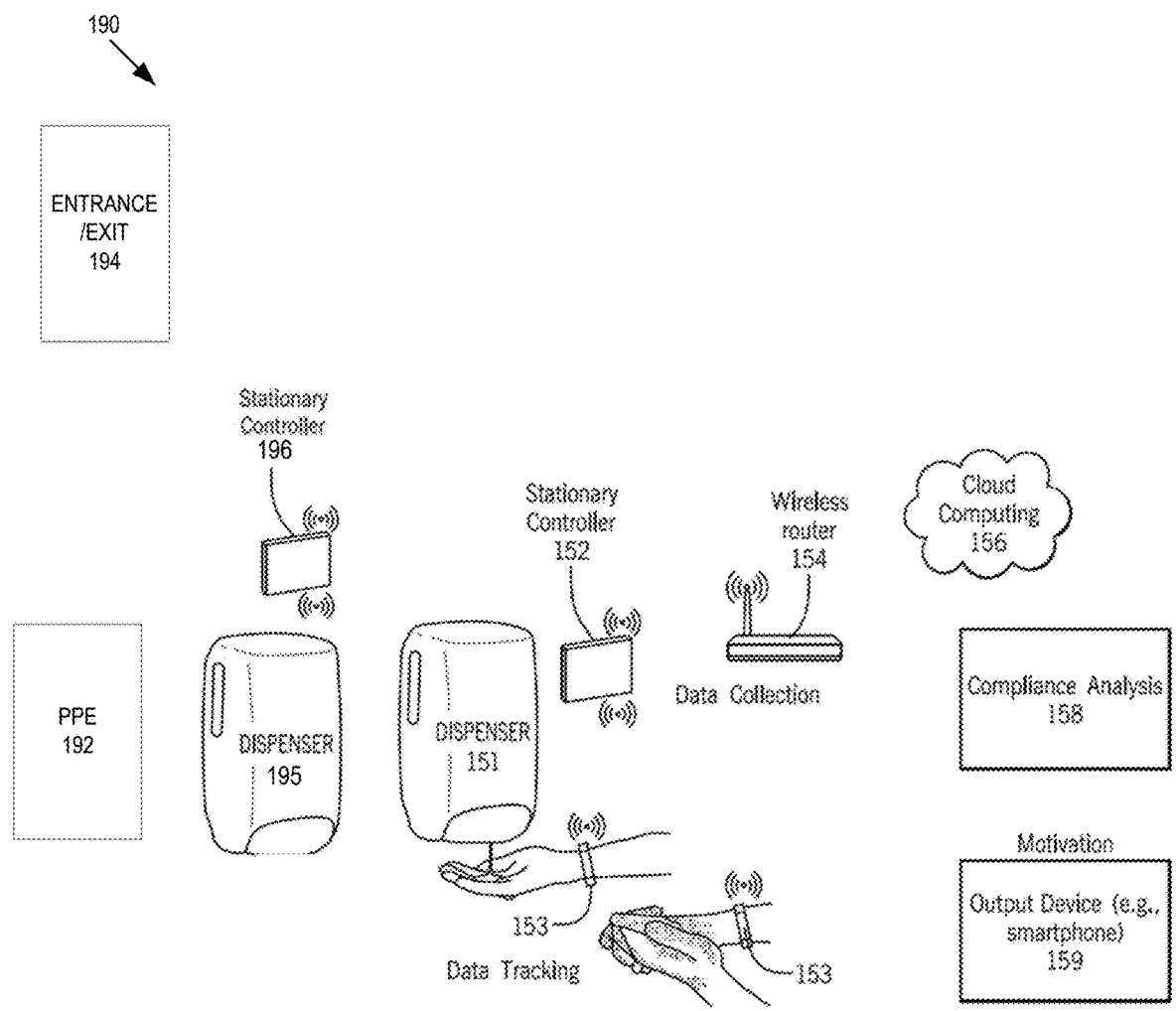
FIG. 1D is an example block diagram of a hand hygiene and personal protective equipment system, with a mobile wristband device, personal protective equipment, an entrance/exit, a dispenser, a local stationary controller, compliance analysis, one or more output devices, and cloud computing.

FIG. 1D is an example block diagram 190 of a hand hygiene and personal protective equipment system, with a mobile wristband device 153, personal protective equipment 192, an entrance/exit 194, one or more dispensers 151, 195, one or more stationary controllers, 152, 196, compliance analysis 158, one or more output devices 159, and cloud computing 156. As discussed further below, the stationary controller may be associated (such as proximate to) entrance/exit 194, which is the entrance and/or exit to a patient area (e.g., a patient room). In one implementation, two dispensers are used, with one dispenser located outside of the room near or proximate to the entrance/exit 194 (e.g., dispenser 151 in FIG. 1D) and a second dispenser located inside the room near or proximate to the entrance/exit 194 (e.g., dispenser 195 in FIG. 1D). For example, one typical clinical setting has a sanitizer dispenser (and/or a washing station) and PPE station positioned at the entrance to a patient room and another sanitizer dispenser (and/or a washing station) inside the patient room.

In practice, when the wristband 153 is proximate to dispenser 151 (as the healthcare provider is outside the room and moving toward the entrance), stationary controller 152 may communicate with wristband 153 in order to trigger the HH and/or PPE event upon entrance. Likewise, when the wristband 153 is proximate to dispenser 195 (as the healthcare provider is inside the room and moving toward the exit to leave), stationary controller 196 may communicate with wristband 153 in order to trigger the HH and/or PPE event upon exit. Alternatively, instead of having two stationary controllers, a single stationary controller (such as stationary controller 152 outside of the room) may be used with an electronic device inside of the room that communicates with stationary controller 152.

Various types of communication between the different electronic devices depicted in FIG. 1D are contemplated. In one implementation, each electronic device depicted in FIG. 1D include Wi-Fi and/or cellular communication functionality in order to communicate, via cloud computing 156, with other devices. For example, stationary controller 152 may communicate with stationary controller 196 via the cloud, and vice-versa. In an alternate implementation, a wireless mesh network may be used. For example, stationary controllers 152, 196 may be organized in a mesh topology with each stationary controller 152, 196 performing different functions. Thus, the wireless mesh network may include an infrastructure of nodes in a mesh topology that are wirelessly connected to each other, with certain nodes piggy-backing off each other to extend a radio signal to route, relay, and proxy traffic to/from clients. In one implementation, stationary controller 196 may comprises a node that communicates with stationary controller 152. Specifically, stationary controller 196, which is positioned inside a patient room, may act as an endpoint, thereby not routing messages for other devices, whereas stationary controller 152, positioned outside the patient room, is responsible for forwarding messages between the endpoints and connecting to the Wi-Fi gateway. The endpoints need not have networking tasks and may enter sleep mode. In this way, the endpoint devices enables a more flexible implementation (e.g., allowing the endpoint devices to be battery-powered), thereby being more conducive for scaling. Further, various electronic devices, such as stationary controller 152 and stationary controller 196, may have unique IDs (e.g., MAC address) within the network.

In this way, a mesh network may be formed, with the stationary controller acting as the access point (communicating with the back-end server via Wi-Fi) and in which the electronic device communicates via near-field communication with the stationary controller.

The personal protective equipment (PPE) 192 may comprise any type of equipment for protecting the person from transmitting a disease to and/or receiving a disease from the patient in the patent area. PPE 192 may include, for example, gloves, mask, goggles, gowns, or the like. As discussed in more detail below, as a person, such as a healthcare provider, enters and/or exits the patient area, one or both of hand hygiene protocols or PPE protocols may be monitored.

As discussed above, one or more electronic devices, such as depicted in FIGS. 1B and 1D, may determine whether a person is entering or exiting the patient area (e.g., patient room) in one of several ways. In one way, one or both of the stationary controllers 152, 196 may determine interaction (and in turn whether the person is entering or exiting the room) based on timing of the interaction. As one example, it may be assumed that the wristband worn by the person who is entering/exiting the room communicates (e.g., via Bluetooth) for a longer period of time than a person who is merely walking past the entrance to the room. In particular, the healthcare provider will remain at the proximity of the entrance for several seconds (to wash hands, don/doff PPE, open door, etc.), unlike someone simply walking by the patient room. Thus, in one implementation, the wristband signal, as detected by stationary controller (e.g., stationary controller 152 positioned at or outside of the entrance to patient room) will be strong (greater than a predetermined threshold) for longer period of time when entering/exiting the room (as compared to walking by). In this way, the stationary controller may count the amount of time this pattern occurs (e.g., greater than the predetermined threshold) and detect if one is entering or exiting the room.

Thus, one or both of the wristband or the stationary controller may determine a period of time that the wristband (with its unique ID) and the stationary controller (also with its unique ID) interact. The wristband and/or the stationary controller may determine an entrance/exit event responsive to determining that the interaction is greater than a predetermined time period. More specifically, the wristband and/or the stationary controller may determine whether the event is an entrance or exit based on timing. For example, responsive to determining that this interaction is less than a predetermined time (such as 30 seconds), the interaction may be determined to be an entrance. Responsive determining that this interaction is greater than a predetermined time (such as 30 seconds), the interaction may be determined to be an exit.

Alternatively, multiple controllers, such as depicted in FIG. 1D, may be used to determine whether a person is entering or exiting the patient area. In particular, one stationary controller, such as stationary controller 152 is positioned outside of the patient room and a second stationary controller, such as stationary controller 196, is positioned inside the patient room. In this way, stationary controller 152 may be tasked with monitoring wristband interaction in order to identify a person entering the room and stationary controller 196 may be tasked with monitoring wristband interaction in order to identify a person exiting the room. Further, the stationary controller network (e.g., such as a stationary controller positioned at respective patient rooms, or multiple stationary controllers positioned at respective patient rooms) may perform multiple tasks, such as monitoring a healthcare provider entering/exiting room, and also monitoring the trace of each provider.

In still an alternate implementation, one or more movements associated with entering or exiting the patient area may be detected. As discussed herein, such as with respect to FIG. 18A, one or more motion sensors may detect movement of a movable item, such as a door opening and/or a door closing. The door may move in one of several ways, such as swinging open/closed or sliding open/closed. In one implementation, the wristband may sense movements (such as using the accelerometer and/or gyroscope housed therein) in order for the wristband to analyze the sensed movement in order to determine whether a door has been opened or a door has been closed (e.g., swing open or swung closed; slid open or slid closed). In an alternate implementation, an electronic device, separate from the wristband and the stationary controller, may sense the movements and may determine whether the door has opened or closed. An example of this is illustrated in FIG. 16D (e.g., see proximity sensing and output generating device 1680 on the front door). In this regard, responsive to the one or more motion sensors sensing a door opening, the one or more motion sensors may transmit a communication (such as a near-field Bluetooth communication) indicative that a door opening has been sensed, which may be received by one or both of the wristband and the stationary controller. Responsive to receipt of the communication indicative that a door opening has been sensed, the wristband and/or the stationary controller may determine that the healthcare provider is entering the room. Conversely, responsive to the one or more motion sensors sensing a door closing, the one or more motion sensors may transmit a communication (such as a near-field Bluetooth communication) indicative that a door closing has been sensed, which may be received by one or both of the wristband and the stationary controller. Responsive to receipt of the communication indicative that a door closing has been sensed, the wristband and/or the stationary controller may determine that the healthcare provider is exiting the room. Alternatively, the separate electronic device may transmit the sensed movements in order for the wristband and/or stationary controller to make the determination.

Alternatively, in the instance where the door is on a spring (and automatically closes after opening), the one or more motion sensors (such as illustrated in FIG. 16D) may still output indications of door openings/closings (e.g., sensor outputs indicative of door opening closing in quick succession).

In the instance where a separate sensor (such as illustrated in FIG. 16D) detects the door opening/closing and transmits the indication of the door opening/closing, responsive to receipt of the communication indicative that a door has opened or closed, the wristband and/or the stationary controller may determine whether the indication is for an entrance or an exit. For example, responsive to the wristband determining that the indication of entrance/exit has not been received within 1 minute (meaning that the wristband has not received an indication within 1 minute of any opening/closing of a door), the wristband may determine that the healthcare provider is entering the room. Conversely, responsive to the wristband determining that the indication of entrance/exit has been received within 1 minute, the wristband may determine that the healthcare provider is exiting the room.

FIG. 2 is a fourth example block diagram of a hand hygiene system 200, with a mobile wristband device 210 and a local stationary controller 230 communicating wirelessly 120 with one another. As shown, hand hygiene system 200 does not include a back-end server. Instead, all analytics discussed herein may be performed by one or both of the mobile wristband device 210 and the local stationary controller 230. Further, in one implementation, the mobile wristband device 210 and the local stationary controller 230 may communicate via near-field communication (e.g., Bluetooth, RFID, ZigBee, etc.), as discussed above.

Figure 3A:
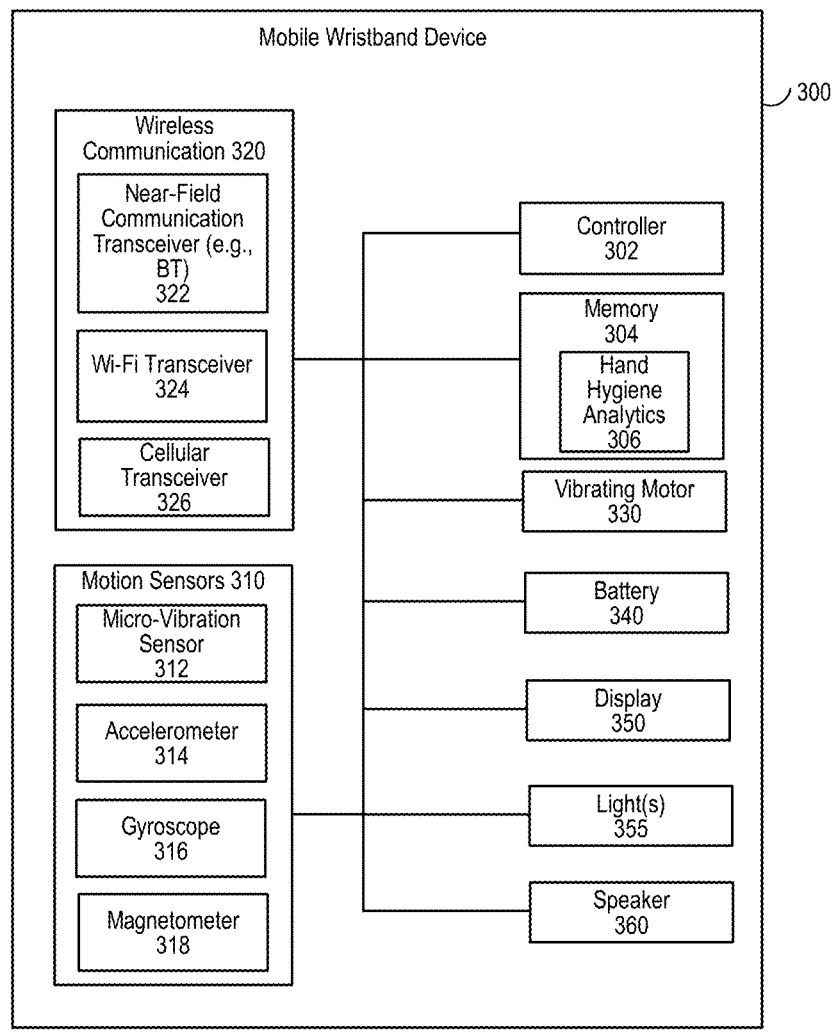
FIG. 3A is a first example block diagram of the mobile wristband device.

FIG. 3A is a first example block diagram of the mobile wristband device 300. As illustrated, the mobile wristband device 300 may include a controller 302, a memory 304, motion sensor(s) 310, wireless communication 320, vibrating motor 330, battery 340, display 350, light(s) 355, and speaker 360. The components illustrated in FIG. 3A may be housed in a mechanical structure that is configured to be attached to a wrist. For example, the mechanical structure may be in the form of a bangle or the like. In one implementation, all of the elements depicted in FIG. 3A are incorporated into the wristband. Alternatively, fewer than all of the elements depicted in FIG. 3A are incorporated into the wristband. For example, vibrating motor 330, display 350, light(s) 355, speaker 360, fewer than all of the motion sensors 310 and fewer than all of the wireless communication 320 need be included in the wristband.

Mobile wristband device 300 may be used in any one of FIG. 1A, 1B 1C, or 2. The controller 302 may comprise a microprocessor, a microcontroller/DSP, PLA, or the like. Further, the memory 304 may include software, such as hand hygiene analytics 306, and may include storage for storing data from motion sensor(s) 310. FIG. 3A illustrates multiple motion sensors. In one implementation, a single motion sensor is used. Thus, in one implementation, mobile wristband device 300 includes only a single motion sensor, such as only accelerometer 314 or only gyroscope 316. Alternatively, multiple motion sensors may be used include any two, any three, or any four of the following: micro-vibration sensor 312, accelerometer 314, gyroscope 316, or magnetometer 318. In an alternative implementation, mobile wristband device 300 includes multiple sensors, such as both accelerometer 314 and gyroscope 316.

In addition, wristband device 300 includes wireless communication 320. In one implementation, a single wireless communication protocol is used. Alternatively, multiple wireless communication protocols may be used include any two, any three, or any four of the following: One or more near-field communication transceiver 308 may comprise functionality to communicate in any one, any combination, or all of the following: near field communication transceiver 322 (e.g., Bluetooth, RFID, and ZigBee); Wi-Fi transceiver 324; cellular transceiver 326; or other far-field communication.

In one implementation, mobile wristband device 300 is configured for low power consumption. Power dissipation of the mobile wristband device 300 may be dominated by one or more components: wireless communication 320; controller 302; motion sensor(s) 310 (including accelerometer 314 and gyroscope 316); vibrating motor 330; display 350; light(s) 355; or speaker 360. In order to reduce power consumption, low-power wireless protocols, such as Bluetooth Low Energy (BLE), RFID (HF/UHF) and ZigBee, may be used. Further, for minimum form factor and low power consumption in mobile applications, mobile wristband device 300 may comprise a system-on-chip (SOC) solution that integrates wireless transceiver and microcontrollers. For instance, DA14580 (Dialog Semiconductor) may be used as a BLE SOC chip developed for beacon, proximity, health and fitness (such as pedometer) applications, and may include a fully integrated BLE radio transceiver and baseband processor (ARM Cortex-M0). Further, the motion sensors may be operated in ultralow power mode and may be triggered into wake-up mode in one of several ways (e.g., by data generated from micro-vibration sensor 312 detecting movement of the mobile wristband device 300 and/or by receiving a communication from local stationary controller, discussed further below). In this regard, motion sensors 310 may include a 6-axis accelerometer/gyroscope combination device that features a configurable 200 µA operating current in normal mode with wake up and back to sleep functions.

Figure 3B:
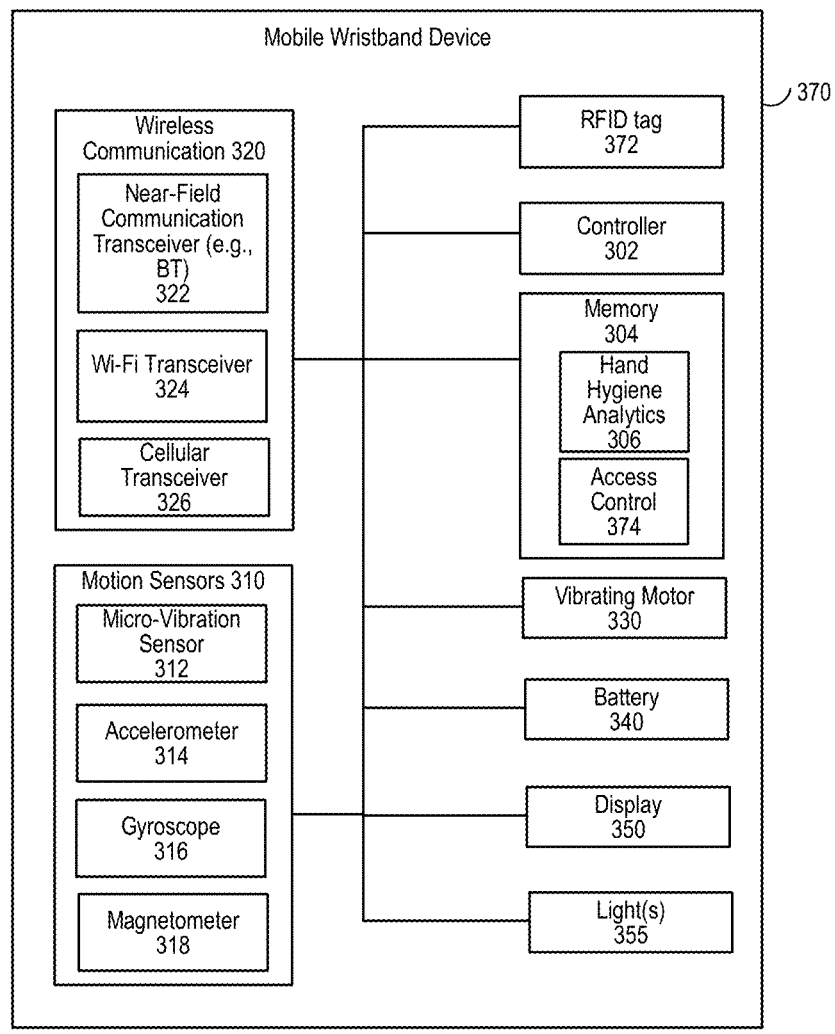
FIG. 3B is a second example block diagram of the mobile wristband device.

FIG. 3B is a second example block diagram of the mobile wristband device 370. Wristband device 370 has functionality similar to wristband device 300, with the additional functionality of access control. In particular, wristband device 370 may be used in combination with an RFID access control system and includes RFID tag 372. Further, wristband device 370 includes access control 374, which may be used to provide additional access control functionality to wristband device 370, as discussed further below.

Figure 3C:
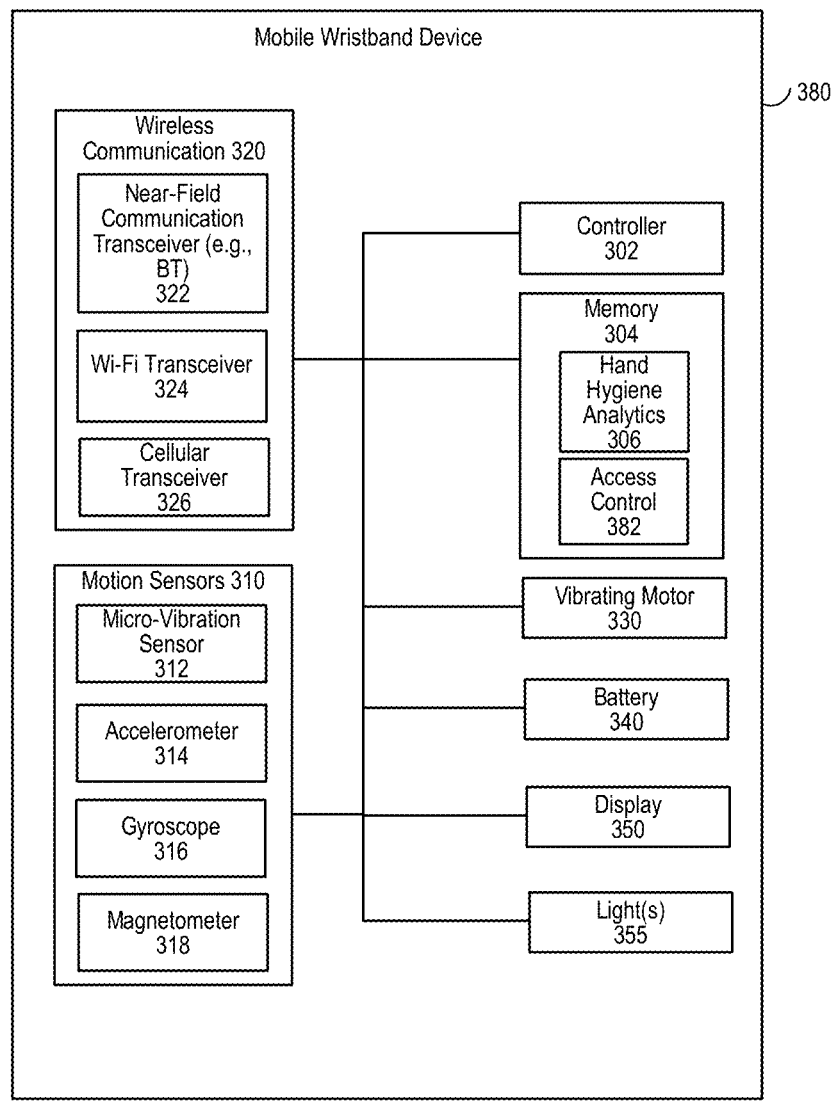
FIG. 3C is a third example block diagram of the mobile wristband device.

FIG. 3C is a third example block diagram of the mobile wristband device 380. Wristband device 380 has functionality similar to wristband device 300, with the additional functionality of access control. In particular, wristband device 380 may be used in combination with an access control system that uses a communication method included in wireless communication 320 (such as using near-field communication transceiver 322). In this regard, the identification code associated with the user of wristband 380 need not be stored in RFID tag 372, but may be stored in access control 382 (or other memory resident in wristband device 380. Further, wristband device 380 includes access control 382, which may be used to provide additional access control functionality to wristband device 380, as discussed further below.

FIG. 4A is a first example block diagram of local stationary controller 400. As illustrated, local stationary controller 400 may include a controller 402, a memory 404, one or more communication protocols, such as near-field communication transceiver 308, and a far-field communication transceiver (such as Wi-Fi transceiver 408 or cellular transceiver (not shown), proximity sensor 410, sound sensor 412, speaker 414, light(s) 416, and display 418. In one implementation, all of the elements depicted in FIG. 4A are incorporated into the stationary controller. Alternatively, fewer than all of the elements depicted in FIG. 4A are incorporated into the wristband. For example, proximity sensor 410, sound sensor 412, speaker 414, light(s) 416, display 418 need be included in the stationary controller.

Local stationary controller 400 may be used in any one of FIG. 1A, 1B, 1C or 2. The controller 402 may comprise a microprocessor, a microcontroller/DSP, PLA, or the like. Further, the memory 404 may include software, such as analytics 406. As discussed above, analytics of the motion sensor data may be performed by the mobile wristband device and/or by the local stationary controller. Further, near-field communication transceiver 308 may be used to communicate via one or more near-field protocols with mobile wristband device. As discussed above, examples of near-field communication protocols include, but are not limited to Bluetooth, RFID, and ZigBee. Other near-field communication protocols are contemplated. Further, local stationary controller 400 may communicate with a back-end server, such as back-end server 130 or cloud computing E.

As discussed further below, in one implementation, stationary controller 400 may sense the proximity of the user (such as the healthcare provider). In a specific implementation, stationary controller 400 may sense the proximity of the wristband worn by the user. Proximity sensor 410 is a representation of the functionality to sense the proximity of the wristband worn by the user. As discussed herein, stationary controller 400 may sense a communication signal, such as a received signal strength indicator (RSSI) signal, which is an example of sensing the proximity of an electronic device. The stationary controller 400, via proximity sensor 410 or the like, may sense the RSSI signal of the wristband at being greater than a predetermined amount or strength (e.g., indicating that the wristband is within 1 meter, within 2 meters, within 3 meters, etc.) for at least a predetermined amount of time (e.g., at least 1 second, at least 2 seconds, at least 3 seconds, etc.) in order to determine whether the wristband is proximate to the stationary controller 400.

Further, as discussed below, sound sensor 412 may be used in order to sense sounds, such as sounds generated by dispenser 151 or sounds generated by user. Speaker 414, light(s) 416, and display 418 may be used as means for output of information to the user.

FIG. 4B is a second example block diagram of the local stationary controller 430. Stationary controller 430 is similar to stationary controller 400, with the addition of access control 434. As discussed further below, access control may be an additional functionality that may be performed by stationary controller 430, such as illustrated in FIGS. 5A-J.

Further, as discussed above, the wristband and stationary controller may interact with one another during various times of a hand hygiene event. As discussed further below with regard to the flow charts, the following may comprise a sequence of interaction: (1) proximity sensing of the stationary controller relative to and wristband or vice-versa as indicative of a hand hygiene event; (2) generation of output on one or both of the stationary controller or the wristband to indicate the hand hygiene event; (3) sensing whether hand cleaning agent has been dispensed (e.g., the stationary controller reviewing audio sensor data to determine whether the motor on the dispenser has dispensed the hand cleaning agent); (4) waking up part of the wristband responsive to determining that the hand cleaning agent has been dispensed (e.g., stationary controller sends a signal to wake-up the microcontroller and/or the accelerometer and/or gyroscope); (5) the awakened motion sensors generate sensor data; and (6) the sensor data is analyzed to determine whether certain hand motions, indicative of sufficient hand hygiene, are detected in order to determine whether there is compliance with hand hygiene protocols.

Figure 6A:
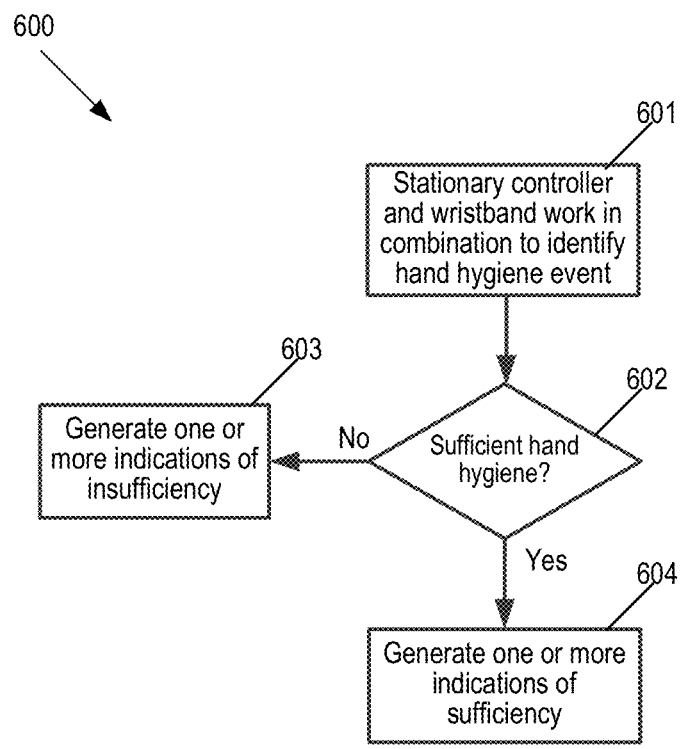
FIG. 6A illustrates a first flow chart of operation of the hand hygiene system.

FIG. 6A illustrates a first flow chart 600 of operation of the hand hygiene system. At 601, the stationary controller and the wristband work in combination in order to identify a hand hygiene event. As discussed above, the stationary controller and the wristband may work in combination in one of several ways. In one way, the stationary controller may sense the presence of the wristband (e.g., via the RSSI signal). In another way, the wristband may sense the presence of the stationary controller. Responsive to identifying the hand hygiene event, one or both of the wristband or the stationary controller may determine whether sufficient hand hygiene was performed. As discussed above, there may be various metrics to determine whether there has been sufficient hand hygiene, such as whether hand cleaning agent has been dispensed, whether the user has performed hand rubbing motions, whether the user has performed hand rubbing motions for a predetermined amount of time, whether the user has performed a plurality of predetermined hand rubbing motions, whether the user has performed a plurality of predetermined hand rubbing motions each for a respective predetermined period of time, etc. Responsive to determining that there was sufficient hand hygiene, at 604, one or both of the stationary controller or the wristband may generate one or more indications of sufficiency. Responsive to determining that there was insufficient hand hygiene, at 603, one or both of the stationary controller or the wristband may generate one or more indications of insufficiency. In one implementation, responsive to determining that there is sufficient hand hygiene, no output is generated, but responsive to determining that there is insufficient hand hygiene, an output is generated. Conversely, in another implementation, responsive to determining that there is insufficient hand hygiene, no output is generated, but responsive to determining that there is sufficient hand hygiene, an output is generated. In still another implementation, responsive to both sufficient and insufficient hand hygiene determination, outputs are generated, as shown in FIG. 6A.

Figure 6B:
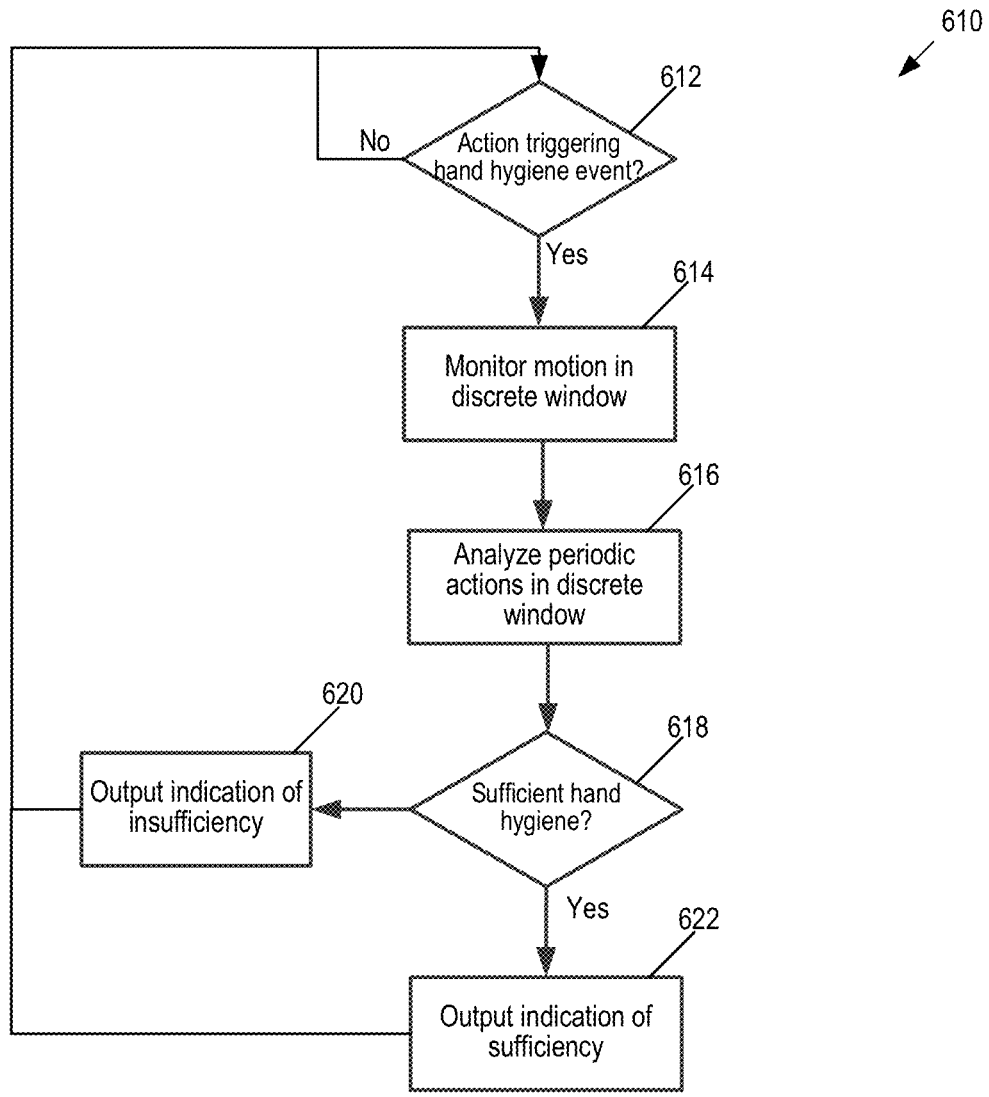
FIG. 6B illustrates a second flow chart of operation of the hand hygiene system.

FIG. 6B illustrates a second flow chart 610 of operation of the hand hygiene system. At 612, it is determined whether an action has occurred which triggered the hand hygiene event. As discussed above, one or more actions may trigger the hand hygiene event, such as proximity to a dispenser, entrance into a room, or the like. If so, at 614, motion is monitored within a discrete window. As discussed above, in one implementation, the motion may be monitored responsive to an indication of a hand hygiene event. In this implementation, the monitoring may take place only responsive to the indication of the hand hygiene event. At 616, periodic actions are analyzed in the discrete window. Again, as discussed above, there may be periodic actions, within the discrete window, that are directed to hand hygiene and other periodic actions (such as arm swinging). In this regard, the analysis may differentiate between the different periodic actions in order to focus on hand hygiene periodic actions.

At 618, it is determined whether, based on the analysis of the periodic action, there is sufficient hand hygiene. If so, at 622, an output may be generated that is indicative of sufficiency of hand hygiene. If not, at 620, an output may be generated that is indicative of insufficiency of hand hygiene.

Figure 6C:
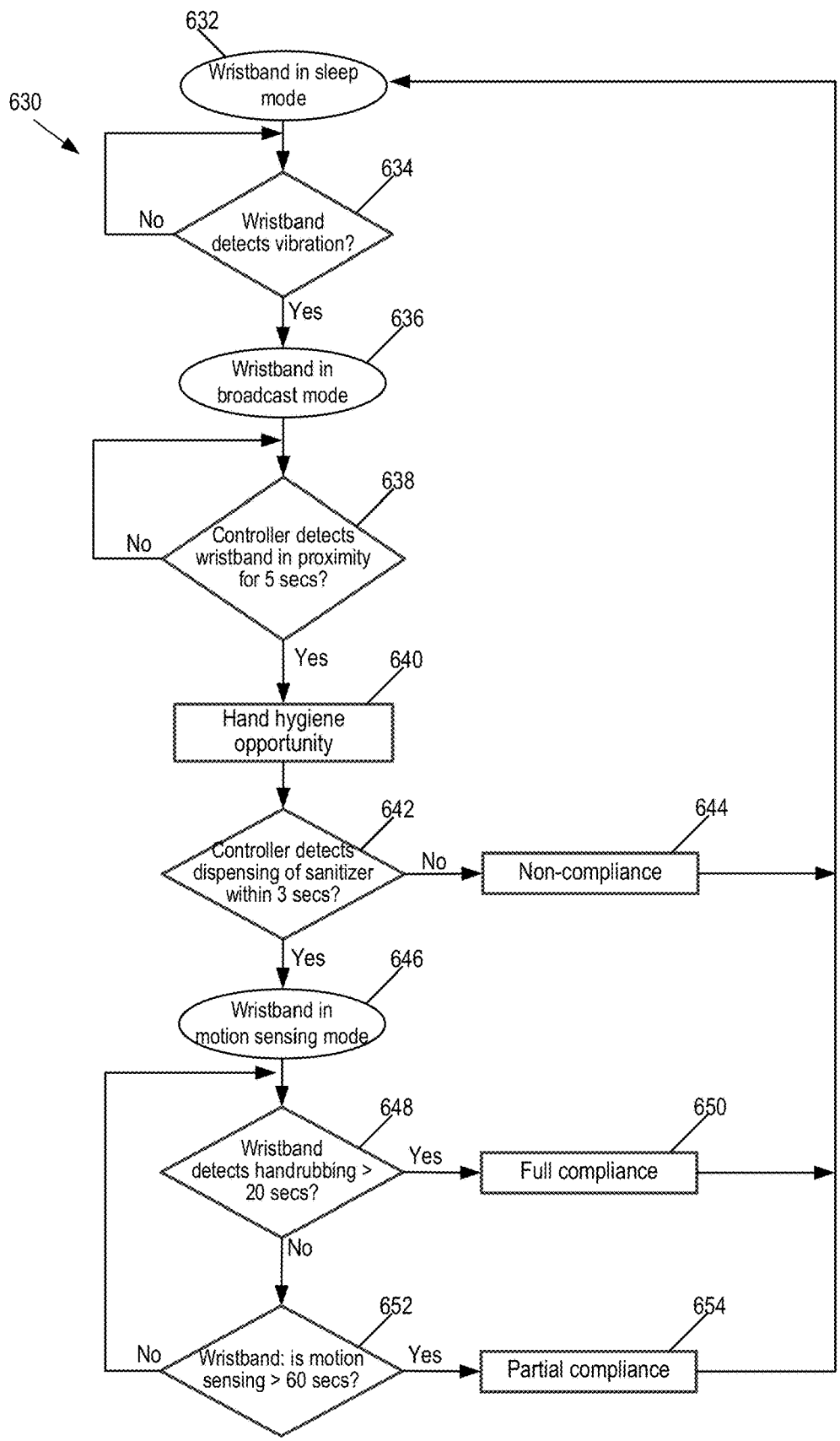
FIG. 6C illustrates a third flow chart of operation of the hand hygiene system.

FIG. 6C illustrates a third flow chart 630 of operation of the hand hygiene system. At 632, the wristband is in sleep mode. As discussed above, various circuits within the wristband may be turned off or in low power mode when the wristband is in sleep mode. At 634, the wristband may detect a vibration, such as via the micro-vibration sensor. In one implementation, even in sleep mode, the micro-vibration sensor remains active. If vibration is detected, at 636, the wristband may transition to broadcast mode. As one example, the wristband may activate one or more of the wireless communication transceivers, such as near-field communication transceiver 322.

For example, when the micro-vibration sensor detects a small movement, the wristband enters broadcast mode and sends Bluetooth low energy beacon continuously until the wristband connects to a stationary controller. The stationary controller may beep to remind the healthcare worker wearing the wristband of hand hygiene (and/or PPE) when its received signal strength indicator (RSSI) from the wristband is over the preset threshold over a preset amount of time. After the stationary controller detects a dispensing sound, the wristband enters motion sensing mode. Motion detection may be active for only 1 minute to reduce power consumption and false detections caused by interfering motions. If no dispensing event is detected by the stationary controller, there will be real-time intervention on the wristband (e.g., vibration) and controller (e.g., voice prompt) with notification "non-compliance" sent to the server.

In this way, at 638, the stationary controller may determine, such as via the RSSI signal, whether the wristband is in proximity for a certain amount of time (e.g., 5 seconds). If so, at 640, it is determined that there is a hand hygiene opportunity.

At 642, the controller determines whether it has detected dispensing of sanitizer within a predetermined amount of time (e.g., 3 seconds) since the hand hygiene opportunity determination. As discussed above, the stationary controller may determine whether sanitizer has been dispensed in one of several ways, such as via a sound sensor, via integration with the motor on the stationary controller, or the like. Alternatively, the wristband may determine whether the sanitizer has been dispensed, such as via a sound sensor resident on the wristband. If it is determined that no sanitizer has been dispensed, at 644, it is determined that there is non-compliance. This determination may be made by the stationary controller and/or the wristband. For example, in response to the wristband making the non-compliance determination, the wristband may send a communication to another electronic device, such as the stationary controller, with the communication indicating the non-compliance (e.g., a field in the communication=0 for non-compliance). Further, in one implementation, non-compliance may be indicative that no sanitizer was even used during the hand hygiene opportunity.

If it is determined that sanitizer has been dispensed, at 646, the wristband may be changed to motion sensing mode. In one implementation, the stationary controller may determine that the sanitizer has been dispensed and then send a signal to the wristband to change its mode to motion sensing mode (e.g., to activate the accelerometer and/or gyroscope and/or magnetometer). In another implementation, the wristband may determine that the sanitizer has been dispensed and then change its mode to motion sensing mode.

At 648, the wristband determines whether it has detected hand rubbing for at least 20 seconds. As discussed above, various analytics on the wristband or on the stationary controller may be used to determine whether there is hand hygiene compliance, one of which is duration of the hand rubbing. If the wristband detects hand rubbing for at least 20 seconds, at 650, the wristband determines that there is full compliance. In response to this determination, the wristband may send a communication to another electronic device, such as the stationary controller, with the communication indicating the compliance (e.g., X=1 for compliance). If the wristband does not detect hand rubbing for at least 20 seconds, at 652, the wristband determines whether 60 seconds has elapsed since the wristband is in motion sensing mode. If not, flow chart 630 loops back to 648. If so, at 654, the wristband determines that there is partial compliance (e.g., sanitizer was taken but the hand rubbing motion was insufficient, such as the hand rubbing motion was not for a long enough time or was not according to the predetermined hand movements). In this regard, the user has a 60 second window in which to be compliant with the hand hygiene guidelines.

Figure 6D:
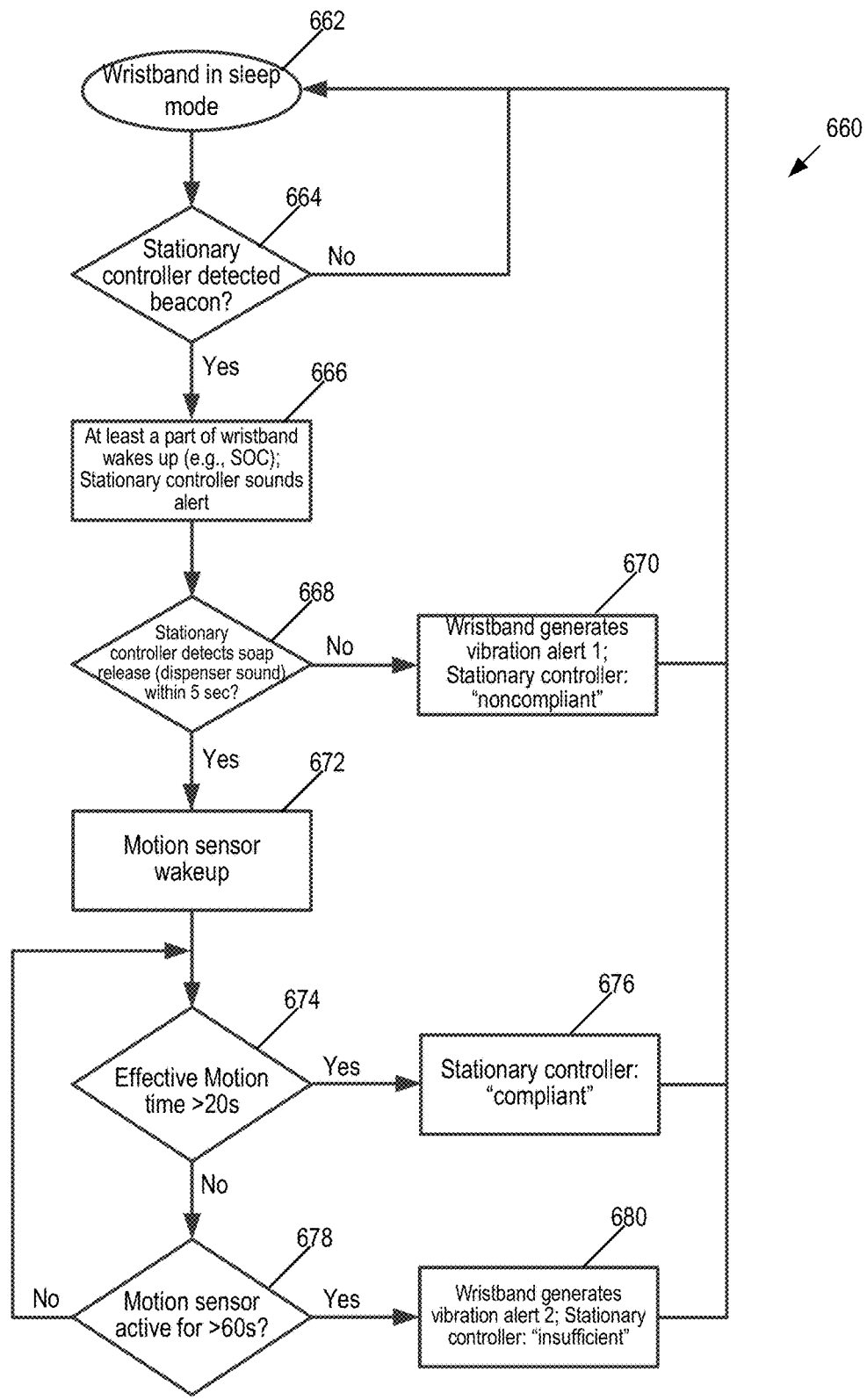
FIG. 6D illustrates a fourth flow chart of operation of the hand hygiene system.
Figure 6E:
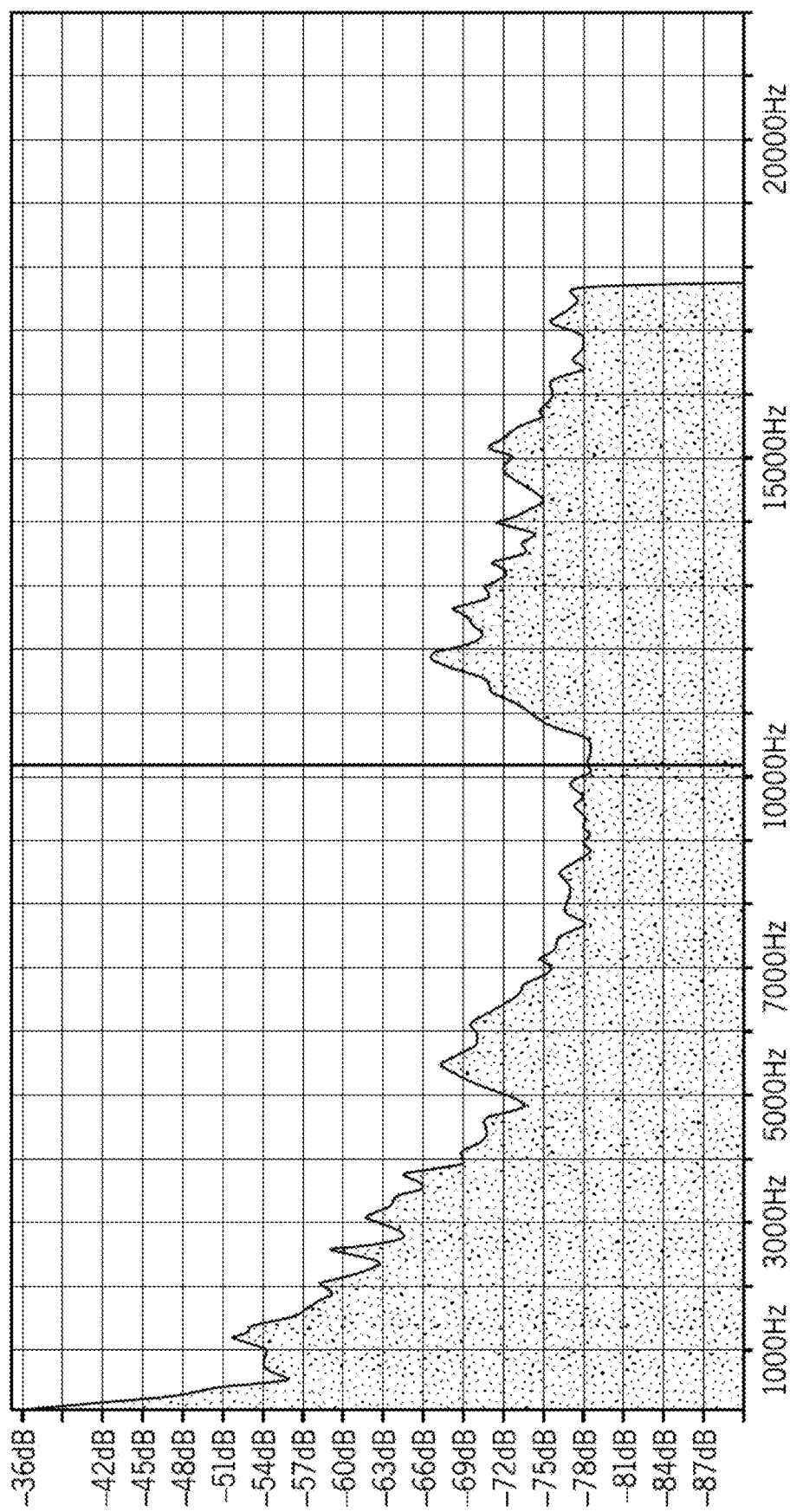
FIG. 6E is a graph of the background sound without dispensing in frequency domain analysis.
Figure 6F:
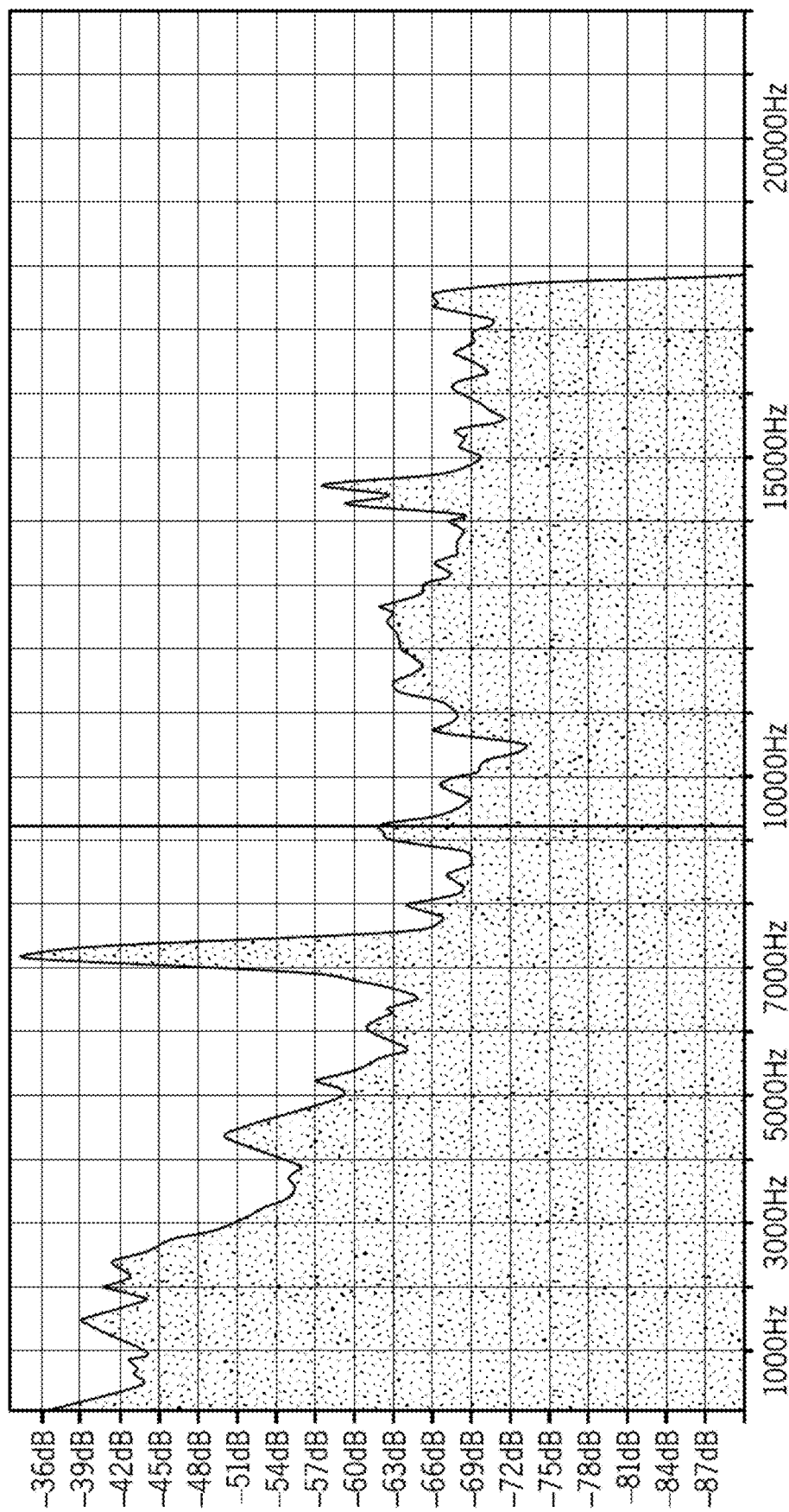
FIG. 6F is a graph of the dispensing sound in frequency domain analysis.

FIG. 6D illustrates a fourth flow chart 660 of operation of the hand hygiene system. At 662, the wristband is in sleep mode. At 664, the stationary controller determines whether it has detected a beacon from the wristband. As discussed above, one of the stationary controller or the wristband may generate a beacon. The other of the stationary controller or the wristband may sense the beacon to determine that a hand hygiene event is occurring. As shown in FIG. 6D, the stationary controller detects a beacon generated by the wristband to determine if a hand hygiene event is occurring. At 666, at least a part of the wristband is woken up, such as the system-on-a-chip. Further, the stationary controller may generate an output (e.g., sound an alert) indicative to the healthcare provider to obtain hand cleaning solution from the dispenser (e.g., output an audio message: "take sanitizer from the dispenser").

At 668, the stationary controller determines whether it has detected the release of the hand cleaning solution (e.g., soap) within a period of time (e.g., 5 seconds). As discussed above, the stationary controller may monitor one or more operations associated with the dispenser, such as the sound associated with the dispensing of the hand cleaning solution. In that regard, the stationary controller may include a sound sensor in order to monitor the sounds generated by the dispenser to determine whether the dispenser has dispensed the hand cleaning solution within the allotted time. If not, at 670, the stationary controller may send a command to the wristband to generate an output, such as a vibration output on the wristband. Alternatively, the stationary controller may generate an output itself. Thus, in one implementation as illustrated in FIG. 6D, a hand hygiene event only starts when the stationary controller detects the following two events in sequence: 1) a healthcare provider is approaching the stationary controller which may be installed next to the dispenser located at ICU/ward entrance or the like; and 2) a dispensing event indicating the healthcare provider has taken sanitizer. These two functions may be achieved by Bluetooth proximity sensing and detection/analysis of dispenser sound respectively.

If so, at 672, the wristband may wakeup the motion sensor(s) and record motion sensor(s) data. At 674, it is determined, based on analysis of the sensor(s) data, whether the effective motion time for hand movement is greater than 20 seconds. This determination may be performed either by the wristband or by the stationary controller. As discussed above, the user may start/stop the hand rubbing motion. In that regard, the wristband may use a counter in order to determine whether the effective total time of the hand rubbing motion is at least 20 seconds. If so, at 676, the stationary controller may determine that the hand hygiene is compliant. Alternatively, the wristband may determine compliance and transmit that determination to the stationary controller. If not, at 678, the wristband may determine whether the motion sensor, which was awakened at 672, has been active for 60 seconds. If not, the flow chart 660 loops back to 674. If so, at 680, the wristband generates vibration alert 2 (indicating that the user has not complied). Further, the stationary controller may determine that the hand rubbing was insufficient. Alternatively, the wristband may determine insufficiency and transmit that determination to the stationary controller. In one implementation, vibration alert 1 may be different from vibration alert 2. For example, vibration alert 1 may be louder or more forceful than vibration alert 2. Alternatively, vibration alert 1 may be the same as vibration alert 2.

As shown in FIG. 6D, there may be multiple alerts issued to the healthcare provider, such as the start of hand hygiene event and a conclusion of the hand hygiene event (e.g., the output of an indication of sufficiency and/or insufficiency of the hand hygiene. Further, the system may monitor the hand hygiene for compliance according to WHO guideline. In addition, as shown in FIGS. 6C-D, the wristband may re-enter sleep mode responsive to one (or both) of a timeout or a determination of sufficiency and/or insufficiency of the hand motions complying with a standard.

Thus, in one design, the SOC may stay in extended sleep mode unless being woken up into "near field" active mode. For example, in the Bluetooth Low Energy (BLE) protocol, 3 ms is used for data transmission. Assuming 3 milliseconds for ARM computing, then during a 60-second hand hygiene event, the current consumption of the wristband SOC is only 3 mA-second and less than 12 mA-second for a KXG07 motion sensor. Assuming 100 hand hygiene events per healthcare provider per day, the total power consumption of the wristband is merely 0.42 mAh per day. Therefore, the wristband can last more than one year on a 200 mAh CR2032 coin battery. The calculation shows that with careful selection of low-power components and optimized power management, the wristband may have a longer battery life.

As discussed above, hand rubbing motions may be difficult to differentiate from other types of motions or other noise factors. In this regard, it may be difficult to detect subtle hand rubbing motions among interfering motions. In practice, when using an alcohol-based formulation, the healthcare provider may walk away from the dispenser and controller while rubbing hands. Therefore, walking and arm swinging are possible noise factors. Likewise, door knocking may cause interference in determining hand rubbing motions.

As discussed herein, one or more sensors may be used to monitor the movement of the wristband. For example, one or both of a miniaturized accelerometer or a gyroscope may be used. The accelerometer may provide information on linear acceleration. The gyroscope may measure the angular velocity rate. In one specific implementation, a 3-axis accelerometer and a 3-axis gyroscope may be used. The accelerometer and gyroscope may sense a variety of movements, such as the hand rubbing movements and various interference movements (e.g., walking, arm swinging and door knocking).

Figure 7:
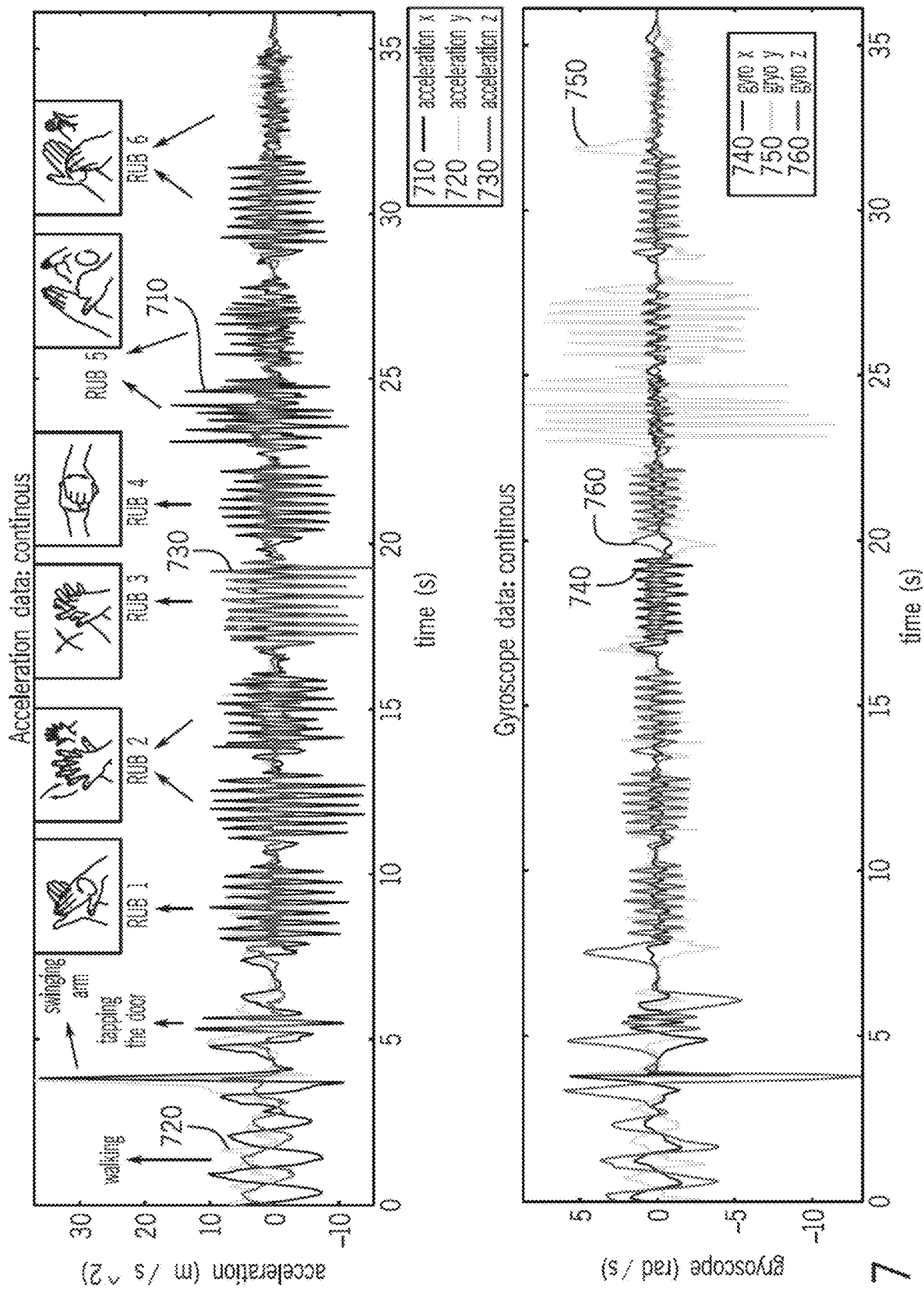
FIG. 7 illustrates graphs of accelerometer data (time versus linear acceleration) and gyroscope data (time versus angular acceleration).

FIG. 7 illustrates graphs of accelerometer data (time versus linear acceleration) and gyroscope data (time versus angular acceleration). Motions tested include three possible interferences during a hand hygiene event (walking, arm swinging and door knocking), followed by the six hand rub motions described in FIG. 10A. Each sensor has outputs on x (710 for accelerometer and 740 for gyroscope), y (720 for accelerometer and 750 for gyroscope) and z (730 for accelerometer and 760 for gyroscope) axis.

As illustrated in FIG. 7, the waveforms indicate: (1) the accelerometer responses to most of the rubbing motions are reasonably large. In many cases, their magnitude is larger or comparable to that of interferences; (2) most hand rubbing motions show large linear acceleration mainly on x- and y-axis. This is because when a person wears a wrist sensor, the x- and y-axis of the accelerometer are parallel to the wrist. Most hand rubbing motions in fact occurs parallel to the wrist; (3) while it is very challenging to distinguish all 6 hand rubbing motions from each other, several hand rubbing motions show their unique characteristics. For instance, rotational rubbing (Rub 5) is the only motion with large rotation rate along y-axis (pitch); rubbing palm to palm with finger interlaced (Rub 3) can be distinguished by its large acceleration along z axis; rubbing hands palm to palm (Rub 1) is a circle motion and therefore shows large acceleration in both x- and y-axis; (4) Hand rub motions in general have shorter periods than periodic noises such as walking and swinging arm. This may be an important property to differentiate the hand rub motions. In this way, the output from one motion sensor may be more indicative of one type of motion whereas another motion sensor may be indicative of another type of motion. Specifically, as illustrated above, the gyroscope output is much more indicative for the motion corresponding to Rub 5 than the accelerometer. For rub 3, the converse is true in that the accelerometer output is more indicative than the gyroscope output. In this regard, in one implementation, the wristband may examine both accelerometer data and gyroscope data in order to determine whether a rubbing motion is being performed. In an alternate implementation, for one or more of the hand rubbing motions, the wristband my use only the output from one motion sensor (and may alternate using the output from different motion sensors depending on the hand rubbing motion).

Figure 8:
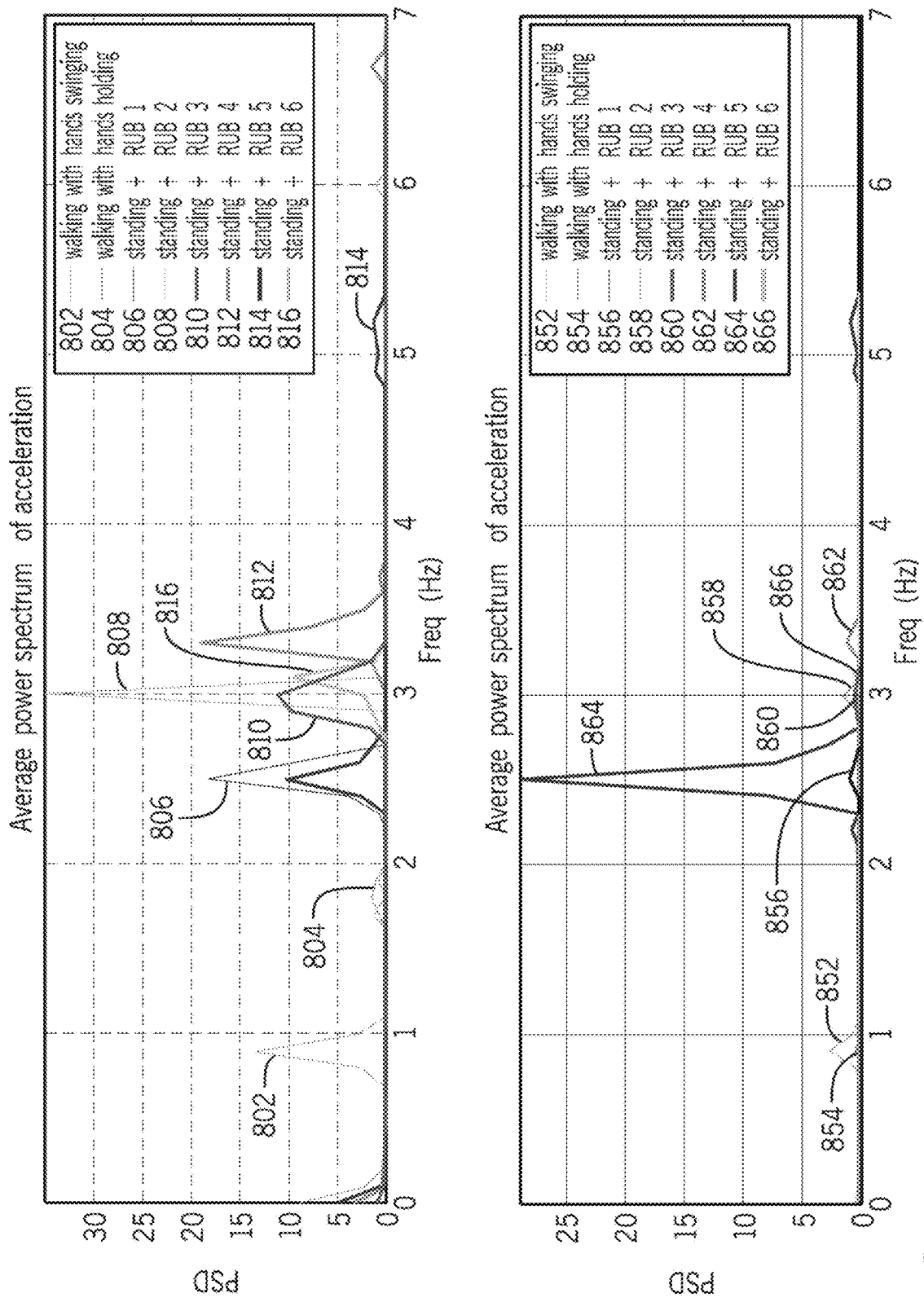
FIG. 8 illustrates graphs of average power spectrum of acceleration (frequency versus power spectrum density) and average power spectrum of rotation (frequency versus power spectrum density).

FIG. 8 illustrates graphs of average power spectrum of acceleration (frequency versus power spectrum density) and average power spectrum of rotation (frequency versus power spectrum density). Analysis of the PSD plot indicates that hand rubbing motions and walking have significantly different peak frequencies. In particular, all hand rubbing motions illustrated have their peak power occurring in the frequency range of 2.5-3.5 Hz, whereas the peak power for normal walking is less than 1 Hz. In this regard, a filter, such as a digital high-pass filter, may be used to attenuate the noise from walking and arm swinging.

As discussed above, the wristband may be configured for a low power mode. Thus, in one implementation, the wristband may have multiple operation modes, such as four operation modes including: sleep (i.e. only micro-vibration sensor 312 active); broadcast (e.g. near-field wireless communication 322 and controller 302 active); motion sensing (e.g. near-field wireless communication 322, controller 302, motion sensors (e.g., accelerometer 314 and/or gyroscope 316 and/or magnetometer 318 active); and motor vibration. In one implementation, an ultra-low-power micro-vibration sensor on the wristband is configured to detect if the wristband is static and, responsive to that detection, for the wristband to enter sleep mode. This power-saving mode applies when the wristband is not worn by providers. When the micro-vibration sensor detects micro-vibration, the wristband device may enter broadcast mode and may send Bluetooth-Low-Energy beacon every second until the wristband connects to a stationary controller. After a hand hygiene opportunity is detected, the wristband enters motion sensing mode and operates for 1 minute before going back to broadcast mode. During a non-compliant hand hygiene event, the wristband may generate a vibration alert that lasts for 1 second.

In one implementation, the average current dissipation is 2.4 μA (sleep), 11.8 μA (broadcast), 613 μA (motion sensing) and 25,400 μA (vibration), respectively. It is estimated that the regular usage time and calculated the power dissipation is assumed to be: (1) an average of 30 hand hygiene opportunities per healthcare provider during an 8-hour shift; and (2) 10 of the 30 hand hygiene opportunities are non-compliant so the motor vibration mode will take no more than 10 seconds per day. Therefore, average daily power consumption of the wristband is ~1800 mAs. A CR2032 coin battery has a capacity of 220 mAh or 792,000 mAs and will last more than one year on the wristband.

Figure 9:
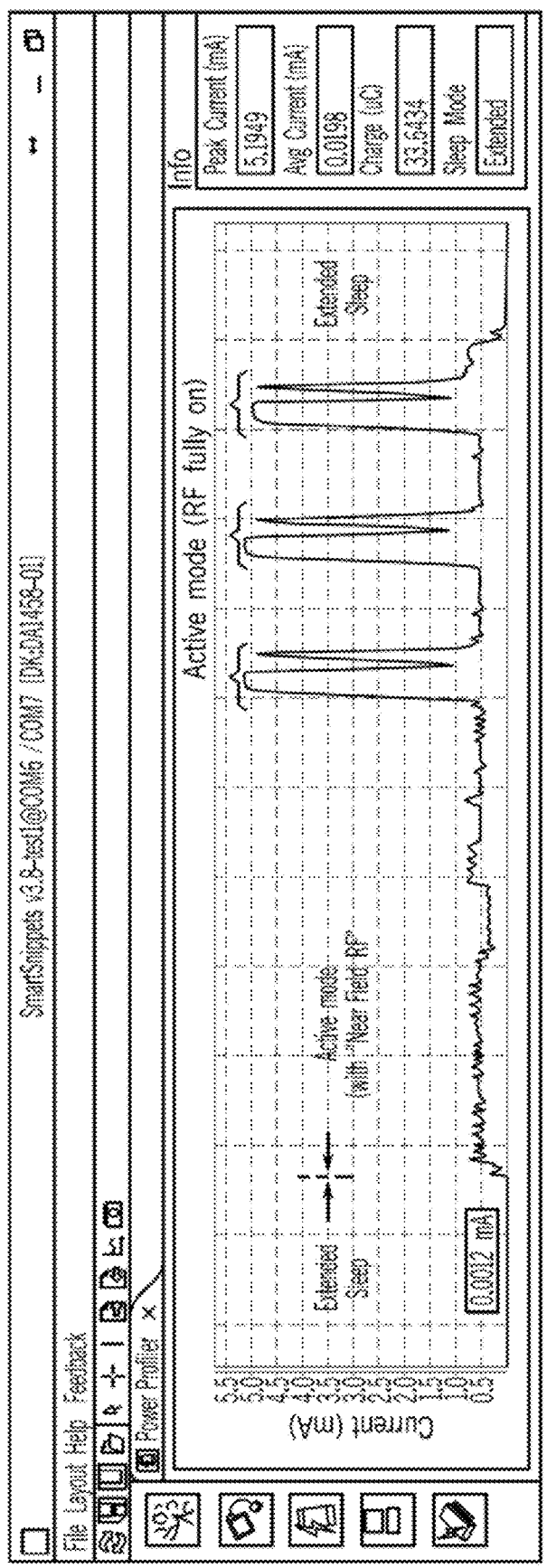
FIG. 9 illustrates a graph of time versus current, including showing in extended sleep mode, the system-on-a-chip (SOC) consumes 1.2 uA, while in full-speed active mode, the SOC current dissipation rises to about 0.45-0.7 mA ("near field RF mode") and 5.2 mA (RF fully on) respectively, with each grid on the x-axis (time) representing 1 milli-second.

FIG. 9 illustrates a graph of time versus current, including showing in extended sleep mode, the system-on-a-chip (SOC) consumes 1.2 uA, while in full-speed active mode, the SOC current dissipation rises to about 0.45-0.7 mA ("near field RF mode") and 5.2 mA (RF fully on) respectively, with each grid on the x-axis (time) representing 1 milli-second.

FIG. 10A illustrates a series of pictures which highlights the recommended hand hygiene techniques with alcohol-based formulation in World Health Organization (WHO) guidelines on hand hygiene in health care, with the duration of the hand hygiene motions (picture #2-7) recommended to last 20-30 seconds.

Figure 11:
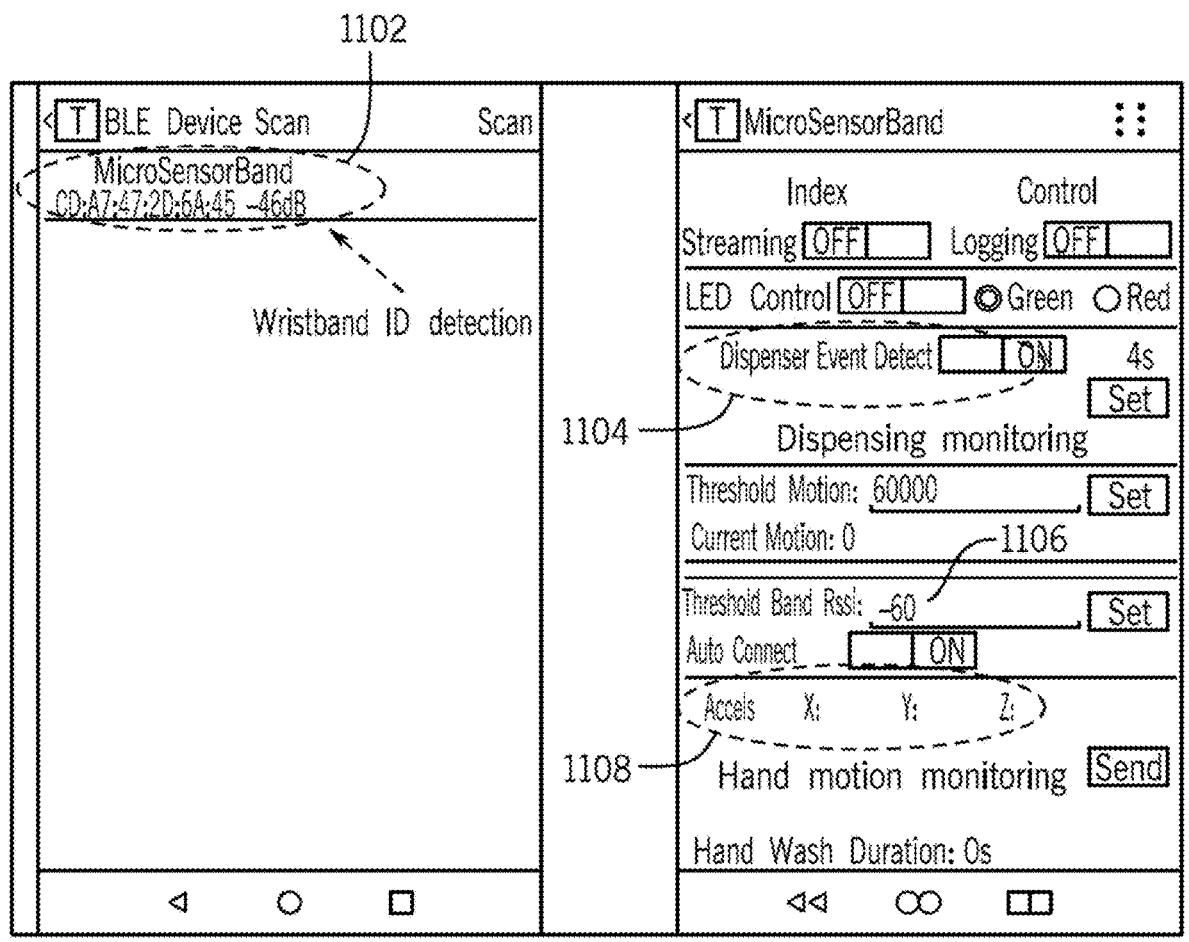
FIG. 11 illustrates a graphical user interface (GUI) for illustration of hand washing event monitoring shown on a stationary controller.

FIG. 11 illustrates a graphical user interface (GUI) for illustration of hand washing event monitoring on a stationary controller. The controller detects a wristband device (MicroSensorBand in the example illustrated in FIG. 11) at its proximity by Bluetooth low-energy (BLE) scan (1102) with signal strength of −46 dB, which is higher than the detection threshold of −60 dB set by 1106. The stationary controller may be configurable to detect how long to wait for the dispensing of sanitizer (1104). As discussed above, at 642 or at 668, the stationary controller waits for 3 or 5 seconds, respectively, to determine whether sanitizer has been dispensed. The threshold RSSI signal (1106) may likewise be set at −60 dB. Finally, if a dispensing event is detected, the controller will start to collect hand motion data from the wristband (1108). All data may then be transmitted to a back-end server for analytics.

As discussed above, various analytics may be generated for various uses. In one use, the analytics may be used for notification of one or more parties, such as the healthcare worker who is the subject of the analytics, an infectious disease specialist, a hospital administrator (e.g., an administrator of nurses or doctors), or the like. In another use, the analytics may be used to track, such as in real time, transmission of pathogens or diseases amongst patients, from healthcare workers to patients, or the like.

In still another use, the analytics may be used to generate one or more graphical user interfaces (GUIs). With regard to GUIs, three components may be used, including a web interface, the background database (such as database 172), and the analytical and computational system (such as application server 162). The web interface allows the user to input the query information and displays the search results, the database stores the data collected by the data collection hardware, and the analytical and computational system implements data analysis and computation, and produces results to be shown on the web interface.

Figure 12A:
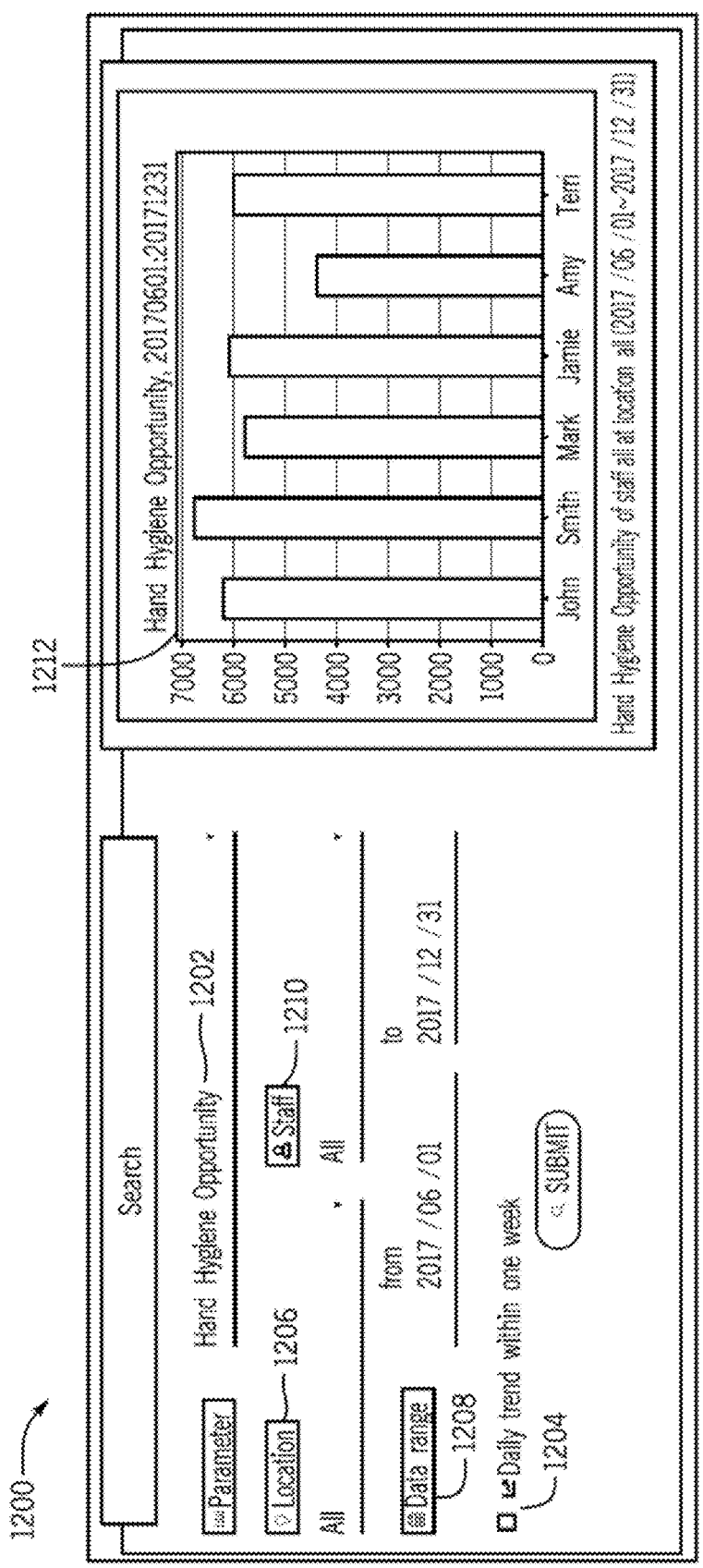
FIG. 12A illustrates a first GUI of a web interface for an electronic device to access the hand hygiene analytical and computational system in which one or more of the following may be selected: hand hygiene opportunity; locations; staff; date range; and/or trend analyses.

FIG. 12A illustrates a first GUI 1200 of a web interface for an electronic device to access the hand hygiene analytical and computational system in which one or more of the following may be selected: hand hygiene opportunity 1202; locations 1206; staff 1210; date range 1208; and/or trend analyses 1204. As one example, various types of hand hygiene opportunities may be listed including: non-compliant hand hygiene (e.g., instances of a non-compliant hand hygiene event); partial compliant hand hygiene; full compliant hand hygiene; non-compliant hand hygiene rate; partial compliant hand hygiene rate; and full compliant hand hygiene rate.

Various locations 1206 may be entered, such as all locations, ICU-A, ICU-B, or ICU-C (e.g., different intensive care units in a hospital). The listing of locations is merely for illustration purposes; other types of locations are contemplated. Likewise, various date ranges 1208 may be entered. Further, staff 1210 may be selected, such as various staff groupings including all staff, all nurses, or all doctors, or such as different individuals. A graph 1212 showing the output may be generated based on the input of hand hygiene opportunity 1202, locations 1206, staff 1210, date range 1208, and/or trend analyses 1204.

In this regard, the back-end server may enable a search function that allows managers (e.g., ICU managers, department manager, infection control team) to analyze the compliance data and obtain detailed infection control compliance reports based on the selection of date, location (e.g., floor, unit and room), role (e.g. nurse, doctor, PSA, etc.) and individual provider. Such reports may be used by the hospital administrators to configure an incentive program to motivate trainees or provide feedback.

Figure 12B:
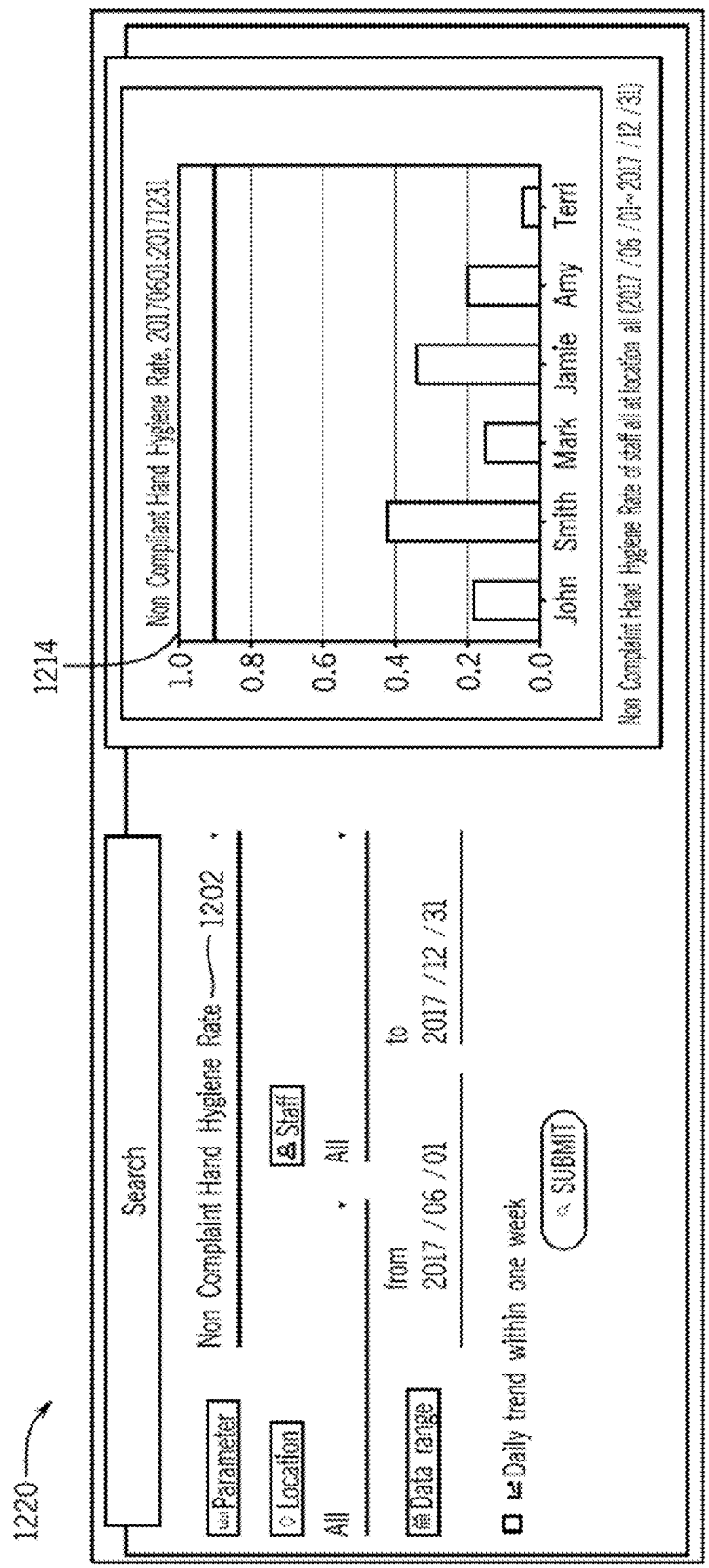
FIG. 12B illustrates a second GUI of a web interface for an electronic device to access the hand hygiene analytical and computational system in which the hand hygiene opportunity selected is non-compliant hand hygiene rate.

FIG. 12B illustrates a second GUI 1220 of a web interface for an electronic device to access the hand hygiene analytical and computational system in which the hand hygiene opportunity 1202 selected is non-compliant hand hygiene rate, with the associated graph 1214.

Figure 12C:
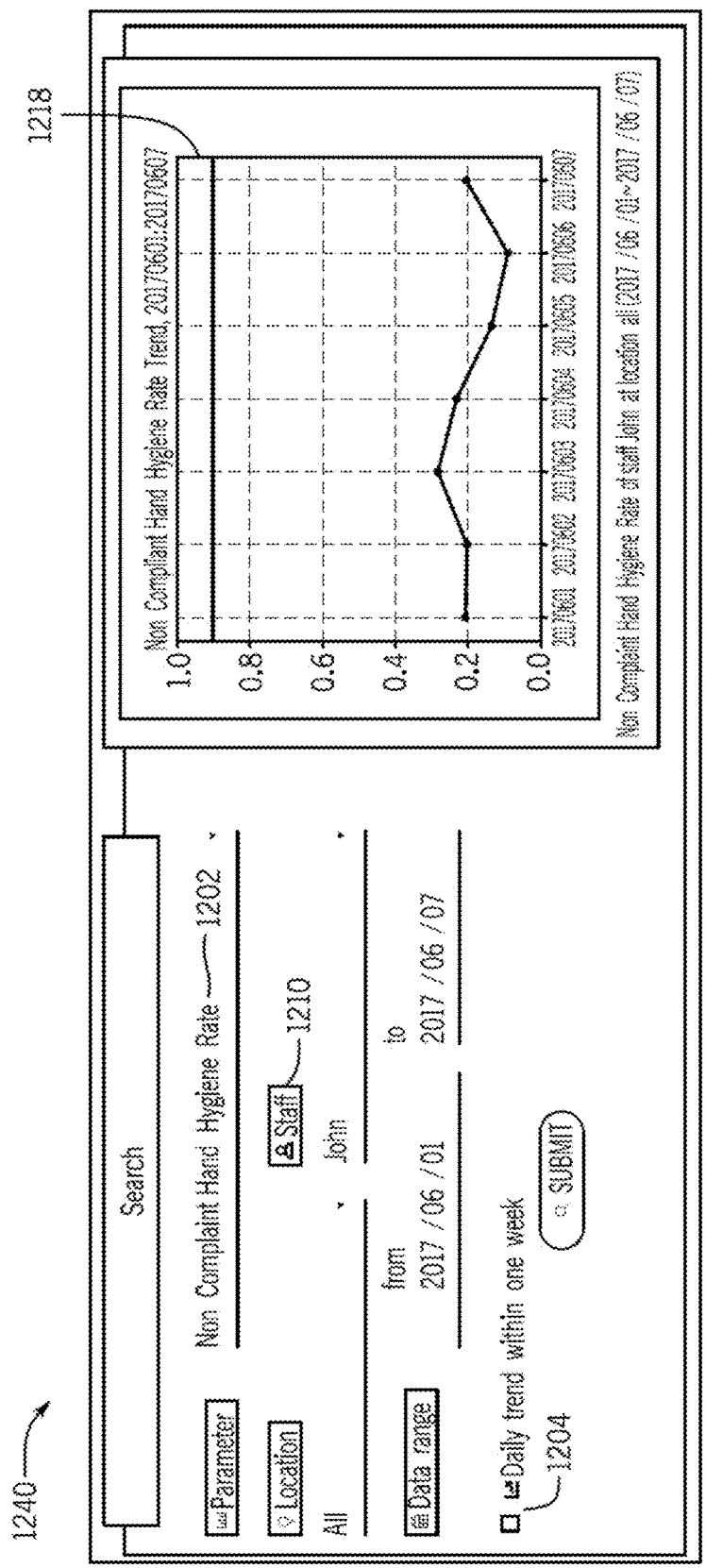
FIG. 12C illustrates a third GUI of a web interface for an electronic device to access the hand hygiene analytical and computational system in which the hand hygiene opportunity selected is non-compliant hand hygiene rate, the staff selected is John, and in which a daily trend is illustrated in an associated graph.

FIG. 12C illustrates a third GUI 1240 of a web interface for an electronic device to access the hand hygiene analytical and computational system in which the hand hygiene opportunity 1202 selected is non-compliant hand hygiene rate, the staff 1210 selected is John, and in which a daily trend 1204 is illustrated in associated graph 1218.

Figure 12D:
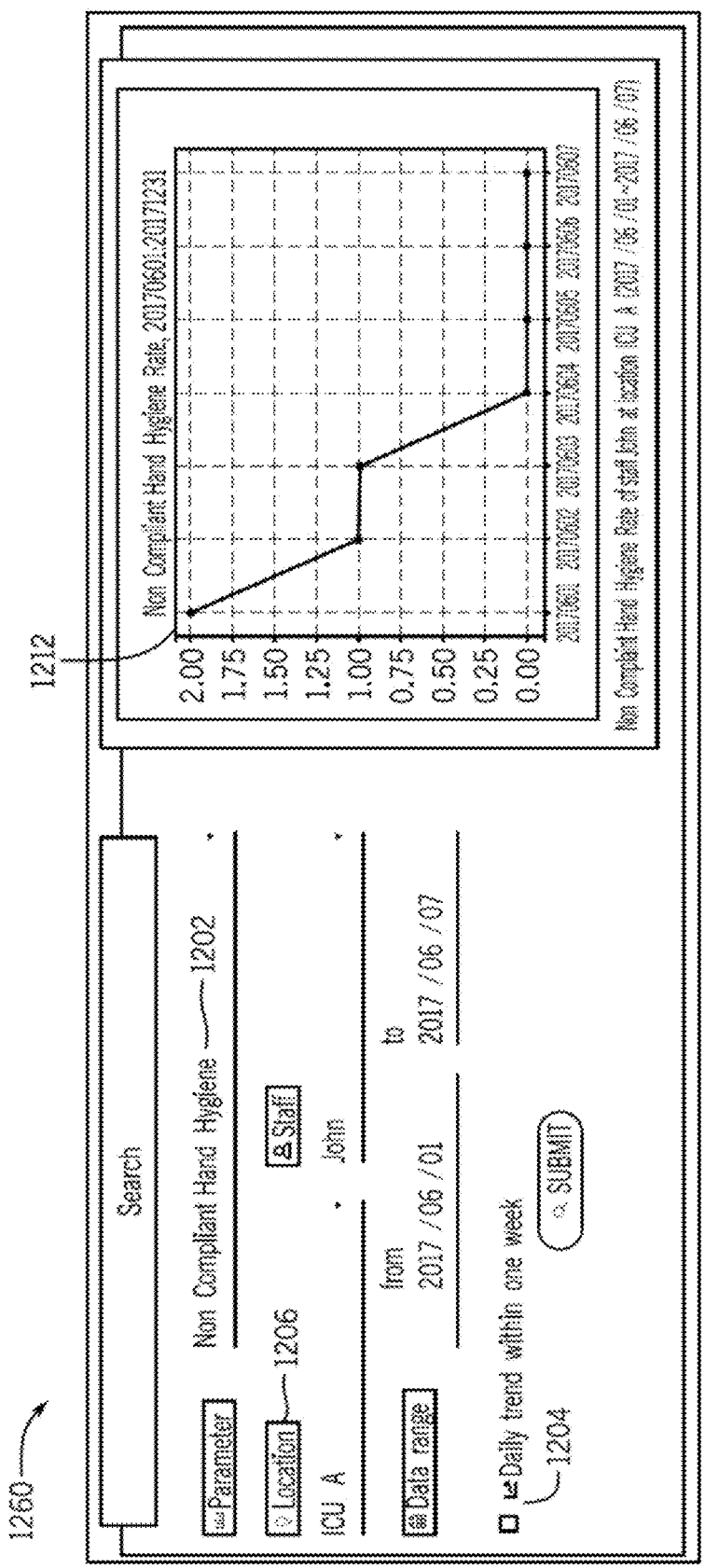
FIG. 12D illustrates a fourth GUI of a web interface for an electronic device to access the hand hygiene analytical and computational system in which the hand hygiene opportunity selected is non-compliant hand hygiene, the staff selected is John, the location is ICU-A, and in which a daily trend is illustrated in an associated graph.

FIG. 12D illustrates a fourth GUI 1260 of a web interface for an electronic device to access the hand hygiene analytical and computational system in which the hand hygiene opportunity 1202 selected is non-compliant hand hygiene, the staff 1210 selected is John, the location 1206 is ICU-A, and in which a daily trend 1204 in associated graph 1222.

As discussed above, responsive to partial compliance or non-compliance, one or more aspects of the system may change. For example, responsive to a single instance of partial compliance or non-compliance, the one or more aspects of the system may change. Alternatively, or in addition, responsive to identifying a pattern of partial compliance or non-compliance (e.g., for an individual or a group of people), the one or more aspects of the system may change. For example, dependent on the analysis of the hand hygiene data (e.g., whether the healthcare provider's non-compliance rate is below a predetermined rate; whether the healthcare provider's number of non-compliant hygiene events is above a predetermined number; whether the healthcare provider's partial-compliance rate is below a predetermined rate; whether the healthcare provider's number of partial-compliant hygiene events is above a predetermined number), the system may modify its operation in one or more aspects. In particular, if the system identifies that a healthcare provider is consistently not washing hands or using sanitizer or consistently not performing the proper hand movements, the system may modify its operation in the one or more aspects.

Example aspects include, but are not limited to: notification; analytics; and alerts. As discussed above, the healthcare provider may be notified of a hand hygiene event, such as via the wristband and/or the stationary controller. As another example, the healthcare provider may be notified of a failure to perform one aspect of the hygiene event (e.g., failure to take hand cleaning agent; failure to perform the proper hand motions; failure to perform the proper hand motions for a long enough time; etc.). Responsive to partial compliance or non-compliance, at least one aspect of the notification may be modified. In one implementation, the modification of notification may be the same responsive to a determination as to partial compliance and as to non-compliance. In an alternate implementation, the modification of notification may be different responsive to a determination as to partial compliance than to a determination as to non-compliance (e.g., non-compliance may comprise additional notifications or louder notifications than partial compliance). In one implementation, the type of notification may remain the same (e.g., a buzzing sound from the stationary controller; a vibration from the wristband); however, the intensity of the notification may change (e.g., a louder buzzing sound in response to a determination of previous partial compliance or non-compliance; a stronger vibration from the wristband in response to a determination of previous partial compliance or non-compliance). In another implementation, a different type of notification may be output. In a first specific implementation, the type of notification responsive to partial compliance or non-compliance may replace the previous notification (e.g., instead of a buzzing sound from the stationary controller, a light is output; instead of vibration from the wristband, an audible output is generated). For example, one metric for hand hygiene compliance is proper hand motions for 20 seconds. Responsive to determining partial compliance or non-compliance, a display on the wristband may display a 20 second countdown, indicating how much proper hand motions the healthcare provider needs to perform. Alternatively, this mode (of displaying the 20 second countdown, which may account for stopping and restarting the proper hand motions) may further be used when a healthcare provider is identified as a trainee (e.g., the wristband is programmed so that the user is identified as a "trainee"). In a second specific implementation, a new type of notification in addition to the standard notification is generated (e.g., a buzzing sound and a light are output from the stationary controller; a vibration and an audible output are generated by the wristband). Thus, in one implementation, the output may be personalized to the healthcare provider based on one or both of status or hand hygiene performance.

Another aspect comprises the analytics of hand hygiene compliance. In one implementation, responsive to partial compliance or non-compliance, the analytics performed on the wristband, the stationary controller, and/or the server may be modified (e.g., more stringent than typical hand hygiene compliance analysis). Still another aspect comprises alerts. As discussed above, various parties may be alerted as to partial compliance and/or non-compliance. As one example, the healthcare provider, subject to the partial compliance and/or non-compliance, may be notified. Alternatively, or in addition, a separate entity or person may be notified. For example, a hospital administrator tasked with overseeing hygiene compliance may be notified, such as responsive to any one, any combination or all of: a hand hygiene event with partial compliance or non-compliance; a non-compliance rate that is below a predetermined rate; a healthcare provider's number of non-compliant hygiene events being above a predetermined number; a healthcare provider's partial-compliance rate being below a predetermined rate; a healthcare provider's number of partial-compliant hygiene events being above a predetermined number.

In this way, detailed hand hygiene compliance reports (such as illustrated in FIGS. 12A-D) may be generated based on the selection of date, location (e.g., floor, unit and/or room), department and individual staff members. They may be available to hospital administrators and may be used to set up an incentive program to motivate healthcare providers. Infection control professionals and unit managers can use this information to identify issues and trends in terms of frequent compliance violators and time of shift variations so that policies and protocols may be revised accordingly. In this way, the analytics is designed to assist and encourage healthcare providers to improve their hand hygiene practices, thus reducing HAIs and costs to the healthcare system. Healthcare providers may login to their own account and compare their performance to colleagues' and be motivated through peer pressure and team competition. The analytics may track the infection source to help hospitals to contain further infections and evaluate the efficacy of any infection control initiatives.

Figure 12E:
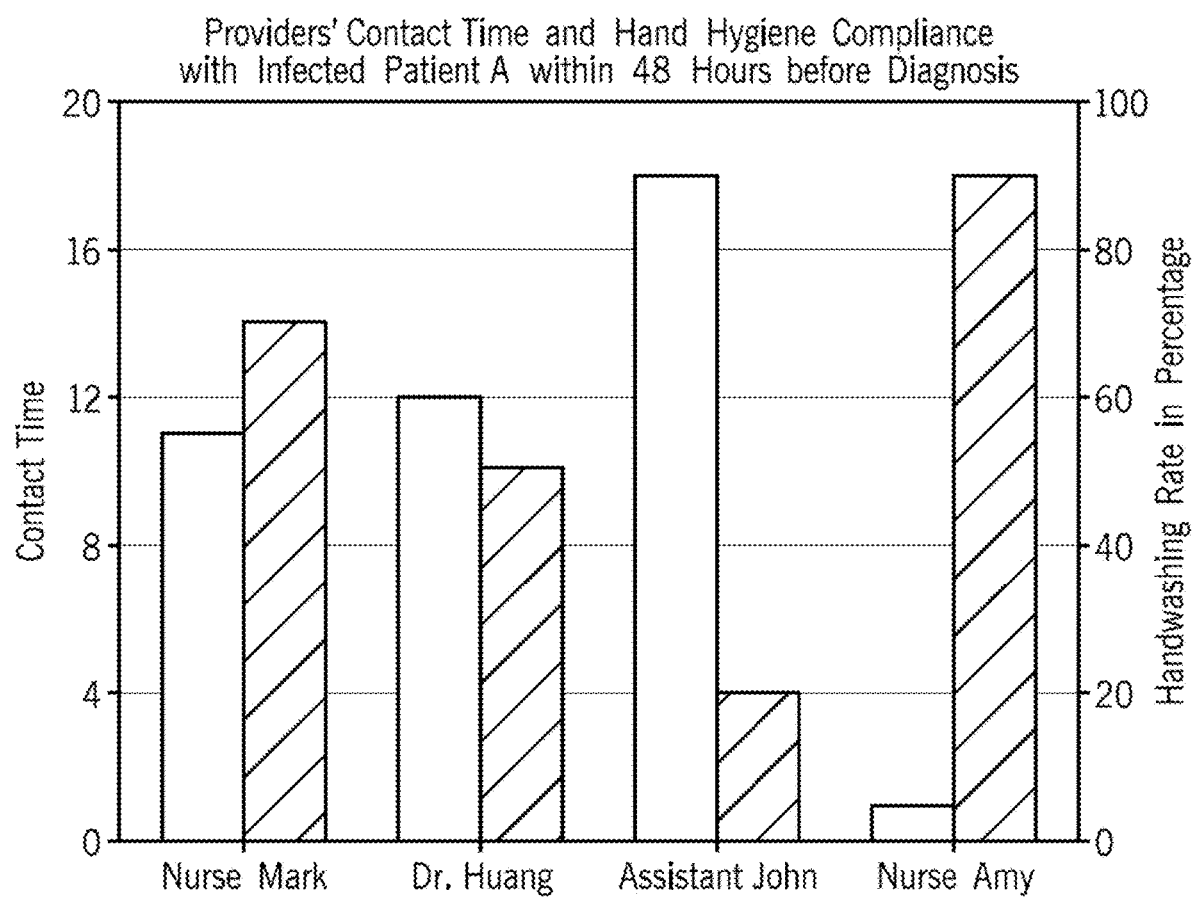
FIG. 12E is a graph of providers' contact time and hand hygiene compliance with infected patient A within 48 hours before diagnosis.

As discussed above, one feature of the analytics may be configured to track infection associated hand hygiene information. Thus, based on mining of data stored in the hand hygiene database and combining with other databases such as infection control data from the hospital, the analytics may be used by the hospital management team to formulate effective strategies against infections. In clinical care, it is very challenging, yet critical, to identify the source of infections in the hospital. Thus, in one implementation, the analytics is configured to track all information associated with a specific infection case. For instance, users may be able to specify the time window and infected patient's room location when searching from the enormous amount of hand hygiene data. This assists in identifying the provider that had the most contact with the infected patient and relatively low hand hygiene compliance rate during the interested time period before diagnosis. Then, potential carriers for this infection may be identified by various statistical inference methods (such as illustrated in FIG. 12E). Furthermore, in the situation of spiked infections of common bacteria in the hospital, the analytics may be configured to instantaneously perform conjoint analysis of all infection events and hand hygiene performance of healthcare providers who have touched these patients, hence tracking bacteria origin down to specific locations and providers.

Specifically, FIG. 12E is a graph of providers' contact time and hand hygiene compliance with infected patient A within 48 hours before diagnosis. In this regard, the graph illustrated in FIG. 12E is an example of tracking information associated with an infected patient. By searching the patient's room location and a predetermined time before diagnosis (e.g., a 48-hr window), the analytics may display the names of all the providers that were in contact with the patient during the time frame, their contact time with the patient and their hand hygiene compliance rate. In this example, Assistant John has the longest contact time and lowest hand hygiene compliance for this soon-to-be infected patient. Thus, the analytics may track the source of infection down to Assistant John for education and isolation strategies.

Further, in one implementation, the analytics may illustrate the correlation between hand hygiene compliance rate and infection rate. With infection data input from hospitals, the analytics may generate detailed analysis and generate visualized reports. For instance, hospital users or researchers from relevant fields may use the software to analyze the correlation between a specific category of infection (e.g., Central Line Infection) and hand hygiene compliance of all providers associated with these patients in that category.

Figure 13A:
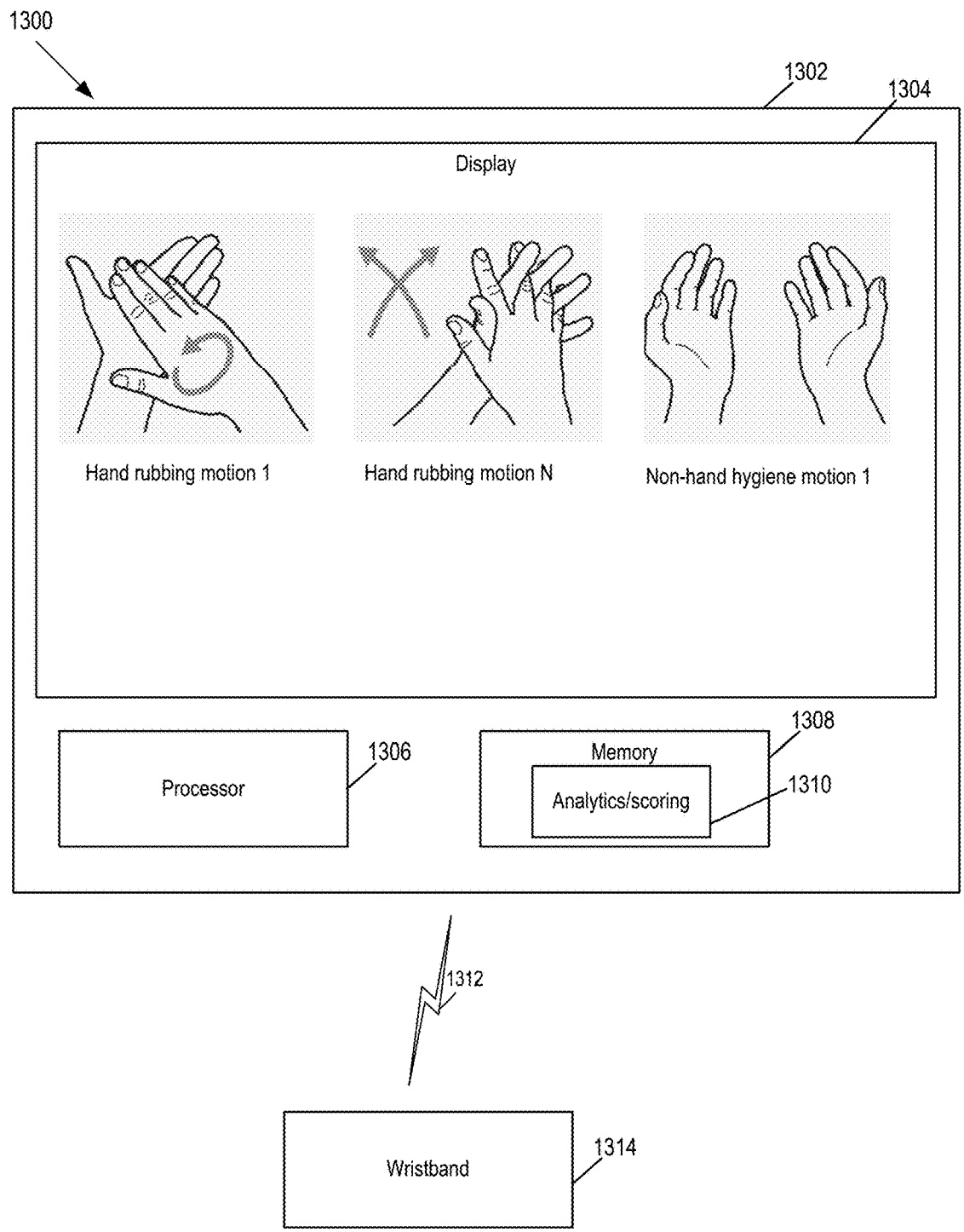
FIG. 13A is a block diagram of a system for instructing and/or scoring a user in hand hygiene compliance.

Users may be instructed in a variety of ways for WHO hand hygiene training. In one way, the users may wear the wristband, and may receive feedback from the wristband and/or the stationary controller. In another way, an electronic device may work in combination with the wristband, such as illustrated in FIG. 13A, and discussed further below. Various types of users may be instructed, including healthcare providers, children, and the elderly. With regard to healthcare providers, the system may train for different hygiene protocols, such as hand hygiene protocols (e.g., WHO hand hygiene guidelines), infectious hygiene protocols (e.g., for treatment of patients with infectious diseases or immunocompromised diseases), etc. In this regard, the training may learn general hygiene protocols or specific hygiene protocols. Further, the system disclosed herein may be integrated with a virtual reality or augmented reality system in which the trainee healthcare provider enters different "rooms" and practices different hygiene protocols, such as hand hygiene protocols, infectious hygiene protocols, etc. (e.g., "walk" from one "room" in ICU #1 with pneumonia with one set of hygiene protocols to another "room" in ICU #2 with a different set of hygiene protocols). In addition, the feedback given to the healthcare provider may be given in one of several ways. In one way, the feedback may be solely based on the current training session. For example, the system may: determine the plurality of hand motions; determine a respective time period for each of the plurality of hand motions; cause the plurality of hand motions to be displayed on the display for the respective times; receive the sensor data, the sensor data indicative of user hand motions and associated respective times for the user hand motions; analyze the sensor data in order to determine a difference between the plurality of hand motions and the user hand motions, and a difference between the respective times and the associated respective times for the user hand motions; and output via the display an indication of the difference between the plurality of hand motions and the user hand motions, and a difference between the respective times and the associated respective times for the user hand motions. In another way, the feedback may compare the difference between the plurality of hand motions and the user hand motions with results from a previous training session, such as a previous difference between previous plurality of hand motions and previous user hand motions in a previous training session, and output the comparison via the display.

Similarly, with regard to children, a wristband in combination with an electronic device may be used to educate, motivate and improve children's hand hygiene. The video game console-like game may make the seemingly boring hand hygiene fun and entertaining. In this regard, the goal of the system is to train the young children with correct hand hygiene behaviors and ultimately reduce infections and absenteeism in daycare centers, schools and pediatric long-term care centers.

FIG. 13A is a block diagram of a system 1300 for instructing and/or scoring a user in hand hygiene compliance. The system 1300 includes a wristband 1314 and an electronic device 1302, which may comprise a mobile electronic device (e.g., tablet or cell phone) installed with a hand hygiene mobile app and includes a display 1304. In this regard, electronic device 1302 may include a processor 1306 and a memory 1308, with analytics/scoring 1310, which may comprise the hand hygiene mobile app. In practice, display 1304 may illustrate various rubbing motions, such as hand rubbing motions and/or non-hand rubbing motions. As shown in FIG. 13A, display 1304 displays two hand rubbing motions (hand rubbing motion 1 and hand rubbing motion N) and a non-hand rubbing motion (non-hand hygiene motion 1). In this regard, display 1304 may display a sequence of the motions.

Though not illustrated in FIG. 13A, electronic device may be in communication with a server, such as back-end server 130. For example, in adult education, a server-based instructional system may be used. In that regard, the server may send motion instructions to a local computer, such as electronic device 1302, for interaction with the person and for central monitoring. Alternatively, the electronic device 1302 is locally operated without server guidance. For example, in child education, central monitoring may not be necessary. In this instance, the electronic device may be a smartphone executing an app for use with wristband 1314.

In either an office setting or a daycare setting, the electronic device 1302 may comprise a tablet or other mobile electronic device, which may be installed in front of the washing station. Further, to avoid the wristband 1314 becoming a fomite, all electronic components may be sealed in the wristband 1314 with silicone, which may make the wristband 1314 easier to clean or sanitize. In one implementation, the wristband 1314 for an office setting (e.g., for adult use) may have the same functionality as the wristband 1314 for a daycare/school setting (e.g., for child use). Alternatively, the wristband 1314 for child use may have less functionality, such as the removal of the vibrating motor.

When the user, such as the healthcare provider or the child, puts on the wristband 1314, the hand hygiene app on the tablet or mobile electronic device may be activated. As one example, the wristband may have built-in motion sensors and Bluetooth chip, such as discussed above. Responsive to the user putting on the wristband, the micro-vibration sensor resident on the wristband may wake-up the wristband. Further, upon wake-up, the wristband 1314 may send a wireless communication via 1312 to electronic device 1302 in order to activate the hand hygiene app. In this way, the battery of the wristband 1314 may last longer and require less recharging or fewer replacements.

With regard to healthcare providers, a series of motions, such as those identical or similar to the motions in the WHO guidelines in FIGS. 10A-B, or those different from the motions in FIGS. 10A-B. Further, the duration for the various motions may be predetermined (e.g., 1 second, 2 seconds, etc.), or may be selected randomly.

With regard to children, the hand hygiene app may comprise a game whose theme is to fight germs. Cartoon monsters, which may represent bacteria on the child's hands, may appear in the game. The game may provide step-by-step video- and/or audio-based instructions to guide the children through all the hand hygiene steps recommended by WHO: wet hands, apply soap, rub hands, clean fingernails, rinse soap and dry hands (see FIGS. 10A-B). Each step of the child's hand hygiene behavior may be detected by the wristband 1314 and sent to the mobile app for evaluation. Alternatively, the wristband 1314 may detect and evaluate the hand hygiene behavior, and transmit the evaluation to the mobile app. The child may be rewarded prizes, such as stars and scores, based on how well the child follows the guidance. If required motions are not completed, the game will provide real-time feedback and remind the child to correct his/her behaviors to be compliant. After each of the required hand hygiene steps is completed, a portion of the monsters may be eliminated to give children an indication of their progress. When adequate hand washing has been achieved, all monsters on the display 1304 will be removed and compliments such as "Good Job!" will be output to encourage children in the correct behavior. Thus, the monsters may represent a plurality of indicia for display. Based on the difference between the plurality of hand hygiene motions and the user hand motions, more or less of the indicia (e.g., the monsters) may be removed from the display, with a greater difference between the plurality of hand hygiene motions and the user hand motions (e.g., the child was further away from the correct hand hygiene motions) resulting in less removal of the number of the monsters on the screen for display and with a lesser difference between the plurality of hand motions and the user hand motions (e.g., the child was closer to the correct hand hygiene motions) resulting in a greater removal of the number of monsters on the screen for display. Alternatively, or in addition, the mobile app may provide a score based on hand hygiene compliance and behavior improvement.

In practice, the wristband may detect the hand hygiene motion of the user by the embedded motion sensor (e.g., an accelerometer and/or gyroscope and/or magnetometer, as discussed above) and transmitted to the mobile app through Bluetooth or other wireless protocol. Various types of hand rubbing motions may be detected. For example, with regard to a healthcare provider, the motions may be detected as described above. For a child, the detection may take into account more gentle rubbing motions that are common in children. In addition, children may move their body dramatically during handwashing or hand rubbing. Therefore, the analytics (present either on the wristband 1314 or on the electronic device 1302) may comprise a robust motion algorithm to detect the hand rubbing motions from interferences such as body movement. Since the wristband 1314 tracks and sends the hand hygiene information to the electronic device (e.g., the smartphone) and receives feedback, the embedded algorithm may be simple to minimize the computing power and thus increase battery life of the wristband 1314. In this way, the system 1300 may provide an entertaining, engaging, and enhancing real-time hand hygiene training for user, such as children, with the goal of helping children to form solid hand-hygiene habits and to develop proper hand hygiene techniques.

Figure 13B:
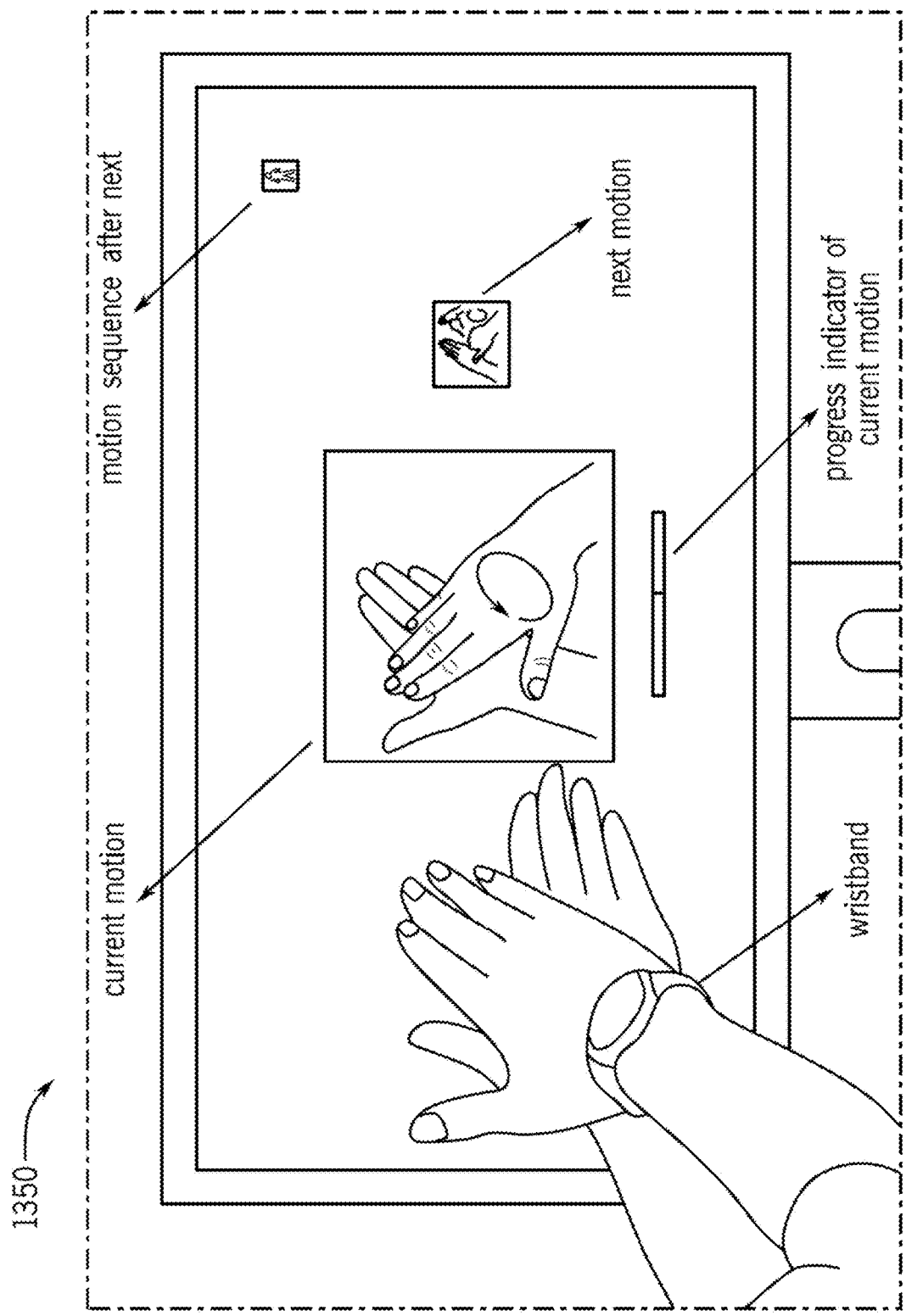
FIG. 13B is an illustration of a GUI illustrated in the system of FIG. 13A.

FIG. 13B is an illustration of a GUI illustrated in the system of FIG. 13A. Each trainee may wear the wristband and perform the motion following the displayed motion image on the display. The image of the current motion is enlarged and located at the center of the screen with a progress bar underneath showing its progress (shown as "progress indicator of current motion"). A small image of the next motion (shown in FIG. 13B as "next motion") is also displayed next to the image of the current motion. This user-friendly interface facilitates the trainee on the transition from one motion to the next.

Specifically, the computer-guided test program may generate a sequence of random motion images, including the 6 hand rubbing motions in WHO guideline (positive motions) and non-hand-hygiene interfering motions (negative motions such as walking, swinging arm, knocking a door, opening a door, etc.). To mimic an actual hand hygiene event, the duration of each motion may be set as a random value, such as between 2 s and 4.5 s. Further, in one implementation, each trial may begin and end with a "rest" action, indicating the trainee to keep hands motionless.

Each trainee may first become familiar with all the possible motions and images displayed on the computer screen. During the tutorial, the computer-guided test program may calculate the sum of the durations of all the positive motions (e.g., the 6 hand rubbing motions in WHO guideline), which may be denoted as TP. The motion duration detected by the sensor algorithm on the wristband may be denoted as TS. For each user, the range of TP and TS may be listed. Further, the duration error ΔT may be calculated as the absolute value of the difference between sensor measurement and the positive hand hygiene duration generated by the program (e.g., |TS-TP|). The error rate may thus be calculated as the ratio of the duration error ΔT to the sum of program generated positive durations TP. For both the duration error and duration error rate, the mean values and standard deviations over all trials may be given.

Further, similar to the computer-guided test program for healthcare providers, the mismatch between the sensor-measured duration and mobile app-generated duration may be used as the basis for scoring for each step. In this way, the game may assist children in developing the correct hand hygiene behavior in their early age.

Figure 14:
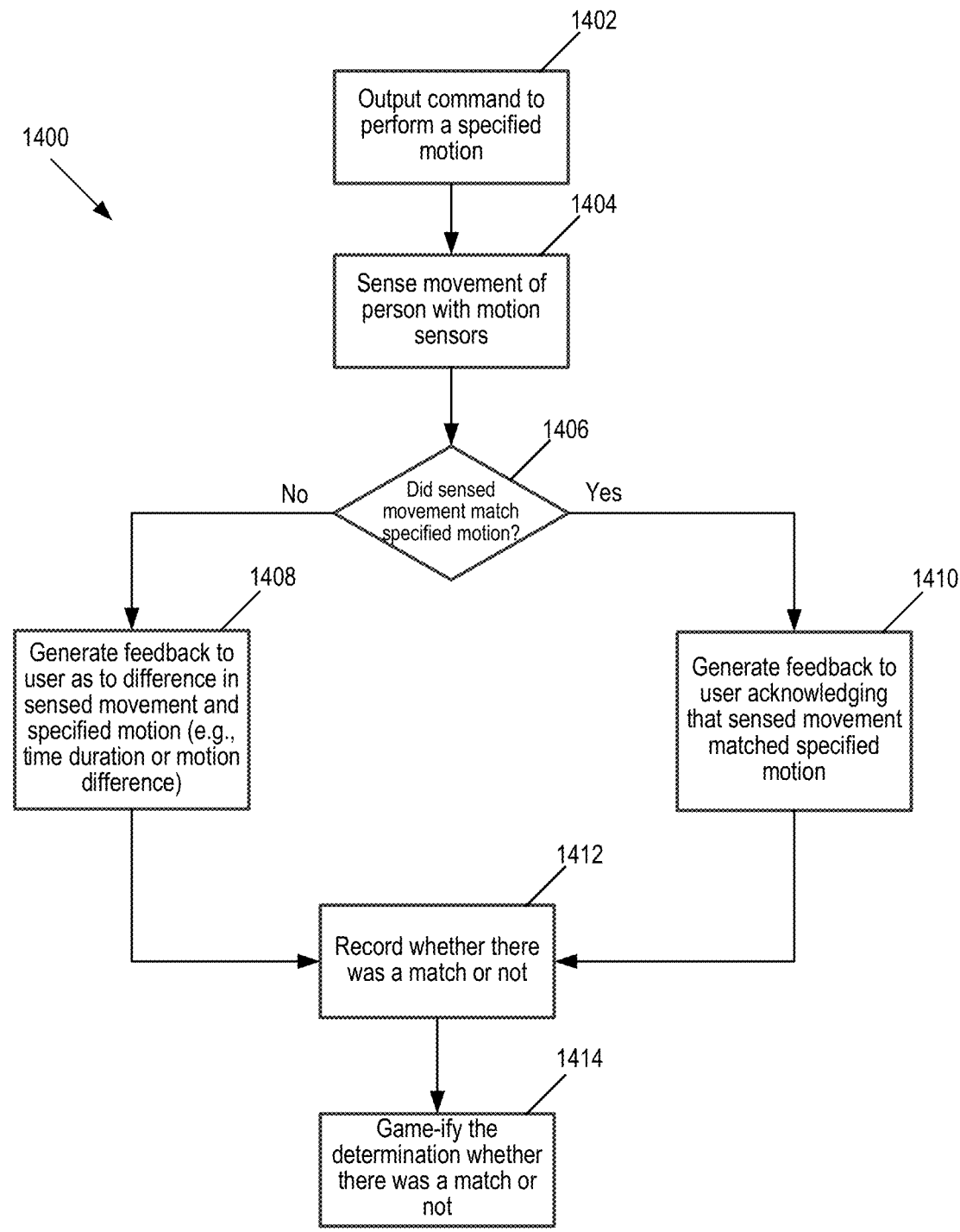
FIG. 14 is flow chart of operation of the system of FIGS. 13A-B.

FIG. 14 is flow chart 1400 of operation of the system of FIGS. 13A-B. At 1402, a command is output to perform a specified motion. At 1404, the movement of the person is sensed with one or more motion sensors. At 1406, it is determined whether the sensed movement matched the specified motion. If yes, at 1410, feedback may be generated acknowledging to the user that the sensed movement matched the specified motion. If no, at 1408, feedback may be generated for output to the user indicating the difference between the sensed movement matched the specified motion. At 1412, it is recorded whether there was a match or not. Finally, at 1414, the determination may be game-ified as to whether there was a match or not.

As discussed above, the hand hygiene monitoring may be integrated with access control. The integration of hand hygiene monitoring and access control may be on one or more levels, including at the mobile electronic device level (e.g., at the wristband), at the local level (e.g., the stationary controller and/or at the local access control reader), and/or at the central level (e.g., the central access control system and/or the hand hygiene monitoring central system).

Hand hygiene monitoring may be integrated with various types of access control systems. One type of access control system is based on RFID technology. In one implementation, a passive RFID tag, which includes an identification code associated with a user, may be included in the mobile electronic device, such as the mobile wristband device. The RFID local access control reader may read the identification code in the RFID tag in order to determine whether the user is to be granted access. One example RFID system comprises HID® Global's multiCLASS reader, which supports a variety of RFID standards including high frequency 13.56 MHz ISO 15693, ISO 14443A/B and low frequency 125 kHz technologies. Another type of access control system is based on a different wireless technology, such as near field (e.g., Bluetooth) wireless communication of the identification code associated with the user.

Figure 5A:
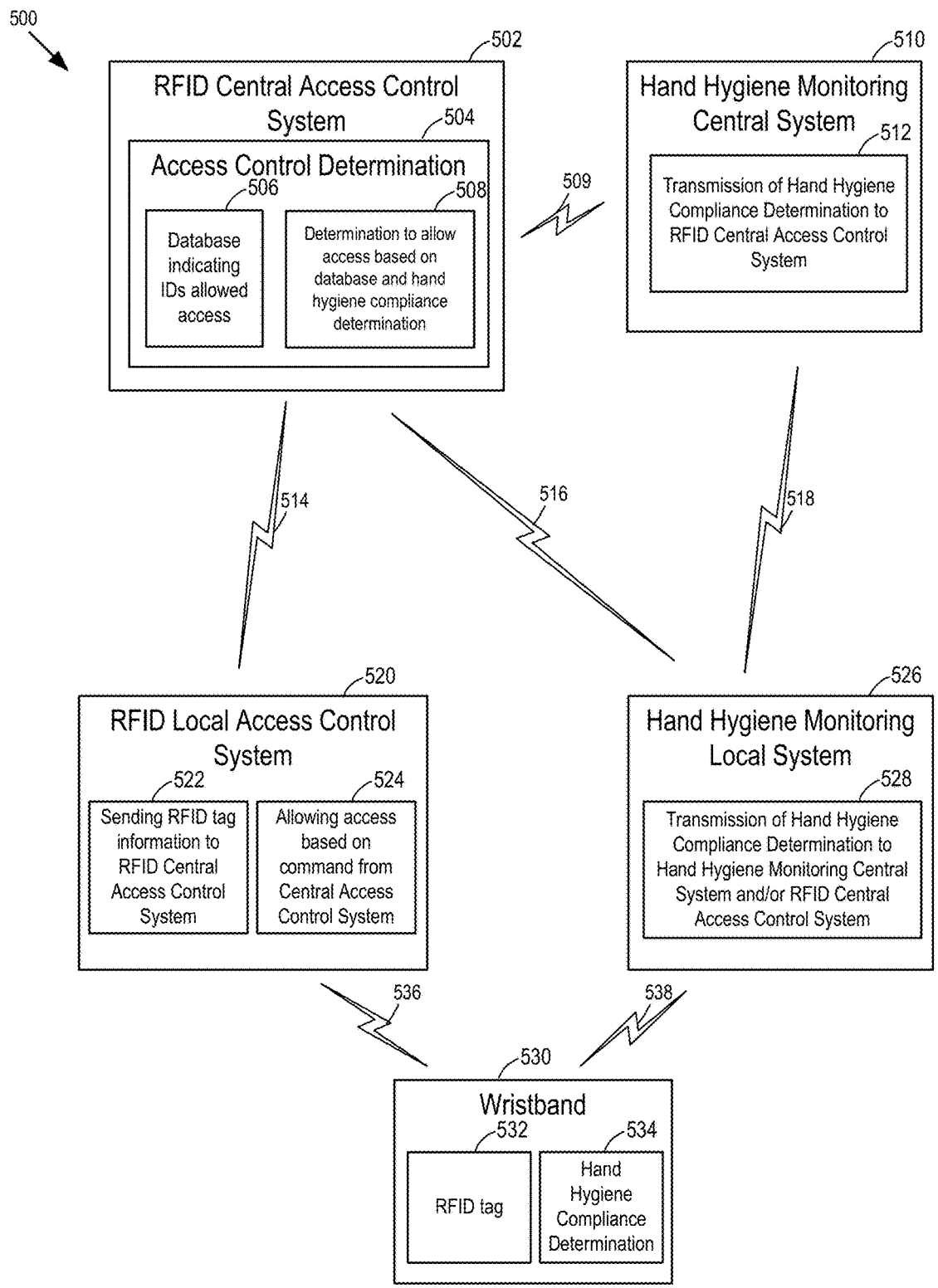
FIG. 5A is a first example block diagram of an access control system (using RFID) and a hand hygiene monitoring system, whereby the access control is centrally determined and whereby the hand hygiene compliance determination is performed at the wristband.

FIG. 5A is a first example block diagram 500 of an access control system (using RFID) and a hand hygiene monitoring system, whereby the access control is centrally determined and whereby the hand hygiene compliance determination is performed at the wristband. In one implementation, the access control determination is independent of hand hygiene compliance. For example, regardless of whether a user has complied with hand hygiene protocols, the user will be granted access if the ID associated with the user is indicative of access. In another implementation, the access control determination is dependent, at least in part, on hand hygiene compliance. For example, the access control determination includes two determinations in order to grant access: (1) compliant hand hygiene determination for a user; and (2) identification of the user indicating allowed access. As discussed above, (1) and (2) may be determined in any order.

FIG. 5A illustrates that RFID central access control system 502 includes access control determination 504, which includes a database 506, whose contents indicate IDs that are allowed access, and determination to allow access based on the database and hand hygiene compliance determination 508. FIG. 5A further illustrates hand hygiene central monitoring system 510, which includes transmission of hand hygiene compliance determination to RFID central access control system 512. As such, FIG. 5A illustrates that the access control determination is dependent, at least in part, on hand hygiene compliance. Alternatively, access control determination may be independent of hand hygiene compliance, in which instance RFID central access control system determines to allow access based on the database (and not based on the hand hygiene compliance determination). Further, FIGS. 5A-H illustrate separate access control and hand hygiene monitoring systems. Alternatively, a single access control system may be used for both access and hand hygiene monitoring. In an implementation with separate systems, the hand hygiene compliance determination may be sent to both systems (either directly from the determining device or via an intermediary device), or may be sent to only one system (such as the hand hygiene monitoring system). Thus, though FIGS. 5A-H illustrate that the hand hygiene compliance determination is sent to at least a part of both the access control system and the hand hygiene monitoring system, alternatively, the hand hygiene compliance determination may only be transmitted within the hand hygiene monitoring system without transmission to the access control system.

Wristband 530, which includes RFID tag 532 (such as a passive RFID tag) and hand hygiene compliance determination 534, is configured to determine whether the hand motions of the user is compliant with hand hygiene standards. Thus, in one implementation, the RFID feature in wristband 530 is independent of other wristband functions, such as the hand hygiene compliance determination. RFID local access control system 520, which may include an RFID reader, may read information from RFID tag 532. In this way, the information from RFID tag 532 may be sent to an electronic device external to wristband 530. Further, in one implementation, the information as to hand hygiene compliance may be transmitted from wristband 530 in a communication that is separate from the information from RFID tag 532 (and potentially may be sent to different external electronic devices). Alternatively, as discussed below, the information as hand hygiene compliance and the identification information of the healthcare provider may be sent in a single communication to an external electronic device (such as to a local access control system).

The wristband 530 may transmit the hand hygiene compliance determination to an external electronic device via near-field wireless transmission 538 to hand hygiene monitoring local system 526, one example of which is the stationary controller discussed above. The hand hygiene compliance determination may comprise a field in a communication indicating that hand hygiene was complied with (e.g., a field in the communication=1) or that hand hygiene was not complied with (e.g., a field in the communication=0). In the implementation in which access control is dependent on hand hygiene compliance, RFID central access control system 502 may receive the hand hygiene compliance determination in one of several ways including: (1) directly from wristband 530; (2) indirectly from hand hygiene monitoring local system 526 (using transmission of hand hygiene compliance determination to hand hygiene monitoring central system and/or RFID central access control system 528); or indirectly from hand hygiene monitoring central system (using transmission of hand hygiene compliance determination to RFID central access control system 502). In the implementation in which access control is independent of hand hygiene compliance, RFID central access control system 502 need not receive the hand hygiene compliance determination.

Communications may be sent wirelessly, such as via 509, 514, 516, 518, 536, 536. Of note, 536 may be a wireless communication via RF for RFID whereas 538 may be a wireless communication via Bluetooth or Wi-Fi. The frequency bands may be different for the RFID transmission versus the Bluetooth or WIFI transmission. RFID transmission may be in the 125 or 134 kHz areas of the spectrum for low-frequency RFID systems, and 13.56 MHz for high-frequency RFID systems. Bluetooth may operate at frequencies between 2402 and 2480 MHz, or 2400 and 2483.5 MHz including guard bands 2 MHz wide at the bottom end and 3.5 MHz wide at the top. Wi-Fi may use five distinct frequency ranges including: 2.4 GHz, 3.6 GHz, 4.9 GHz, 5 GHz, and 5.9 GHz bands.

Because of the central access determination, RFID local access control system 520 transmits the RFID tag information using sending RFID tag information to RFID central access control system 522, and allows access (e.g., unlocks an electronic lock) responsive to a command from the RFID central access control system 502 using allowing access based on command from central access control system 524.

Figure 5B:
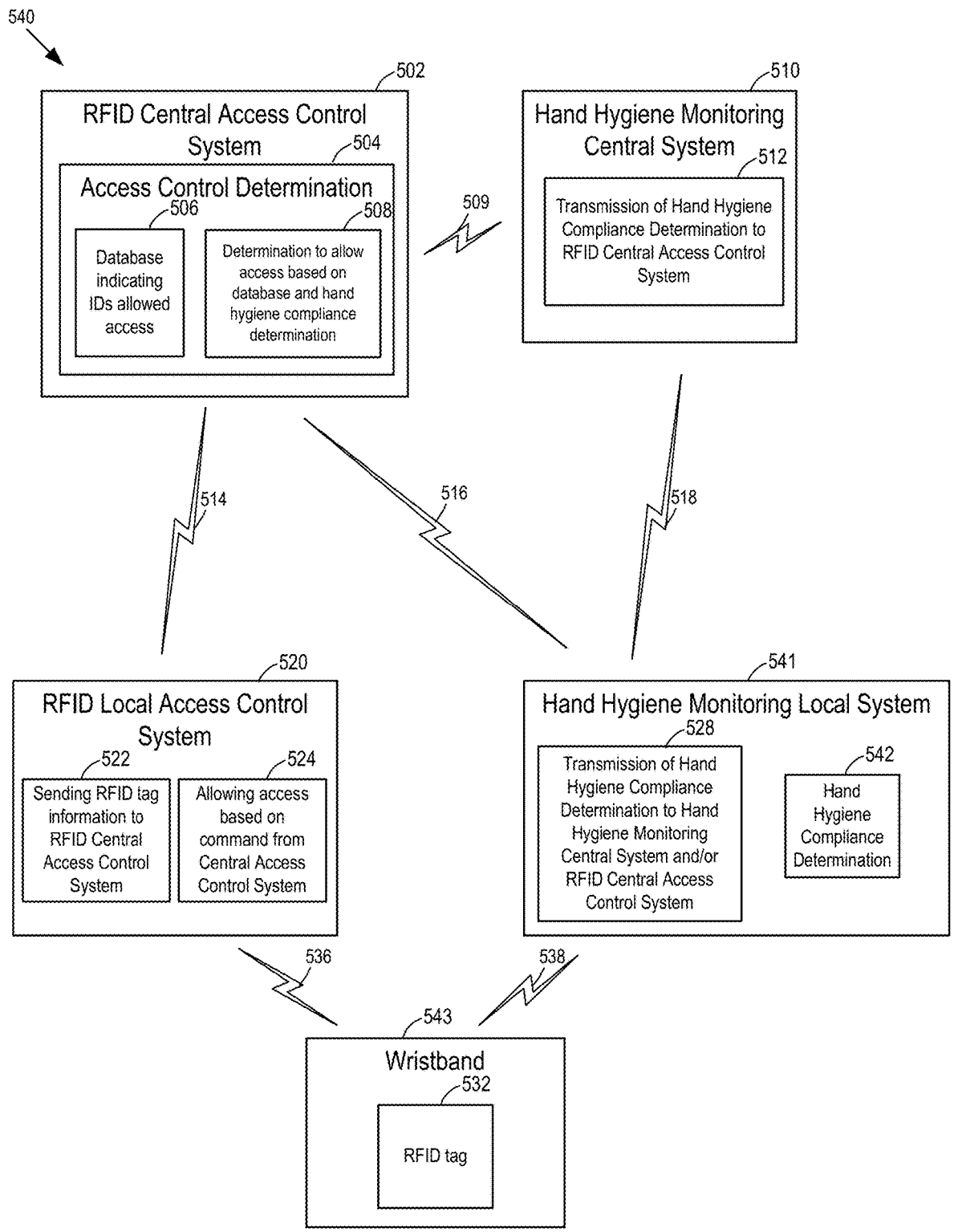
FIG. 5B is a second example block diagram of an access control system (using RFID) and a hand hygiene monitoring system, whereby the access control is centrally determined and whereby the hand hygiene compliance determination is performed at the stationary controller.

FIG. 5B is a second example block diagram 540 of an access control system (using RFID) and a hand hygiene monitoring system, whereby the access control is centrally determined and whereby the hand hygiene compliance determination is performed at the stationary controller. Thus, in contrast to FIG. 5A, hand hygiene monitoring local system 541 includes hand hygiene compliance determination 542, and not on wristband 543.

Figure 5C:
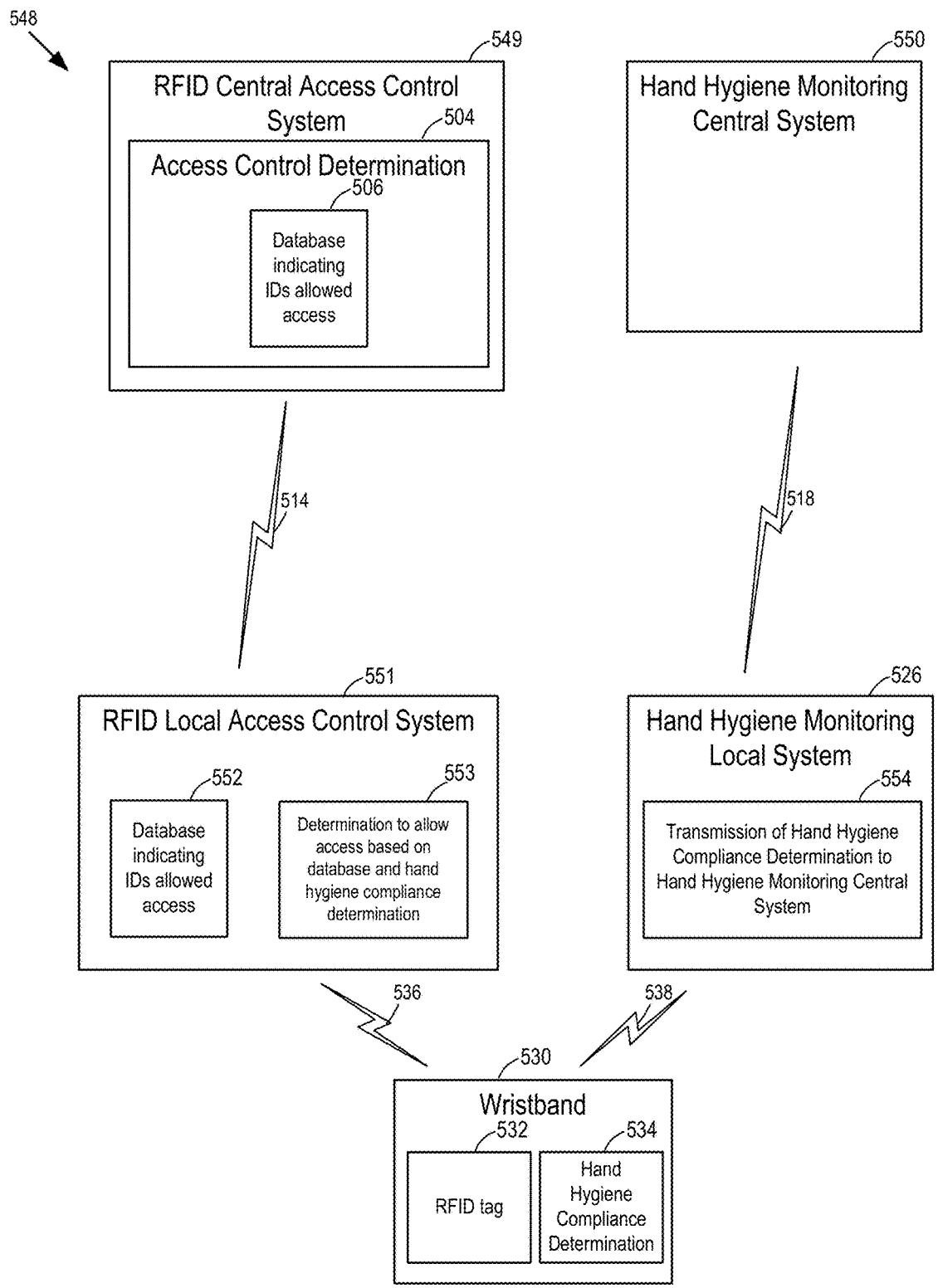
FIG. 5C is a third example block diagram of an access control system (using RFID) and a hand hygiene monitoring system, whereby the access control is locally determined and whereby the hand hygiene compliance determination is performed at the wristband.

FIG. 5C is a third example block diagram 548 of an access control system (using RFID) and a hand hygiene monitoring system, whereby the access control is locally determined and whereby the hand hygiene compliance determination is performed at the wristband 530. FIG. 5C illustrates that RFID local access control system 551 includes database indicating IDs allowed access 552, whose contents indicate IDs that are allowed access, and determination to allow access based on the database and hand hygiene compliance determination 553. As such, FIG. 5C illustrates that the access control determination is dependent, at least in part, on hand hygiene compliance. Alternatively, access control determination may be independent of hand hygiene compliance, in which instance RFID local access control system determines to allow access based on the database (and not based on the hand hygiene compliance determination). Further, hand hygiene monitoring local system 526 may use transmission of hand hygiene compliance determination to hand hygiene monitoring central system 554 in order to transmit the hand hygiene compliance determination to hand hygiene monitoring central system 550.

Figure 5D:
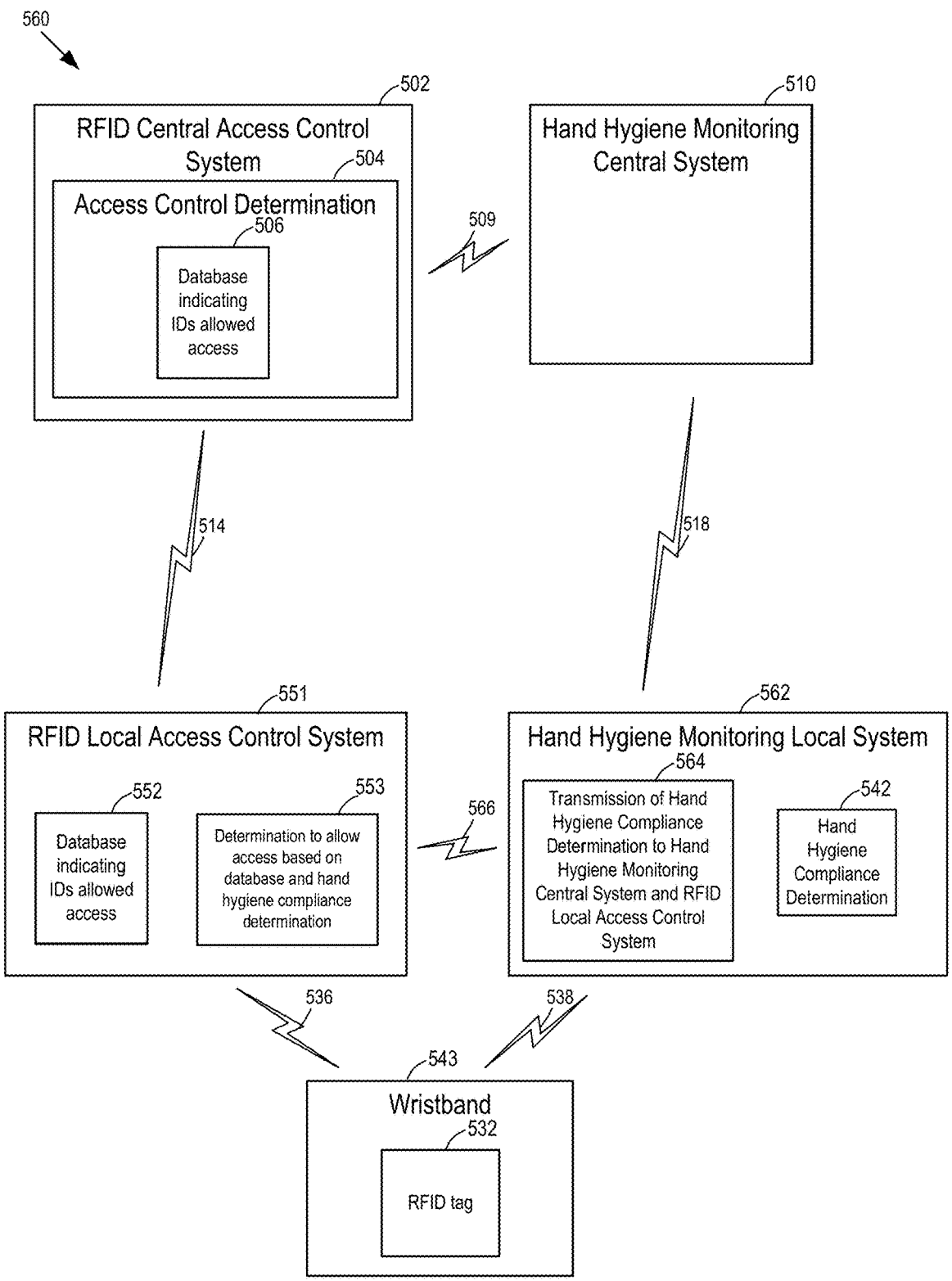
FIG. 5D is a fourth example block diagram of an access control system (using RFID) and a hand hygiene monitoring system, whereby the access control is locally determined and whereby the hand hygiene compliance determination is performed at the stationary controller.

FIG. 5D is a fourth example block diagram 560 of an access control system (using RFID) and a hand hygiene monitoring system, whereby the access control is locally determined and whereby the hand hygiene compliance determination is performed at the stationary controller. Thus, in contrast to FIG. 5C, hand hygiene monitoring local system 562 includes hand hygiene compliance determination 542, and not on wristband 543. Further, hand hygiene monitoring local system 562 includes transmission of hand hygiene compliance determination to hand hygiene monitoring central system and RFID local access control system 564. Thus, FIG. 5D illustrates that access control is dependent on hand hygiene compliance. In the instance of independence of access control from hand hygiene compliance, the hand hygiene compliance determination need not be transmitted to RFID local access control system 551.

Figure 5E:
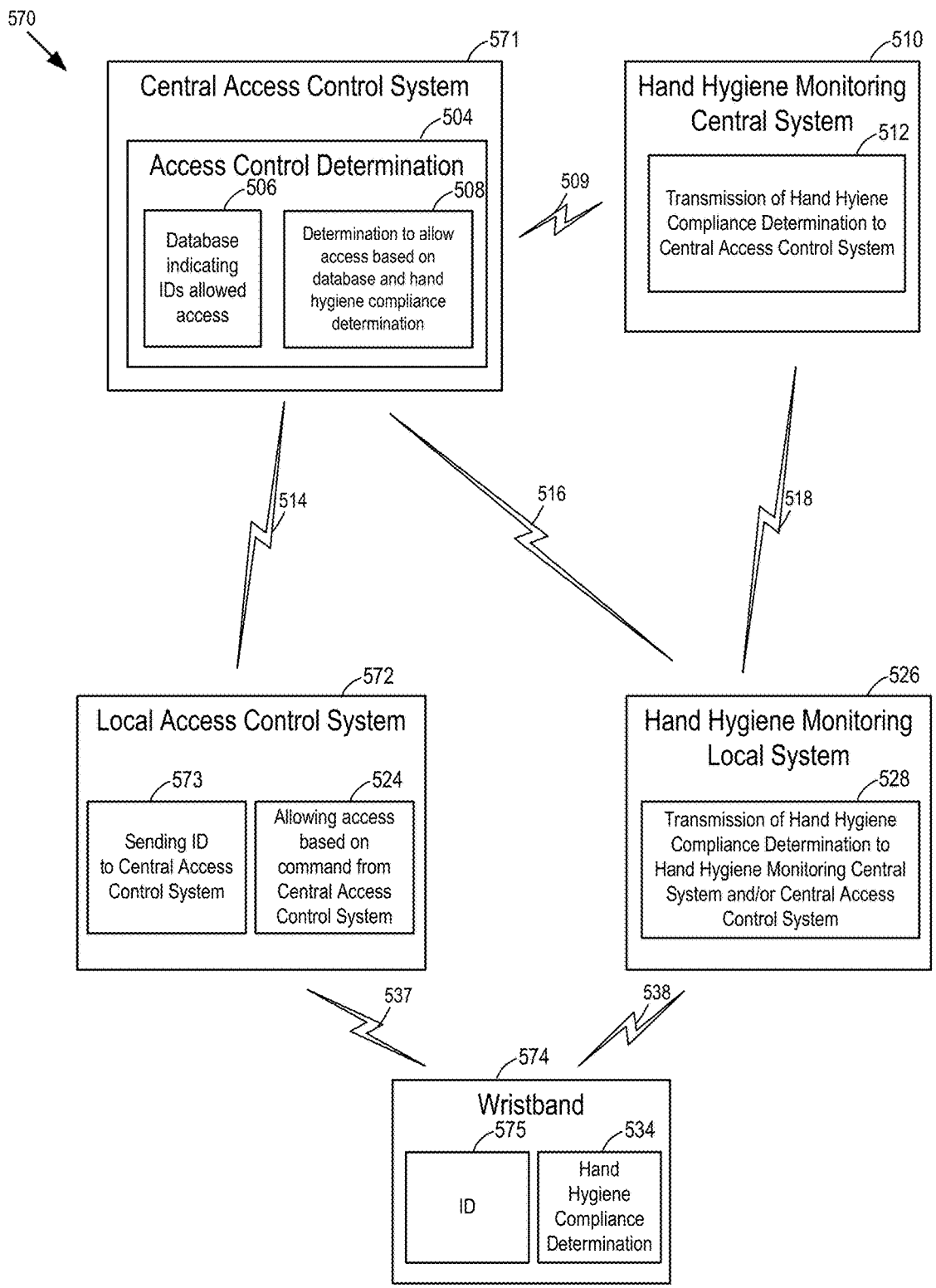
FIG. 5E is a fifth example block diagram of an access control system and a hand hygiene monitoring system, whereby the access control and hand hygiene communication communicate via the same wireless protocol, whereby access control is centrally determined and whereby the hand hygiene compliance determination is performed at the wristband.

As discussed above, access control in one implementation may be based on RFID technology and may be based on non-RFID technology. FIG. 5E is a fifth example block diagram 570 of an access control system which is based on non-RFID technology and a hand hygiene monitoring system, whereby the access control and hand hygiene communication communicate via the same wireless protocol, whereby access control is centrally determined and whereby the hand hygiene compliance determination is performed at the wristband. Specifically, central access control system 571 is similar to that in FIG. 5A. However, wristband 574 includes ID 575, which is not an RFID tag, but instead may be an identification in stored memory. Wireless communication 537 may comprise a non-RFID frequency band, such as Bluetooth or Wi-Fi, thereby communicating the ID 575 to local access control system 572. Local access control system 572 uses sending ID to central access control system 573. Similar to FIG. 5A, FIG. 5E illustrates that the access control determination is dependent on the hand hygiene compliance determination. Alternatively, in the implementation in which access control is independent of hand hygiene compliance, central access control system 571 need not receive the hand hygiene compliance determination and the determination to grant access need not be dependent on the hand hygiene compliance determination.

Figure 5F:
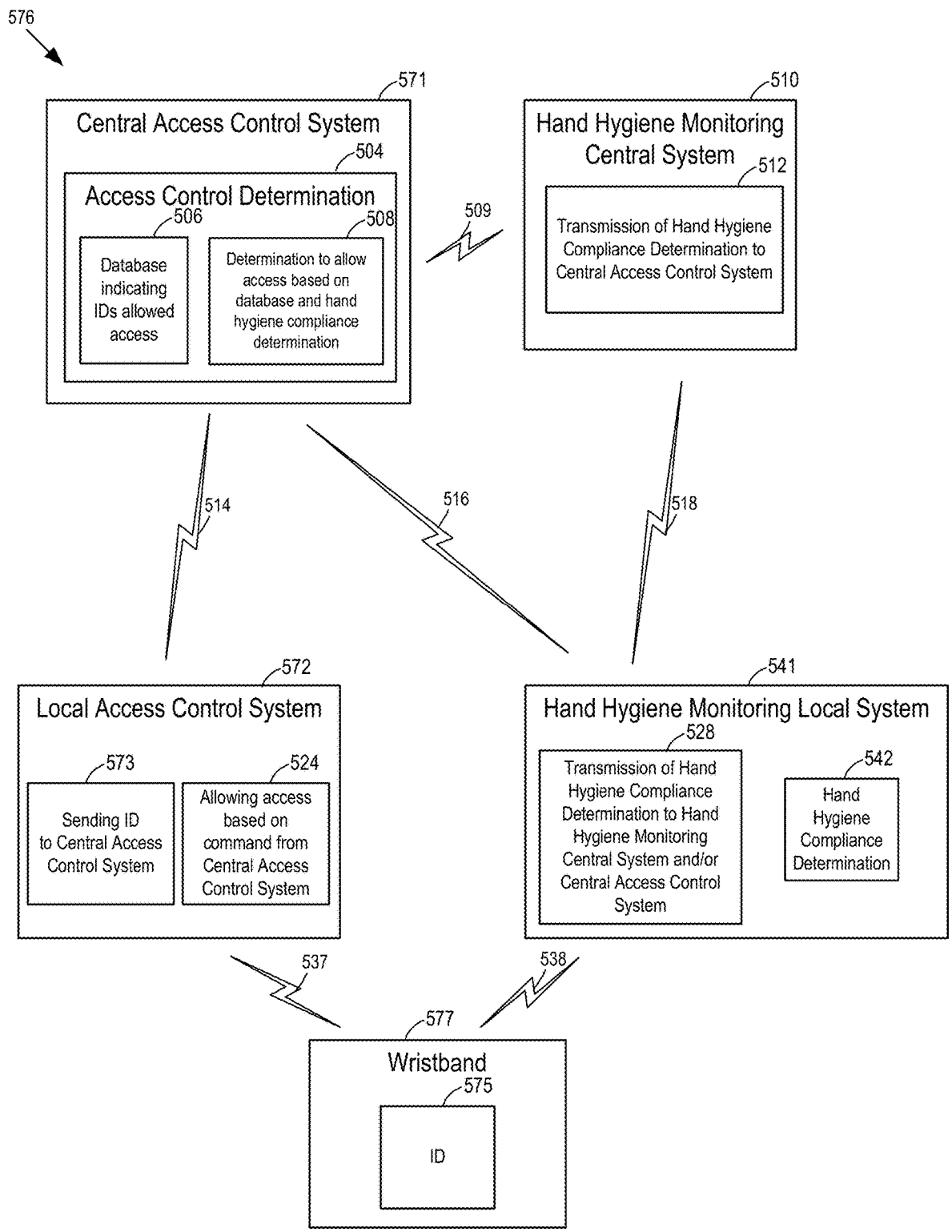
FIG. 5F is a sixth example block diagram of an access control system and a hand hygiene monitoring system, whereby the access control and hand hygiene communication communicate via the same wireless protocol, whereby access control is centrally determined and whereby the hand hygiene compliance determination is performed at the stationary controller.

FIG. 5F is a sixth example block diagram 576 of an access control system and a hand hygiene monitoring system, whereby the access control and hand hygiene communication communicate via the same wireless protocol, whereby access control is centrally determined and whereby the hand hygiene compliance determination is performed at the hand hygiene monitoring local system 541 (e.g., the stationary controller). FIG. 5F is similar to FIG. 5B except that the wristband 577 includes ID 575, and the central access control system 571 and local access control system 572 (with sending ID to central access control system 573) are not RFID based.

Figure 5G:
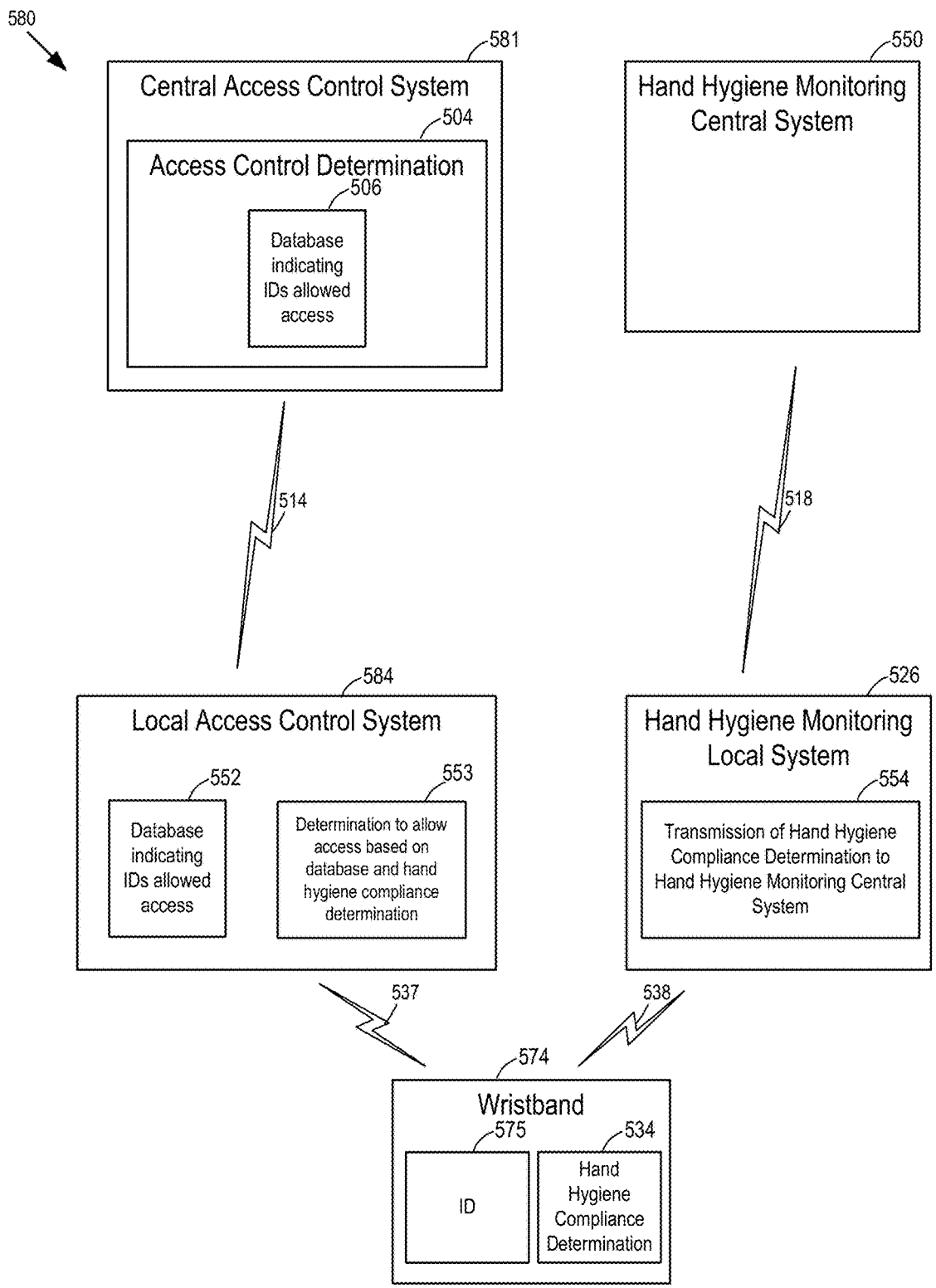
FIG. 5G is a seventh example block diagram of an access control system and a hand hygiene monitoring system, whereby the access control and hand hygiene communication communicate via the same wireless protocol, whereby access control is locally determined and whereby the hand hygiene compliance determination is performed at the wristband.

FIG. 5G is a seventh example block diagram 580 of an access control system and a hand hygiene monitoring system, whereby the access control and hand hygiene communication communicate via the same wireless protocol, whereby access control is locally determined and whereby the hand hygiene compliance determination is performed at the wristband 574. FIG. 5G is similar to FIG. 5C except that the wristband 577 includes ID 575, and the central access control system 581 and local access control system 584 are not RFID based.

Figure 5H:
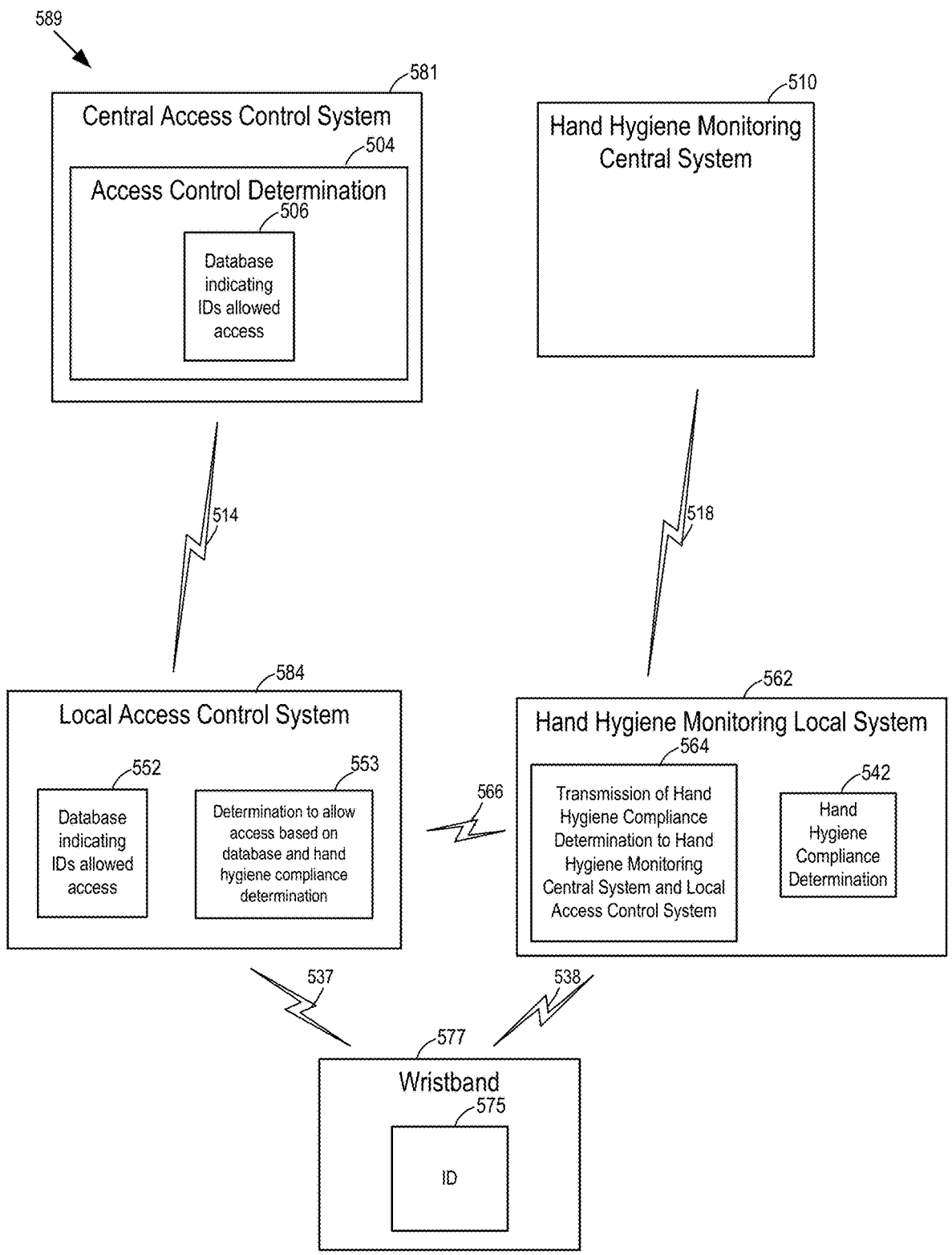
FIG. 5H is an eighth example block diagram of an access control system and a hand hygiene monitoring system, whereby the access control and hand hygiene communication communicate via the same wireless protocol, whereby access control is locally determined and whereby the hand hygiene compliance determination is performed at the stationary controller.

FIG. 5H is an eighth example block diagram 589 of an access control system and a hand hygiene monitoring system, whereby the access control and hand hygiene communication communicate via the same wireless protocol, whereby access control is locally determined and whereby the hand hygiene compliance determination is performed at the stationary controller.

Figure 5I:
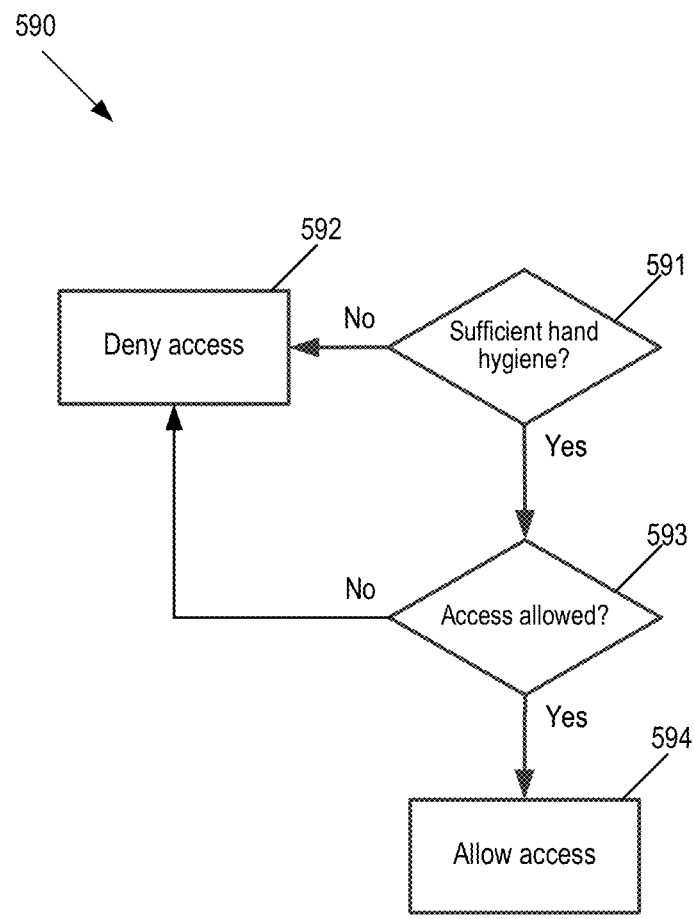
FIG. 5I illustrates a first flow chart of operation to determine access control, such as resident at the central or local RFID access control system.

FIG. 5I illustrates a first flow chart 590 of operation to determine access control, such as resident at the central or local RFID access control system. At 591, it is determined (either at the central or at the local access control system) whether there is sufficient or compliant hand hygiene. If not, at 592, access is denied. If so, it is determined (either at the central or at the local access control system) whether access should be allowed (e.g., the ID of the user indicates access is to be granted. If not, flow chart 590 loops back to 592 and access is denied. If so, at 594, access is granted (e.g., an electronic lock is unlocked).

Figure 5J:
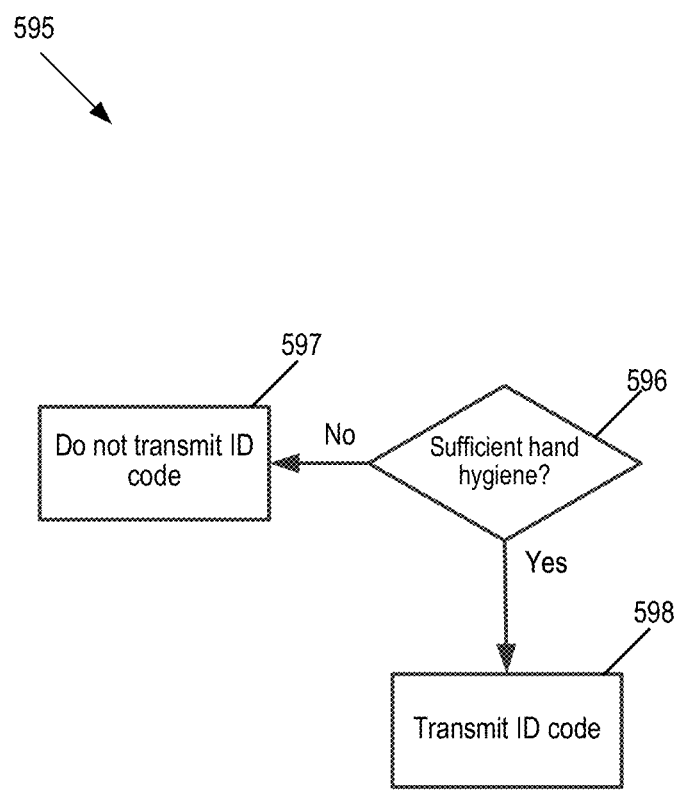
FIG. 5J illustrates a first flow chart of operation for the wristband to determine whether to send an ID to an access control system, such as a local access control system.

FIG. 5J illustrates a first flow chart 595 of operation for the wristband to determine whether to send an ID to an access control system, such as a local access control system. At 596, the wristband determines whether there is sufficient hand hygiene. If not, at 597, the wristband determines not to transmit the ID code to the local access control system (with the wristband effectively denying access to the user based on a failure to comply with hand hygiene). If so, at 598, the wristband determines to transmit the ID code to the local access control system (with the local access control system making the access determination).

As discussed above, dementia is a syndrome associated with a decline in memory or thinking skills that is severe enough to interfere with daily life, with Alzheimer's disease (AD) being the most common type of dementia. Dementia is not only devastating for the person with it, but also is overwhelming for their caregivers and families with substantial physical, emotional and financial pressures. Therefore, in one implementation, a proximity sensing and output generating device is disclosed that is cost-effective and includes user-friendly technology with accessible interventions that reduces the burden of dementia care.

In particular, the proximity sensing and output generating device comprises a smart voice-cueing device that reminds and guides dementia individuals to perform everyday tasks in real time. The tasks may comprise any type of human task, including various tasks related to hygiene and safety (e.g., toileting, cooking, and going outdoors). The proximity sensing and output generating device may be small (e.g., the size of a US quarter or smaller) and ultra-low-power.

The proximity sensing and output generating device may be placed in a variety of places for a variety of tasks, such as illustrated in FIG. 16D. As illustrated, the proximity sensing and output generating device may be placed in the bathroom (see proximity sensing and output generating device 1670 on door of bathroom for toileting), the kitchen (see proximity sensing and output generating device 1660 on drawer for preparing food), and the main entrance (see proximity sensing and output generating device 1680 on front door for going outdoors). As discussed further below, the proximity sensing and output generating device may include a housing or other type of mechanical structure that has a fastener configured to fasten the proximity sensing and output generating device to a part of the premises. The fastener may comprise an adhesive on the housing (e.g., glue) so that the proximity sensing and output generating device may be attached to a part of the premises. Alternatively, the fastener may comprise a connector, such as a screw with the housing including a hole through which the screw may traverse and connect to the part of the premises.

As discussed further below, various parts of the premises are contemplated at which the proximity sensing and output generating device may be attached. For example, doors (such as front doors, interior doors, cabinet doors, electrical appliance doors (e.g., refrigerator door), and the like), drawers, etc. may be parts of the premises to which the proximity sensing and output generating device may be attached. In this regard, doors and drawers are examples of movable portions of the premises. Other movable portions of the premises are contemplated.

In one implementation, the proximity sensing and output generating device includes various functionalities, such as motion sensing and sound detection. For example, the proximity sensing and output generating device, using the data from motion sensing and/or sound detection, determine a task (e.g., toileting, preparing food, going outdoors) is occurring, responsive thereto, generate an output. As one example, responsive to the motion sensor sensing movement of the front door, the controller of the proximity sensing and output generating device may determine that the person is going outdoors. As another example, responsive to the motion sensor sensing movement of an interior door, the controller of the proximity sensing and output generating device may determine that the person is going into a certain room of the premises (such as the bathroom). As still another example, responsive to the motion sensor sensing movement of the kitchen drawer, the controller of the proximity sensing and output generating device may determine that the person is preparing food. As another example, responsive to the motion sensor sensing movement in the kitchen, the proximity sensing and output generating device may access a heat sensor (e.g., an IR sensor) in order to determine whether the person has turned on the stove. If so, the proximity sensing and output generating device may generate an output to remind the person to turn off the stove after use. As yet another example, responsive to the sound sensor sensing the toilet flushing or running water from the faucet, the controller of the proximity sensing and output generating device may determine that the person is using the bathroom. Further, responsive to the proximity sensing and output generating device determining a task, the proximity sensing and output generating device may generate an output (e.g., a pre-recorded voice message to remind the person to perform an act related to the task). For example, responsive to determining that the person is going outdoors, the pre-recorded message may remind the person to carry cellular phones or location-monitoring devices before going outside. As another example, responsive to determining that the person is preparing food, the pre-recorded message may remind the person to wash hands prior to preparing food. As still another example, responsive to determining that the person is using the toilet, the pre-recorded message may remind the person to remember to flush the toilet, remember to wash hands after using the toilet, and/or remember to turn off the faucet after washing hands. Further, the analytics in the proximity sensing and output generating device recording daily activities of the dementia persons may also be used for health evaluation, as discussed further below. In this way, the proximity sensing and output generating device may provide interventions and prevent accidents, such as wandering outside or a water leak.

In one implementation, family members or caregivers may pre-record their personal messages for storage within the proximity sensing-output generating device. In one implementation, a button (not shown) on the housing of the proximity sensing-output generating device may be pressed, activating a microphone on the proximity sensing-output generating device in order to record the personal message. Alternatively, the message may be recorded onto another electronic device, such as a smartphone, and transferred to the proximity sensing-output generating device (such as via Bluetooth) and stored in the memory of the proximity sensing-output generating device (e.g., in microcontroller memory).

Figure 15A:
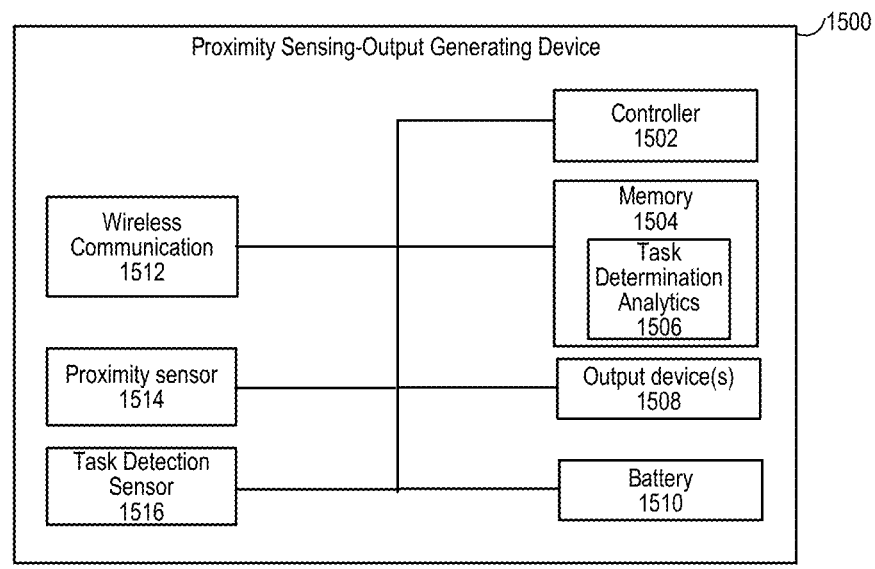
FIG. 15A is a first example block diagram of a proximity sensing-output generating device.

FIG. 15A is a first example block diagram of a proximity sensing-output generating device 1500. The proximity sensing-output generating device 1500 includes a controller 1502, a memory 1504, output device(s) 1508, a battery 1510, wireless communication 1512, proximity sensor 1514, and task detection sensor 1516. Though FIG. 15A depicts separate blocks for various elements, the blocks may be combined. For example, the controller 1502, memory 1504 and wireless communication 1512 may be combined, such as discussed below.

As discussed further below, proximity sensing-output generating device 1500 performs multiple functions, including: sensing, using proximity sensor 1514, the proximity of a person to the proximity sensing-output generating device 1500; determining, using task detection sensor 1516 and task determination analytics 1506, whether a specific task is occurring; and outputting, using output device(s) 1508, an output in response to determining that the specific task is occurring. Proximity sensor 1514, which may generate proximity sensor output indicative of a person proximate to the proximity sensing-output generating device 1500, may take one of several forms. In one form, proximity sensor 1514 may comprise a micro vibration sensor, discussed further below. In another form, proximity sensor 1514 may comprise a sound sensor, such as a microphone. Further, various task detection sensors 1516 may be used, such as one or more motion sensors, one or more sound sensors, or the like. Further, the task determination analytics 1506 may determine whether a specific task (e.g., toileting, preparing food, going outdoors) is occurring.

Thus, in one implementation, the following components may be used: wireless transceiver, microcontroller, sensors (microphone, accelerometer & gyroscope) and speaker. Various low-power wireless protocols may be used, such as Bluetooth Low Energy (BLE), RFID and ZigBee. For small form factor and low power consumption, a system-on-chip (SOC) solution may be used that integrates wireless transceiver and microcontrollers. For instance, DA14580 (Dialog Semiconductor) is a BLE SOC chip configured for wearable applications. It has a fully integrated BLE radio transceiver and baseband processor (ARM Cortex-M0) and dissipates 4.9 mA in typical working condition with transceiver fully on, 0.5 mA with RF in "Near Field Mode" and 1.2 uA in extended sleep mode (ARM idle, RAM retention, RF off).

One motion sensor may comprise an ultralow power, 3-axis MEMS accelerometer that consumes less than 2 µA at a 100 Hz output data rate, and 270 nA when in motion triggered wake-up mode. Another motion sensor may comprise KXG07 (Kionix), which is a 6-axis accelerometer/gyroscope combination device that features a configurable 200 µA operating current in normal mode with wake up and back to sleep functions.

For the sound sensor, a microphone may be used. One type of microphone is ICS-40310 from InvenSense, which is a MEMS microphone with a combination of very low power consumption (~16 µA), high SNR, and a tiny package. With such a low power consumption, the microphone may always remain on.

For the speaker circuit, Texas Instrument TLV320AIC3 from and Cirrus Logic CS42L52 each integrate low-power stereo codec and mono class-D speaker amplifier. Since the voice cueing device is for use in small space, such as a bathroom, kitchen and front entrance, a speaker that delivers 80 dB (or ~10 mW) power may be satisfactory.

Figure 15B:
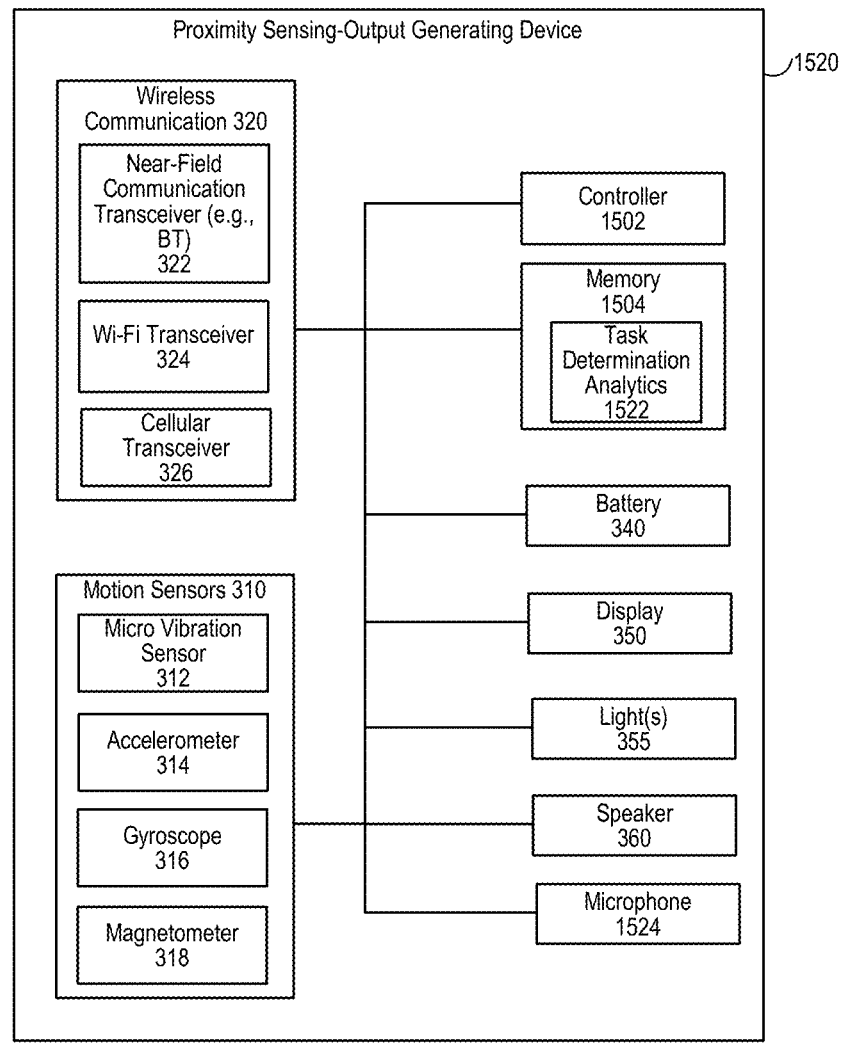
FIG. 15B is a second example block diagram of a proximity sensing-output generating device.

FIG. 15B is a second example block diagram of a proximity sensing-output generating device 1520. As illustrated, various type of wireless communication 320 may be used, as discussed above. Though three types of wireless communication 320 are illustrated, fewer or greater numbers of wireless communication protocols may be used. Further, one or more motion sensors 310 may be used. Though three types of motion sensors 310 are illustrated, fewer or greater numbers of motion sensors may be used. As discussed above, for power management purposes, micro-vibration sensor 312 may be always on and/or microphone 1524 may be always on, with its output used to awaken various other parts of the proximity sensing-output generating device 1520, such as wireless communication 320 and/or other motion sensors (such as accelerometer 313 and gyroscope 316). Finally, task determination analytics 1522 may be used to determine, based on sensor input, whether a specific task is being performed, as discussed above.

In one implementation, the speaker and microcontroller, both of which may consume mWs of power, will only work when the low-power sensor(s) (such as micro-vibration sensor 312, which operates on the order of ~µWs) detect a signal over the threshold level. For instance, for sound monitoring, since most of the time the output of the microphone 1524 is just background noise, instead of activating the microcontroller and analyze the sound all the time, proximity sensing-output generating device 1520 may include a hardware comparator to check the sound level, awakening the microcontroller only when the detected sound level is over a threshold.

Figure 15C:
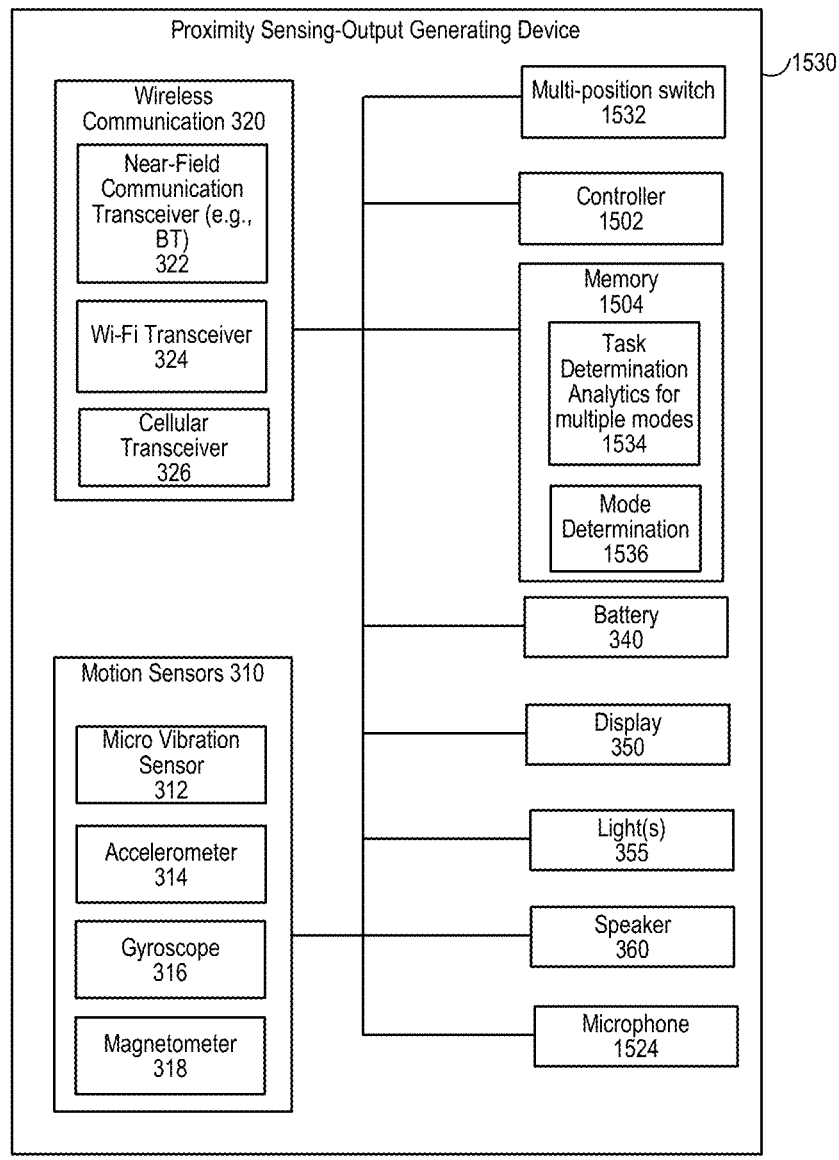
FIG. 15C is a third example block diagram of a proximity sensing-output generating device.

FIG. 15C is a third example block diagram of a proximity sensing-output generating device 1530. As discussed above, the proximity sensing-output generating device may be placed in different parts of the premises, such as the kitchen, the bathroom, the front door, etc. The tasks monitored and/or the output generated may be different depending on the placement, such as toileting for the bathroom, food preparation for the kitchen, and going outdoors for the front door. For example, with regard to the placement in the bathroom, the controller 1502, using the task determination analytics for multiple modes 1534, may determine that the placement is in the bathroom and whether a task specific to the bathroom (toilet flushing or faucet running water) is being performed based on comparing the sound generated by the microphone with pre-recorded sound(s). Further, responsive to determination that a specific task is occurring (e.g., using the toilet in the bathroom), the proximity sensing-output generating device 1530 may generate an output specific to the specific task (e.g., "remember to flush the toilet after use").

The proximity sensing-output generating device 1530 may determine the placement of the proximity sensing-output generating device 1530 in one of several ways. In one way, the proximity sensing-output generating device 1530 may include a multi-position switch 1532. The multi-position switch 1532 may be placed on an external housing of a proximity sensing-output generating device 1530. The multi-position switch 1532 may have two positions, three positions, or more. The different positions of the multi-position switch 1532 may be correlated to different placements. For example, when the multi-position switch 1532 is set to the first position, this is indicative to controller 1502, using mode determination 1536, that the proximity sensing-output generating device 1530 is positioned in the kitchen. Responsive to determining that the proximity sensing-output generating device 1530 is positioned in the kitchen, the controller 1502 may determine the task(s) for monitoring and the output(s) to generate. When the multi-position switch 1532 is set to the second position, this is indicative to controller 1502, using mode determination 1536, that the proximity sensing-output generating device 1530 is positioned in the bathroom. When the multi-position switch 1532 is set to the third position, this is indicative to controller 1502, using mode determination 1536, that the proximity sensing-output generating device 1530 is positioned on the front door. The example positions of the multi-position switch 1532 are merely for illustration purposes. In another way, the proximity sensing-output generating device 1530 may receive a communication via wireless communication 320 indicative of the placement of the proximity sensing-output generating device 1530. The communication may be sent via the Internet, such as via electronic device 1630, discussed further below.

Figure 16A:
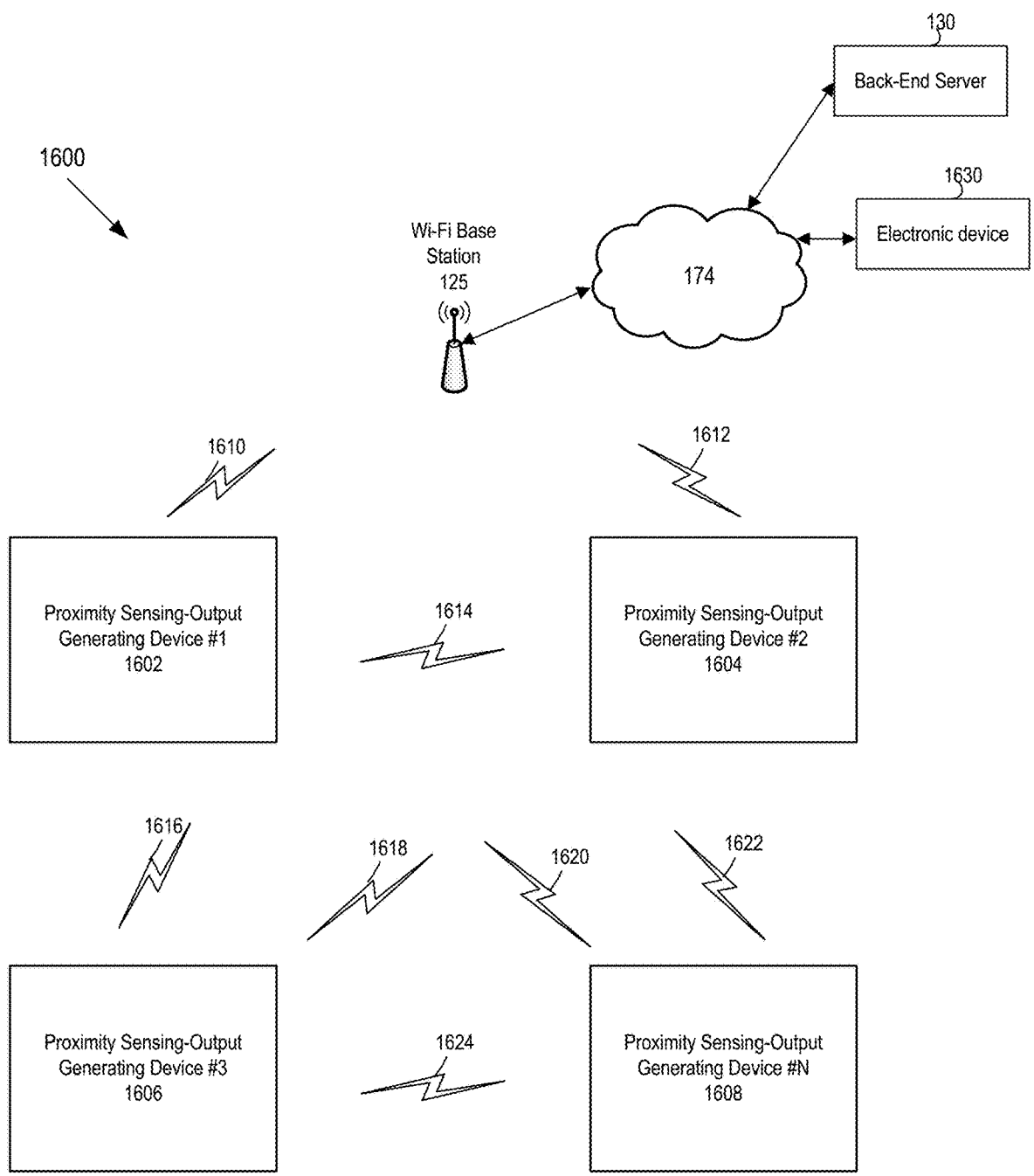
FIG. 16A is a first example block diagram of a system that uses a plurality of a proximity sensing-output generating devices.

FIG. 16A is a first example block diagram of a system 1600 that uses a plurality of a proximity sensing-output generating devices, including proximity sensing-output generating device #1 (1602), proximity sensing-output generating device #2 (1604), proximity sensing-output generating device #3 (1606), and proximity sensing-output generating device # N (1608). Any number of proximity sensing-output generating devices may be used and may be placed in various parts of the premises. As discussed above, the proximity sensing-output generating device may include wireless communication functionality. In that regard, the proximity sensing-output generating devices may communicate wirelessly amongst themselves or with base station 125. For example, proximity sensing-output generating device #1 (1602) may communicate wirelessly via 1610 with base station 125, via 1614 with proximity sensing-output generating device #2 (1604), via 1616 with proximity sensing-output generating device #3 (1606), and via 1620 with proximity sensing-output generating device #4 (1608). Similarly, proximity sensing-output generating device #2 (1604) may communication wirelessly via 1612 with base station 125, via 1618 with proximity sensing-output generating device #3 (1606) and via 1622 with proximity sensing-output generating device #4 (1608). The wireless communications illustrated in FIGS. 16A-B are merely for illustration purposes.

As discussed above, the proximity sensing-output generating device that monitors the task may be the same proximity sensing-output generating device that generates the output (e.g., the vocal reminder). Alternatively, or in addition, the proximity sensing-output generating device may send a communication to an external device (such as another proximity sensing-output generating device located in the same premises and/or an electronic device remote from the premises). As one example, responsive to determining that the person has likely left the part of the premises where the task is being monitoring (e.g., the water in the faucet is continuing to run, likely meaning that the person left the bathroom and is in another part of the premises), the proximity sensing-output generating device may send a communication, such as a wireless communication, to another proximity sensing-output generating device in order for the another proximity sensing-output generating device to generate an output (e.g., "please return to the bathroom to turn off the water in the faucet). As another example, the proximity sensing-output generating device may monitor the front door of the premises. Responsive to determining that a person has exited the premises, the proximity sensing-output generating device may send (e.g., via the Internet or a cellular communication) an alert to an electronic device (e.g., a smartphone) external to the premises, with the alert indicating: "the resident has left the premises". In this way, the smart voice reminder device sends real-time notification to mobile electronic devices and can be easily integrated into smart home network through Bluetooth low energy (BLE) wireless communication.

Figure 16B:
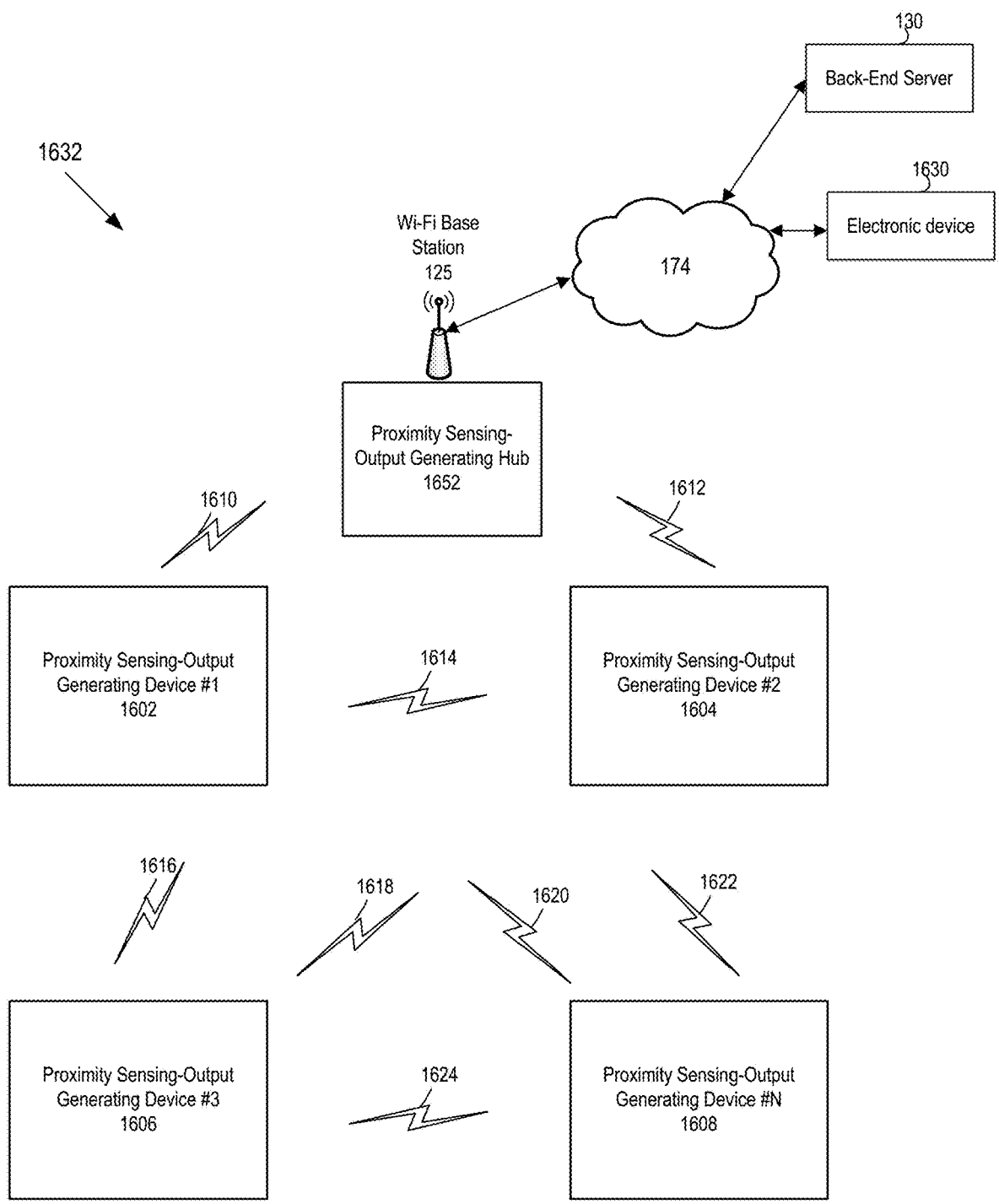
FIG. 16B is a second example block diagram of a system that uses a plurality of a proximity sensing-output generating devices.

FIG. 16B is a second example block diagram of a system 1632 that uses a plurality of a proximity sensing-output generating devices. FIG. 16B is similar to FIG. 16A, except with the addition of proximity sensing-output generating hub 1652, which may coordinate communications amongst the different proximity sensing-output generating devices on the premises. For example, the proximity sensing-output generating hub 1652 may route communications received from one proximity sensing-output generating device to another proximity sensing-output generating device on the premises. Alternatively, or in addition, the proximity sensing-output generating hub 1652 may route communications received from one proximity sensing-output generating device to electronic device 1630, which is external to the premises (e.g., a smartphone of a family member of the person living on the premises), or to back-end server 130, which may record various tasks performed. For example, one proximity sensing-output generating device may be positioned in the bathroom (e.g., the door into the bathroom) and may record bathroom habits. This information may be sent to back-end server 130 for recording and potential subsequent analysis. As another example, one proximity sensing-output generating device may be positioned in the kitchen (e.g., the drawer for the cutlery, the cabinet door for the dishes, the refrigerator door) and may record eating habits. Similarly, this information may be sent to back-end server 130 for recording and potential subsequent analysis.

Figure 16C:
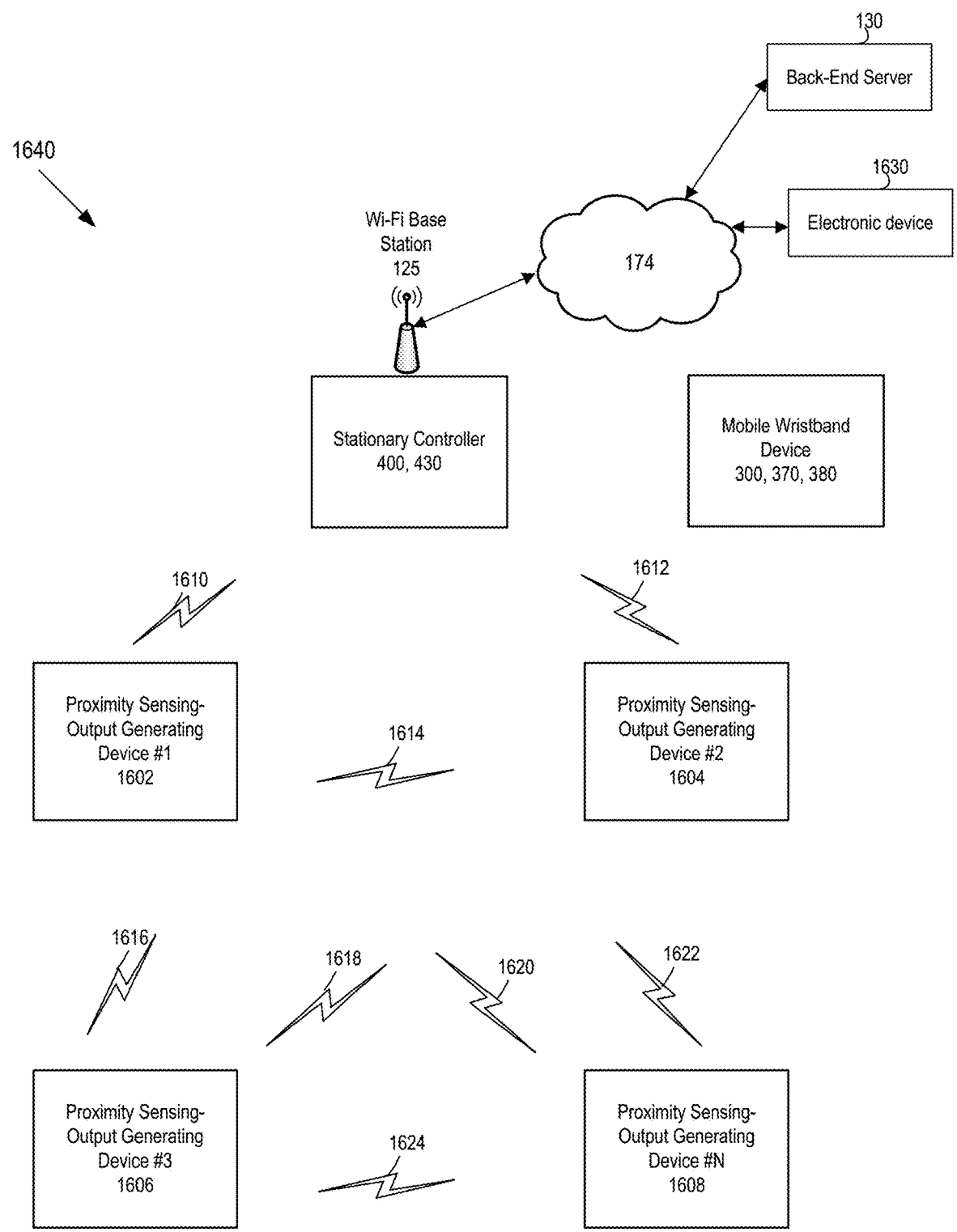
FIG. 16C is a third example block diagram of a system that uses a plurality of a proximity sensing-output generating devices, a stationary controller and a mobile wristband device.
Figure 16D:
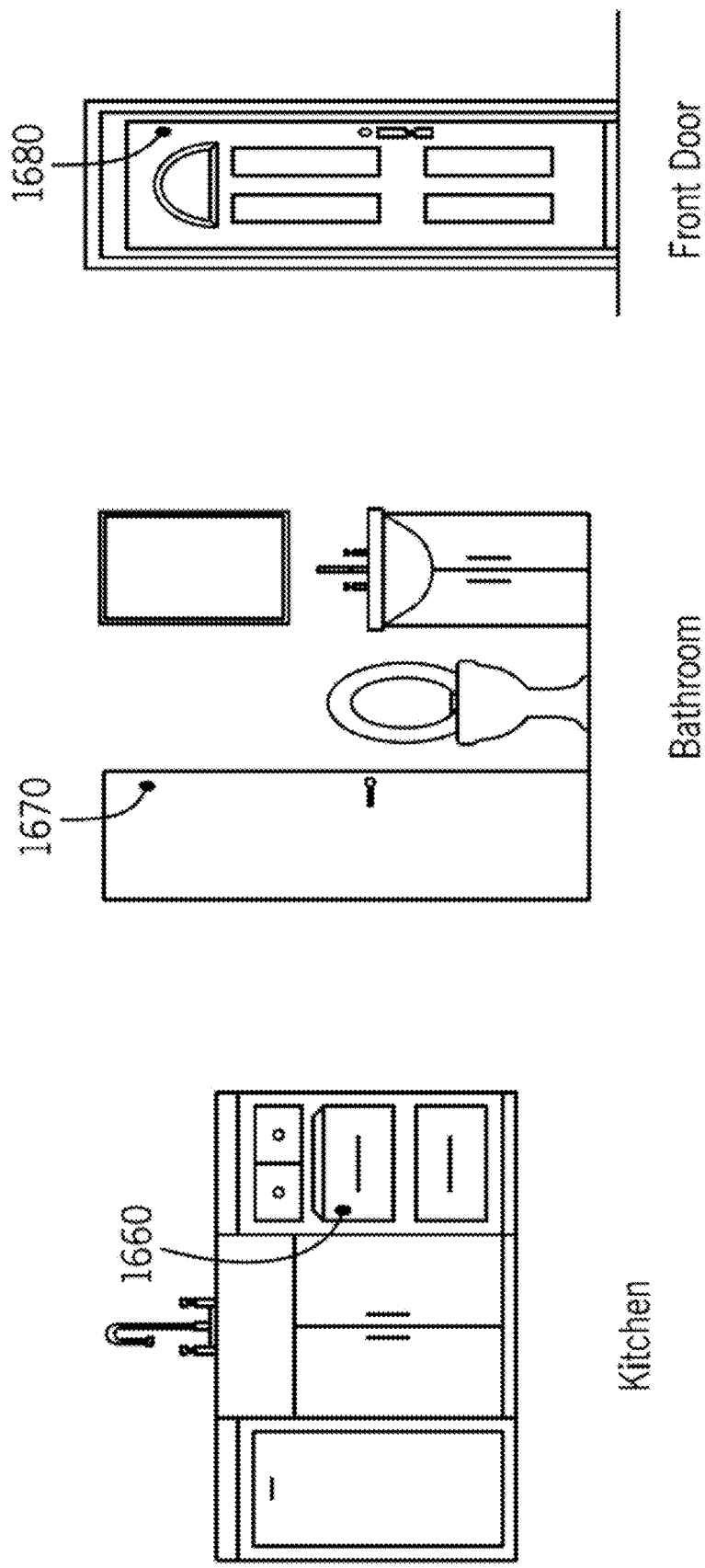
FIG. 16D are illustrations of locations in a premises where the proximity sensing-output generating device may be placed.

FIG. 16C is a third example block diagram of a system 1640 that uses a plurality of a proximity sensing-output generating devices 1602, 1604, 1606, 1608, a stationary controller 400, 430 and a mobile wristband device 300, 370, 380. For background, a healthcare provider may have 5 moments or phases with a patient: (1) before touching a patient; (2) before clean/aseptic procedure; (3) after body fluid exposure risk; (4) after touching the patient; and (5) after touching the patient surrounds. As discussed above, the stationary controller 400, 430 may identify when the healthcare provider has entered the room (such as when the RSSI signal is greater than a predetermined amount for a certain period of time). Similarly, the stationary controller 400, 430 may determine when the healthcare provider is exiting the room (e.g., after the initial identification of the healthcare provider, the stationary controller may continue to monitor the RSSI signal. When the RSSI signal increases again (presumably when the healthcare provider has finished with the patient and moves toward the door), the stationary controller may determine that the healthcare provider is exiting the room. In this way, the stationary controller may determine moments (1), (4) and (5).

Alternatively, or in addition, the proximity sensing-output generating devices 1602, 1604, 1606, 1608 may be installed at the door, thereby indicating whether the door is first being opened (so that the entrance of the healthcare provider may be identified) or whether the door is being opened again (so that the exit of the healthcare provider may be identified). In one implementation, the proximity sensing-output generating devices 1602, 1604, 1606, 1608 may be placed in a hospital room in order to determine moments (2) and/or (3). For example, the proximity sensing-output generating devices 1602, 1604, 1606, 1608 may be positioned on a drawer or a cabinet, such as a central line cart, a drawer containing medical supplies, and/or a medicine cabinet. Responsive to the proximity sensing-output generating devices 1602, 1604, 1606, 1608 sensing the drawer opening, it may be presumed that the healthcare provider is performing a procedure, such as performing a clean/aseptic procedure. In this regard, the proximity sensing-output generating devices 1602, 1604, 1606, 1608 may identify moment (2), and may generate an output (e.g., "remember to wash hands before the aseptic procedure").

Alternatively, or in addition, the proximity sensing-output generating devices 1602, 1604, 1606, 1608 may send a communication to one or both of the stationary controller 400, 430 or the wristband 300, 370, 380, with the communication indicative that the proximity sensing-output generating devices 1602, 1604, 1606, 1608 identified a drawer opening. Responsive to the communication, one or both of the stationary controller 400, 430 or wristband 300, 370, 380 may generate an output. In a first implementation, the output generated by one or both of the stationary controller 400, 430 or wristband 300, 370, 380 may be independent of the status of the person and may remind the healthcare provider to wash hands before the aseptic procedure. In a second implementation, the output generated by one or both of the stationary controller 400, 430 or wristband 300, 370, 380 may be dependent on the status of the person. As one example, if the healthcare worker is designated as a "trainee" (e.g., based on an indicator that is stored in the memory in the wristband 300, 370, 380), the output reminds the healthcare provider to wash hands before the aseptic procedure. In particular, the controller 302 may access memory 304 for an indication of the status of the healthcare worker. Responsive to the controller determining that the indication of the status is that of a trainee, the controller 302 may cause an output from the wristband 300, 370, 380. The output may be indicative to the healthcare worker as part of training for the HH event (e.g., aural output: "take soap from the dispenser") and/or for the PPE event (e.g., aural output responsive to detecting entry into a patient area: "first put on mask and then put on gloves"). In this regard, responsive to the communication between the wristband and the stationary controller identifying the HH event and/or the PPE event (and potentially before a determination as to whether there is compliance with the HH event and/or the PPE event), the wristband may generate the output. As another example, if the healthcare worker is designated as an "employee" (e.g., not a "trainee"), the stationary controller 400, 430 or wristband 300, 370, 380 may determine not to output the reminder. In this way, the stationary controller 400, 430 and/or the mobile wristband 300, 370, 380 may work in combination with the proximity sensing-output generating devices 1602, 1604, 1606, 1608 to remind the healthcare worker about hygiene protocols.

In this way, the proximity sensing-output generating devices 1602, 1604, 1606, 1608 may be installed in various parts of the patient's room, such as at the door into the patient's room, at the medicine cabinet, and/or the drawers inside a patient's room. For instance, when healthcare providers open the medicine cabinet, or a drawer of a central line cart (e.g. before an aseptic task), they will be reminded for hand hygiene. This way we can claim we can capture 4 out of 5 moments for hand hygiene. In addition, a reminder device installed on the door of the patient's room will also allow us to know better if someone is leaving the room or entering the room (being alternative or complementary to RSSI detection).

Figure 17A:
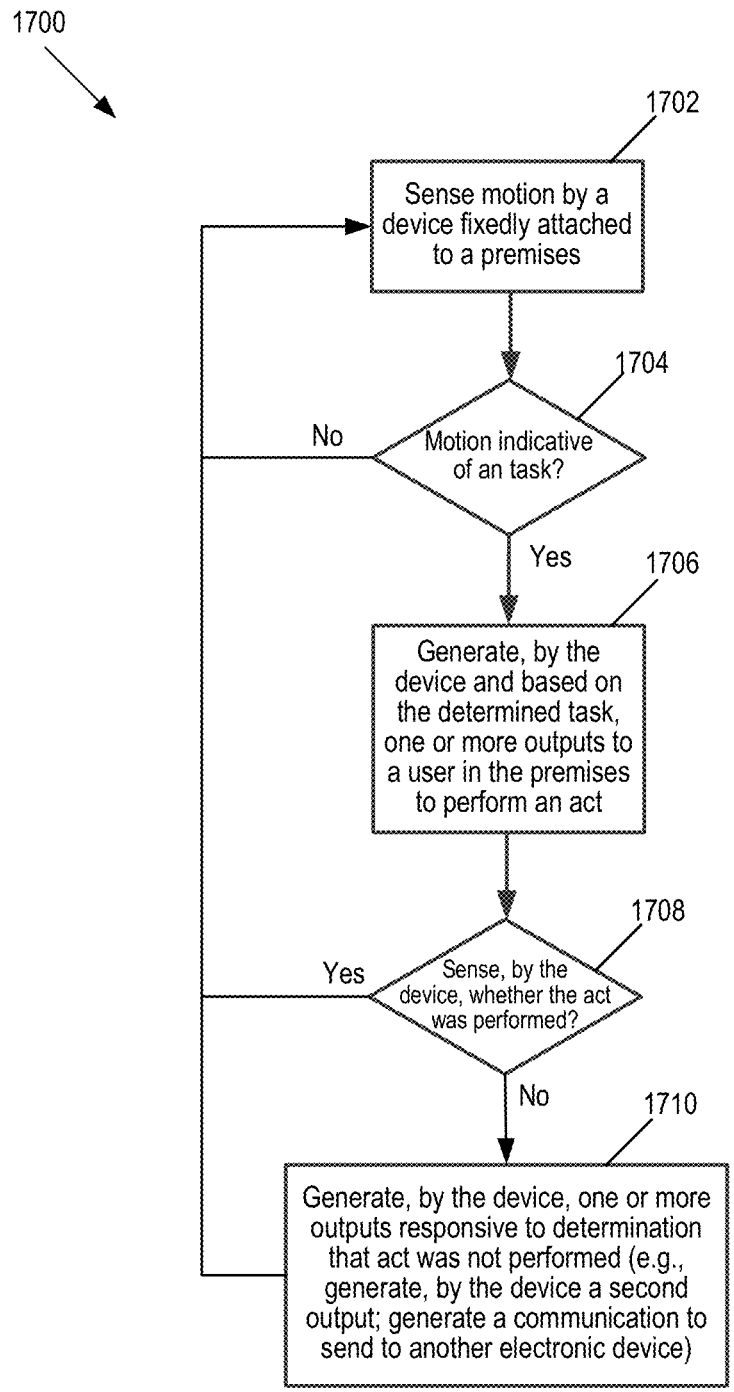
FIG. 17A is a first flow chart of operation of the proximity sensing-output generating device.

FIG. 17A is a first flow chart 1700 of operation of the proximity sensing-output generating device. At 1702, the proximity sensing-output generating device, fixedly attached to a part of the premises, may sense motion. In this way, motion sensing may begin the process of determining whether a task is being performed. Alternatively, the proximity sensing-output generating device may begin the process of determining whether a task is being performed by analyzing sound. For example, the proximity sensing-output generating device may use a microphone to generate sound data to determine whether the sound data is indicative of a person entering the bathroom (which may indicate that the person is preparing to use the toilet and should be reminded to flush the toilet and/or wash hands). As another example, the proximity sensing-output generating device may use a microphone to generate sound data to determine whether the sound data is indicative of a toilet flushing (which may indicate that the person has already used the toilet and should be reminded to wash hands). In particular, in the instance of the proximity sensing-output generating device determining, based on the sound data, that the toilet has flushed, an output may be generated, such as by the proximity sensing-output generating device and/or by another electronic device, such as a wristband (such as wristband 300, 370, 380) which may output the reminder as well. At 1704, the proximity sensing-output generating device may determine whether the sensed motion is indicative of a task, such as going to the toilet, preparing food, going outdoors, or the like. If so, at 1706, the proximity sensing-output generating device may generate an output based on the determined task, with the output indicative of performing an act (e.g., "remember to flush the toilet"; "remember to wash your hands"; "remember to turn off the water in the faucet"; "remember to take your cellphone and ID"). At 1708, the proximity sensing-output generating device may sense whether the act was performed. For example, responsive to outputting a reminder to flush the toilet, the proximity sensing-output generating device, analyzing sound data generated by a sound sensor, may determine whether the toilet was flushed. As another example, responsive to outputting a reminder to wash hands and turn off the faucet, the proximity sensing-output generating device, analyzing sound data generated by a sound sensor, may determine first whether the faucet was turned on and subsequently whether the faucet was turned off. At 1710, responsive to sensing that the act was not performed, generating one or more outputs. For example, responsive to determining that the faucet was not turned off, the proximity sensing-output generating device located in the bathroom may generate an output reminding the person to turn off the faucet. Alternatively, or in addition, the proximity sensing-output generating device may send a communication so that another proximity sensing-output generating device, such as located in the kitchen or in the main entranceway, may output the reminder to the person to turn off the faucet.

Figure 17B:
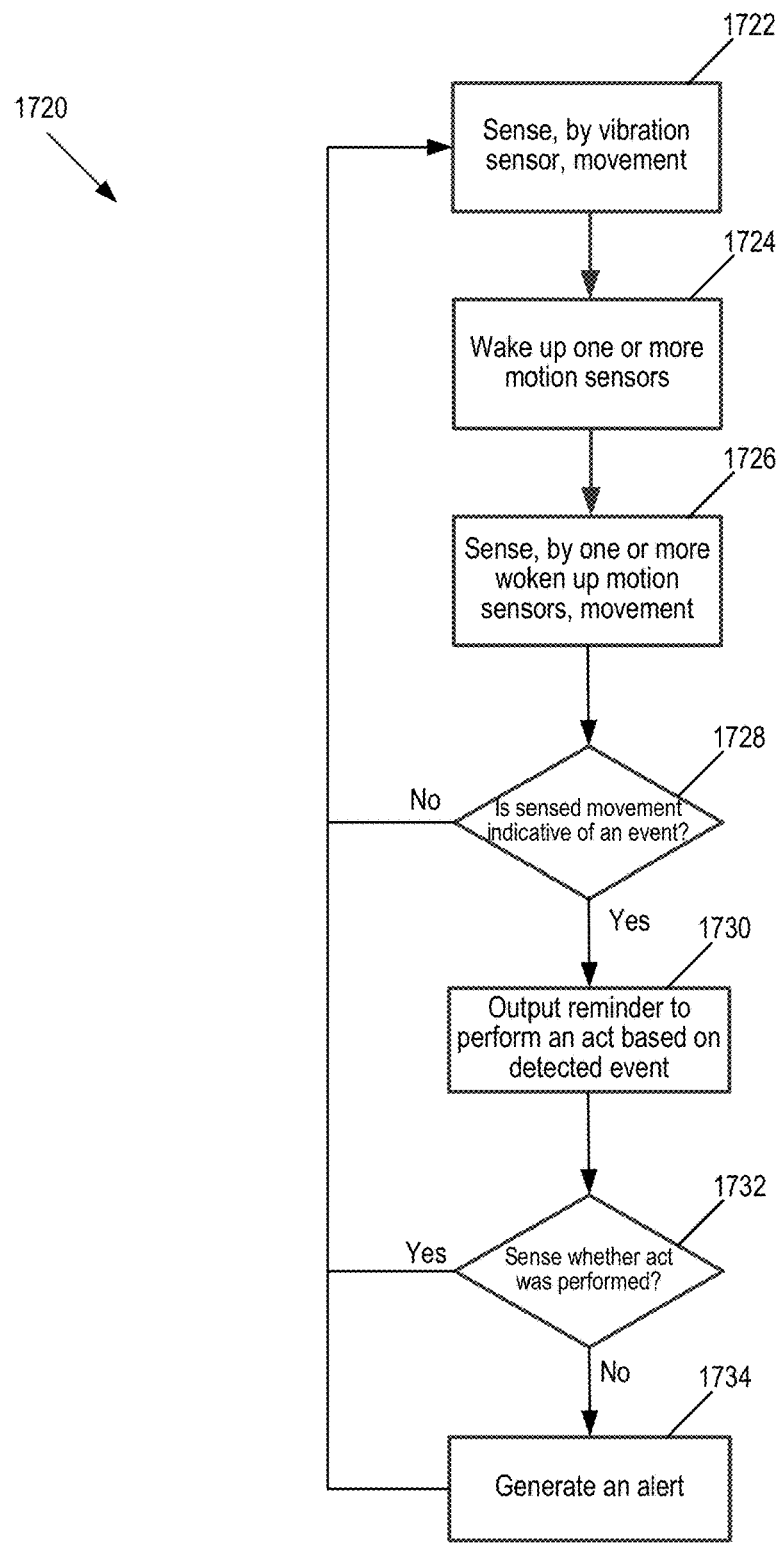
FIG. 17B is a second flow chart of operation of the proximity sensing-output generating device.

FIG. 17B is a second flow chart 1710 of operation of the proximity sensing-output generating device. At 1722, a vibration sensor of the proximity sensing-output generating device may sense movement. Responsive to sensing the vibration, at 1724, one or more of the motion sensors in the proximity sensing-output generating device may be activated (e.g., transitioned from sleep mode to normal mode). At 1726, the activated one or more motion sensors may sense movement. At 1728, the proximity sensing-output generating device may determine whether the sensed movement is indicative of a task. If so, at 1730, the proximity sensing-output generating device may output a reminder to perform an act based on the detected task. At 1732, the proximity sensing-output generating device may determine whether the act was performed. If not, at 1734, the proximity sensing-output generating device (and/or another electronic device) may generate an alert.

Figure 18A:
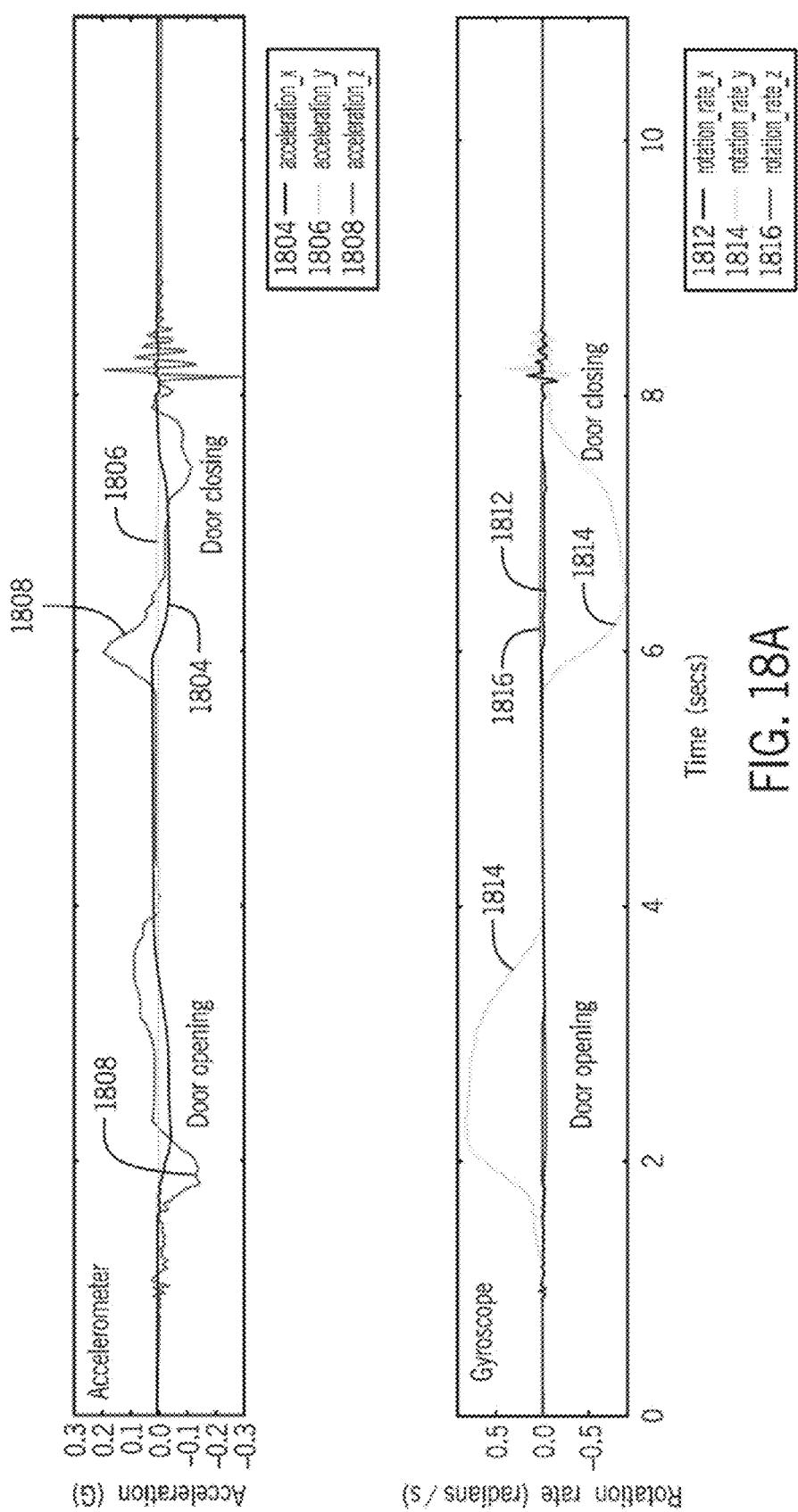
FIG. 18A are graphs of outputs of motion sensors, including an accelerometer and a gyroscope, for a door opening and a door closing.
Figure 18B:
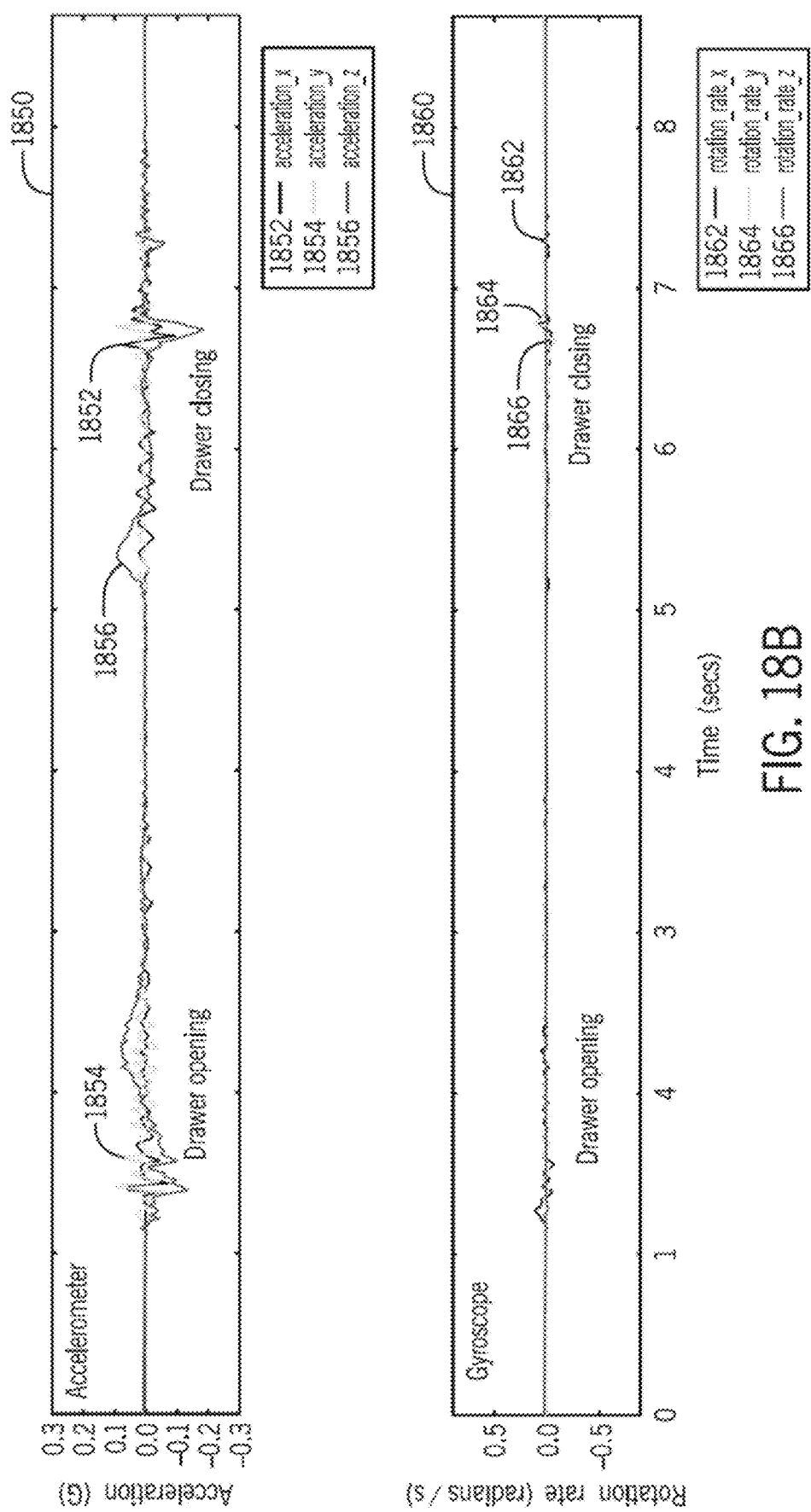
FIG. 18B are graphs of outputs of motion sensors, including an accelerometer and a gyroscope, for a drawer opening and a drawer closing.

FIG. 18A are graphs 1802, 1810 of outputs of motion sensors, including an accelerometer and a gyroscope, for a door opening and a door closing. Specifically, 1804 illustrates acceleration in the x direction, 1806 illustrates acceleration in the y direction, and 1808 illustrates acceleration in the z direction. Further, 1812 illustrates rotation rate in the x direction, 1814 illustrates rotation rate in the y direction, and 1816 illustrates rotation rate in the z direction. FIG. 18B are graphs 1850, 1860 of outputs of motion sensors, including an accelerometer and a gyroscope, for a drawer opening and a drawer closing. Specifically, 1852 illustrates acceleration in the x direction, 1854 illustrates acceleration in the y direction, and 1856 illustrates acceleration in the z direction. Further, 1862 illustrates rotation rate in the x direction, 1864 illustrates rotation rate in the y direction, and 1866 illustrates rotation rate in the z direction. For the device to send the correct voice reminder, the corresponding events may be detected. In one implementation, one or more motion sensors and/or one or more sound sensors may detect the following events: front door opening, drawer opening, running water and toilet flushing. Detection of other events is contemplated.

For example, analysis of motion sensor data may be used to determine whether a door or drawer has been opened. For example, opening a front door is an indication of going outside. As another example, opening a kitchen drawer (e.g., to get flatware) may indicate that the person has finished cooking and is preparing to eat a meal. Therefore, monitoring the events of door/drawer opening may be used to trigger outputs, such as voice messages including as "carrying your cell phone" or "wash your hand before meal and shut off fire/water". As discussed above, one or more motion sensors may be used. For example, an accelerometer may provide information on linear acceleration whereas gyroscope may measure the angular velocity rate (e.g., the rotational rate). The linear and angular motion recorded by the accelerometer and gyroscope along x-, y- and z-axis are illustrated in FIG. 18A. The waveforms indicate several aspects. For example, FIG. 18A indicates that the door opening and closing have clear acceleration on the two axes (e.g., x and z) on the rotation plane (detected by accelerometer) and angular velocity along 1 axis (detected by the gyroscope). FIG. 18B indicates that drawer movement causes linear acceleration mainly in one axis (z) and no detectable rotation. Further, FIGS. 18A-B indicate that opening and closing causes different acceleration and rotation directions. Thus, as illustrated in FIGS. 18A-B, the movement data for the door and the drawer have unique characteristics, are distinguishable, and what may be used by the proximity sensing-output generating device to identify a direction of movement (e.g., opening or closing).

Figure 19:
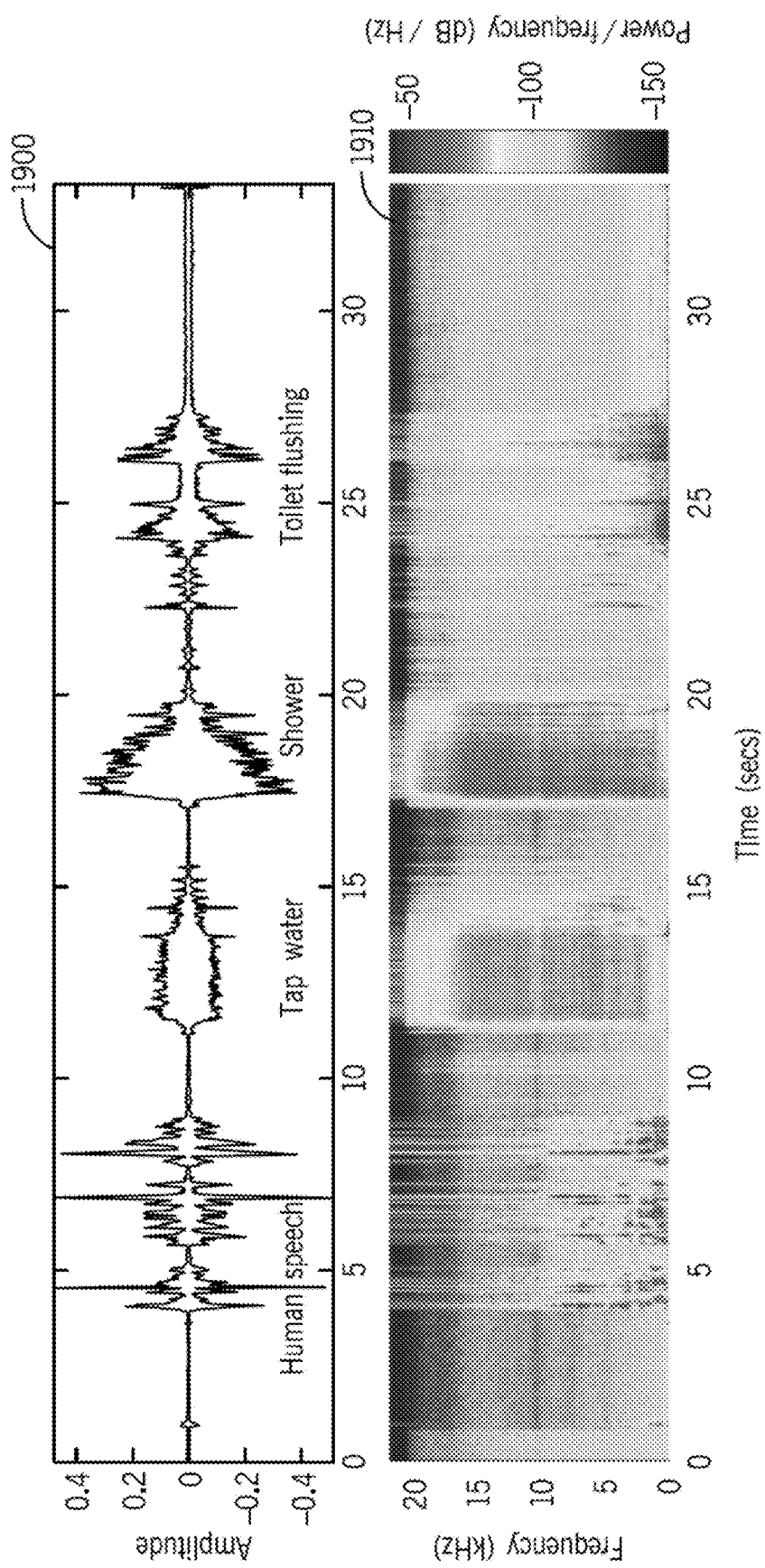
FIG. 19 are graphs of recorded waveforms of a sequence of typical sounds in a bathroom (such as human speech, tap water, shower and toilet flushing) and the corresponding spectrograms.

FIG. 19 are graphs 1900, 1910 of recorded waveforms of a sequence of typical sounds in a bathroom (such as human speech, tap water, shower and toilet flushing) and the corresponding spectrograms.

The spectrogram illustrated in FIG. 19 shows how the frequency spectrum and magnitude of a sound vary with time. The fundamental frequency of a typical voiced speech usually varies from 80 to 250 Hz (male: 80-180 Hz and female 160 to 250 Hz) with the formant frequencies usually lower than 8 KHz; running water has white-noise characteristics, where the power is almost uniformly distributed in a wide range of frequency bands. For toilet flushing measurement, the toilet tank lever was turned at 22.5 seconds in FIG. 19. The amplitude reaches to the first peak level at 24 seconds at the flushing and its second peak level around 26 seconds when the toilet valve is closed, followed by multiple seconds of water tank refilling. Thus, FIG. 19 illustrates the unique sound measurements that may be used to identify whether a specific task, such as toileting, using the shower, running the water in the faucet, is being performed.

Figure 20A:
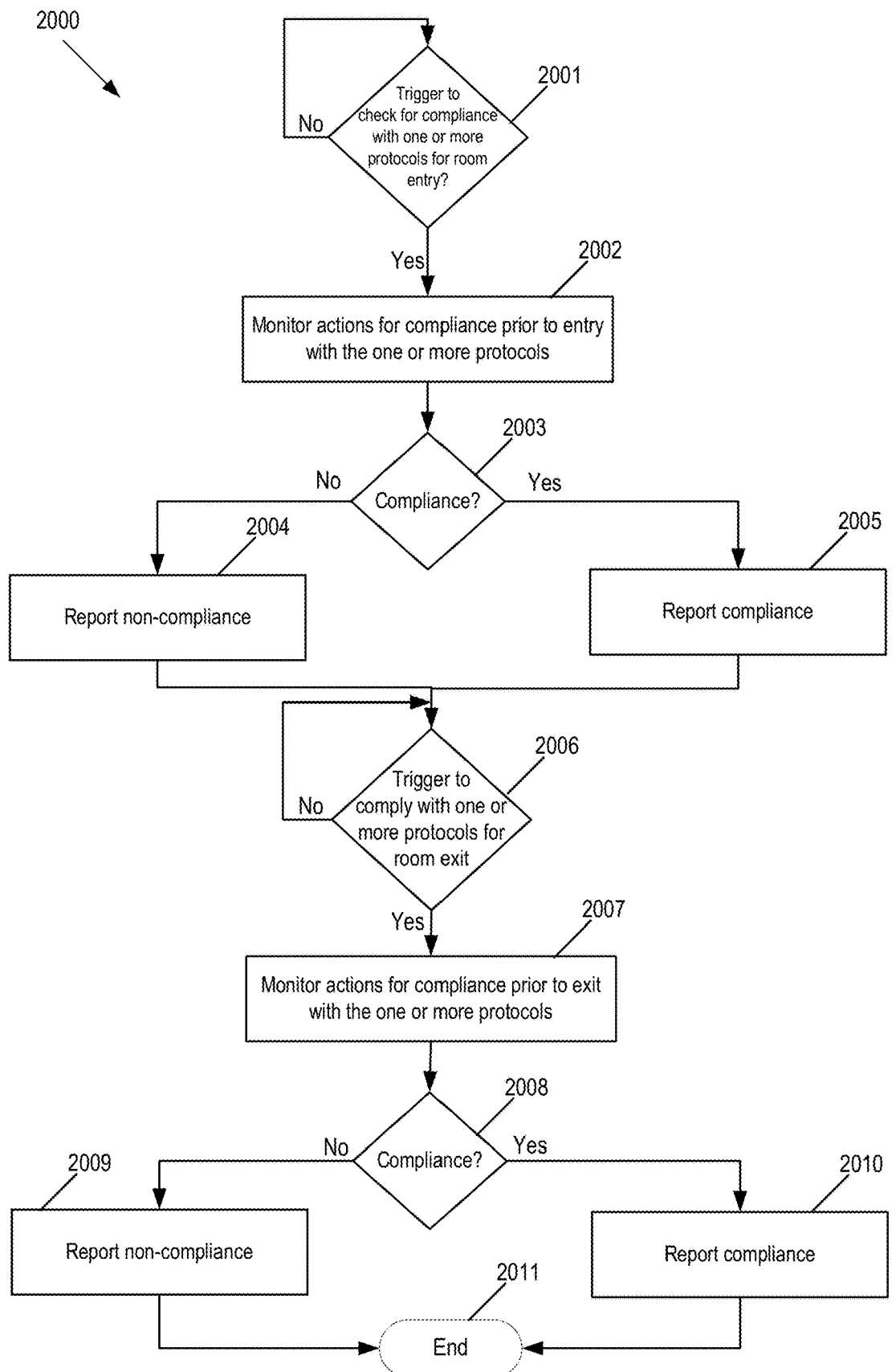
FIG. 20A is a flow chart of one example of monitoring compliance with one or more protocols when entering and exiting a patient area.

FIG. 20A is a flow chart 2000 of one example of monitoring compliance with one or more protocols when entering and exiting a patient area. As discussed above, one or more protocols may be monitored for compliance. At 2001, it is determined whether there is a trigger to check for compliance with one or more protocols for room entry. Examples of protocols include, but are not limited to, HH protocol(s) and/or PPE protocol(s). As discussed above, the stationary controller and/or the wristband may make the determination as to whether there has been a trigger to check for compliance with the one or more protocols for room entry.

At 2002, one or more actions are monitored for compliance with the one or more protocols prior to or attendant to entry. As discussed above, one or more types of actions may be monitored, such as movements of the body and/or actions taken with regard to a device (such as receiving alcohol-based formulation, turning on the faucet, or receiving soap).

At 2003, it is determined whether there is compliance with the one or more protocols for entry. If so, at 2005, the compliance is reported. There are a multitude of ways in which to report compliance, such as to output (via the wristband and/or via the stationary controller of an indication of compliance), and/or reporting the compliance to a separate electronic device (e.g., a back-end server and/or a separate mobile electronic device). If compliance is not determined, at 2003, the non-compliance is reported. Again, there are a multitude of ways in which to report non-compliance, such as to output (via the wristband and/or via the stationary controller of an indication of compliance), and/or reporting the compliance to a separate electronic device (e.g., a back-end server and/or a separate mobile electronic device, such as the chief of the nurses station).

At 2006, it is determined whether there is a trigger to comply with one or more protocols for room exit. Again, examples of protocols include, but are not limited to, HH protocol or PPE protocol. As discussed above, the stationary controller and/or the wristband may make the determination as to whether there has been a trigger to comply with the one or more protocols for room exit.

At 2007, one or more actions are monitored for compliance with the one or more protocols prior to or shortly after exit. As discussed above, one or more types of actions may be monitored, such as movements of the body and/or actions taken with regard to a device (such as receiving alcohol-based formulation, turning on the faucet, or receiving soap).

At 2008, it is determined whether there is compliance with the one or more protocols for exit. If so, at 2010, the compliance is reported. Again, there are a multitude of ways in which to report compliance, such as to output (via the wristband and/or via the stationary controller of an indication of compliance), and/or reporting the compliance to a separate electronic device (e.g., a back-end server and/or a separate mobile electronic device). If non-compliance is determined, at 2009, the non-compliance is reported. Again, there are a multitude of ways in which to report non-compliance, such as to output (via the wristband and/or via the stationary controller of an indication of compliance), and/or reporting the compliance to a separate electronic device (e.g., a back-end server and/or a separate mobile electronic device, such as the chief of the nurses station). FIG. 20A illustrates that protocol(s) are examined both upon entry to and exit from the patient area. Alternatively, protocol(s) are examined only upon entry to the patient area. In still an alternate implementation, protocol(s) are examined only upon exit from the patient area.

Figure 20B:
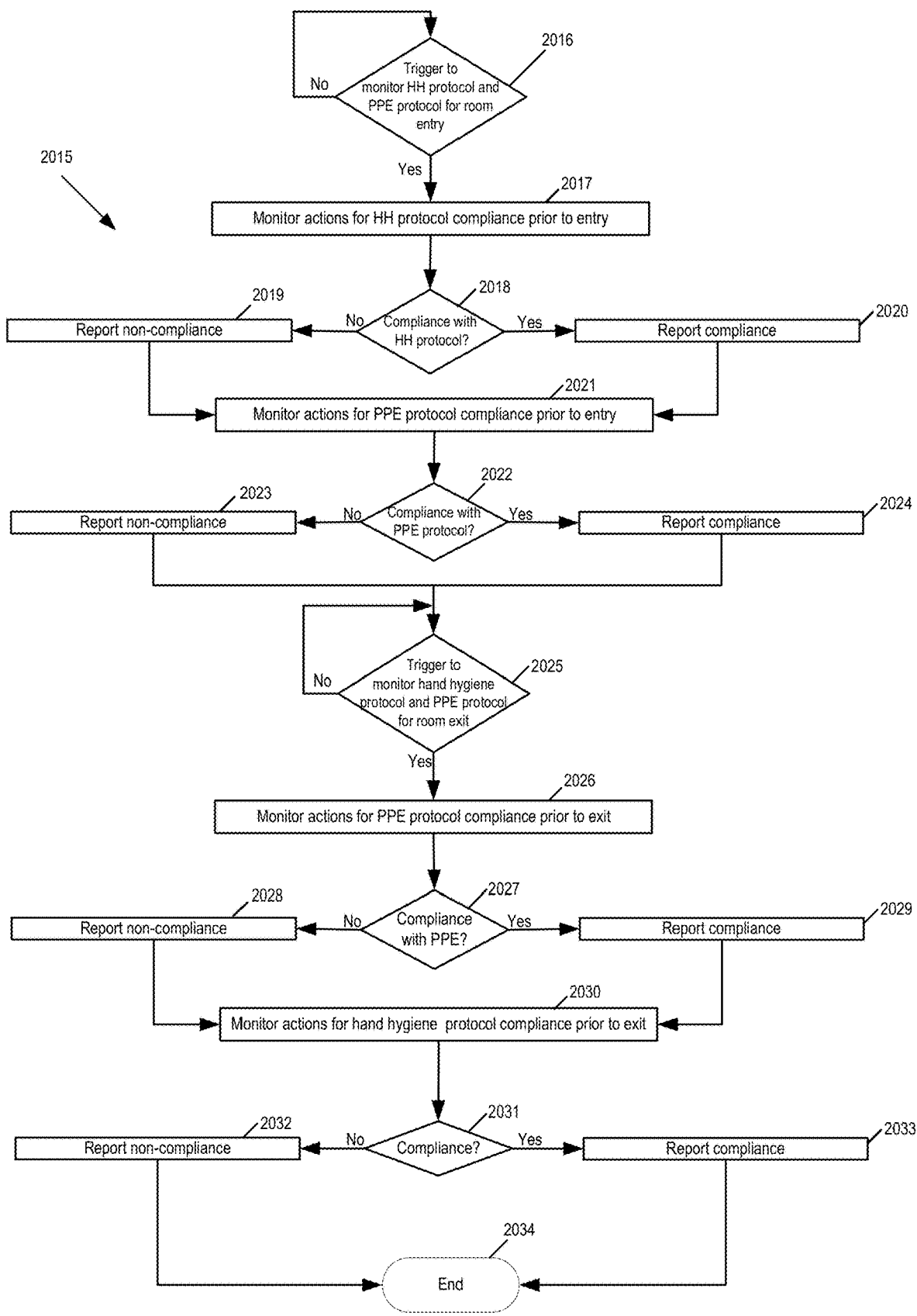
FIG. 20B is a flow chart of one example of monitoring compliance for hand hygiene (HH) and personal protective equipment (PPE) protocols for entry and exit from a patient area.

FIG. 20B is a flow chart 2015 of one example of monitoring compliance for hand hygiene (HH) and personal protective equipment (PPE) protocols for entry and exit from a patient area. At 2016, it is determined whether there has been a trigger to monitor the HH protocol and the PPE protocol for room entry. As discussed above, in one implementation, a single interaction may serve as a trigger to monitor both the HH protocol and the PPE protocol. Alternatively, separate interactions may server as respective triggers to monitor both the HH protocol and the PPE protocol.

At 2017, actions are monitored for the HH protocol compliance prior to entry. As discussed above, in certain instances, the different protocols may have a specific sequence in which to perform. For example, upon or prior to entry of the patient room, the HH protocol is to be performed prior to the PPE protocol. In this regard, FIG. 20B illustrates that movements after triggering the HH and PPE events are examined for HH protocol compliance. Movements thereafter are monitored for PPE protocol compliance.

At 2018, it is determined whether there is compliance with the HH protocol for entry. As discussed above, compliance with the HH protocol may comprise any one, any combination, or all of: determining whether hand cleaning solution has been dispensed; determining whether the proper type of hand cleaning solution has been dispensed (e.g., as discussed below, multiple types of hand cleaning solutions (such as an alcohol-based cleaning solution or soap-based cleaning solution) may be dispensed; certain HH protocols require that a specific type of handing cleaning solution be dispensed); determining whether the hand movements have been for at least a certain time period; determining whether a set of movements have been performed; or determining whether a certain sequence of movements have been performed. If not, at 2019, the non-compliance is reported. If so, at 2020, the compliance is reported. In one implementation, the reporting of compliance with the HH protocol may be silent to the healthcare provider; rather, the back-end server may receive the report of compliance for record-keeping purposes. Alternatively, the reporting of compliance with the HH protocol may be evident to the healthcare provider. For example, for a HH protocol requiring 20 seconds of rubbing, and responsive to the system determining compliance with the required 20 seconds of rubbing, an output (such as a light output and/or a sound output (aural output stating "you can now proceed to putting on your gloves") on the wristband and/or by the stationary controller) may be generated indicative of compliance with the HH protocol. In this way, the healthcare provider may receive feedback in order to proceed to the next protocol in the sequence, such as the PPE protocol. Alternatively, or in addition, responsive to determination of compliance with the HH protocol, one or more actions with regard to the PPE may be generated. As one example, responsive to determination of compliance with the HH protocol, a command may be sent to unlock a lock that housing the PPE, thereby allowing the healthcare provider to access the PPE.

Thus, as one example, one or more electronic devices (such as the stationary controller, the wristband, the stationary controller/wristband in combination) may monitor whether the specific type of hand cleaning solution, dictated by the HH protocol, has been dispensed. The one or more electronic devices may analyze the sound to determine whether the sound is indicative of a dispensing from an alcohol-based solution dispenser (which may have a certain sound) or indicative of a dispensing from a soap-based solution dispenser (which may have a different sound). Alternatively, or in addition, the one or more electronic device may analyze the sound to determine whether the sound is indicative of running water, which may indicate that the healthcare provider is using water to clean his or her hands. In a specific implementation, the one or more electronic devices may analyze whether the dispensing sound and the sound indicative of running water are contemporaneous with one another (e.g., the dispensing sound is within a predetermined time (such as 2 seconds) from the beginning of the water sound; and/or the dispensing sound is within the time that the water sound is registered). Responsive to determining that the dispensing sound and the sound indicative of running water are contemporaneous with one another, the one or more electronic devices may determine compliance with that part of the HH protocol.

At 2021, actions are monitored for the PPE protocol compliance prior to entry. At 2022, it is determined whether there is compliance with the PPE protocol for entry. If not, at 2023, the non-compliance is reported. If so, at 2024, the compliance is reported. In one implementation, the reporting of compliance with the PPE protocol may be silent to the healthcare provider; rather, the back-end server may receive the report of compliance for record-keeping purposes. Alternatively, the reporting of compliance with the PPE protocol may be evident to the healthcare provider. For example, for a PPE protocol requiring removal of gloves, and responsive to the system determining compliance with the removal of gloves, an output (such as a light output and/or a sound output (aural output stating "you can now proceed to washing your hands") on the wristband and/or by the stationary controller) may be generated indicative of compliance with the PPE protocol. In this way, the healthcare provider may receive feedback in order to proceed to the next protocol in the sequence, such as the HH protocol.

At 2025, it is determined whether there has been a trigger to monitor the HH protocol and the PPE protocol for room exit. Similar to entering, for exiting, there may be a sequence for following the multiple protocols. As one example, in one implementation, upon exiting, the PPE protocol are to be followed prior to the HH protocol. In particular, when the healthcare provider is wearing latex rubber gloves, the first movement at exit is removal of the gloves. In this regard, the sequence of monitoring the protocols upon exit is the reverse as the sequence upon entry.

At 2026, actions are monitored for the PPE protocol compliance prior to exit. At 2027, it is determined whether there is compliance with the PPE protocol for exit. If not, at 2028, the non-compliance is reported. If so, at 2029, the compliance is reported.

At 2030, actions are monitored for the HH protocol compliance prior to exit. At 2031, it is determined whether there is compliance with the HH protocol for exit. If not, at 2032, the non-compliance is reported. If so, at 2033, the compliance is reported. After which, flow chart 2015 ends at 2034.

Thus, in one implementation, the stationary controller is programmable, based on a specific patient in the patient area, for a specific PPE action and/or a specific HH action. Responsive to interaction of the wristband with the stationary controller, the wristband receives from the stationary controller, the specific PPE action and/or the specific HH action responsive to identifying the PPE event and/or responsive to identifying the HH event. The mobile electronic device may determine, based on the specific PPE action and/or the specific HH action received from the stationary controller and the stored motion data (motion data generated by and stored in the wristband), one or both of compliance or non-compliance with regard to the PPE event and/or the HH event.

Figure 21:
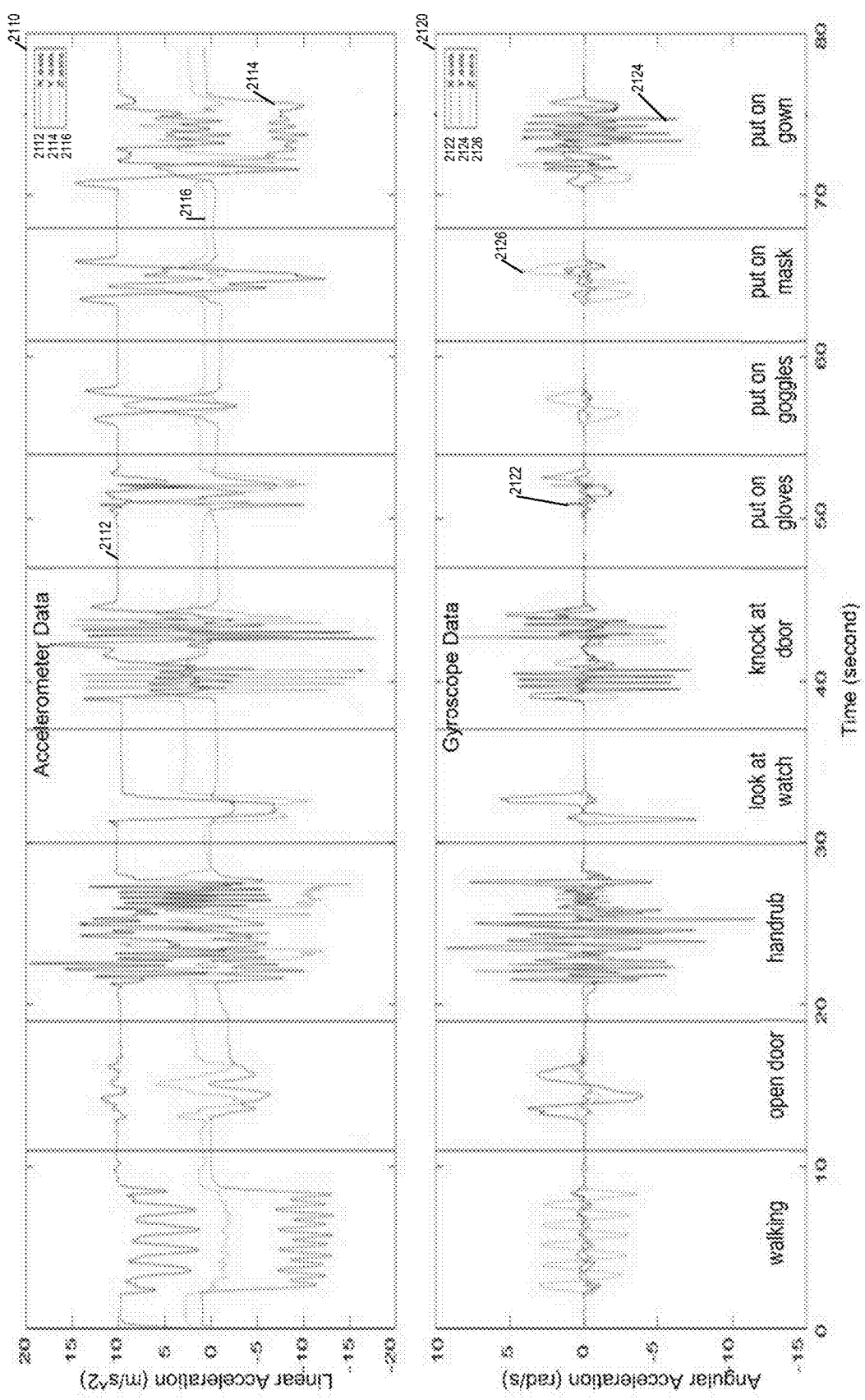
FIG. 21 are graphs of outputs of motion sensors, including an accelerometer and a gyroscope, for donning PPE motions and interfering motions measured by accelerometer (upper) and gyroscope (lower).

In one implementation, the stationary controller that is associated with the specific patient in the patient area, may be programmed with one or more specific PPE indicators and/or one or more specific HH indicators. For example, the specific PPE indicators may be indicative of specific PPE, such as one or both of specific PPE movements (such as illustrated in FIG. 21) or specific PPE (e.g., putting on a gown is coded with a "0001"; taking off a gown is coded with a "0010"; putting on gloves is coded with "0011", etc.). As another example, the specific HH indicators may be indicative of specific HH, such as one or both of specific HH movements (such as illustrated in FIG. 7) or specific HH (e.g., using ABHR is coded with a "1000"; using soap/water is coded with a "1001"; etc.).

In practice, the wristband may store in its memory a table that correlates a plurality of PPE indicators with respective movement markers. Each of the plurality of PPE indicators correlates to one or both of a respective PPE movement or a respective PPE. The respective movement markers indicative of the one or both of the respective PPE movement or the respective PPE (e.g., the code "0001" may be correlated to one or more movement markers indicative of putting on a gown). Thus, using the table, glove movements may be associated with the glove indicator, mask movements may be associated with the mask indicator, gown movements may be associated with the gown indicator, and protective eyewear movements may be associated with the protective eyewear indicator. The wristband may receive the specific PPE indicators programmed for the specific patient room. For example, the healthcare provider must use gloves and a gown; hence, the stationary controller is programmed to send codes "0001" and "0011" to the wristband (which is a subset of the all of the correlated movements (i.e., the mask code and the protective eyewear codes are not sent). Responsive to receipt of the codes "0001" and "0011", the wristband uses the table to access the respective movement markers (e.g., the movement markers for putting on the gown and the movement markers for putting on gloves), and determines, using the movement data that was generated and stored in the wristband, whether there is compliance with the PPE protocol. In a specific implementation, the stationary controller may arrange the codes in a specific sequence in order to indicate to the wristband a specific sequence that the movements should be performed. In the example given above, the stationary controller may arrange the codes as "0001" and thereafter "0011" to indicate to the wristband that the wristband should check whether movements associated with putting on the gown were performed prior to the movements associated with putting on the gloves.

Thus, in one implementation, the wristband, in its determination of compliance or non-compliance with PPE protocols, may be dependent on the stationary controller. In one implementation, the wristband may determine compliance or non-compliance with regard to the HH event based on its stored sensor data and without reliance on any indication from the stationary controller of sequence of HH movement or the HH movement. Specifically, the wristband may be programmed to perform the HH compliance determination responsive to identifying the HH event, without anything further from the stationary controller.

Figure 20C:
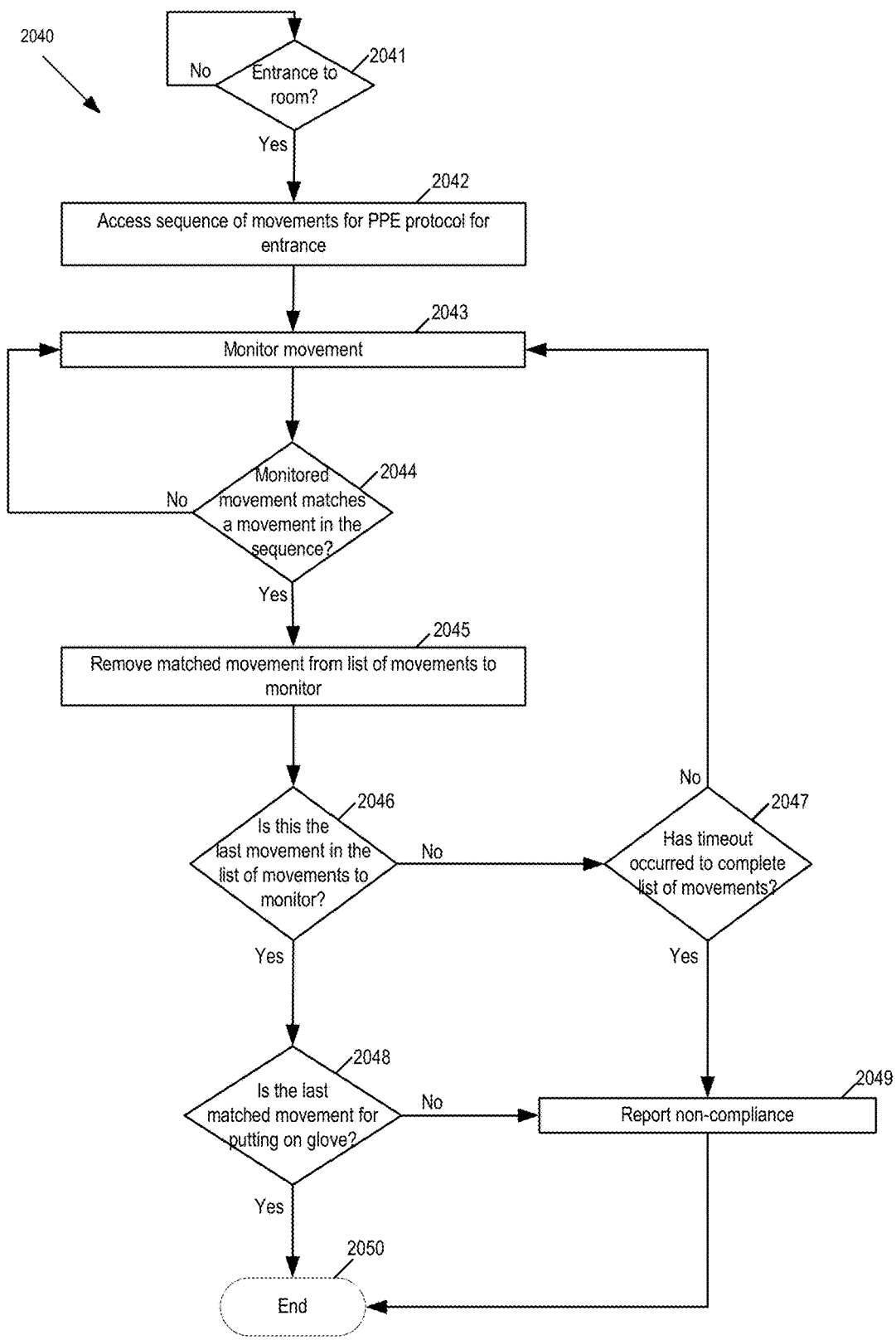
FIG. 20C is a flow chart of one example of monitoring PPE protocols for entry into a patient area.

FIG. 20C is a flow chart 2040 of one example of monitoring PPE protocols for entry into a patient area. At 2041, it is determined whether the healthcare provider has approached the entrance or entered a room, such as a particular patient's room. If so, at 2042, the sequence of movements for the PPE protocol at entrance are accessed. As discussed above, different patients may have different PPE protocols. An example table of the different protocols are shown below:

| Scenario | Isolation Precaution | ABHR or Soap/Water | PPE |
| --- | --- | --- | --- |
| Patient with Methicillin-resistant *Staphylococcus aureus* (MRSA) in a first patient situation (e.g., would to particular body part necessitating certain precautions and dressings) | Standard Precautions; Contact Precautions | ABHR | Glove Gown Face Shield or mask and goggles |
| Patient with pneumonia caused by a certain drug resistant bacteria | Standard Precautions; Contact Precautions | ABHR | Glove Gown |
| Patient with urinary tract infection caused by a first bacterium exhibiting certain symptoms | Standard Precautions; Contact Precautions | ABHR | Glove Gown |

| Scenario | Isolation Precaution | ABHR or Soap/Water | PPE |
| --- | --- | --- | --- |
| Patient with active diarrhea (>3 loose stools in 24 hours) with positive stool culture for a second bacterium | Standard Precautions; Contact Precautions | Soap and water | Glove Gown |
| Patient with influenza Type A with heavy cough and requiring particular treatments | Standard Precautions; Droplet Precautions | ABHR | Glove Gown Surgical Mask |
| Pediatric Patient with adenovirus with certain symptoms and having a particular bacterial infection | Standard Precautions; Contact Precautions; Droplet Precautions | ABHR | Glove Gown Surgical Mask |
| Patient arriving at Emergency Department with vomiting and diarrhea. A certain virus is suspected due to outbreak in community. | Standard Precautions; Contact Precautions; Droplet Precautions | Soap and Water | Glove Gown Surgical Mask |

As shown above, patients with different illnesses may require different precautions, such as standard precautions, contact precautions, and/or droplet precautions. Further, the different illnesses may necessitate different types of hand hygiene, such as in certain instances using ABHR or soap/water for hand hygiene. In addition, the different illnesses may necessitate different types of personal protective equipment (e.g., gloves, gown, surgical mask, face shield, goggles, etc.).

The determination as to the type of HH protocol (e.g., ABHR or soap/water) and/or the PPE protocol may be performed in one of several ways. In one way, a specific area (such as a room) may be assigned a particular patient (e.g., patient #3357). The HH protocol and/or the PPE protocol may be correlated to the specific area (which is in turn correlated to the particular patient). Alternatively, the HH protocol and/or the PPE protocol may be correlated directly to the particular patient. Thus, responsive to a healthcare provider entering and/or exiting the specific area, the HH protocol and/or PPE protocol may be accessed.

In either implementation, the HH protocol and/or the PPE protocol for the particular patient may be manifested by using particular patient HH indicators and/or particular patient PPE indicators. Merely by way of example, and not to be interpreted as limiting, ABHR may be assigned indicator="0" and soap/water may be assigned indicator="1". The stationary controller for the room of the particular patient may be programmed, such as by back-end server 130, with the particular patient HH indicator (either "0" for ABHR or "1" for soap/water) based on the needs of the particular patient.

In practice, when the wristband communicates with the stationary controller, the stationary controller may send the particular patient HH indicator. Responsive to receipt, the wristband may access a table (or other type of memory construct that correlates HH indicators with corresponding movements. In the given example, the memory in the wristband may store a correlation of "0" for ABHR with one or more movement markers associated with the movements for ABHR. Likewise, the memory in the wristband may store a correlation of "1" for soap/water with one or more movement markers associated with the movements for using soap/water for cleaning the hands of the healthcare provider. Thus, responsive to receipt of a "0" (indicative of ABHR), the wristband may access the one or more movement markers associated with the movements for ABHR in order for the wristband to check whether the movements registered by the sensors on the wristband match with the movement markers associated with the movements for ABHR. Conversely, responsive to receipt of a "1" (indicative of soap/water), the wristband may access the one or more movement markers associated with the movements for soap/water in order for the wristband to check whether the movements registered by the sensors on the wristband match with the movement markers associated with the movements for soap/water.

Again, merely by way of example, and not to be interpreted as limiting, PPE may include: gloves; mask; gown; and goggles. Gloves may be assigned indicator="2"; mask may be assigned indicator="3"; gown may be assigned indicator="4"; and goggles may be assigned indicator="5". The stationary controller for the room of the particular patient may be programmed, such as by back-end server 130, with the particular patient PPE indicator (any one, any combination or all of: "2" for gloves; "3" for mask; "4" for gown; or "5" for goggles) based on the needs of the particular patient.

In practice, when the wristband communicates with the stationary controller, the stationary controller may send the particular patient PPE indicator(s). Responsive to receipt, the wristband may access a table or other type of memory construct that correlates PPE indicators with corresponding movements. In the given example, the memory in the wristband may store: a correlation of "2" for gloves with one or more movement markers associated with the movements for putting on and/or removing gloves; a correlation of "3" for mask with one or more movement markers associated with the movements for putting on and/or removing a mask; a correlation of "4" for gown with one or more movement markers associated with the movements for putting on and/or removing a gown; and a correlation of "5" for goggles with one or more movement markers associated with the movements for putting on and/or removing goggles. Thus, responsive to receipt of a "2" (indicative of gloves), the wristband may access the one or more movement markers associated with the movements for gloves in order for the wristband to check whether the movements registered by the sensors on the wristband match with the movement markers associated with the movements for gloves. Responsive to receipt of a "2" and a "3" (indicative of gloves and mask), the wristband may access the one or more movement markers associated with the movements for gloves and for a mask in order for the wristband to check whether the movements registered by the sensors on the wristband match with the movement markers associated with the movements for gloves and with the movements for mask. In one implementation, the sequence of the indicators (with "2" included after "3") is indicative that the movement for gloves should be checked after checking for the movements for the mask. Further, the receipt of fewer than all of the PPE indicators (such as "2" and "3") results in the wristband checking for fewer than all of the PPE movements stored in the wristband (e.g., checking for movements for gloves and mask, but not checking for movements for gown and goggles).

Alternatively, different PPE indicators may be received based on entrance into and/or exit from the patient area. As one example, putting on gloves may be assigned indicator="2"; putting on mask may be assigned indicator="3";

putting on gown may be assigned indicator="4"; putting on goggles may be assigned indicator="5"; removing gloves may be assigned indicator="6"; removing mask may be assigned indicator="7"; removing gown may be assigned indicator="8"; and removing goggles may be assigned indicator="9". Responsive to receipt of the specific PPE indicator(s), the wristband may check whether the respective PPE movements have been detected.

Further, the device which performs the determination as to whether the protocol has been followed may receive an indication as to the protocol in one of several ways. In one implementation, the wristband performs the determination as to whether the protocol has been followed. In a first specific implementation, the wristband may receive from the stationary controller the indication as to what protocols to monitor.

In particular, multiple HH protocols and/or multiple PPE protocols may be resident in the wristband. For example, the ABHR protocol and the soap/water protocol (including associated movements indicating compliance with the ABHR protocol and the soap/water protocol) may be resident within the wristband. As another example, different PPE protocols may be resident within the wristband. In particular, the wristband may include a putting on glove protocol (such as movements indicative of putting on a glove); removing a glove protocol (such as movements indicative of removing a glove); a putting on a gown protocol (such as movements indicative of putting on a gown); a removing a gown protocol (such as movements indicative of removing a gown); a putting on face shield protocol (such as movements indicative of putting on a face shield); a removing a face shield protocol (such as movements indicative of removing a face shield); a putting on mask protocol (such as movements indicative of putting on a mask); a removing mask protocol (such as movements indicative of removing a mask); a putting on goggles protocol (such as movements indicative of putting on goggles); a removing goggles protocol (such as movements indicative of removing goggles).

In practice, the stationary controller may receive an indication from a separate electronic device (such as back-end server 130) as to the protocols to follow for a specific patient area (such as a specific room in a hospital). For example, a first specific patient area may be subject to ABHR protocol and subject to mask protocol and gloves protocol, and a second patient area may be subject to soap/water protocol and subject to gown protocol and gloves protocol. The back-end server 130 may transmit the protocols to the respective stationary controllers (e.g., transmit to the first stationary controller, associated with the first specific patient area, an indication that the ABHR protocol, the mask protocol and the gloves protocol are to be followed; transmit to the second stationary controller, associated with the second specific patient area, an indication that the soap/water protocol, the gown protocol and the gloves protocol are to be followed).

Responsive to the interaction of the wristband with the stationary controller, the stationary controller may send the specific HH protocol and/or specific PPE protocol to the wristband (such as whether ABHR or soap/water is used or whether all or a subset of the PPE are used). Thus, in the example give above, the first stationary controller may transmit to the wristband an indication that the ABHR protocol, the mask protocol and the gloves protocol to be followed. Alternatively, responsive to interaction with the stationary controller, the wristband may communicate directly with the back-end server in order to receive the indication of the protocols to follow (e.g., responsive to interacting with the first stationary controller, the wristband communicates with the back-end server 130 (with the communication having a field indicating the stationary controller) requesting the protocols associated with the room for the first stationary controller). Thus, the wristband may have stored therein a set of HH protocols and/or a set of PPE protocols. Responsive to interaction with another device (such as the stationary controller and/or the back-end server), the wristband may access a subset of the set of HH protocols (e.g., less than all of the HH protocols stored in the wristband) and/or access a subset of the set of PPE protocols (e.g., less than all of the PPE protocols stored in the wristband).

In one implementation, both the movements and a sequence of the movements are monitored. As one example with regard to PPE upon entrance, the gloves are put on last. If there are other PPE to be used, such as putting on gowns, mask, etc., movements associated with those other PPE may be performed in any sequence prior to the last step of putting on the gloves. Optionally, movements other than for PPE (such as hand sanitizing) may be monitored as well. For example, taking an alcohol-based sanitizer or soap, and performing hand movements consistent with hand washing may be monitored prior to monitoring for any PPE movements.

As discussed above, in one implementation, upon entry to a patient room, the healthcare provider is to perform hand hygiene (either using ABHR or soap/water) and thereafter perform one or more PPE movements. In this regard, after identifying the entry of the healthcare provider into the room, sensor data from the one or more sensors configured to indicate movement may be stored. The stored sensor data may thereafter be examined by comparing the stored sensor data with predetermined movements, such as predetermined hand hygiene movements and/or predetermined PPE movements. Alternatively, upon entry to a patient room, the healthcare provider is to perform one or more PPE movements. In this regard, after identifying the entry of the healthcare provider into the room, sensor data from the one or more sensors configured to indicate movement may be stored. The sensor data may thereafter be examined for comparison with predetermined movements, such as predetermined PPE movements.

Referring back to FIG. 20C, at 2043, the movement is monitored. At 2044, it is determined whether the monitored movement matches the movement in the designated sequence. In this regard, the monitored movement may be matched with one or both of predetermined hand movements or predetermined PPE movements. At 2045, the matched movement is removed from the list of movements. For example, responsive to the identifying a match with the putting on a gown movement, that matched movement is removed from the list of movements to be tracked.

At 2046, it is determined whether all of the movements in the list of movements for tracking have been matched. If not, at 2047, it is determined whether a timeout has occurred. The timeout may be a predetermined time period, such as 30 seconds or 1 minute after identifying the entrance of the healthcare provider. If the timeout has occurred, at 2049, the non-compliance is reported. In this instance, the non-compliance may be reported in one of several ways. In one way, a general indication of non-compliance may be reported along with the identification of the healthcare provider who is entering the room. In another way, an indication of what movements the healthcare provider performed and/or did not perform in the time allotted along with the identification of the healthcare provider who is entering the room may be reported. If the timeout has not occurred, flow chart 2040 loops back to 2043 in order to continue monitoring for movement of the healthcare provider.

If all of the movements subject to tracking have been matched, at 2048, it is determined whether the last matched movement is for putting on the gloves. As discussed above, separate from identifying movements, a sequence of movements may be tracked. In one instance, the last tracked PPE movement upon entrance is the putting on of gloves. If the last matched movement upon entrance is not putting on of gloves, at 2049, this non-compliance may be reported. Again, the report of non-compliance may comprise a general indication of non-compliance and the identification of the healthcare provider, or may comprise an indication of non-compliance of putting on the gloves as the last step and the identification of the healthcare provider. After which, at 2050, flow chart 2040 ends.

Figure 20D:
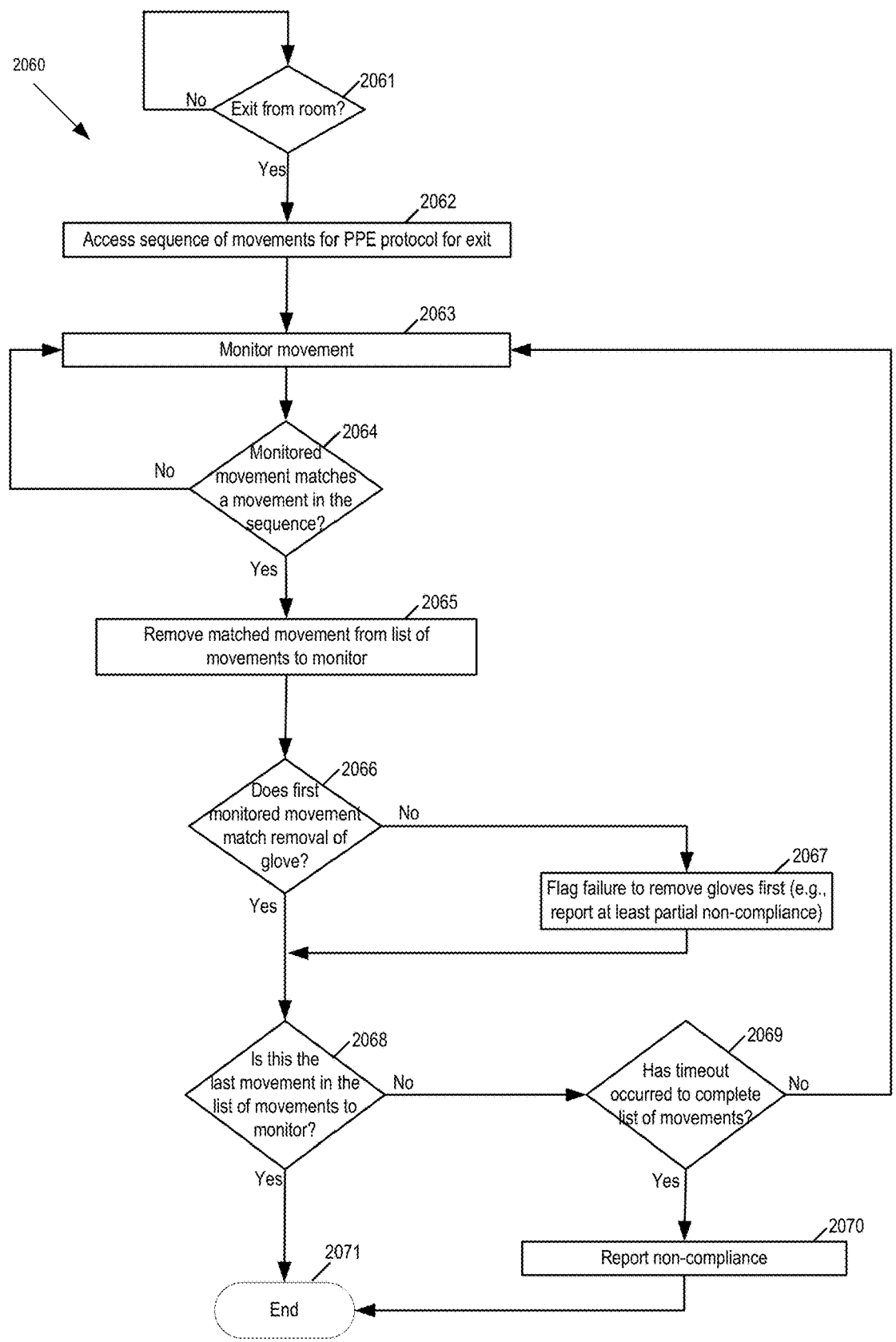
FIG. 20D is a flow chart of one example of monitoring PPE protocols for exit from a patient area.

FIG. 20D is a flow chart 2060 of one example of monitoring PPE protocols for exit from a patient area. Similar to entering the patient area, exiting the patient area may comprise monitoring a set of tracked movements and/or a sequence of the set of tracked movements. At 2061, it is determined whether the healthcare provider has approached the exit or exited a room, such as a particular patient's room. If so, at 2062, the sequence of movements for the PPE protocol at exit are accessed. As discussed above, there are several ways to determine what protocols to access for monitoring.

At 2063, the movement is monitored. At 2064, it is determined whether the monitored movement matches the movement in the designated sequence. In this regard, the monitored movement may be matched with one or both of predetermined hand movements or predetermined PPE movements associated with exiting the patient area. At 2065, the matched movement is removed from the list of movements. For example, responsive to the identifying a match with the removing a gown movement, that matched movement is removed from the list of movements to be tracked.

At 2066, it is determined whether the first matched movement is for removing the gloves. As discussed above, separate from identifying movements, a sequence of movements may be tracked. In one instance, the first tracked PPE movement upon or at exit is the removal of gloves. If the first matched movement upon or at exit is not removing the gloves, at 2067, this non-compliance may be reported (e.g., flagging failure to remove gloves first, indicating at least partial non-compliance). Again, the report of non-compliance may comprise a general indication of non-compliance and the identification of the healthcare provider, or may comprise an indication of non-compliance of removing the gloves as the first step and the identification of the healthcare provider. Alternatively, or in addition, the non-compliance may be generated for notification of the particular healthcare provider that failed to comply with protocols (e.g., aural or light output indicative of non-compliance).

At 2068, it is determined whether all of the movements in the list of movements for tracking have been matched. If not, at 2069, it is determined whether a timeout has occurred. The timeout may be a predetermined time period, such as 30 seconds or 1 minute after identifying the entrance of the healthcare provider. If the timeout has occurred, at 2070, the non-compliance is reported. In this instance, the non-compliance may be reported in one of ways. In one way, a general indication of non-compliance may be reported along with the identification of the healthcare provider who is exiting the room. In another way, an indication of what movements the healthcare provider performed and/or did not perform in the time allotted along with the identification of the healthcare provider who is exiting the room may be reported. Alternatively, or in addition, the non-compliance may be generated for notification of the particular healthcare provider that failed to comply with protocols (e.g., aural or light output indicative of non-compliance). If the timeout has not occurred, flow diagram 2060 loops back to 2063 in order to continue monitoring for movement of the healthcare provider. If all of the movements subject to tracking have been matched, at 2071, flow chart 2060 ends.

Figure 20E:
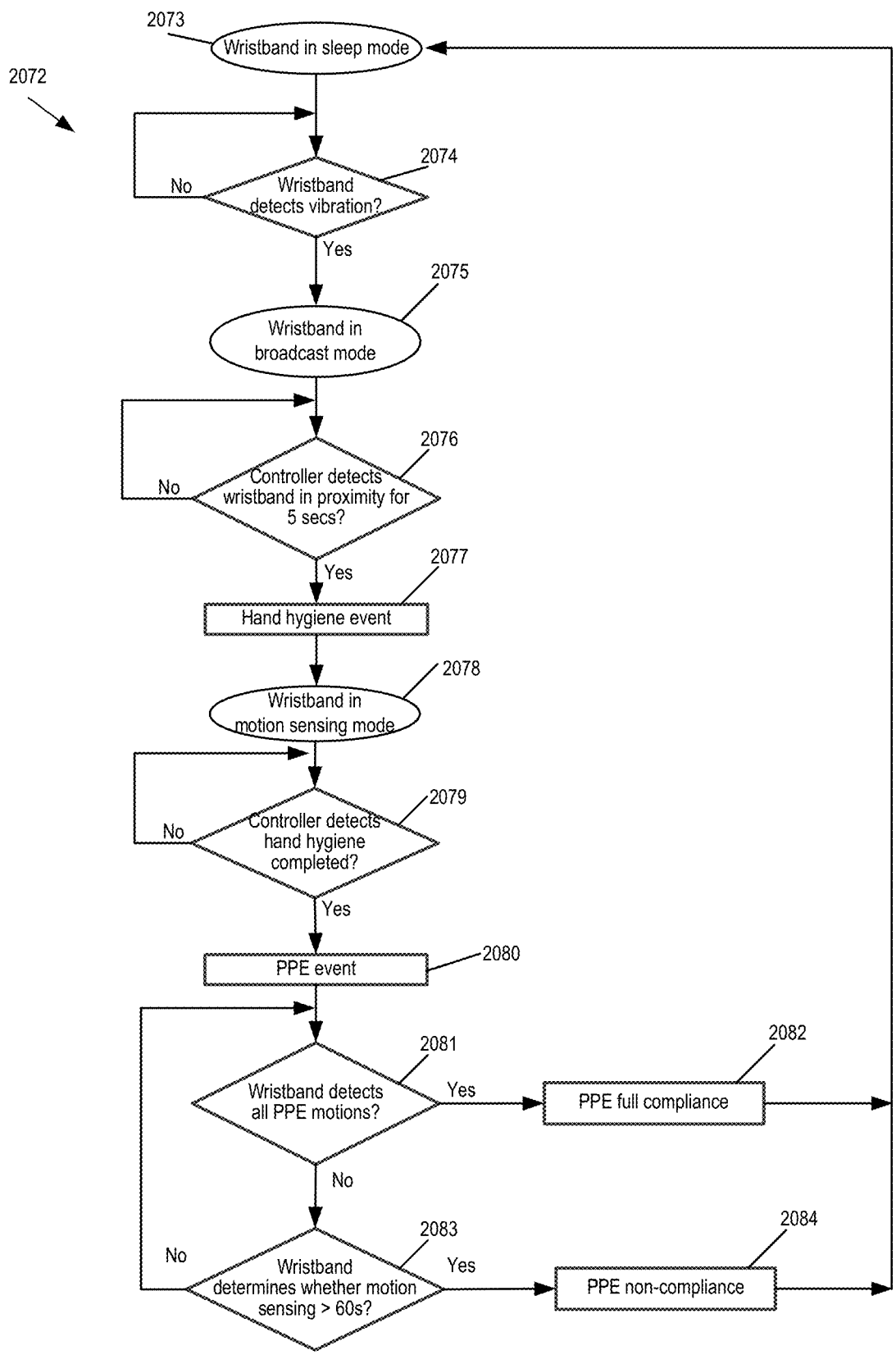
FIG. 20E is a flow chart of another example of monitoring HH and PPE protocols for entry to a patient area.

FIG. 20E is a flow chart 2072 of another example of PPE compliance monitoring when entering a patient area. At 2073, the wristband is in sleep mode. As discussed above, various circuits within the wristband may be turned off or in low power mode when the wristband is in sleep mode. At 2074, the wristband may detect a vibration, such as via the micro-vibration sensor. In one implementation, even in sleep mode, the micro-vibration sensor remains active. If vibration is detected, at 2075, the wristband may transition to broadcast mode. As one example, the wristband may activate one or more of the wireless communication transceivers, such as near-field communication transceiver 322.

In this way, at 2076, the stationary controller may determine, such as via the RSSI signal, whether the wristband is in proximity for a certain amount of time (e.g., 5 seconds). If so, at 2077, it is determined that there is a hand hygiene event.

At 2078, the wristband may be changed to motion sensing mode. At 2079, the controller (and/or the wristband) may detect that hand hygiene has been completed. In one implementation, the stationary controller may determine whether the hand cleaning agent (e.g., sanitizer) has been dispensed. If not, non-compliance may be noted and/or a notification may be output. If it is detected that hand hygiene has been completed, at 2080, it is determined that there is a PPE event (e.g., an entrance PPE event). At 2081, the wristband detects whether all PPE motions have been detected. If so, at 2082, PPE full compliance is determined (and notification of PPE compliance may be output via the wristband and/or the stationary controller, and/or a communication indicating PPE compliance may be send to the back-end server for recordal purposes).

If not, at 2083, the wristband detects whether the period for motion sensing is greater than 60 seconds. If so, at 2084, PPE non-compliance is determined (and notification of PPE non-compliance may be output via the wristband and/or the stationary controller, and/or a communication indicating PPE non-compliance may be send to the back-end server for recordal purposes). If the wristband has not performed motion sensing for 60 seconds, flow chart 2072 loops back to 2081.

Thus, the PPE event may comprise an entrance PPE event associated with entering the patient area and/or an exit PPE event associated with exiting the patient area. The entrance PPE event may include a first PPE putting-on movement associated with putting on the first PPE (e.g., one of a mask putting-on movement, a gown putting-on movement, etc.), a second PPE putting-on movement associated with putting on the second PPE (e.g., another of a mask putting-on movement, a gown putting-on movement, etc.), and a glove putting-on movement associated with putting on the gloves. The exit PPE event may include a first PPE taking-off movement associated with taking off the first PPE, a second PPE taking-off movement associated with taking off the second PPE, and a glove taking-off movement associated with taking off the gloves. The glove putting-on movement and the glove taking-off movement are examples of glove movements. Likewise, the mask putting-on movement and the mask taking-off movement are examples of mask movements, the gown putting-on movement and the gown taking-off movement are examples of gown movements, and the protective eyewear putting-on movement and the protective eyewear taking-off movement are examples of protective eyewear movements. One or both of compliance or non-compliance determination with regard to the PPE event may comprise: determining whether both of the first PPE putting-on movement and the second PPE putting-on movement, in any order, are performed prior to the glove putting-on movement; and determining whether both of the first PPE taking-off movement and the second PPE taking-off movement, in any order, are performed after the glove taking-off movement.

In one implementation, the stationary controller may be implemented with sound and light interventions whereas the wristband may be implemented with vibration reminders. For instance, when the healthcare worker (e.g., trainee) is not compliant with the infection control measures, the wristband may vibrate while the stationary controller will flash in red light. Further, since the system tracks each trainee's performance, the system may also implement reminders that targets those trainees with poor behaviors (e.g., compliance rate less than a pre-determined percentage). For instance, if a trainee with a low compliance rate approaches the entrance of a patient room, the controller may beep to prompt the trainee for hand wash and/or PPE. By identifying the target trainees and sending personalized reminders, the system may improve the target trainee's performance while avoiding annoyance to other trainees.

Thus, in one implementation, the motion sensor inside the wristband may monitor whether the trainee performed the proper motions (e.g., hand rubbing for 20 seconds; donning or removing PPEs in the correct order) and sends real-time alert (to any one, any combination, or all of: the trainee; the back-end server; a supervisor) indicative of compliance and/or non-compliance. In a more specific implementation, in addition to the compliance and non-compliance data, the wristband may send related data, such as timestamps, stationary controller ID and wristband ID, to the back-end server in order to generate a compliance report. In one implementation, each trainee may compare his/her performance with peers from a web or mobile app login, thereby motivating trainees through peer pressure and team competition.

The training and/or monitoring methodology provides one or more benefits. As one example, the training and/or monitoring methodology provides just-in-time infection control training in practice settings. In particular, the training and/or monitoring methodology may educate and train students in both simulation and practice settings, and track their performance in practice to ensure they achieve a high infection-control compliance rate. For instance, the training and/or monitoring methodology may capture three out of five of the "critical moments" specified by WHO (e.g., before touching a patient, after touching a patient, and after touching patient surroundings) to ensure a significant impact on the reduction of HAIs.

In addition, the training and/or monitoring methodology may be tailored to trainees' and/or healthcare workers' practice setting and their roles. As one example, training may be tailored in one instance to a first site (surgical site infection (SSI) prevention specifically for operating room (OR) nurses) as opposed to another instance (general infection control overview). In this way, the training may be more effective. In addition, different infection control measures are required based on the patient infection and/or the nature of the patient contact. The training and/or monitoring methodology may be easily configured to accommodate different patient scenarios and healthcare settings (e.g., community, homecare, hospital).

Further, the training and/or monitoring methodology may provide real-time feedback and interventions for non-compliant incidences. In particular, the training and/or monitoring methodology may provide real-time intervention to poor performance through various types of alerts/reminders and immediate supervisor notification.

Also, the training and/or monitoring methodology may use electronic sensors to track each trainee's or healthcare worker's performance on hand hygiene and PPE use. Such information may be used by the infection control team or the supervisors to evaluate the progress of the trainees or healthcare workers, to identify issues, and to provide feedback. Detailed infection control compliance reports may also be available by any one, any combination, or all of: date; location (e.g., floor, unit and room); or group or individual trainee/healthcare worker.

In addition, the wristbands, which in one implementation include low power modes, may operate for a longer time (e.g., over 1 year) with a coin battery. The use of the wristband may result in little, if any, interruption in workflow for the person.

Figure 20F:
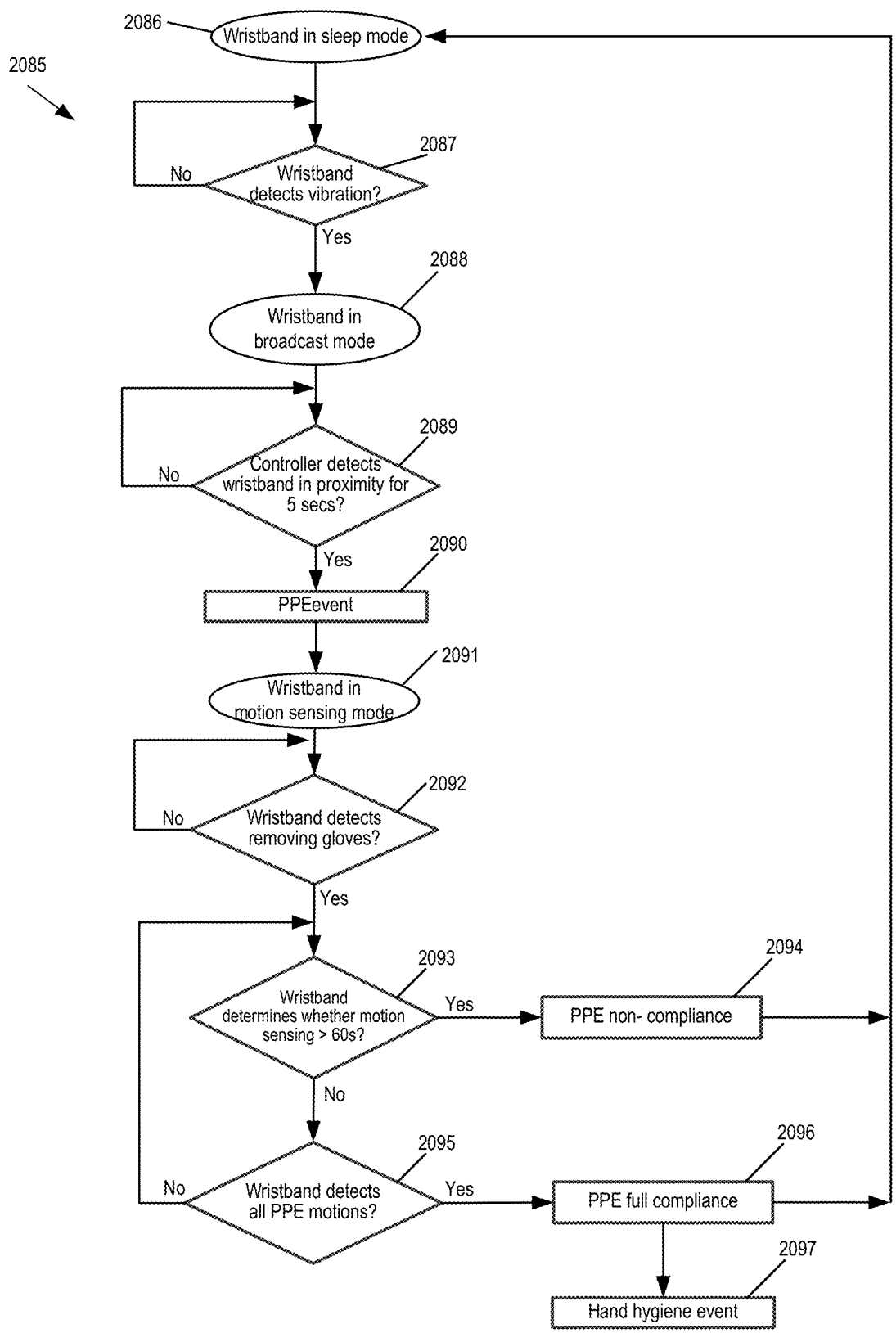
FIG. 20F is a flow chart of another example of monitoring HH and PPE protocols for exit from a patient area.

FIG. 20F is a flow chart 2085 of another example of PPE compliance monitoring when exiting a patient area. At 2086, the wristband is in sleep mode. At 2087, the wristband may detect a vibration, such as via the micro-vibration sensor. If vibration is detected, at 2088, the wristband may transition to broadcast mode. At 2089, the stationary controller may determine, such as via the RSSI signal, whether the wristband is in proximity for a certain amount of time (e.g., 5 seconds). If so, at 2090, it is determined that there is a PPE event (e.g., an exit PPE event).

At 2091, the wristband may be changed to motion sensing mode. At 2092, the wristband detects whether the gloves have been removed. As discussed above, when exiting the patient room, the recommended first motion is the removal of the gloves. If glove removal is detected, at 2093, the wristband detects whether the period for motion sensing is greater than 60 seconds. If so, at 2094, PPE non-compliance is determined (and notification of PPE non-compliance may be output via the wristband and/or the stationary controller, and/or a communication indicating PPE non-compliance may be send to the back-end server for recordal purposes). If not, at 2095, the wristband detects whether all PPE motions have been detected. If so, at 2096, PPE full compliance is determined (and notification of PPE compliance may be output via the wristband and/or the stationary controller, and/or a communication indicating PPE compliance may be send to the back-end server for recordal purposes). After which, at 2097, it is determined that there is a hand hygiene event, with the attendant checking of compliance with one or more hand hygiene protocols. If not, flow chart 2085 loops back to 2093.

FIG. 21 are graphs of outputs of motion sensors, including a graph 2110 of accelerometer data (time versus linear acceleration) and a graph 2120 of gyroscope data (time versus angular acceleration), for donning PPE motions and interfering motions. Each sensor has outputs on x-axis (2112 in graph 2110 and 2122 in graph 2120), y-axis (2114 in graph 2110 and 2124 in graph 2120) and z-axis (2116 in graph 2110 and 2126 in graph 2120). Donning/doffing PPEs may cause very close responses. In this regard, only responses from donning PPE motions are illustrated in FIG. 21. PPE-donning motions have unique characteristics and may be clearly distinguished from interfering motions. For instance, donning goggles cause a large response in accelerometer (x- and y-axis) and gyroscope (z-axis) (due to raising and lowering arms); donning a mask comprises (or consists) of the following motions in sequence (raise arm, tie the mask and lower arm) so that its response is similar to donning goggles but with a longer interval; donning gloves generates large and short pulses on the accelerometer due to sudden arm stretching; donning a gown comprises (or consists) of motions of raising arms, lowering arms then tying the gown behind waist, so its response is close to donning goggles followed by several seconds of large responses on accelerometer and gyroscope cause by tying the gown; opening door has a noticeable gyroscope response in x-axis; and both hand rubbing and walking are periodic motions with frequency of hand rubbing being much higher. Though FIG. 21 illustrates donning PPE, accelerometer and gyroscope data may be analyzed for doffing PPE in order to detect whether the doffing motions associated with PPE have been performed. Further, in one implementation, the detection of the movements, such as the hand washing and/or PPE movements, may be limited in time and responsive to a certain trigger event (e.g., communication with a stationary controller). In this way, limiting the time in which the movements are detected may reduce the possibility of false detections.

As discussed above, the monitoring of the HH protocols and/or PPE protocols may be used in a variety of contexts. In one context, the monitoring of the HH protocols and/or PPE protocols may be used for overseeing healthcare providers' treatment of patients. This is illustrated, for example, in the reports in FIGS. 12A-E. In another context, the monitoring of the HH protocols and/or PPE protocols may be used for training healthcare providers. Thus, in one implementation, the status of the healthcare provider (e.g., trainee versus non-trainee; nurse versus doctor; etc.) may implicate whether the respective healthcare provider is subject to HH protocol and/or PPE protocol monitoring.

In one implementation, the status may be determined based on interaction with the wristband. For example, the wristband may include an identification of the person wearing the wristband. The identification may comprise an ID associated with the person (with the ID then being correlated to the status of the person) or may comprise the status of the person. In one implementation, a first device may identify the status of the person and a second device may determine, based on the identified status, whether to monitor HH protocols and/or PPE protocol. For example, the wristband may identify the status of the person and the stationary controller, having received the status from the wristband, may determine whether to monitor HH protocols and/or PPE protocol. In another implementation, a single device may identify the status of the person and determine, based on the identified status, whether to monitor HH protocols and/or PPE protocol. For example, the wristband may identify the status of the person (e.g., the status is stored in a memory resident in the wristband) and the wristband may determine, based on the stored status, whether to monitor HH protocols and/or PPE protocol. In particular, responsive to an electronic device identifying the particular status of the person (such as the wristband indicating a trainee) and to the particular status indicating that monitoring of HH protocols and/or PPE protocols are to be performed, the electronic device may monitor for the HH protocols and/or PPE protocols.

Responsive to determining compliance and/or non-compliance of one or both of the HH or the PPE protocols, a device (such as the wristband and/or the stationary controller and/or the back-end server) may generate an electronic message indicative of an intervention. The electronic message may be generated in any one, any combination, or all of: (1) prior to performing the respective protocol; (2) during the performance of the respective protocol; or (3) after the respective protocol should have been performed. As one example, responsive to the stationary controller identifying a HH event or a PPE event, the stationary controller may output a message (e.g., a light and/or a sound) indicative of the HH event or the PPE event (e.g., "please wash your hands"). As another example, responsive to the wristband monitoring a HH event or a PPE event, the wristband may output a message (e.g., a light and/or a sound) indicative of the HH event or the PPE event (e.g., playing music for 20 seconds indicative to the healthcare worker to rub hands for 20 seconds during the HH event). As still another example, responsive to the determination that the HH event or the PPE event is over (either due to compliance or due to non-compliance), an electronic device (e.g., the stationary controller and/or the wristband) may generate an output indicative of at least one aspect of the event (e.g., indicative of compliance, indicative of non-compliance, or indicative that the event is completed).

In one implementation, the trigger for intervention may comprise the determination of non-compliance of a protocol. As one example, an electronic device may determine non-compliance with the HH protocol. As discussed above, one aspect of compliance with the HH protocol is the dispensing of hand-cleaning agent, such as ABHR or soap. An electronic device, such as the stationary controller which may be positioned within or proximate to the dispenser of the hand-cleaning agent, may sense whether the dispenser has dispensed the hand-cleaning agent. In particular, responsive to the stationary controller determining that the wristband has been within Bluetooth range of the stationary controller for at least a predetermined amount of time (e.g., 3-5 seconds, indicating that the person wearing the wristband is likely entering the room), the stationary controller may wait a predetermined amount of time (e.g., 3-5 seconds) to determine whether the dispenser has dispensed the hand-cleaning agent. If the stationary controller determines that the dispenser has dispensed the hand-cleaning agent within the predetermined amount of time, the stationary controller may determine that this portion of the HH protocol has been satisfied. However, if the stationary controller determines that the dispenser has not dispensed the hand-cleaning agent within the predetermined amount of time (e.g., the stationary controller has not sensed the sound indicative that the dispenser has dispensed hand-cleaning agent) and/or that the healthcare worker has moved into the patient area (e.g., a first stationary controller exterior to the patient room senses the healthcare worker and thus triggers the HH event; a second stationary controller interior to the patient room senses that the healthcare worker has moved into the room; the proximity sensing and output generating device has identified that the door into the patient room has been opened, indicating that the person has entered into the room), the stationary controller may determine that this portion of the HH protocol has not been satisfied, thereby triggering an intervention. Thus, based on a timeout (e.g., not taking the hand-cleaning agent within a predetermined amount of time) and/or based on a movement into the patient area without performing the requisite action, the intervention may be triggered.

Another aspect of compliance with the HH protocol may comprise the amount of time spent rubbing hands (e.g., 20 seconds). An electronic device, such as the wristband, may sense whether the healthcare worker has spent the requisite time rubbing hands. If the wristband determines that the healthcare worker has spent the requisite time rubbing hands, the wristband may determine that this portion of the HH protocol has been satisfied. However, if the wristband determines that the healthcare worker has not spent the requisite time rubbing hands (e.g., within a period of 60 seconds from trigger of the HH event, the healthcare worker has not rubbed for 20 total seconds), the wristband may determine that this portion of the HH protocol has not been satisfied, thereby triggering an intervention. In this regard, responsive to determining that the healthcare worker has taken hand-cleaning agent but has not rubbed hands for the requisite amount of time, the system may determine partial compliance. In one implementation, the intervention for partial compliance may be different from the intervention for non-compliance.

Still another aspect of compliance with the HH protocol may comprise the requisite motions, such as illustrated in FIGS. 10A-B. An electronic device, such as the wristband, may sense whether the healthcare worker has spent the requisite time rubbing hands. If the wristband determines that the healthcare worker has performed the requisite motions, the wristband may determine that this portion of the HH protocol has been satisfied. However, if the wristband determines that the healthcare worker has not performed the requisite motions (e.g., within a period of 60 seconds from trigger of the HH event, the healthcare worker has performed steps 2-7 in FIG. 10A), the wristband may determine that this portion of the HH protocol has not been satisfied, thereby triggering an intervention.

As another example, an electronic device may determine non-compliance with the PPE protocol. As discussed above, one aspect of compliance with the PPE protocol is the donning or doffing of certain PPE. Responsive to an electronic device (e.g., the wristband) determining that the requisite movements (e.g., indicating the donning or doffing of the certain PPE) have not been performed within a predetermined amount of time (e.g., 60 seconds) or were not performed in the proper order, the system may trigger an intervention. Alternatively, or in addition, responsive to determining that the healthcare worker has moved into the patient area without performing the requisite movements, the system may trigger an intervention.

In one implementation, the trigger for an intervention for a first protocol may be independent of the trigger for an intervention for a second protocol. For example, the trigger to intervene based on non-compliance with the HH protocol may be independent of the trigger to intervene based on non-compliance with the PPE protocol. In particular, prior to entry to a patient area and a failure to take hand-cleaning agent, the intervention may be performed regardless of whether the healthcare worker complied with the PPE protocol. In an alternative implementation, the trigger for an intervention for the first protocol may be dependent of the trigger for the intervention for the second protocol.

Responsive to triggers, various types of intervention may be performed including any one, any combination, or all of: light output (e.g., on the wristband and/or on the stationary controller); aural output (e.g., on the wristband and/or on the stationary controller); or electronic notification (e.g., to the back-end server and/or to a supervisor). For example, light and/or sound may be indicative that an action should be taken. For example, responsive to the stationary controller determining that the dispenser has not dispensed hand-cleaning agent, the stationary controller may output a beep and/or a sound stating: "please take hand-sanitizer from the dispenser". As another example, responsive to non-compliance, the supervisor may be notified in real-time. In particular, responsive to the stationary controller determining the non-compliance, the stationary controller may send a communication to the back-end server indicating the non-compliance of a certain individual (such as identified by the wristband worn by the individual) and/or of a certain part of the building (such as the neonatal intensive care unit). The back-end server may access a look-up table, correlating the identity of the individual and/or the certain part of the building in order to immediately notify a supervisor in real-time (e.g., send a text to the mobile phone number associated with the supervisor).

Further, in one implementation, the intervention may be based on any one, any combination, or all of the following: determination of compliance or non-compliance; determination of partial compliance; status of the person subject to the compliance, non-compliance, or partial compliance (e.g., whether the person is a trainee or a full-time employee); history of compliance of the person (e.g., whether trends indicate that the person has a history of compliance, non-compliance, or partial compliance); or location of the compliance, non-compliance, or partial compliance (e.g., whether the setting is a home, an intensive care unit, a long-term care facility, or a community care facility). As one example, in response to determining compliance, the healthcare worker may not be notified; however, the back-end server may be notified. in response to determining non-compliance, the healthcare worker, the supervisor, and the back-end server are notified. In response to determining that the status of the person is a trainee, the person is notified regardless of compliance, non-compliance, or partial compliance. In response to determining that the status of the person is a full-time employee, the person is notified only responsive to determination of non-compliance or partial compliance. As still another example, responsive to determining that the person has a history of non-compliance or partial-compliance (e.g., the percentage of non-compliance or partial compliance is greater than a predetermined percentage; certain number of times indicative of non-compliance or partial compliance), the system generate an output (e.g., light and/or aural) to the person. Conversely, responsive to determining that the person does not have a history of non-compliance or partial-compliance, the system does not generate an output to the person.

Figure 22:
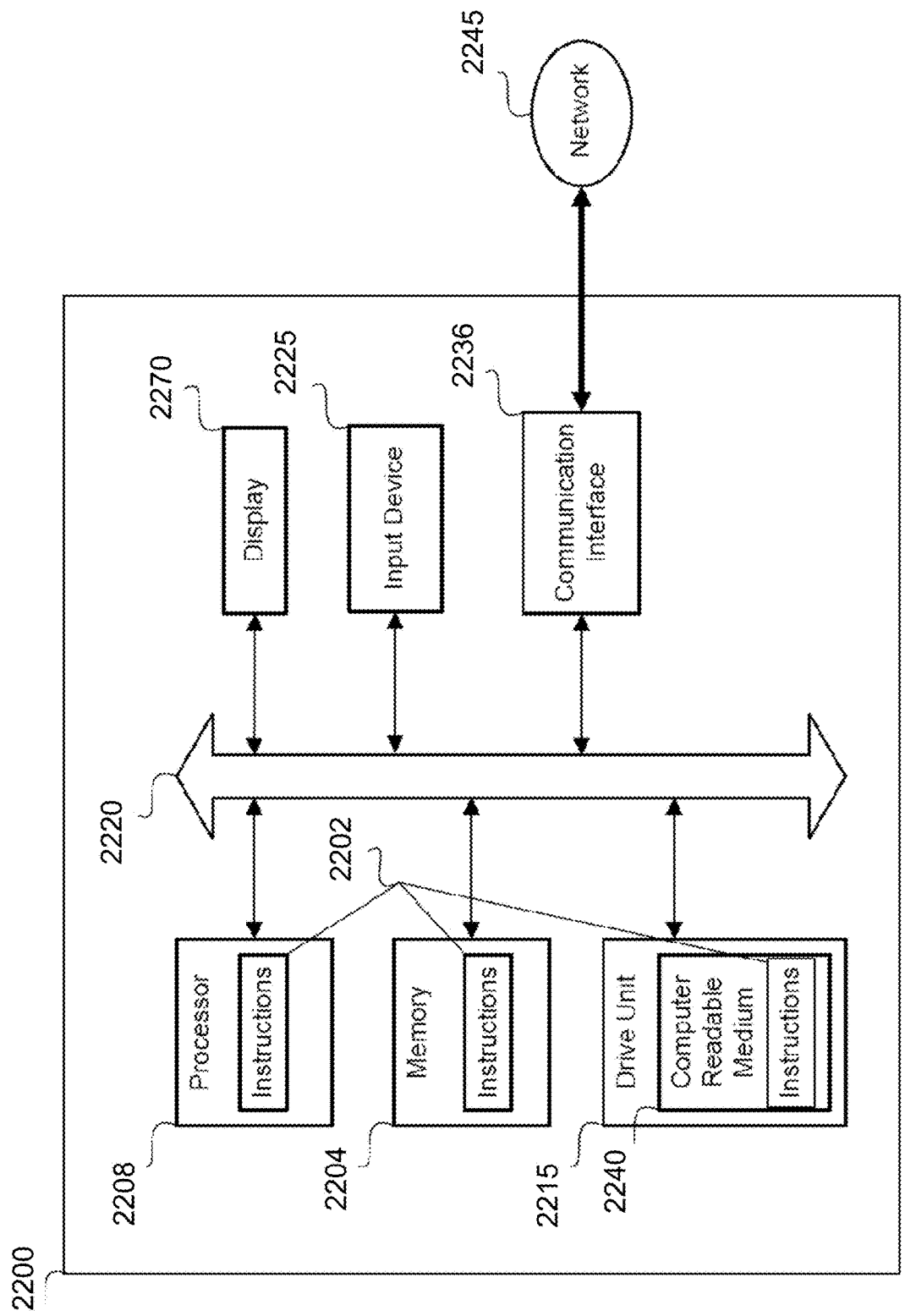
FIG. 22 is a general computer system, programmable to be a specific computer system, which may represent any of the computing devices referenced herein.

FIG. 22 is a general computer system 2200, programmable to be a specific computer system, which may represent any of the computing devices referenced herein, such as the wristband, the stationary controller, or the back-end. The computer system 2200 may include an ordered listing of a set of instructions 2202 that may be executed to cause the computer system 2200 to perform any one or more of the methods or computer-based functions disclosed herein. The computer system 2200 can operate as a stand-alone device or can be connected, e.g., using the network 2245, to other computer systems or peripheral devices.

In a networked deployment, the computer system 2200 can operate in the capacity of a server or as a client-user computer in a server-client user network environment, or as a peer computer system in a peer-to-peer (or distributed) network environment. The computer system 2200 can also be implemented as or incorporated into various devices, such as a personal computer or a mobile computing device capable of executing a set of instructions 2202 that specify actions to be taken by that machine, including and not limited to, accessing the Internet or Web through any form of browser. Further, each of the systems described can include any collection of sub-systems that individually or jointly execute a set, or multiple sets, of instructions to perform one or more computer functions.

The computer system 2200 can include a memory 2204 on a bus 2220 for communicating information. Code operable to cause the computer system to perform any of the acts or operations described herein can be stored in the memory 2204. The memory 2204 can be a random-access memory, read-only memory, programmable memory, hard disk drive or any other type of volatile or non-volatile memory or storage device.

The computer system 2200 can include a processor 2208, such as a central processing unit (CPU) and/or a graphics processing unit (GPU). In one implementation, one example of a processor is a controller. Further, one example of a controller is a microcontroller. The processor 2208 can include one or more general processors, digital signal processors, application specific integrated circuits, field programmable gate arrays, digital circuits, optical circuits, analog circuits, combinations thereof, or other now known or later-developed devices for analyzing and processing data. The processor 2208 can implement the set of instructions 2202 or other software program, such as manually programmed or computer-generated code for implementing logical functions. The logical function or any system element described can, among other functions, process and convert an analog data source such as an analog electrical, audio, or video signal, or a combination thereof, to a digital data source for audio-visual purposes or other digital processing purposes such as for compatibility for computer processing.

The computer system 2200 can also include a disk or optical drive unit 2215. The disk drive unit 2215 can include a computer-readable medium 2240 in which one or more sets of instructions 2202, e.g., software, can be embedded. Further, the instructions 2202 can perform one or more of the operations as described herein. The instructions 2202 can reside completely, or at least partially, within the memory 2204 or within the processor 2208 during execution by the computer system 2200.

The memory 2204 and the processor 2208 also can include computer-readable media as discussed above. A "computer-readable medium," "computer-readable storage medium," "machine readable medium," "propagated-signal medium," or "signal-bearing medium" can include any device that has, stores, communicates, propagates, or transports software for use by or in connection with an instruction executable system, apparatus, or device. The machine-readable medium can selectively be, but not limited to, an electronic, magnetic, optical, electromagnetic, infrared, or semiconductor system, apparatus, device, or propagation medium.

Additionally, the computer system 2200 can include an input device 2225, such as a keyboard or mouse, configured for a user to interact with any of the components of system 2200. It can further include a display 2270, such as a liquid crystal display (LCD), a cathode ray tube (CRT), or any other display suitable for conveying information. The display 2270 can act as an interface for the user to see the functioning of the processor 2208, or specifically as an interface with the software stored in the memory 2204 or the drive unit 2215.

The computer system 2200 can include a communication interface 2236 that enables communications via the communications network 2245. The network 2245 can include wired networks, wireless networks, or combinations thereof. The communication interface 2236 network can enable communications via any number of communication standards, such as 802.11, 802.17, 802.20, WiMAX, 802.15.4, cellular telephone standards, or other communication standards, as discussed above. Simply because one of these standards is listed does not mean any one is preferred, as any number of these standards can never actually be adopted in a commercial product.

Block diagrams of different aspects of the system, including FIGS. 1A-5H, 13A, and 15A-16D, may be implemented using the computer functionality disclosed in FIG. 22. Further, the flow diagrams illustrated in FIGS. 5I-6D, 14, 17A-C and 20A-F may use computer readable instructions that are executed by one or more processors in order to implement the functionality disclosed.

The present disclosure contemplates a computer-readable medium that includes instructions or receives and executes instructions responsive to a propagated signal, so that a device connected to a network can communicate voice, video, audio, images or any other data over the network. Further, the instructions can be transmitted or received over the network via a communication interface. The communication interface can be a part of the processor or can be a separate component. The communication interface can be created in software or can be a physical connection in hardware. The communication interface can be configured to connect with a network, external media, the display, or any other components in system, or combinations thereof. The connection with the network can be a physical connection, such as a wired Ethernet connection or can be established wirelessly as discussed below. In the case of a service provider server, the service provider server can communicate with users through the communication interface.

The computer-readable medium can be a single medium, or the computer-readable medium can be a single medium or multiple media, such as a centralized or distributed database, or associated caches and servers that store one or more sets of instructions. The term "computer-readable medium" can also include any medium that can be capable of storing, encoding or carrying a set of instructions for execution by a processor or that can cause a computer system to perform any one or more of the methods or operations disclosed herein.

The computer-readable medium can include a solid-state memory such as a memory card or other package that houses one or more non-volatile read-only memories. The computer-readable medium also can be a random access memory or other volatile re-writable memory. Additionally, the computer-readable medium can include a magneto-optical or optical medium, such as a disk or tapes or other storage device to capture carrier wave signals such as a signal communicated over a transmission medium. A digital file attachment to an email or other self-contained information archive or set of archives can be considered a distribution medium that can be a tangible storage medium. The computer-readable medium is preferably a tangible storage medium. Accordingly, the disclosure can be considered to include any one or more of a computer-readable medium or a distribution medium and other equivalents and successor media, in which data or instructions can be stored.

Alternatively, or in addition, dedicated hardware implementations, such as application specific integrated circuits, programmable logic arrays and other hardware devices, can be constructed to implement one or more of the methods described herein. Applications that can include the apparatus and systems of various embodiments can broadly include a variety of electronic and computer systems. One or more embodiments described herein can implement functions using two or more specific interconnected hardware modules or devices with related control and data signals that can be communicated between and through the modules, or as portions of an application-specific integrated circuit. Accordingly, the present system can encompass software, firmware, and hardware implementations.

The methods described herein may be implemented by software programs executable by a computer system. Further, implementations may include distributed processing, component/object distributed processing, and parallel processing. Alternatively, or in addition, virtual computer system processing may be constructed to implement one or more of the methods or functionality as described herein.

Although components and functions are described that may be implemented in particular embodiments with reference to particular standards and protocols, the components and functions are not limited to such standards and protocols. For example, standards for Internet and other packet switched network transmission (e.g., TCP/IP, UDP/IP, HTML, and HTTP) represent examples of the state of the art. Such standards are periodically superseded by faster or more efficient equivalents having essentially the same functions. Accordingly, replacement standards and protocols having the same or similar functions as those disclosed herein are considered equivalents thereof.

The illustrations described herein are intended to provide a general understanding of the structure of various embodiments. The illustrations are not intended to serve as a complete description of all of the elements and features of apparatus, processors, and systems that utilize the structures or methods described herein. Many other embodiments can be apparent to those of skill in the art upon reviewing the disclosure. Other embodiments can be utilized and derived from the disclosure, such that structural and logical substitutions and changes can be made without departing from the scope of the disclosure. Additionally, the illustrations are merely representational and cannot be drawn to scale. Certain proportions within the illustrations may be exaggerated, while other proportions may be minimized. Accordingly, the disclosure and the figures are to be regarded as illustrative rather than restrictive.

Thus, in one implementation, a method is disclosed. The method includes: identifying a hand hygiene event based on interaction of a mobile electronic device and a stationary controller, the mobile electronic device configured to be associated with a person, the stationary controller configured to be associated with a dispenser configured to dispense hand cleaning agent; responsive to identifying the hand hygiene event, monitoring at least one aspect of the hand hygiene event; and determining, based on monitoring the at least one aspect of the hand hygiene event, one or both of compliance or non-compliance with regard to the hand hygiene event.

The method may further include wherein identifying the hand hygiene event based on the interaction of the mobile electronic device and the stationary controller comprises the stationary controller receiving a signal from the mobile electronic device of at least a predetermined strength for a predetermined time indicative that the mobile electronic device is proximate to the stationary controller.

The method may further include wherein monitoring at least one aspect of the hand hygiene event comprises monitoring whether the dispenser has dispensed the hand cleaning agent within a predetermined time since identifying the hand hygiene event.

The method may further include wherein the stationary controller monitors whether the dispenser has dispensed the hand cleaning agent by analyzing sound data to determine whether the sound data is indicative of the dispenser dispensing the hand cleaning agent; and wherein the stationary controller is configured to transmit and receive data.

The method may further include wherein monitoring at least one aspect of the hand hygiene event comprises monitoring hand motions of the person.

The method may further include wherein monitoring the hand of the person comprises using one or more motion sensors to generate sensor data in order to sense the hand motions of the person; and wherein determining one or both of compliance or non-compliance with regard to the hand hygiene event comprises analyzing the sensor data in order to determine whether the sensor data is indicative of a predetermined hand movement.

The method may further include wherein determining one or both of compliance or non-compliance with regard to the hand hygiene event comprises analyzing the sensor data in order to determine whether the sensor data is indicative of the predetermined hand movement for at least a predetermined amount of time.

The method may further include wherein determining whether the sensor data is indicative of the predetermined hand movement for at least a predetermined amount of time comprises: determining a starting time of the predetermined hand movement; subsequent to determining the starting time of the predetermined hand movement, determining a stopping time of the predetermined hand movement; subsequent to determining the stopping time of the predetermined hand movement, determining a restarting time of the predetermined hand movement; and determining, based on the determined starting time, stopping time, and restarting time, an effective time in which the predetermined hand movement has been performed.

The method may further include wherein the mobile electronic device comprises a wristband electronic device.

The method may further include wherein the wristband electronic device determines the one or both of compliance or non-compliance with regard to the hand hygiene event.

The method may further include wherein monitoring at least one aspect of the hand hygiene event comprises the wristband electronic device using one or more motion sensors to generate sensor data in order to sense hand motions of the person; and wherein the wristband determines compliance with regard to the hand hygiene event by determining whether the sensor data is indicative of a plurality of predetermined hand movements.

The method may further include, responsive to identifying the hand hygiene event, generating by the stationary controller an output, the output indicative to the person to obtain the hand cleaning agent from the dispenser.

The method may further include wherein, responsive to determining non-compliance with regard to the hand hygiene event, generating an output on one or both of the mobile electronic device and stationary controller.

The method may further include wherein the output generated comprises vibrating the mobile electronic device.

In another implementation, a mobile wearable electronic device is disclosed. The mobile wearable electronic device comprises: at least one mechanical structure configured for attachment onto at least a part of a body of a person; communication functionality configured to communicate with a stationary controller, the stationary controller configured to be associated with a dispenser configured to dispense hand cleaning agent; one or more motion sensors configured to generate sensor data indicative of hand movement of the person; and a controller in the mechanical structure and in communication with the communication functionality and the one or more sensors. The controller configured to: responsive to communication with the stationary controller, store sensor data generated by the one or more motion sensors in order to determine compliance or non-compliance of the hand movement of the person with regard to a hand hygiene event.

The mobile wearable electronic device may further include wherein the controller is further configured to: analyze the sensor data in order to determine whether the hand movement of the person is compliant or non-compliant.

The mobile wearable electronic device may further include wherein responsive to a signal generated by the communication functionality, the communication functionality is configured to receive one or more signals from the stationary controller; and wherein the controller is further configured to wake-up at least one of the one or more motion sensors responsive to the one or more signals from the stationary controller.

The mobile wearable electronic device may further include wherein the mobile wearable electronic device is a wristband electronic device; wherein the one or more motion sensors comprises a vibration sensor and an accelerometer; wherein, responsive to the vibration sensor sensing vibration, the communication functionality is configured to be awakened; responsive to awakening of the communication functionality, the signal is generated by the communication functionality; and responsive to the one or more signals from the stationary controller, the mobile wearable electronic device is configured to enter motion sensing mode.

The mobile wearable electronic device may further include wherein the controller is configured to analyze the sensor data in order to determine whether the hand movement of the person is compliant or non-compliant by: determining a starting time of a hand movement; subsequent to determining the starting time of the hand movement, determining a stopping time of the hand movement; subsequent to determining the stopping time of the hand movement, determining a restarting time of the hand movement; determining, based on the determined starting time, stopping time, and restarting time, an effective time in which the hand movement has been performed; and comparing the effective time with a predetermined hand movement time; and responsive to determining that the effective time is equal or greater than the predetermined hand movement time, determining that the hand movement of the person is compliant.

In another implementation, a hand hygiene analytics and notification system is disclosed. The hand hygiene analytics and notification system comprises: a plurality of electronic device wristbands, the plurality of electronic device wristbands each correlated to a healthcare provider and including one or more motion sensors configured to generate sensor data indicative of movement of a person during a hand hygiene event; one or more databases configured to correlate hand hygiene data with the healthcare providers, the hand hygiene data being based on the sensor data and indicative of compliance or non-compliance of the hand hygiene event; communication functionality configured to communicate with one or more electronic devices; and a controller in communication with the one or more databases and the communication functionality. The controller is configured to: analyze the hand hygiene data; and responsive to the analysis of the hand hygiene data, transmit an alert via the communication functionality to an electronic device.

The hand hygiene analytics and notification system further includes wherein the plurality of electronic device wristbands are configured to analyze the sensor data in order to generate the hand hygiene data; and wherein the hand hygiene data includes compliance, non-compliance, and partial compliance.

The hand hygiene analytics and notification system further includes wherein the controller configured to analyze the hand hygiene data by determining a specific healthcare provider suspected of cross-contamination amongst patients.

The hand hygiene analytics and notification system further includes wherein the controller configured to analyze the hand hygiene data by determining whether a rate of non-compliant hand hygiene events is lower than a predetermined rate or a number of non-compliant hand hygiene events is lower than a predetermined rate.

In another implementation, a proximity sensing and output generating device is disclosed. The proximity sensing and output generating device comprises: a fastener configured to fasten the proximity sensing and output generating device to a movable portion of a premises; a motion sensor configured to generate motion sensor data, the motion sensor configured to be activated based on sensor input from another sensor; an output device configured to generate an output; and a controller in communication with the motion sensor and the output device. The controller is configured to: determine, based on the motion sensor data, a direction of movement of the movable portion of the premises, the direction of movement of the movable portion indicative of an event; determine, based on the direction of movement, an output message, the output message related to the event; and responsive to determining the output message, output, via the output device, the output message.

The proximity sensing and output generating device further includes wherein the fastener comprises one of an adhesive or a connector.

The proximity sensing and output generating device further includes wherein the movable portion of a premises comprises a door or a drawer.

The proximity sensing and output generating device further includes where the controller is configured to determine whether the motion sensor data is indicative of the door or drawer opening; and responsive to determining that the motion sensor data is indicative of the door or drawer opening, outputting an audio message.

The proximity sensing and output generating device further includes wherein the controller is further configured to: after outputting the output message, analyze audio sensor data related to the event; and determine whether to output a second audio message based on the analysis of the audio sensor data.

The proximity sensing and output generating device further includes a multi-position switch on a housing of the proximity sensing and output generating device; wherein a first position of the multi-position switch is indicative of fastening the proximity sensing and output generating device to a first movable portion of the premises; wherein a second position of the multi-position switch is indicative of fastening the proximity sensing and output generating device to a second movable portion of the premises; wherein, responsive to the multi-position switch in the first position, the controller is configured to determine a first output message related to movement of the first movable portion of the premises; and wherein, responsive to the multi-position switch in the second position, the controller is configured to determine a second output message related to movement of the second movable portion of the premises.

The proximity sensing and output generating device further includes wherein the motion sensor is configured to be activated based on the sensor input from another motion sensor.

The proximity sensing and output generating device further includes wherein the motion sensor comprises one of an accelerometer or gyroscope; and wherein the another sensor comprises a vibration sensor.

In another implementation, a proximity sensing and output generating device is disclosed. The proximity sensing and output generating device comprises: a fastener configured to fasten the proximity sensing and output generating device to a movable portion of a premises; a proximity sensor configured to generate proximity sensor output indicative of a person proximate to the movable portion of the premises; a motion sensor configured to generate motion sensor data, the motion sensor configured for operation in a sleep mode and an active mode, the motion sensor transitioning from the sleep mode into the active mode responsive to the proximity sensor output being indicative of the person proximate to the movable portion of the premises; an output device configured to generate an output; and a controller in communication with the proximity sensor, the motion sensor and the output device. The controller is configured to: determine whether the motion sensor data is indicative of an event; responsive to determining that the motion sensor data is indicative of an event, determine an output message, the output message related to the event; and responsive to determining the output message, output, via the output device, the output message.

The proximity sensing and output generating device further includes wherein the proximity sensor comprises an always-on vibration sensor.

The proximity sensing and output generating device further includes wherein the fastener is configured to fasten the proximity sensing and output generating device to a first movable portion of the premises; wherein the fastener is configured to fasten the proximity sensing and output generating device to a second movable portion of the premises; wherein a first event is associated with the first movable portion of the premises; wherein a second event is associated with the second movable portion of the premises; wherein the controller is further configured to determine an indication of whether the proximity sensing and output generating device is connected to the first movable portion of the premises or the second movable portion of the premises; wherein the controller is configured to determine a first output message related to the first event based on determining that the proximity sensing and output generating device is connected to the first movable portion of the premises; and wherein the controller is configured to determine a second output message related to the second event based on determining that the proximity sensing and output generating device is connected to the second movable portion of the premises.

The proximity sensing and output generating device further includes wherein the motion sensor comprises a first motion sensor and a second motion sensor, the first motion sensor configured to generate first motion sensor data, the second motion sensor configured to generate second motion sensor data; wherein the controller is configured to, responsive to determining that the proximity sensing and output generating device is connected to the first movable portion of the premises, use the first motion sensor data to determine whether the first motion sensor data is indicative of the first event; and wherein the controller is configured to, responsive to determining that the proximity sensing and output generating device is connected to the second movable portion of the premises, not use the first motion sensor data but use the second motion sensor data to determine whether the second motion sensor data is indicative of the second event.

The proximity sensing and output generating device further includes wherein the first movable portion of the premises comprises a door; wherein the second movable portion of the premises comprises a drawer; wherein the first motion sensor comprises a gyroscope; wherein the second motion sensor comprises an accelerometer; wherein the first event comprises the door opening; and wherein the second event comprises the drawer opening.

The proximity sensing and output generating device further includes a multi-position switch on a housing of the proximity sensing and output generating device; wherein a first position of the multi-position switch is indicative of fastening the proximity sensing and output generating device to the door; wherein a second position of the multi-position switch is indicative of fastening the proximity sensing and output generating device to the drawer; and wherein the controller is configured to determine the indication of whether the proximity sensing and output generating device is connected to the door or the drawer based on the multi-position switch.

The proximity sensing and output generating device further includes wireless communication functionality; and wherein the controller is further configured to transmit, via the wireless communication functionality a message to an external electronic device, the message indicative to the external electronic device to output an alert.

In another implementation, an output alert system is disclosed. The output alert system comprises: an electronic device comprising: wireless communication functionality; and output functionality configured to output an alert; and a proximity sensing and output generating device comprising: a fastener configured to fasten the proximity sensing and output generating device to a movable portion of a premises; wireless communication functionality; a proximity sensor configured to generate proximity sensor output indicative of a person proximate to the movable portion of the premises; a motion sensor configured to generate motion sensor data, the motion sensor configured for operation in a sleep mode and an active mode, the motion sensor transitioning from the sleep mode into the active mode responsive to the proximity sensor output being indicative of the person proximate to the movable portion of the premises; and a controller in communication with the wireless communication functionality, the proximity sensor, and the motion sensor. The controller is configured to: determine whether the motion sensor data is indicative of an event; and responsive to determining that the motion sensor data is indicative of an event, transmit, via the wireless communication functionality, a communication indicative of the alert, wherein responsive to receipt of the alert, the electronic device is configured to output the alert.

The output alert system further includes wherein the electronic device comprises a mobile wristband electronic device configured for wearing on a person's wrist; wherein the controller is configured to determine whether the motion sensor data is indicative of an event by determining whether the motion sensor data is indicative of opening a drawer or a cabinet; wherein the wireless communication functionality comprises near-field communication functionality; and wherein the alert is indicative to the person of a procedure related to opening of the drawer or the cabinet.

The output alert system further includes wherein the electronic device comprises a stationary electronic device; wherein the controller is configured to determine whether the motion sensor data is indicative of an event by determining whether the motion sensor data is indicative of opening a drawer or a cabinet; and wherein the communication functionality comprises near-field communication functionality; and wherein the alert is indicative to the person of a procedure related to opening of the drawer or the cabinet.

In another implementation, a mobile wearable electronic device is disclosed. The mobile wearable electronic device comprises: at least one mechanical structure configured for attachment onto at least a part of a body of a person; communication functionality configured to communicate with a hand hygiene external electronic device; one or more motion sensors configured to generate sensor data indicative of hand movement of the person; a radio frequency identification (RFID) tag configured to communicate with an external RFID reader; and a controller in communication with the communication functionality and the one or more sensors, the controller configured to: store the sensor data generated by the one or more motion sensors in order to determine compliance or non-compliance of the hand movement of the person with regard to a hand hygiene event.

The mobile wearable electronic device further includes wherein the controller is further configured to: determine, based on the sensor data, the compliance or the non-compliance of the hand movement of the person with regard to the hand hygiene event; and transmit the determination of the compliance or the non-compliance to an external device.

The mobile wearable electronic device further includes wherein the mobile wearable electronic device is configured for wear on a wrist of a person.

In another implementation, a mobile wearable electronic device is disclosed. The mobile wearable electronic device comprises: at least one mechanical structure configured for attachment onto at least a part of a body of a person; communication functionality configured to communicate with one or more external devices regarding hand hygiene and access control; one or more motion sensors configured to generate sensor data indicative of hand movement of the person; an identification of the person; and a controller in communication with the communication functionality and the one or more sensors. The controller is configured to: determine, based on the sensor data generated by the one or more motion sensors, compliance or non-compliance of the hand movement of the person with regard to a hand hygiene event; transmit, via the communication functionality, the determination of compliance or non-compliance of the hand movement of the person with regard to the hand hygiene event; and transmit, via the communication functionality, the identification of the person to an access control device.

The mobile wearable electronic device further includes wherein the mobile wearable electronic device is a wristband.

The mobile wearable electronic device further includes wherein the controller is configured to transmit the determination of compliance or non-compliance and the identification of the person in a single communication to an external device.

The mobile wearable electronic device further includes wherein the controller is configured to transmit the determination of compliance or non-compliance and the identification of the person in separate communications.

In another implementation, a mobile wearable electronic device is disclosed. The mobile wearable electronic device comprises: at least one mechanical structure configured for attachment onto at least a part of a body of a person; communication functionality configured to communicate with one or more external devices regarding hand hygiene and access control; one or more motion sensors configured to generate sensor data indicative of hand movement of the person; an identification of the person; and a controller in communication with the communication functionality and the one or more sensors, the controller configured to: determine, based on the sensor data generated by the one or more motion sensors, compliance or non-compliance of the hand movement of the person with regard to a hand hygiene event; responsive to determining compliance of the hand movement of the person, transmit, via the communication functionality, the identification of the person to an access control device; and responsive to determining non-compliance of the hand movement of the person, do not transmit the identification of the person to the access control device.

The mobile wearable electronic device further includes wherein the mobile wearable electronic device is a wristband electronic device.

In another implementation, a system for instructing hand hygiene is disclosed. The system comprises: a mobile wristband electronic device comprising: a mechanical structure configured for attachment onto a wrist of a user; communication functionality configured to communicate with an electronic instruction display system; one or more motion sensors configured to generate sensor data indicative of user hand motions; and a controller in the mechanical structure and in communication with the communication functionality and the one or more sensors, the controller configured to: responsive to communication with the electronic instruction display system, store sensor data generated by the one or more motion sensors. The system also includes the electronic instruction display system comprising: communication functionality configured to communicate with an electronic instruction display system; a display to display a plurality of hand motions; and a controller in communication with the communication functionality and the display, the controller configured to: determine the plurality of hand motions; determine a respective time period for each of the plurality of hand motions; cause the plurality of hand motions to be displayed on the display for the respective times; receive the sensor data, the sensor data indicative of user hand motions and associated respective times for the user hand motions; analyze the sensor data in order to determine a difference between the plurality of hand motions and the user hand motions, and a difference between the respective times and the associated respective times for the user hand motions; and output via the display an indication of the difference between the plurality of hand motions and the user hand motions, and a difference between the respective times and the associated respective times for the user hand motions.

The system further includes wherein the controller is configured to output the indication of the difference between the plurality of hand motions and the user hand motions by: initially displaying on the display a plurality of indicia; and based on the difference between the plurality of hand motions and the user hand motions, removing a number of the plurality of indicia from the display, with a greater difference between the plurality of hand motions and the user hand motions resulting in less removal of the number of the plurality of indicia on the screen for display and with a lesser difference between the plurality of hand motions and the user hand motions resulting in a greater removal of the number of the plurality of indicia on the screen for display.

The system further includes wherein the controller is further configured to: compare the difference between the plurality of hand motions and the user hand motions with a previous difference between previous plurality of hand motions and previous user hand motions in a previous training session; and output the comparison via the display.

The above disclosed subject matter is to be considered illustrative, and not restrictive, and the appended claims are intended to cover all such modifications, enhancements, and other embodiments, which fall within the true spirit and scope of the description. Thus, to the maximum extent allowed by law, the scope is to be determined by the broadest permissible interpretation of the following claims and their equivalents, and shall not be restricted or limited by the foregoing detailed description.

The invention claimed is:

1. A method comprising:
    identifying a personal protective equipment (PPE) event based on interaction of a mobile electronic device and a stationary controller, the mobile electronic device associated with a person and including one or more motion sensors configured to generate motion data, the stationary controller associated with an area that is assigned one or more specific PPE protocols, the one or more specific PPE protocols comprising one or more specific PPE movements;
    responsive to identifying the PPE event based on the interaction of the mobile electronic device and the stationary controller:
        monitoring movement of a person by storing the motion data generated by the one or more motion sensors;
        accessing, by the mobile electronic device, the one or more specific PPE movements for the one or more specific PPE protocols assigned to the area; and
        determining, based on the one or more specific PPE movements and the stored motion data, at least one of compliance or non-compliance with regard to the PPE event.

2. The method of claim 1, wherein the area comprises a patient area; and
    wherein the stationary controller is associated with a dispenser configured to dispense hand cleaning agent, the dispenser proximate to an entrance of the patient area.

3. The method of claim 2, wherein the PPE comprises a first PPE and a second PPE;
    wherein the PPE event comprises one of a PPE entrance event or a PPE exit event;
    wherein the PPE entrance event has an associated first PPE putting-on protocol comprising a putting-on movement associated with putting on the first PPE and has an associated second PPE putting-on protocol comprising a putting-on movement associated with putting on the second PPE;
    wherein the PPE exit event has an associated second PPE taking-off protocol comprising a taking-off movement associated with taking off the second PPE and has an associated first PPE a taking-off protocol comprising a taking-off movement associated with taking off the first PPE; and
    wherein determining at least one of compliance or non-compliance with regard to the PPE event comprises determining whether the movements of the person match one or both of the first PPE putting-on protocol and the second PPE putting-on protocol or the second PPE taking-off protocol and the first PPE taking-off protocol.

4. The method of claim 3, wherein the PPE entrance event comprises a predetermined sequence of the putting-on movement associated with putting on the first PPE being performed prior to the putting-on movement associated with putting on the second PPE;
    wherein the PPE exit event comprises a predetermined sequence of the taking-off movement associated with taking off the second PPE being performed prior to the taking-off movement associated with taking off the first PPE; and
    wherein determining at least one of compliance or non-compliance with regard to the PPE event comprises determining whether the movements of the person match the predetermined sequence of the putting-on movement associated with putting on the first PPE being performed prior to the putting-on movement associated with putting on the second PPE and match the predetermined sequence of the taking-off movement associated with taking off the second PPE being performed prior to the taking-off movement associated with taking off the first PPE.

5. The method of claim 1, wherein the area comprises a patient area;
    wherein the PPE comprises a first PPE and gloves;
    wherein the PPE event comprises an entrance PPE event associated with entering the patient area and an exit PPE event associated with exiting the patient area;
    wherein the entrance PPE event has an associated first PPE putting-on protocol that includes a first PPE putting-on movement associated with putting on the first PPE and has an associated glove putting-on protocol that includes a glove putting-on movement associated with putting on the gloves;
    wherein the exit PPE event has an associated first PPE taking-off protocol that includes a first PPE taking-off movement associated with taking off the first PPE and has an associated glove taking-off protocol that includes a glove taking-off movement associated with taking off the gloves; and
    wherein determining the at least one of compliance or non-compliance with regard to the PPE event comprises:
        determining whether the first PPE putting-on movement is performed prior to the glove putting-on movement; and
        determining whether the first PPE taking-off movement is performed after the glove taking-off movement.

6. The method of claim 5, wherein responsive to determining a first proximity of the mobile electronic device with the stationary controller, determination of compliance of the entrance PPE event is performed; and
    wherein, responsive to determining a second proximity of the mobile electronic device with the stationary controller, determination of compliance of the exit PPE event is performed, wherein the second proximity is later in time than the first proximity.

7. The method of claim 1, further comprising:
    identifying a hand hygiene (HH) event based on the interaction of the mobile electronic device and the stationary controller;
    responsive to identifying the HH event, monitoring at least one aspect of the HH event; and determining, based on monitoring the at least one aspect of the HH event, at least one of compliance or non-compliance with regard to the HH event.

8. The method of claim 7, further comprising monitoring a sequence of performing at least one PPE action and at least one HH action in order to determine whether the person complied or did not comply with a predetermined sequence of performing the at least one PPE action and the at least one HH action.

9. The method of claim 8, wherein the area comprises a patient area;
    wherein the stationary controller is programmable, based on a specific patient in the patient area, for a specific PPE action;
    wherein the mobile electronic device receives from the stationary controller the specific PPE action responsive to identifying the PPE event; and
    wherein the mobile electronic device determines, based on the specific PPE action received from the stationary controller and the stored motion data, the at least one of compliance or non-compliance with regard to the PPE event.

10. The method of claim 9, wherein the stationary controller is programmed with a designation of status;
    comparing the designation of status with an indication of status as programmed in the mobile electronic device;
    responsive to the comparison of the designation of status with the indication of status as programmed in the mobile electronic device, determining whether to output an instruction regarding one or both of the PPE event or the HH event; and
    responsive to determining to output the instruction, outputting the instruction on one or both of the mobile electronic device or the stationary controller.

11. The method of claim 10, wherein the designation of status comprises a trainee status; and
    responsive to determining that the person, as indicated by the mobile electronic device, is a trainee, determining to output the instruction regarding one or both of the PPE event or the HH event.

12. The method of claim 8, wherein the area comprises a patient area;
    wherein the at least one aspect of the HH event comprises dispensing hand cleaning agent from a dispenser, the dispenser proximate to an entrance of the patient area; and
    wherein responsive to identifying the HH event, the stationary controller monitors whether the hand cleaning agent is dispensed from the dispenser.

13. The method of claim 8, further comprising generating an output responsive to determining the at least one of compliance or non-compliance of the PPE event and responsive to determining the at least one of compliance or non-compliance of the HH event.

14. The method of claim 13, wherein the output responsive to determining the at least one of compliance or non-compliance of the PPE event is different from the output responsive to determining the at least one of compliance or non-compliance of the HH event.

15. The method of claim 14, wherein timing for generating the output responsive to determining the at least one of compliance or non-compliance of the PPE event is different from timing for generating the output responsive to determining the non-compliance of the HH event.

16. The method of claim 8, wherein the area comprises a patient area;
    wherein the stationary controller is programmable, based on a location of the patient area, for a specific PPE action;
    wherein the mobile electronic device receives from the stationary controller the specific PPE action responsive to identifying the PPE event; and
    wherein the mobile electronic device determines, based on the specific PPE action received from the stationary controller and the stored motion data, the at least one of compliance or non-compliance with regard to the PPE event.

17. A mobile wearable electronic device comprising:
    at least one mechanical structure configured for attachment onto at least a part of a body of a person;
    communication functionality configured to wirelessly communicate with a stationary controller, the stationary controller configured to be associated with an area, the area being assigned one or more specific personal protection equipment (PPE) protocols, the one or more specific PPE protocols comprising one or more specific PPE movements;
    one or more motion sensors configured to generate sensor data indicative of movement of the person; and
    a controller in the mechanical structure and in communication with the communication functionality and the one or more motion sensors, the controller configured to:
        communicate with the stationary controller in order to identify a PPE event;
        responsive to the PPE event being identified:
            monitor the movement of the person by storing the sensor data generated by the one or more motion sensors;
            access the one or more specific PPE movements for the one or more specific PPE protocols assigned to the area; and
            determine, based on the one or more specific PPE movements and the stored sensor data, at least one of compliance or non-compliance of the movement of the person with regard to the PPE event.

18. The mobile wearable electronic device of claim 17, wherein the mobile wearable electronic device comprises a wristband;
    wherein the controller is configured to monitor one or more hand movements of the person; and
    wherein the controller is further configured to generate an output responsive to the at least one of compliance or non-compliance of the one or more hand movements of the person with regard to the PPE event.

19. The mobile wearable electronic device of claim 18, further comprising a memory configured to store an indication that the person is a trainee; and
    wherein the controller is further configured to:
        determine, based on accessing the indication in the memory, whether the person is a trainee; and
        responsive to determining that the person is a trainee and responsive to the communication with the stationary controller, output an instruction to the person in order to comply with the PPE event.

20. The mobile wearable electronic device of claim 17, wherein the area comprises a patient area;
    further comprising a memory configured to:
        store a plurality of PPE indicators, each of the plurality of PPE indicators correlated to one or both of one or more respective PPE movements or a respective PPE protocol;

store, for each of the plurality of PPE indicators, respective movement markers, the respective movement markers indicative of the one or both of the one or more respective PPE movements or the respective PPE protocol;

wherein the mobile wearable electronic device is configured to receive one or more indicators of the one or more specific PPE protocols assigned to the patient area;

wherein the controller is configured to access the one or more respective PPE movements correlated to the one or more indicators for the one or more specific PPE protocols; and wherein the controller is further configured to determine, based on the accessed one or more respective PPE movements correlated to the one or more indicators for the one or more specific PPE protocols, the at least one of compliance or non-compliance of the movement of the person with regard to the PPE event.

21. The mobile wearable electronic device of claim 20, wherein the plurality of PPE indicators comprise a glove indicator, a mask indicator, a gown indicator, and a protective eyewear indicator;

wherein the memory is configured to store glove movements associated with the glove indicator, mask movements associated with the mask indicator, gown movements associated with the gown indicator, and protective eyewear movements associated with the protective eyewear indicator;

wherein the controller is configured to receive, from the stationary controller, the the one or more indicators of the one or more specific PPE protocols for the patient area, the one or more indicators consisting of a subset of the glove indicator, the mask indicator, the gown indicator, and the protective eyewear indicator;

responsive to the controller receiving the one or more indicators for interacting with a specific patient assigned to the patient area, the controller is configured to:

check, based on the one or more indicators and for less than all of the glove movements, the mask movements, the gown movements, and the protective eyewear movements, whether movements of the person comply with a subset of the glove movements, the mask movements, the gown movements, and the protective eyewear movements.

22. The mobile wearable electronic device of claim 21, wherein the one or more indicators are indicative of a sequence of movements of the person for the subset of the glove movements, the mask movements, the gown movements, and the protective eyewear movements; and wherein the controller is configured to check whether the movements of the person comply with the subset of the glove movements, the mask movements, the gown movements, and the protective eyewear movements in the sequence.

23. The mobile wearable electronic device of claim 17, wherein a first stationary controller associated with a first patient area for a first patient, interaction with the first patient according to a first PPE protocol, the first PPE protocol comprising a first set of personal protective equipment for a healthcare provider to wear;

a second stationary controller associated with a second patient area for a second patient, interaction with the second patient according to a second PPE protocol, the second PPE protocol comprising a second set of personal protective equipment for the healthcare provider to wear, the second PPE protocol being different from the first PPE protocol such that the PPE for the healthcare provider to wear when interacting with the second patient is different from the PPE for the healthcare provider to wear when interacting with the first patient;

wherein the mobile wearable electronic device is configured to receive, from the first stationary controller, an indication of the first PPE protocol;

wherein, responsive to receiving the indication of the first PPE protocol, the controller is configured to check movements of the person to determine whether the person has complied with the first PPE protocol;

wherein the mobile wearable electronic device is configured to receive, from the second stationary controller, an indication of the second PPE protocol; and wherein, responsive to receiving the indication of the second PPE protocol, the controller is configured to check the movements of the person to determine whether the person has complied with the second PPE protocol.

24. The mobile wearable electronic device of claim 17, wherein, responsive to communication with the stationary controller, the controller is further configured to determine, based on the stored sensor data, at least one of compliance or non-compliance with regard to the PPE event and with regard to a hand hygiene (HH) event.

25. The mobile wearable electronic device of claim 24, wherein the mobile wearable electronic device is configured to receive one or both of an indication of PPE movements or an indication of a sequence of PPE movements;

wherein the controller is further configured to determine, based on the stored sensor data and the one or both of the indication of a set of PPE movements or the indication of a sequence of the PPE movements, at least one of compliance or non-compliance with regard to the PPE event; and wherein the controller is further configured to determine, based on the stored sensor data and without reliance on any indication from the stationary controller of a set of HH movements or the HH movements, at least one of compliance or non-compliance with regard to the HH event.

26. The mobile wearable electronic device of claim 24, wherein the area comprises a patient area;

wherein the controller is configured to determine whether the person is entering or exiting the patient area;

wherein, responsive to determining that the person is entering the patient area, the controller is configured to determine compliance based on determining whether the person complies with an entrance sequence of PPE movements and HH movements;

wherein, responsive to determining that the person is exiting the patient area, the controller is configured to determine compliance based on determining whether the person complies with an exit sequence of PPE movements and HH movements; and wherein the entrance sequence of PPE movements and HH movements is different from the exit sequence of PPE movements and HH movements.

27. A mobile wearable electronic device comprising:
at least one mechanical structure configured for attachment onto at least a part of a body of a person;
communication functionality configured to communicate with a stationary controller, the stationary controller configured to be associated with a patient area;
one or more motion sensors configured to generate sensor data indicative of hand movement of the person; and a controller in the mechanical structure and in communication with the communication functionality and the one or more motion sensors, the controller configured to:
- responsive to communication with the stationary controller, store sensor data generated by the one or more motion sensors in order to determine compliance or non-compliance of the hand movement of the person with regard to a personal protective equipment (PPE) event; and
- cause the stored sensor data to be transmitted for determination by an electronic device, other than the mobile wearable electronic device, of compliance with regard to the PPE event.

28. The mobile wearable electronic device of claim 27, wherein the controller is configured to cause the stored sensor data to be transmitted to the stationary controller for determination by the electronic device, other than the mobile wearable electronic device, of compliance of the PPE event.

29. The method of claim 1, wherein the area comprises a patient area; and
further comprising, responsive the PPE event being identified based on interaction of the mobile electronic device and the stationary controller, wirelessly receiving, by the mobile electronic device, at least one of an indication of the one or more specific PPE protocols for the patient area or the one or more specific PPE movements for the patient area in order for the mobile electronic device to determine the at least one of compliance or non-compliance with regard to the PPE event.

30. The method of claim 29, wherein the mobile electronic device comprises a wristband; and
wherein the wristband receives, from the stationary controller, the at least one of the indication of the one or more specific PPE protocols for the patient area or the one or more specific PPE movements for the patient area.

31. The mobile wearable electronic device of claim 17, wherein the area comprises a patient area; and
wherein the controller is further configured to, responsive the identification of the PPE event based on interaction of the mobile wearable electronic device and the stationary controller, wirelessly receiving at least one of an indication of the one or more specific PPE protocols for the patient area or the one or more specific PPE movements for the patient area in order for the mobile wearable electronic device to determine the at least one of compliance or non-compliance with regard to the PPE event.

32. The mobile wearable electronic device of claim 31, wherein the mobile wearable electronic device comprises a wristband; and
wherein, responsive to the PPE event being identified, the wristband is configured to receive, from the stationary controller, the at least one of the indication of the one or more specific PPE protocols for the patient area or the one or more specific PPE movements for the patient area.

* * * * *